(12) United States Patent
Shen et al.

(10) Patent No.: US 9,702,001 B2
(45) Date of Patent: *Jul. 11, 2017

(54) SCAFFOLD-BASED POLYMERASE ENZYME SUBSTRATES

(71) Applicant: Pacific Biosciences of California, Inc., Menlo Park, CA (US)

(72) Inventors: Gene Shen, Santa Clara, CA (US); Lubomir Sebo, Redwood City, CA (US); Stephen Yue, Eugene, OR (US); Wei-Chuan Sun, Mountain View, CA (US); Louis Brogley, Santa Cruz, CA (US); Andrei Fedorov, San Bruno, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 266 days.

This patent is subject to a terminal disclaimer.

(21) Appl. No.: 14/531,506

(22) Filed: Nov. 3, 2014

(65) Prior Publication Data
US 2015/0307933 A1    Oct. 29, 2015

Related U.S. Application Data

(63) Continuation of application No. 13/218,382, filed on Aug. 25, 2011, now Pat. No. 8,906,612.
(Continued)

(51) Int. Cl.
*C12Q 1/68* (2006.01)
*C07H 19/04* (2006.01)
(Continued)

(52) U.S. Cl.
CPC ......... *C12Q 1/6869* (2013.01); *C07D 209/14* (2013.01); *C07D 401/14* (2013.01);
(Continued)

(58) Field of Classification Search
CPC .............................. C12Q 1/6869; C07H 19/10
(Continued)

(56) References Cited

U.S. PATENT DOCUMENTS

| | | |
|---|---|---|
| 5,437,977 A | 8/1995 | Segev |
| 5,925,517 A | 7/1999 | Tyagi et al. |

(Continued)

FOREIGN PATENT DOCUMENTS

| | | |
|---|---|---|
| WO | 03014743 A2 | 2/2003 |
| WO | 2012054749 A1 | 4/2012 |
| WO | 2012054784 A1 | 4/2012 |

OTHER PUBLICATIONS

Chekasov et al., "New Nucleotide Analogues with Enhanced Signal Properties." Bioconjugate Chem. (2010) 21:122-129.
(Continued)

*Primary Examiner* — Jezia Riley
(74) *Attorney, Agent, or Firm* — Robert H. Reamey

(57) ABSTRACT

The invention provides a novel class of scaffold-based labeled polymerase enzyme substrates. The polymerase enzyme substrates have a multivalent core or scaffold to which is attached fluorescent dye moieties and nucleoside phosphate moities. The polymerase enzyme substrates have multiple fluorescent dye moities and/or multiple nucleoside phosphate moieties. Preferred multivalent cores comprise trifunctional six membered aromatic moities. The invention also provides for sequencing methods and kits with scaffold-based labeled polymerase enzyme substrates.

28 Claims, 53 Drawing Sheets

Related U.S. Application Data

(60) Provisional application No. 61/377,022, filed on Aug. 25, 2010, provisional application No. 61/377,048, filed on Aug. 25, 2010, provisional application No. 61/377,038, filed on Aug. 25, 2010, provisional application No. 61/377,004, filed on Aug. 25, 2010, provisional application No. 61/377,031, filed on Aug. 25, 2010.

(51) Int. Cl.
| | |
|---|---|
| *C09B 23/10* | (2006.01) |
| *C07D 209/14* | (2006.01) |
| *C07D 401/14* | (2006.01) |
| *C07D 405/14* | (2006.01) |
| *G01N 33/58* | (2006.01) |
| *C09B 23/01* | (2006.01) |
| *C09B 23/06* | (2006.01) |
| *C09B 23/08* | (2006.01) |
| *C07H 19/10* | (2006.01) |
| *C07K 5/09* | (2006.01) |
| *C07K 5/11* | (2006.01) |

(52) U.S. Cl.
CPC ........... *C07D 405/14* (2013.01); *C07H 19/10* (2013.01); *C07K 5/0815* (2013.01); *C07K 5/1019* (2013.01); *C09B 23/0025* (2013.01); *C09B 23/0033* (2013.01); *C09B 23/0066* (2013.01); *C09B 23/06* (2013.01); *C09B 23/083* (2013.01); *C09B 23/105* (2013.01); *C12Q 1/6844* (2013.01); *C12Q 1/6876* (2013.01); *G01N 33/582* (2013.01)

(58) Field of Classification Search
USPC .......................................... 536/26.6; 435/6.1
See application file for complete search history.

(56) References Cited

U.S. PATENT DOCUMENTS

| | | | |
|---|---|---|---|
| 7,462,452 | B2 | 12/2008 | Williams et al. |
| 8,906,612 | B2 * | 12/2014 | Shen .................... C07D 401/14 435/6.1 |
| 2002/0102590 | A1 | 8/2002 | Taing et al. |
| 2002/0115076 | A1 | 8/2002 | Williams |
| 2003/0219783 | A1 | 11/2003 | Puglisi et al. |
| 2004/0262585 | A1 | 12/2004 | Cummins et al. |
| 2005/0158761 | A1 | 7/2005 | Korlach et al. |
| 2006/0127940 | A1 | 6/2006 | Bao et al. |
| 2009/0186343 | A1 | 7/2009 | Wang et al. |
| 2009/0208957 | A1 | 8/2009 | Korlach et al. |
| 2010/0152424 | A1 | 6/2010 | Korlach et al. |
| 2010/0167299 | A1 | 7/2010 | Korlach |
| 2011/0165652 | A1 | 7/2011 | Hardin et al. |
| 2011/0313129 | A1 | 12/2011 | Hu et al. |

OTHER PUBLICATIONS

Martin et al., "Amplified Fluorescent Molecular Probes Based on 1,3,5,7-Tetrasubstituted Adamantane," Tetrahedron Letters (1999) 40:223-226.

Randolph et al., "Stability, Specificity and Fluorescence Brightness of Multiply-Labeled Fluorescent DNA Probes." Nucleic Acids Research (1997) 25(14):2923-2929.

* cited by examiner

Aminoproline

Piperidine

Phenylalanine

Diaminopropanoic Acid

Aspartic Acid

Trifluoroacetamidosuccinic Anhydride

Lysine

Glutamic Acid

Carbobenzyloxy Glutamic Anhydride

Serine

Aminoadipic Acid

Carboxyproline

Dicarboxypyrrolidine

| Entry # | R1 | R2 | R3 | R4 | R5 | R1' | R2' | R3' | R4' | R5' | absorption |
|---|---|---|---|---|---|---|---|---|---|---|---|
| 1 | H | H | H | H | D | H | H | H | H | D | 642 nm |
| 2 | H | H | COOH | H | D | H | H | COOH | H | D | 650 nm |
| 3 | H | A | H | A | D | H | H | H | COOH | D | 642 nm |
| 4 | H | A | H | A | D | H | H | H | B | D | 641 nm |
| 5 | H | A | H | A | D | H | A | H | A | D | 640 nm |
| 6 | H | A | H | A | D | H | H | COOH | H | D | 648 nm |
| 7 | H | H | SO$_3$H | H | D | H | H | COOH | H | D | 650 nm |
| 8 | H | H | SO$_3$H | H | D | H | H | SO$_3$H | H | D | 649 nm |
| 9 | H | H | G | H | D | H | H | G | H | D | 671 nm |
| 10 | H | H | H | F | D | H | H | H | F | D | 650 nm |
| 11 | H | H | F | H | D | H | H | F | H | C | 671 nm |
| 12 | H | H | F | H | D | H | H | F | H | D | 672 nm |
| 13 | H | H | F | H | C | H | H | F | H | C | 671 nm |
| 14 | OCH$_3$ | H | F | H | D | OCH$_3$ | H | F | H | C | 690 nm |
| 15 | H | SO$_3$H | H | E | D | H | H | H | COOH | D | 637 nm |
| 16 | H | E | H | E | D | H | H | H | COOH | D | 638 nm |
| 17 | H | E | H | E | D | H | SO$_3$H | H | COOH | D | 640 nm |
| 18 | H | SO$_3$H | H | E | D | H | SO$_3$H | H | COOH | D | 640 nm |
| 19 | H | SO$_3$H | H | COOH | D | H | SO$_3$H | H | COOH | D | 641 nm |
| 20 | H | A | H | A | D | H | SO$_3$H | H | COOH | D | 641 nm |
| 21 | H | SO$_3$H | H | SO$_3$H | D | H | SO$_3$H | H | COOH | D | 648 nm |
| 22 | SO$_3$H | H | SO$_3$H | H | D | H | SO$_3$H | H | COOH | D | 650 nm |
| 23 | H | H | NH$_2$CH$_2$ | H | D | H | H | SO$_3$H | H | C | 648 nm |
| 24 | H | SO$_3$H | H | E | D | H | SO$_3$H | H | E | D | 640 nm |
| 25 | H | A | H | A | D | H | SO$_3$H | H | E | D | 640 nm |
| 26 | H | SO$_3$H | H | SO$_3$H | D | H | H | H | COOH | D | 648 nm |
| 27 | SO$_3$H | H | SO$_3$H | H | D | H | H | H | COOH | D | 650 nm |
| 28 | H | SO$_3$H | H | SO$_3$H | D | H | H | COOH | H | D | 653 nm |
| 29 | SO$_3$H | H | SO$_3$H | H | D | H | H | COOH | H | D | 658 nm |
| 30 | H | SO$_3$H | H | SO$_3$H | D | H | H | SO$_3$H | H | C | 651 nm |
| 31 | SO$_3$H | H | SO$_3$H | H | D | H | H | SO$_3$H | H | C | 653 nm |
| 32 | H | A | H | A | D | H | COOH | H | E | D | 641 nm |
| 33 | H | E | H | E | D | H | COOH | H | E | D | 639 nm |

FIGURE 31b

| Entry # | R1 | R2 | R3 | R4 | R5 | R1' | R2' | R3' | R4' | R5' | absorption |
|---|---|---|---|---|---|---|---|---|---|---|---|
| 1 | H | H | H | H | D | H | H | H | H | D | 546 nm |
| 2 | H | H | COOH | H | D | H | H | COOH | H | D | 557 nm |
| 3 | H | H | H | COOH | D | H | H | H | COOH | D | 546 nm |
| 4 | H | A | H | A | D | H | H | H | COOH | D | 546 nm |
| 5 | H | H | H | A | D | H | H | COOH | H | D | 551 nm |
| 6 | H | A | H | A | D | H | H | COOH | H | D | 551 nm |
| 7 | H | OCH₃ | H | H | D | H | H | H | COOH | D | 549 nm |
| 8 | H | H | SO₃H | H | D | H | H | COOH | H | D | 553 nm |
| 9 | H | H | COOH | H | D | H | H | COOH | H | D | 556 nm |
| 10 | H | COOH | H | COOH | D | H | COOH | H | COOH | D | 545 nm |
| 11 | H | COOH | H | COOH | D | H | A | H | A | C | 551 nm |
| 12 | H | A | H | A | D | H | COOH | H | COOH | D | 547 nm |
| 13 | H | COOH | H | COOH | D | H | H | SO₃H | H | C | 549 nm |
| 14 | SO₃H | H | F | H | D | SO₃H | H | F | H | D | 568 nm |
| 15 | H | H | H | F | D | H | H | H | F | C | 552 nm |
| 16 | H | H | H | F | D | H | F | H | F | D | 552 nm |
| 17 | OCH₃ | H | F | H | D | OCH₃ | H | F | H | C | 593 nm |
| 18 | H | H | SO₃H | H | D | H | H | SO₃H | H | D | 550 nm |
| 19 | SO₃H | H | SO₃H | H | D | H | H | SO₃H | H | C | 560 nm |
| 20 | H | SO₃H | H | SO₃H | D | H | H | SO₃H | H | C | 558 nm |
| 21 | H | H | SO₃H | H | D | H | H | SO₃H | H | C | 551 nm |
| 22 | H | H | H | H | D | H | H | SO₃H | H | C | 547 nm |
| 23 | H | H | SO₃H | H | D | H | H | H | H | C | 549 nm |
| 24 | H | H | H | H | C | H | H | H | H | C | 549 nm |
| 25 | H | H | H | H | CH₃ | H | H | H | H | C | 545 nm |
| 26 | H | H | H | H | CH₃ | H | H | H | H | CH₃ | 543 nm |
| 27 | H | H | SO₃H | H | C | H | H | SO₃H | H | C | 553 nm |
| 28 | H | H | H | H | CH₃ | H | H | SO₃H | H | C | 548 nm |
| 29 | H | H | NH₂CH₂ | H | D | H | H | COOH | H | C | 549 nm |
| 30 | H | E | H | E | D | H | SO₃H | H | COOH | D | 542 nm |
| 31 | H | E | H | E | D | H | E | H | E | D | 540 nm |
| 32 | H | SO₃H | H | COOH | D | H | SO₃H | H | COOH | D | 543 nm |
| 33 | H | SO₃H | H | E | D | H | SO₃H | H | COOH | D | 543 nm |
| 34 | H | A | H | A | D | H | SO₃H | H | COOH | D | 544 nm |
| 35 | H | SO₃H | H | E | D | H | SO₃H | H | E | D | 540 nm |
| 36 | H | A | H | A | D | H | SO₃H | H | E | D | 543 nm |
| 37 | H | SO₃H | H | SO₃H | D | H | H | H | COOH | D | 550 nm |
| 38 | SO₃H | H | SO₃H | H | D | H | H | H | COOH | D | 554 nm |

FIGURE 32b

| Entry # | R1 | R2 | R3 | R4 | R5 | R6 | R1' | R2' | R3' | R4' | R5' | R6' | absorption |
|---|---|---|---|---|---|---|---|---|---|---|---|---|---|
| 1 | H | H | H | H | D | CH₃ | H | H | H | H | D | CH₃ | 546 nm |
| 2 | H | H | COOH | H | D | CH₃ | H | H | COOH | H | D | CH₃ | 557 nm |
| 3 | H | H | H | COOH | D | CH₃ | H | H | H | COOH | D | CH₃ | 546 nm |
| 4 | H | A | H | A | D | CH₃ | H | H | H | COOH | D | CH₃ | 546 nm |
| 5 | H | H | H | A | D | CH₃ | H | H | COOH | H | D | CH₃ | 551 nm |
| 6 | H | A | H | A | D | CH₃ | H | H | COOH | H | D | CH₃ | 551 nm |
| 7 | H | OCH₃ | H | H | D | CH₃ | H | H | H | COOH | D | CH₃ | 549 nm |
| 8 | H | H | SO₃H | H | D | CH₃ | H | H | COOH | H | D | CH₃ | 553 nm |
| 9 | H | H | COOH | H | D | CH₃ | H | H | COOH | H | D | CH₃ | 556 nm |
| 10 | H | COOH | H | COOH | D | CH₃ | H | COOH | H | COOH | D | CH₃ | 545 nm |
| 11 | H | COOH | H | COOH | D | CH₃ | H | A | H | A | C | CH₃ | 551 nm |
| 12 | H | A | H | A | D | CH₃ | H | COOH | H | COOH | D | CH₃ | 547 nm |
| 13 | H | COOH | H | COOH | D | CH₃ | H | H | SO₃H | H | C | CH₃ | 549 nm |
| 14 | SO₃H | H | F | H | D | CH₃ | SO₃H | H | F | H | D | CH₃ | 568 nm |
| 15 | H | H | H | F | D | CH₃ | H | H | H | F | C | CH₃ | 552 nm |
| 16 | H | H | H | F | D | CH₃ | H | F | H | F | D | CH₃ | 552 nm |
| 17 | OCH₃ | H | F | H | D | CH₃ | OCH₃ | H | F | H | C | CH₃ | 593 nm |
| 18 | H | H | SO₃H | H | D | CH₃ | H | H | SO₃H | H | D | CH₃ | 550 nm |
| 19 | SO₃H | H | SO₃H | H | D | CH₃ | H | H | SO₃H | H | C | CH₃ | 560 nm |
| 20 | H | SO₃H | H | SO₃H | D | CH₃ | H | H | SO₃H | H | C | CH₃ | 558 nm |
| 21 | H | H | SO₃H | H | D | CH₃ | H | H | SO₃H | H | C | CH₃ | 551 nm |
| 22 | H | H | H | H | D | CH₃ | H | H | SO₃H | H | C | CH₃ | 547 nm |
| 23 | H | H | SO₃H | H | D | CH₃ | H | H | H | H | C | CH₃ | 549 nm |
| 24 | H | H | H | H | C | CH₃ | H | H | H | H | C | CH₃ | 549 nm |
| 25 | H | H | H | H | CH₃ | CH₃ | H | H | H | H | C | CH₃ | 545 nm |
| 26 | H | H | H | H | CH₃ | CH₃ | H | H | H | H | CH₃ | CH₃ | 543 nm |
| 27 | H | H | SO₃H | H | C | CH₃ | H | H | SO₃H | H | C | CH₃ | 553 nm |
| 28 | H | H | H | H | CH₃ | CH₃ | H | H | SO₃H | H | C | CH₃ | 548 nm |
| 29 | H | H | NH₂CH₂ | H | D | CH₃ | H | H | COOH | H | C | CH₃ | 549 nm |
| 30 | H | E | H | E | D | CH₃ | H | SO₃H | H | COOH | D | CH₃ | 542 nm |
| 31 | H | E | H | E | D | CH₃ | H | E | H | E | D | CH₃ | 540 nm |
| 32 | H | SO₃H | H | COOH | D | CH3 | H | SO₃H | H | COOH | D | CH₃ | 543 nm |
| 33 | H | SO₃H | H | E | D | CH₃ | H | SO₃H | H | COOH | D | CH₃ | 543 nm |
| 34 | H | A | H | A | D | CH₃ | H | SO₃H | H | COOH | D | CH₃ | 544 nm |
| 35 | H | SO₃H | H | E | D | CH₃ | H | SO₃H | H | E | D | CH₃ | 540 nm |
| 36 | H | A | H | A | D | CH₃ | H | SO₃H | H | E | D | CH₃ | 543 nm |

FIGURE 32b, continued

| Entry # | R1 | R2 | R3 | R4 | R5 | R6 | R1' | R2' | R3' | R4' | R5' | R6' | absorption |
|---|---|---|---|---|---|---|---|---|---|---|---|---|---|
| 37 | H | SO₃H | H | SO₃H | D | CH₃ | H | H | H | COOH | D | CH₃ | 550 nm |
| 38 | SO₃H | H | SO₃H | H | D | CH₃ | H | H | H | COOH | D | CH₃ | 554 nm |
| 39 | H | H | SO₃H | H | D | D | H | COOH | H | E | D | CH₃ | 550 nm |
| 40 | H | A | H | A | D | CH₂ | H | COOH | H | E | D | D | 545 nm |
| 41 | H | E | H | E | D | CH₂ | H | COOH | H | E | D | D | 542 nm |
| 42 | H | H | SO₃H | H | D | CH₂ | H | H | SO₃H | H | C | D | 555 nm |

FIGURE 33b

| Entry # | R1 | R2 | R3 | R4 | R5 | R1' | R2' | R3' | R4' | R5' | absorption |
|---|---|---|---|---|---|---|---|---|---|---|---|
| 1 | H | J | H | SO₃H | D | H | J | H | SO₃H | D | 674 nm |
| 2 | H | J | H | SO₃H | D | H | J | H | SO₃H | C | 674 nm |
| 3 | H | J | H | SO₃H | C | H | J | H | SO₃H | C | 675 nm |
| 4 | H | SO₃H | H | J | D | H | SO₃H | H | J | D | 675 nm |
| 5 | H | SO₃H | H | J | D | H | SO₃H | H | J | C | 675 nm |
| 6 | H | J | H | J | D | H | J | H | J | D | 675 nm |
| 7 | H | J | H | J | D | H | J | H | J | C | 676 nm |
| 8 | H | J | H | J | C | H | J | H | J | C | 677 nm |
| 9 | H | K | H | SO₃H | D | H | K | H | SO₃H | D | 675 nm |
| 10 | H | K | H | SO₃H | D | H | K | H | SO₃H | C | 676 nm |
| 11 | H | K | H | SO₃H | C | H | K | H | SO₃H | C | 676 nm |
| 12 | H | SO₃H | H | K | D | H | SO₃H | H | K | D | 675 nm |
| 13 | H | K | H | K | D | H | K | H | K | D | 677 nm |
| 14 | H | H | F | H | D | H | H | F | H | D | 691 nm |
| 15 | SO₃H | H | F | H | D | SO₃H | H | F | H | C | 689 nm |
| 16 | H | H | SO₃H | H | D | H | H | H | H | C | 682 nm |
| 17 | H | H | SO₃H | H | D | H | H | SO₃H | H | C | 686 nm |
| 18 | H | SO₃H | H | SO₃H | D | H | SO₃H | H | SO₃H | C | 677 nm |

FIGURE 34b

| Entry # | R1 | R2 | R3 | R4 | R5 | R1' | R2' | R3' | R4' | R5' | absorption |
|---|---|---|---|---|---|---|---|---|---|---|---|
| 1 | H | J | H | SO₃H | D | H | J | H | SO₃H | D | 579 nm |
| 2 | H | J | H | SO₃H | D | H | J | H | SO₃H | C | 579 nm |
| 3 | H | SO₃H | H | J | D | H | SO₃H | H | J | D | 581 nm |
| 4 | H | SO₃H | H | J | D | H | SO₃H | H | J | C | 581 nm |
| 5 | H | J | H | J | D | H | J | H | J | D | 579 nm |
| 6 | H | J | H | J | D | H | J | H | J | C | 580 nm |
| 7 | H | J | H | J | C | H | J | H | J | C | 581 nm |
| 8 | H | K | H | SO₃H | D | H | K | H | SO₃H | D | 580 nm |
| 9 | H | SO₃H | H | K | D | H | SO₃H | H | K | D | 578 nm |
| 10 | H | K | H | K | D | H | K | H | K | D | 580 nm |
| 11 | H | K | H | SO₃H | D | H | K | H | SO₃H | C | 580 nm |
| 12 | H | H | F | H | D | H | H | F | H | D | 602 nm |
| 13 | SO₃H | H | F | H | D | SO₃H | H | F | H | C | 595 nm |
| 14 | H | H | SO₃H | H | D | H | H | H | H | C | 587 nm |
| 15 | H | SO₃H | H | SO₃H | D | H | H | H | H | C | 582 nm |
| 16 | H | SO₃H | H | SO₃H | D | H | H | SO₃H | H | C | 584 nm |
| 17 | H | H | SO₃H | H | D | H | H | SO₃H | H | D | 587 nm |
| 18 | H | H | SO₃H | H | D | H | H | SO₃H | H | C | 587 nm |
| 19 | H | H | SO₃H | H | C | H | H | SO₃H | H | C | 590 nm |
| 20 | H | H | NH₂CH₂ | H | D | H | H | SO₃H | H | C | 585 nm |
| 21 | H | SO₃H | H | SO₃H | D | H | SO₃H | H | SO₃H | C | 581 nm |
| 22 | H | SO₃H | H | SO₃H | D | H | SO₃H | H | SO₃H | D | 581 nm |
| 23 | SO₃H | H | COOH | H | D | SO₃H | H | COOH | H | D | 590 nm |

FIGURE 35b

| Entry # | R1 | R2 | R3 | R4 | R5 | R6 | R7 | R1' | R2' | R3' | R4' | R5' | R6' | absorption |
|---|---|---|---|---|---|---|---|---|---|---|---|---|---|---|
| 1 | H | H | SO₃H | H | D | D | L | H | H | SO₃H | H | D | D | 650 nm |
| 2 | H | H | SO₃H | H | D | D | L | H | H | SO₃H | H | D | D | 653 nm |
| 3 | H | H | SO₃H | H | D | D | M | H | H | SO₃H | H | D | D | 650 nm |
| 4 | H | H | SO₃H | H | D | D | M | H | H | SO₃H | H | D | D | 650 nm |
| 5 | H | H | SO₃H | H | D | CH₃ | M | H | H | SO₃H | H | D | D | 645 nm |
| 6 | H | A | H | A | D | CH₃ | M | H | A | H | A | D | CH₃ | 638 nm |
| 7 | H | A | H | A | D | CH₃ | P | H | A | H | A | D | CH₃ | 640 nm |
| 8 | | | | | | | | | | | | | | |
| | | | | | | | | | | | | | | |

FIGURE 36b

| Entry # | R1 | R2 | R3 | R4 | R5 | R6 | R7 | R1' | R2' | R3' | R4' | R5' | R6' | absorption |
|---|---|---|---|---|---|---|---|---|---|---|---|---|---|---|
| 1 | H | SO$_3$H | H | SO$_3$H | D | CH$_3$ | M | H | SO$_3$H | H | SO$_3$H | D | CH$_3$ | 672 nm |
| 2 | H | SO$_3$H | H | SO$_3$H | D | D | M | H | SO$_3$H | H | SO$_3$H | D | D | 680 nm |
| 3 | H | SO$_3$H | H | SO$_3$H | D | D | M | H | SO$_3$H | H | SO$_3$H | D | D | 678 nm |
| 4 | H | SO$_3$H | H | SO$_3$H | D | CH$_3$ | N | H | SO$_3$H | H | SO$_3$H | D | CH$_3$ | 666 nm |
| 5 | | | | | | | | | | | | | | |
| 18 | | | | | | | | | | | | | | |

FIGURE 37b

| Entry # | R1 | R2 | R3 | R4 | R5 | R1' | R2' | R3' | R4' | R5' | absorption |
|---|---|---|---|---|---|---|---|---|---|---|---|
| 2009 | SO$_3$H | H | H | F | D | SO$_3$H | H | H | L | D | 612 nm |
| 2010 | SO$_3$H | H | H | L | D | SO$_3$H | H | H | L | D | 612 nm |
| 2011 | SO$_3$H | H | H | F | D | SO$_3$H | H | H | F | D | 612 nm |
| 2013 | H | H | H | F | D | H | H | H | L | D | 614 nm |
| 2014 | H | H | H | L | D | H | H | H | L | D | 616 nm |
| 2016 | H | H | H | F | D | H | H | H | F | D | 616 nm |
| 2018 | H | H | H | SO$_3$H | D | H | H | H | SO$_2$NXY* | D | 607 nm |
| 2019 | H | H | H | SO$_3$H | D | H | H | H | SO$_2$NHZ* | D | 606 nm |
| 2021 | H | H | H | SO$_3$H | D | H | H | H | SO$_3$H | D | 594 nm |
| 2022 | H | H | H | F | D | H | H | H | M | D | 617 nm |
| 2023 | H | H | H | M | D | H | H | H | M | D | 616 nm |
| 2024 | SO$_3$H | H | H | M | D | SO$_3$H | H | H | N | D | 611 nm |
| 2026 | H | H | H | F | D | H | H | H | N | D | 611 nm |
| 2027 | H | H | H | N | D | H | H | H | N | D | 610 nm |
| 2028 | SO$_3$H | H | H | F | D | SO$_3$H | H | H | M | D | 611 nm |
| 2029 | SO$_3$H | H | H | F | D | SO$_3$H | H | H | N | D | 610 nm |
| 2030 | H | H | H | F | D | H | H | H | O | D | 613 nm |
| 2031 | SO$_3$H | H | H | SO$_3$H | C | SO$_3$H | H | H | SO$_3$H | D | 606 nm |
| 2032 | SO$_3$H | SO$_3$H | H | SO$_3$H | D | SO$_3$H | H | H | SO$_3$H | D | 607 nm |
| 2033 | SO$_3$H | H | H | M | D | SO$_3$H | H | H | M | D | 614 nm |

*X = Me; Y = (CH$_2$)$_3$CO$_2$H; Z = (CH$_2$)$_5$CO$_2$H

SCAFFOLD-BASED POLYMERASE ENZYME SUBSTRATES

BACKGROUND OF THE INVENTION

This application is a continuation application of U.S. patent application Ser. No. 13/218,382 filed Aug. 25, 2011, which claims the benefit of Provisional Patent Application 61/377,022 filed on Aug. 25, 2010, Provisional Patent Application 61/377,048 filed on Aug. 25, 2010, Provisional Patent Application 61/377,038 filed on Aug. 25, 2010, Provisional Patent Application 61/377,004 filed on Aug. 25, 2010, Provisional Patent Application 61/377,031 filed on Aug. 25, 2010, the full disclosures of which are incorporated by reference herein in their entirety.

BACKGROUND

The ability to read the genetic code has opened countless opportunities to benefit humankind. Whether it involves the improvement of food crops and livestock used for food, the identification of the causes of disease, the generation of targeted therapeutic methods and compositions, or simply the better understanding of what makes us who we are, a fundamental understanding of the blueprints of life is an integral and necessary component.

A variety of techniques and processes have been developed to obtain genetic information, including broad genetic profiling or identifying patterns of discrete markers in genetic codes and nucleotide level sequencing of entire genomes. With respect to determination of genetic sequences, while techniques have been developed to read, at the nucleotide level, a genetic sequence, such methods can be time-consuming and extremely costly.

Approaches have been developed to sequence genetic material with improved speed and reduced costs. Many of these methods rely upon the identification of nucleotides being incorporated by a polymerization enzyme during a template sequence-dependent nucleic acid synthesis reaction. In particular, by identifying nucleotides incorporated against a complementary template nucleic acid strand, one can identify the sequence of nucleotides in the template strand. A variety of such methods have been previously described. These methods include iterative processes where individual nucleotides are added one at a time, washed to remove free, unincorporated nucleotides, identified, and washed again to remove any terminator groups and labeling components before an additional nucleotide is added. Still other methods employ the "real-time" detection of incorporation events, where the act of incorporation gives rise to a signaling event that can be detected. In particularly elegant methods, labeling components are coupled to portions of the nucleotides that are removed during the incorporation event, eliminating any need to remove such labeling components before the next nucleotide is added (See, e.g., Eid, J. et al., Science, 323(5910), 133-138 (2009)).

In any of the enzyme mediated template-dependent processes, the overall fidelity, processivity and/or accuracy of the incorporation process can have direct impacts on the sequence identification process, e.g., lower accuracy may require multiple fold coverage to identify the sequence with a high level of confidence. One of the key components of sequencing is the labeled nucleotide probe (labeled polymerase enzyme substrate). To enhance the sensitivity of analyses and assays there is a need for labeled nucleotide probes that are good enzyme substrates, are bright and readily detectable at low concentrations, and can be readily engineered to have a particular absorbance and/or emission pattern spectrum. The present invention provides methods, systems and compositions that provide for improved polymerase enzyme probes, among other benefits.

BRIEF SUMMARY OF THE INVENTION

In some aspects the invention comprises a composition comprising a compound of the structure:

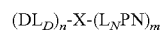

$(DL_D)_n\text{-}X\text{-}(L_NPN)_m$ wherein each D is a fluorescent dye moiety, X is a multifunctional core with multiple linking sites, P is a polyphosphate moiety having 2 to 10 phosphates, N is a nucleoside moiety, m+n=3 or greater, and $L_D$ and $L_N$ are either direct bonds or linkers.

In some embodiments the compound has the structure:

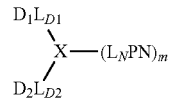

wherein $D_1$ and $D_2$ are each fluorescent dye moieties, $L_{D1}$ and $L_{D2}$ are each either direct bonds or linkers, N is a nucleoside moiety, and m is one or greater.

In some embodiments, the compound has the structure

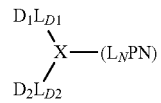

wherein $D_1$ and $D_2$ are each fluorescent dye moieties, $L_{D1}$ and $L_{D2}$ are each either direct bonds or linkers, and N is a nucleoside moiety.

In some embodiments $D_1$ is a FRET donor and $D_2$ is a FRET acceptor.

In some embodiments, the compound has the structure:

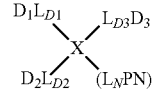

wherein $D_1$, $D_2$, and $D_3$ are each fluorescent dye moieties, $L_{D1}$, $L_{D2}$, and $L_{D3}$ are each either direct bonds or linkers. In some embodiments $D_1$ and $D_2$ are FRET donors and $D_3$ is a FRET acceptor.

In some embodiments, the compound has the structure

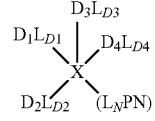

wherein $D_1$, $D_2$, $D_3$, and $D_4$ are each fluorescent dye moieties, $L_{D1}$, $L_{D2}$, $L_{D3}$, and $L_{D4}$ are each either direct bonds or linkers.

In some embodiments $D_1$, $D_2$, and $D_3$ are FRET donors and $D_4$ is a FRET acceptor. The composition of claim 2 or 3 wherein X comprises a trifunctional six-membered aromatic moiety. In some embodiments the trifunctional six-membered aromatic moiety comprise either a tri-substituted benzene or a tri-substituted triazine. In some embodiments the trifunctional six-membered aromatic moiety comprise a tri-substituted triazine and also comprises one, two, or three piperidine moieties attached to the triazine.

In some embodiments X comprises two trifunctional six-membered aromatic moities bonded to each other to form tetrafunctional core. In some embodiments the trifunctional six-membered aromatic moities comprise one or more tri-substituted benzene or tri-substituted triazine. In some embodiments X comprises two td-substituted triazines bonded to each other to form a tetrafunctional core. In some embodiments X comprises three trifunctional six-membered aromatic moities bonded to each other to form pentafunctional core. In some embodiments the trifunctional six-membered aromatic moities comprise one or more tri-substituted benzene or tri-substituted triazine. In some embodiments X comprises three tri-substituted triazines bonded to each other to form a pentafunctional core.

In some embodiments one or more of the linkers comprise linear or branched alkyl chains having from 2 to 20 carbons. In some embodiments one or more of the fluorescent dye moieties comprise cyanine dyes.

In some embodiments all the fluorescent dye moieties in the compound comprise cyanine dye. In some embodiments m+n is from 3 to 12.

In some embodiments X comprises the structure:

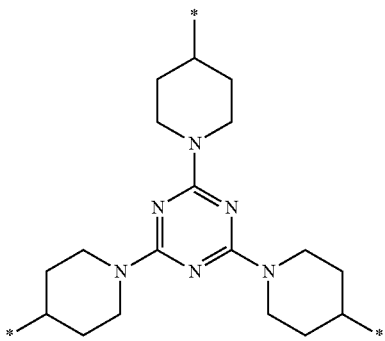 [SMILES: *C1CCN(c2nc(N3CCC(*)CC3)nc(N3CCC(*)CC3)n2)CC1]

In some embodiments X comprises the structure:

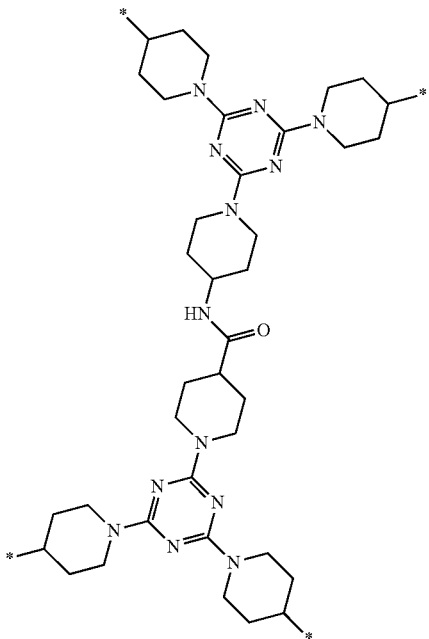 [SMILES: *C1CCN(c2nc(N3CCC(*)CC3)nc(N3CCC(NC(=O)C4CCN(c5nc(N6CCC(*)CC6)nc(N6CCC(*)CC6)n5)CC4)CC3)n2)CC1]

In some embodiments X comprises the structure:

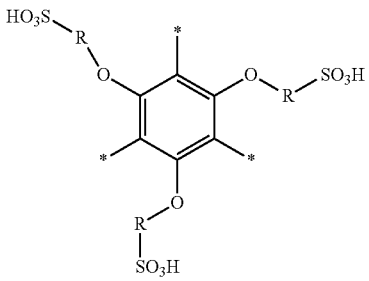

wherein R comprises a linear or branched alkyl chain with from 1 to 10 carbons.

In some embodiments X comprises an aminoproline moiety. In some embodiments R is a linear alkyl chain with 1 to 5 carbons. In some embodiments the compound comprises 4 to 40 sulfonate groups.

In some aspects the invention comprises a sequencing mixture comprising a set of 4 nucleotide analog substrates, each having one of the bases A, G, C, T, or A, G, C, U, at least two of the substrates having a structure described herein, and each substrate having at least one fluorescent dye moiety different from the fluorescent dye moieties on the other three substrates.

In some aspects the invention comprises a method for nucleic acid sequencing comprising: immobilizing a polymerase enzyme complex comprising a polymerase enzyme and a template nucleic acid; exposing the immobilized polymerase enzyme complex to a plurality of labeled nucleotide analog substrates, at least one of the substrates comprising a compound having the structure of described herein; detecting the incorporation of substrates by observing fluorescence from the nucleotide analog substrates; and using the detected incorporation over time to obtain sequence information about the template nucleic acid.

In some aspects the invention comprises a kit comprising a set of 4 nucleotide analog substrates, each having one of the bases A, G, C, T, or A, G, C, U, at least one of the substrates having the structure described herein, and each substrate having at least one fluorescent dye moiety different from the fluorescent dye moieties on the other three substrates.

In some aspects the invention comprises a composition comprising a compound having the structure:

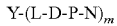

wherein Y is a multifunctional core having m linking sites, L is either a direct bond or a linker, D is a fluorescent dye moiety, P is a polyphosphate having from 2 to 10 phosphates, and N is a nucleoside moiety, and in is greater than 2.

In some embodiments m is from 2 to about 10. In some embodiments each L-D-P-N in the compound is the same. In some embodiments Y comprises a trifunctional six-membered aromatic moiety. In some embodiments the trifunctional six-membered aromatic moiety comprise either a tri-substituted benzene or a tri-substituted triazine. In some embodiments the trifunctional six-membered aromatic moiety comprise a tri-substituted triazine and also comprises one, two, or three piperidine moieties attached to the triazine. In some embodiments L is a linker having a linear or branched alkyl chain with 2 to 20 carbons.

In some aspects the invention comprises a composition comprising a compound having the structure:

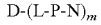

wherein D is a fluorescent dye moiety having m linking sites, L is either a direct bond or a linker, P is a polyphosphate moiety having 2 to 10 phosphates, N is a nucleoside moiety, and m is from 2 to 8.

In some embodiments D comprises a cyanine dye. In some embodiments m is from 2 to 4. In some embodiments the compound has 2 to 40 sulfonate groups. In some embodiments compound is water soluble. In some embodiments L is a linker having a linear or branched alkyl chain with 2 to 20 carbons.

In some aspects the invention comprises a composition comprising a compound having the structure:

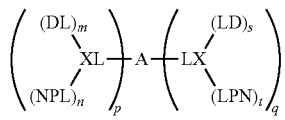

wherein X is a multifunctional linker, A is a FRET acceptor dye moiety, each D is a FRET donor each L is a direct bond or a linker, each N is a nucleoside, each P is a polyphosphate having from 2 to 10 phosphates, m, n, s, t, p, and q are each independently either 1, 2, or 3.

In some embodiments, the compound has the structure:

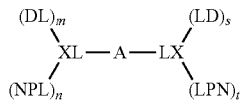

In some embodiments m, n, s, and t=1. In some embodiments A comprises a cyanine dye. In some embodiments each D comprises a cyanine dye. In some embodiments A comprises a CY3, CY3.5, CY5 or CY5.5 dye.

In some embodiments the compound is a symmetrical compound in which each D, each N, each P, and each X are the same in the compound.

In some embodiments each X comprises a trifunctional six-membered aromatic moiety. In some embodiments the trifunctional six-membered aromatic moiety comprise either a tri-substituted benzene or a tri-substituted triazine. In some embodiments trifunctional six-membered aromatic moiety comprise a tri-substituted triazine and also comprises one, two, or three piperidine moieties attached to the triazine.

In some embodiments at least one X comprises the structure:

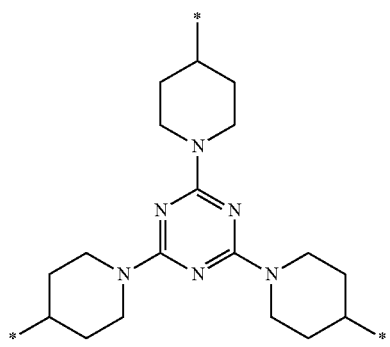 [SMILES: *C1CCN(c2nc(N3CCC(*)CC3)nc(N3CCC(*)CC3)n2)CC1]

In some embodiments at least one X comprises the structure:

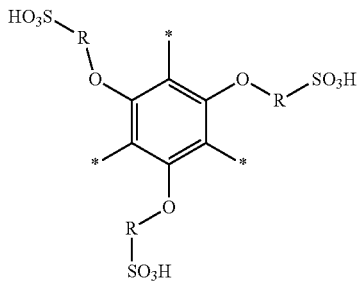

In some embodiments R comprises a linear or branched alkyl chain with from 1 to 10 carbons. In some embodiments X comprises an aminoproline moiety. In some embodiments R is a linear alkyl chain with 1 to 5 carbons.

BRIEF DESCRIPTION OF THE DRAWINGS

FIG. 30(b) is a tabulation of exemplary dye component precursors according to the generic structure of FIG. 30(a).

FIG. 31(b) is a tabulation of exemplary dye component precursors according to the generic structure of FIG. 31(a).

FIG. 32(b) is a tabulation of exemplary dye component precursors according to the generic structure of FIG. 32(a).

FIG. 33(b) is a tabulation of exemplary dye component precursors according to the generic structure of FIG. 33(a).

FIG. 34(b) is a tabulation of exemplary dye component precursors according to the generic structure of FIG. 34(a).

FIG. 35(b) is a tabulation of exemplary dye component precursors according to the generic structure of FIG. 35(a).

FIG. 36(b) is a tabulation of exemplary dye component precursors according to the generic structure of FIG. 36(a).

FIG. 37(b) is a tabulation of exemplary dye component precursors according to the generic structure of FIG. 37(a).

DETAILED DESCRIPTION OF THE INVENTION

Abbreviations

Figure 1:
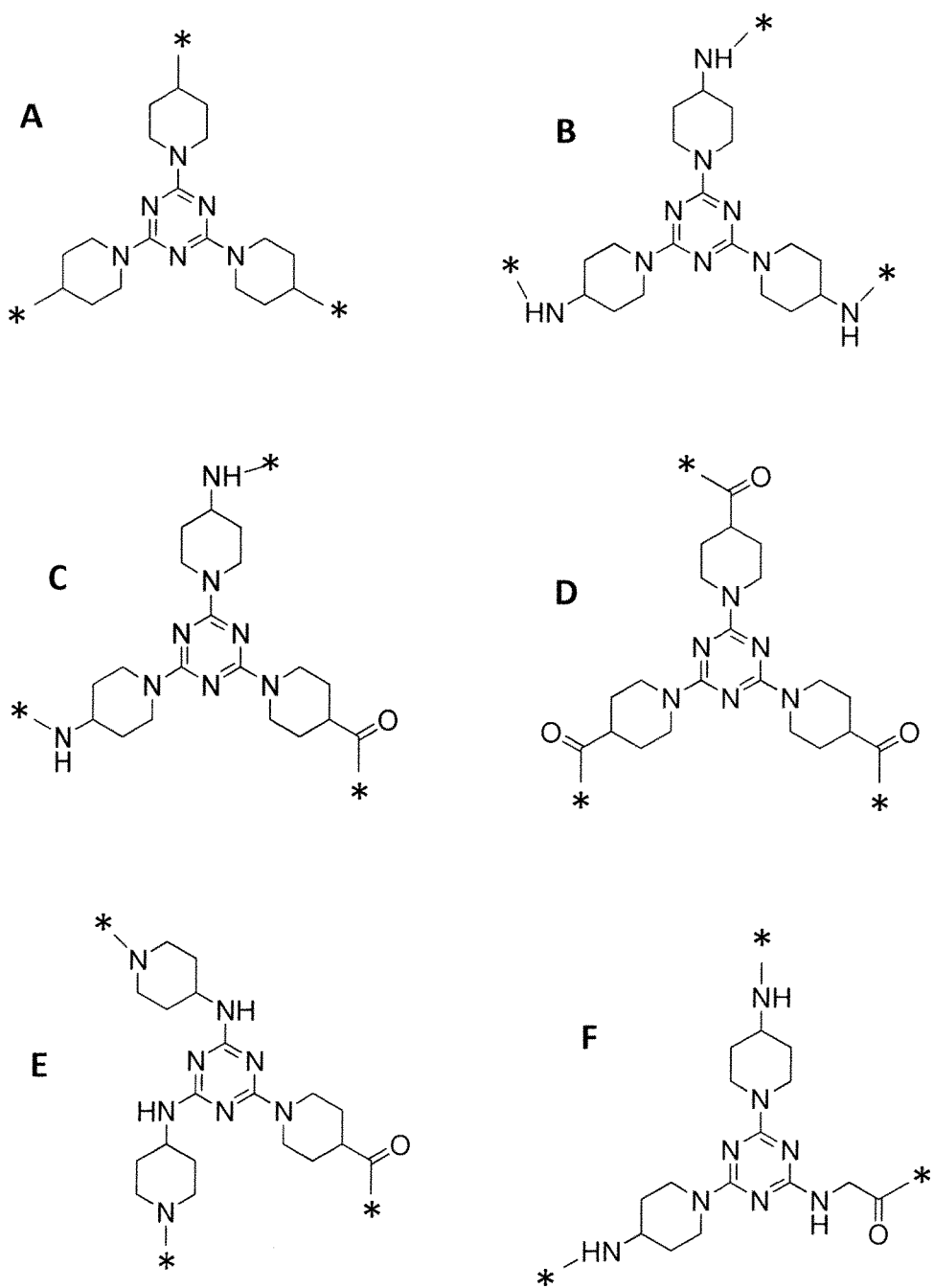
FIG. 1 shows representative triazine based core units.

"FRET," as used herein, refers to "Fluorescence Resonance Energy Transfer." These terms are used herein to refer to both radiative and non-radiative energy transfer processes. For example, processes in which a photon is emitted and those involving long-range electron transfer are included within these terms. Throughout this specification, both of these phenomena are subsumed under the general term "donor-acceptor energy transfer."

Any of the dyes set forth herein can be a component of an FRET pair as either the donor or acceptor. Conjugating a donor and an acceptor through reactive functional groups on the donor, acceptor and an appropriate linker or carrier molecule is well within the abilities of those of skill in the art.

Definitions

Where chemical moieties are specified by their conventional chemical formulae, written from left to right, they optionally equally encompass the moiety which would result from writing the structure from right to left, e.g., —CH$_2$O— is intended to also recite —OCH$_2$—; —NHS(O)$_2$— is also intended to optionally represent. —S(O)$_2$HN—, etc. Moreover, where compounds can be represented as free acids or free bases or salts thereof, the representation of a particular form, e.g., carboxylic or sulfonic acid, also discloses the other form, e.g., the deprotonated salt form, e.g., the carboxylate or sulfonate salt. Appropriate counterions for salts are well-known in the art, and the choice of a particular counterion for a salt of the invention is well within the abilities of those of skill in the art. Similarly, where the salt is disclosed, this structure also discloses the compound in a free acid or free base form. Methods of making salts and free acids and free bases are well-known in the art.

"Cyanine," as used herein, refers to polymethine dyes such as those based upon the cyanine, merocyanine, styryl and oxonol ring. Cyanine dyes include, for example, CY3, CY3.5, CY5 and CY5.5 type dyes.

As used herein, "nucleic acid" means any natural or non-natural nucleotide or nucleoside phosphate oligomer or polymer; e.g., DNA, RNA, single-stranded, double-stranded, triple-stranded or more highly aggregated hybridization motifs, and any chemical modifications thereof. Modifications include, but are not limited to, conjugation with a compound of the invention or a construct that includes a compound of the invention covalently attached to a linker that tethers the compound to the nucleic acid, and those providing the nucleic acid with a group that incorporates additional charge, polarizability, hydrogen bonding, electrostatic interaction, fluxionality or functionality to the nucleic acid. Exemplary modifications include the attachment to the nucleic acid, at any position, of one or more hydrophobic or hydrophilic moieties, minor groove binders, intercalating agents, quenchers, chelating agents, metal chelates, solid supports, and other groups that are usefully attached to nucleic acids. Exemplary nucleic acids of the invention include one or more dye moiety of the invention bound thereto.

Exemplary modified nucleic acids include, but are not limited to, peptide nucleic acids (PNAs), those with phosphodiester group modifications (e.g., replacement of O⁻ with OR, NR, or SR), 2'-, 3'- and 5'-position sugar modifications, modifications to the base moiety, e.g., 5-position pyrimidine modifications, 8-position purine modifications, modifications at exocyclic amines, substitution of 4-thiouridine, substitution of 5-bromo or 5-iodo-uracil; backbone modifications, i.e., substitution of P(O)O$_3$ with another moiety, methylations, unusual base-pairing combinations such as the isobases, isocytidine and isoguanidine and the like. Nucleic acids can also include non-natural bases, e.g., nitroindole. Non-natural bases include bases that are modified with a compound of the invention or a linker-compound of the invention construct, a minor groove binder, an intercalating agent, a hybridization enhancer, a chelating agent, a metal chelate, a quencher, a fluorophore, a fluorogenic compound, etc. Modifications within the scope of "nucleic acid" also include 3' and 5' modifications with one or more of the species described above.

The nucleic acid can comprise DNA, RNA or chimeric mixtures or derivatives or modified versions thereof. Both the probe and target nucleic acid can be present as a single strand, duplex, triplex, etc. Moreover, as discussed above, the nucleic acid can be modified at the base moiety, sugar moiety, or phosphate backbone with other groups such as radioactive labels, minor groove binders, intercalating agents, donor and/or acceptor moieties and the like.

Nucleic acids, nucleotides and nucleosides contain nucleobases. In addition to the naturally occurring "nucleobases," adenine, cytosine, guanine and thymine, nucleic acid components of the compounds of the invention optionally include modified bases. These components can also include modified sugars. For example, the nucleic acid can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methyl inosine, 2,2-dimethylguanine, 2-methyladenine, 2-methylguanine, 3-methylcytosine, 5-methylcytosine, N$^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine. The cyanine dye of the invention or another probe component can be attached to the modified base.

Typically the nucleic acids, nucleotides, and nucleosides of the invention comprise either ribose (RNA) or deoxyribose (DNA). In other embodiments, the nucleic acid, nucleotide, or nucleoside comprises a modified sugar moiety selected from the group including, but not limited to, arabinose, 2-fluoroarabinose, xylulose, and hexose. The cyanine dye or another probe component can be attached to the modified sugar moiety.

In yet another embodiment, the nucleic acid, nucleotide, or nucleoside phosphate comprises at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof. The cyanine dye or another probe component can be attached to the modified phosphate backbone.

Nucleic acids, nucleotides and nucleotide phosphates of the invention also include species that are modified at one or more internucleotide bridges (e.g., P(O)O$_3$) by replacing or derivatizing an oxygen of the bridge atom with a compound of the invention or a species that includes a compound of the invention attached to a linker. For example a "nucleic acid" also refers to species in which the P(O)O$_2$ moiety (the O$^-$ moiety remains unchanged or is converted to "OR") of a natural nucleic acid is replaced with a non-natural linker species, e.g., —ORP(O)O—, —ROP(O)R—, —ORP(O)OR—, —ROP(O)OR—, or —RP(O)R— in which the symbol "—" indicates the position of attachment of the linker to the 2'-, 3'- or 5'-carbon of a nucleotide sugar moiety, thus allowing the placement of the exemplified, and other, non-natural linkers between adjacent nucleoside sugar moieties. Exemplary linker subunits ("R") include substituted or unsubstituted alkyl and substituted or unsubstituted heteroalkyl moieties. "R" can include a compound of the invention or a construct of a linker and a compound of the invention.

Further exemplary nucleic acids of the invention include a polyphosphate moiety, e.g., pyrophosphate or a higher homologue, such as the 3-mer, 4-mer, 5-mer, 6-mer, 7-mer, 8-mer and the like. The polyphosphate moities of the invention generally comprise from 2 to 10 phosphates. In preferred embodiments, the polyphosphate moieties comprise 4, 5, 6, 7 or 8 phosphates. In other some embodiments, a methylene moiety, NH moiety, or S moiety bridges two or more phosphorus atoms, replacing the OPO link with an PCH$_2$P, PNHP, or PSP link.

Furthermore, "nucleic acid" includes those species in which one or more internucleotide bridge does not include phosphorus: the bridge being optionally modified with a compound of the invention or a linker arm-cyanine dye construct. An exemplary bridge includes a substituted or unsubstituted alkyl or substituted or unsubstituted heteroalkyl moiety in which a carbon atom is the locus for the interconnection of two nucleoside sugar residues (or linker moieties attached thereto) and a compound of the invention or a linker construct that includes a compound of the invention. The discussion above is not limited to moieties that include a carbon atom as the point of attachment; the locus can also be another appropriate linking atom, such as nitrogen or another atom.

Phosphodiester linked nucleic acids of the invention can be synthesized by standard methods known in the art, e.g. by use of an automated DNA synthesizer using commercially available amidite chemistries (Ozaki et al., *Nucleic Acids Research,* 20: 5205-5214 (1992); Agrawal et al., *Nucleic Acids Research,* 18: 5419-5423 (1990); Beaucage et al., *Tetrahedron,* 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679). Nucleic acids bearing modified phosphodiester linking groups can be synthesized by methods known in the art. For example, phosphorothioate nucleic acids may be synthesized by the method of Stein et al. (*Nucl. Acids Res.* 16:3209 (1988)), methylphosphonate nucleic acids can be prepared by use of controlled pore glass polymer supports (Sarin et al., *Proc. Natl. Acad. Sci. U.S.A.* 85:7448-7451 (1988)). Other methods of synthesizing both phosphodiester- and modified phosphodiester-linked nucleic acids will be apparent to those of skill in the art.

The nucleotides and nucleoside phosphates of the invention are generally meant to be used as substrates for polymerase enzymes, particularly in the context of nucleic acid sequencing. Therefore, generally, any non-natural base, sugar, or phosphate of the nucleotide or nucleoside phosphate can be included as a nucleotide or nucleoside phosphate of the invention if the nucleoside phosphate is capable of acting as a substrate for any natural or modified polymerase enzyme.

As used herein, "quenching group" refers to any fluorescence-modifying group of the drug, dye, nutrient, growth factor, etc., without limitation. "Carrier molecule" also refers to species that might not be considered to fall within the classical definition of "a molecule," e.g., solid support (e.g., synthesis support, chromatographic support, membrane), virus and microorganism. An exemplary carrier molecule of use in the present invention is a polyphosphate nucleic acid, or a polyphosphate nucleic acid linker cassette. Exemplary conjugates between the dyes of the invention and the polyphosphate nucleic linker cassette are conjugated by covalent binding of the linker to both the dye and the polyphosphate nucleic acid. In an exemplary embodiment, the linker is bound to the polyphosphate moiety through a phosphodiester bond. In an exemplary embodiment, the linker is attached to the dye through a bond formed with an activated derivative of a carboxyl moiety on the dye. In various embodiments, the bond is an amide bond.

"Activated derivatives of carboxyl moieties," and equivalent species, refers to moiety on a dye of the invention or another component of a conjugate of the invention in which an oxygen-containing, or other, leaving group is formally accessed through a carboxyl moiety, e.g., an active ester, acyl halide, acyl imidazolide, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene," "alkynyl" and, optionally, those derivatives of alkyl defined in more detail below, such as "heteroalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P and S, and wherein the nitrogen and sulfur atoms may optionally be oxidized and the nitrogen heteroatom may optionally be quaternized. The heteroatom(s) O, N, S, P and Si may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene, alkynyl, and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di- and multivalent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C$_1$-C$_4$)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like).

Each of the above terms (e.g., "alkyl," "heteroalkyl," "aryl" and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', SO$_3$R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, i-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The substituents set forth in the paragraph above are referred to herein as "alkyl group substituents."

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', SO$_3$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)alkyl.

The substituents set forth in the two paragraphs above are referred to herein as "aryl group substituents."

"Analyte", "target", "substance to be assayed", and "target species," as utilized herein refer to the species of interest in an assay mixture. The terms refer to a substance, which is detected qualitatively or quantitatively using a material, process or device of the present invention. Examples of such substances include nucleic acids, cells and portions thereof, enzymes, antibodies, antibody fragments and other biomolecules, e.g., antigens, nucleic acids, polypeptides, glycoproteins, polysaccharides, complex glycolipids, nucleic acids, effector molecules, receptor molecules, enzymes, inhibitors and the like and drugs, pesticides, herbicides, agents of war and other bioactive agents.

More illustratively, such substances include, but are not limited to, tumor markers such as α-fetoprotein, carcinoembryonic antigen (CEA), CA 125, CA 19-9 and the like; various proteins, glycoproteins and complex glycolipids such as β$_2$-microglobulin (β$_2$ m), ferritin and the like; various hormones such as estradiol (E$_2$), estriol (E$_3$), human chorionic gonadotropin (hCG), luteinizing honnone (LH), human placental lactogen (hPL) and the like; various virus-related antigens and virus-related antibody molecules such as HBs antigen, anti-HBs antibody, HBc antigen, anti-HBc antibody, anti-HCV antibody, anti-HIV antibody and the like; various allergens and their corresponding IgE antibody molecules; narcotic drugs and medical drugs and metabolic products thereof; and nucleic acids having virus- and tumor-related polynucleotide sequences.

The term, "assay mixture," refers to a mixture that includes the analyte and other components. The other components are, for example, diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like.

As used herein, the term "environmentally sensitive dye," refers to a dye that begins to fluoresce, ceases fluorescing, fluoresces at an altered wavelength or altered intensity upon a binding event in which the dye participates. An example of a binding event is the interaction of the dye with a protein. An exemplary protein is a DNA polymerase. An exemplary dye is essentially non-fluorescent until it binds to a DNA polymerase at which point it fluoresces with detectable intensity.

When referring to components of the compounds of the invention, the term "residue derived from," refers to a residue formed by the reaction of a first reactive functional group on a first component (e.g., scaffold, dye or a linker) and a second reactive functional group on a second component (e.g., scaffold, a linker or dye moiety) to form a covalent bond. In exemplary embodiments, an amine group on the first component is reacted with an activated carboxyl group on the second component to form a residue including one or more amide moieties. Other permutations of first and second reactive functional groups are encompassed by the invention.

Introduction

The present invention provides a class of core or scaffold-based substrates for polymerase enzymes, particularly for use in nucleic acid sequencing. Compounds of the invention have at least one fluorescent dye moiety and at least one nucleoside polyphosphate moiety and generally have multiple fluorescent dye moieties and/or multiple nucleoside phosphate moieties. The compounds of the invention are covalent compounds formed around a small molecule core with a defined number of substituents, where the substituents comprise a combination of both fluorescent dye moieties and nucleoside polyphosphate moieties. The number of substituents can be, for example, 3, 4, 5, 6, 7, 9, or more.

The compounds of the invention can be useful for carrying out real time single-molecule nucleic acid sequencing as described, for example in Eid et al., Science 323, 133 (2009). When carrying out such sequencing, it can be advantageous to have a substrate for the polymerase enzyme having multiple labels, multiple nucleoside polyphosphates or having both multiple labels and multiple nucleoside phosphates.

A polymerase enzyme substrate with multiple dyes can in some cases result in higher brightness, which can result from having 2, 3, 4, 5, 6, 7, 8, 9, 10, 11, 12 or more dyes of the same type attached to a central core. In other cases, the constructs of the invention having multiple dyes will have two or more different types of dyes. A substrate with multiple dyes can have a FRET donor-acceptor pair. Having a FRET dye pair as part of the substrate allows for constructing dye sets having desirable brightness, quantum yield, and Stokes shift values. The compounds of the invention also allow for the production of FRET systems having multiple FRET donors and/or multiple FRET acceptors. For example, we have found that it can be desirable in single molecule sequencing to have an enzyme substrate comprising two FRET donors and one acceptor.

A polymerase enzyme substrate with multiple nucleoside polyphosphate moieties can also be desirable for single molecule sequencing. Multiple nucleoside polyphosphates on the substrate results in a higher concentration of nucleoside phosphate to the enzyme for a given concentration of substrate compound, increasing the rate of incorporation. Having both multiple fluorescent dye moieties and multiple nucleoside polyphosphate moieties allows for both increased brightness and for increased local concentration. The various compounds of the present invention allow for adjusting these properties in order to improve the overall performance of the sequencing system.

For example, in real-time single molecule sequencing, e.g. as discussed in Eid et al., Science 323, 133 (2009), there are typically four different enzyme substrates, corresponding to A, G, T, C or A, G, T, U, each with a distinct fluorescent label. The excitation and emission spectra of each of the dyes must be selected in order to independently detect the presence of each type of base in order to determine the identity of the base which is incorporated. In some cases, two different excitation wavelengths are used, each excitation wavelength exciting the label corresponding to two bases. In other cases, a single excitation wavelength (laser) is used to excite all four labeled enzyme substrates. Where one laser excites all four substrates, the Stokes shifts (difference between the dye's excitation and emission maxima) is selected in order to provide four distinct excitation spectra. The compounds of the present invention that incorporate multiple dyes, especially those incorporating different FRET donor/acceptor combinations, provide for constructing sets of polymerase substrates with the required spectral characteristics.

In some aspects the invention describes multi-dye constructs having a multifunctional core. The multi-dye constructs can be used to label proteins or nucleic acids.

The scaffold or core of the polymerase enzyme substrate in some preferred embodiments comprises a trifunctional aromatic moiety, for example a tri-substituted benzene or tri-substituted triazine moiety. The tri-substituted aromatic moiety acts as a rigid central core about which the fluorescent dye moieties and nucleoside polyphosphate moieties are attached. The aromatic core is generally a 6 membered ring. In some cases, the aromatic core can be heterocyclic, containing, for example, one nitrogen (pyridine), two nitrogens (diazine), or preferably three nitrogens (triazine). The heterocyclic aromatic core can also comprise silicon, germanium, tin, phosphorous, or arsenic. The aromatic core is preferably substituted at the 1, 3, and 5 positions (or the 2, 4, and 6 positions), but can have other substitutions in some embodiments.

In some cases, the compounds of the invention have a single tri-substituted aromatic moiety at its core, resulting in a trifunctional molecule having either two fluorescent dye moities and one nucleoside polyphosphate moieties or two nucleoside phosphate moieties and one dye moiety.

In some cases the compounds of the invention have two or more trifunctional moieties linked together to form the core. The core can comprise, for example, two trifunctional units, e.g. two aromatic trifunctional units, linked together to form a tetrafunctional core. The tetrafunctional core can have one fluorescent dye moities and three nucleotide polyphosphates, two fluorescent dye moieties and two nucleoside polyphosphates, or three fluorescent dye moieties and one nucleoside phosphate.

In some cases the core comprises three tri-functional units, e.g. three aromatic trifunctional units, thereby producing a penta-functional core. The penta-functional core can have any combination of fluorescent dye moieties and nucleoside polyphosphate moities from one fluorescent dye moiety and four nucleoside polyphosphate moities to four fluorescent dye moieties and one nucleoside phosphate moiety. Compounds with one nucleoside polyphosphate moiety and four fluorescent dye moieties can have, for example two FRET donors and two FRET acceptors, three FRET donors and one FRET acceptor, or one FRET donor and three FRET acceptors.

Various scaffolds or cores described herein include a functionalized linker arm that is readily converted into an array of reactive derivatives without requiring a modification of the polyvalent nucleus or the dye moieties attached thereto. Accordingly, the compounds of the invention provide an, as yet, undisclosed advantage, allowing facile access to an array of conjugates between the linker arm-scaffold-based fluorophore and a carrier molecule.

The polymerase enzyme substrates comprise fluorescent labels. Fluorescent labels have the advantage of requiring few precautions in handling, and being amenable to high-throughput visualization techniques (optical analysis including digitization of the image for analysis in an integrated system comprising a computer). Exemplary labels exhibit one or more of the following characteristics: high sensitivity, high stability, low background, low environmental sensitivity and high specificity in labeling. Many fluorescent labels based upon the cyanine-nucleus are commercially available from the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., Life Technologies, Inc., Fluka Chemica-Biochemika Analytika (Fluka Chemie AG, Buchs, Switzerland), Anaspec, Inc., (Fremont, Calif.) and Biotium, Inc., (Hayward, Calif.) as well as many other commercial sources known to one of skill. Furthermore, those of skill in the art will recognize how to select an appropriate cyanine-based fluorophore for a particular application and, if it not readily available commercially, will be able to synthesize the necessary fluorophore de novo or synthetically modify commercially available cyanine compounds to arrive at the desired fluorescent label. It is generally desirable that the polymerase enzyme substrates of the invention are water soluble, and therefore include water soluble fluorescent dye moieties. The water soluble fluorescent dye moieties generally include one or more charged groups, such as sulfonate, phosphate, ammonium, or carboxylate. Suitable fluorescent dye moities are described, for example in U.S. Provisional Patent Application 61/377,048 filed Aug. 25, 2010, U.S. Provisional Patent Application 61/377,038 filed Aug. 25, 2010, U.S. Provisional Patent Application 61/377,004 filed Aug. 25, 2010, and U.S. Provisional Patent Application 61/377,031 filed Aug. 25, 2010. It will be understood that where fluorescent dyes are described, such dyes can be used as fluorescent dye moieties herein by performing the appropriate functionalization using chemical synthesis techniques well known in the art.

The compounds, probes and methods discussed in the following sections are generally representative of the compositions of the invention and the methods in which such compositions can be used. The following discussion is intended as illustrative of selected aspects and embodiments of the present invention and it should not be interpreted as limiting the scope of the present invention.

Embodiments

In some aspects, the invention comprises composition having a multivalent core or scaffold that is at least trifunctional, having at least three linking sites and having covalently attached at the linking sites one or more fluorescent dye moiety and one or more nucleoside polyphosphate moiety. Where three moities are attached, there can be either one fluorescent dye moiety and two nucleoside phosphate moities, or two fluorescent dye moieties and one nucleoside phosphate moiety. The compounds of the invention are covalently connected "small molecules" as opposed to polymeric materials, particles, or association complexes. These types of molecules are desirable in that while they may have a number of similar or identical units, they can be synthesized as single compound rather than a mixture of compounds having some average composition. Having a defined chemical structure can be useful in purification, quality control, and in consistency of performance. This type of consistency can be particularly useful for applications such as nucleic acid sequencing where accurately and reproducibly calling out bases is very important. For example, with particles such as beads, with association complexes, such as with streptavidin-biotin or antibody-antigen, and with polymers it is difficult to obtain a homogeneous population having exactly the same molecular weight and level of substitution. Generally with non-covalent or polymeric compounds, a distribution of related compounds, for example within a range of molecular weights is formed. With the small molecules of the invention, a single type of molecule can be formed, providing a sample that can be purified and subjected to quality control in a more rigorous manner.

In some aspects, the invention includes compositions comprising a compound of the structure:

$$(DL_D)_n\text{-}X\text{-}(L_NPN)_m$$

wherein each D is a fluorescent dye moiety, X is a multifunctional core with multiple linking sites, P is a polyphosphate moiety having 2 to 10 phosphates, N is a nucleoside moiety, m+n is 3 or greater, and $L_D$ and $L_N$ are either direct bonds or linkers. Each of the n ($DL_D$) and the m ($L_NPN$) can be the same or different. For example, in some cases all of the fluorescent dye moieties (D) are the same type of dye. This type of structure allows for increased brightness with similar spectral properties. In some cases the fluorescent dye moities are different. For example, one or more fluorescent dye moieties are FRET donors and one or more fluorescent dye moieties are FRET acceptors. Typically each of the polyphosphate (P) and the Nucleoside (N) moieties are the same. For example, where there are two or more nucleosides in the compound, and one nucleoside represents the A base, the other nucleosides on that compound also typically represent the A base. In this way, the detection of a single compound in the proximate to the polymerase enzyme can be used to indicate the incorporation of an A base, thereby indicating the presence of a T in the template nucleic acid.

The number of moieties attached to the multifunctional core (m+n) is generally from 3 to about 12. The number of moieties can be, for example, 3, 4, 5, 6, 7, 8, 9, 10, 1 or 12. There can be any combination of fluorescent dye moieties and nucleoside polyphosphate moieties as long as there is at least one fluorescent dye moiety and one nucleoside polyphosphate moiety.

One important use for the compounds of the invention is in real time single molecule nucleic acid sequencing such as that described in Eid et al., Science 323, 133 (2009). In order to be used in this type of sequencing, the substrates have a nucleoside that the polymerase enzyme recognizes as one of the nucleic acid bases (or in some cases a non-natural or artificial base). In the compounds of the invention, the nucleoside is attached such that when the nucleoside is incorporated into a growing strand in nucleic acid synthesis, the nucleoside is cleaved from the rest of the compound, releasing the fluorescent dye moiety or moieties from the polymerase enzyme complex. The nucleoside is generally attached to the complex through a nucleoside polyphosphate. In nucleic acid synthesis using natural NTPs, the bond between the alpha phosphate, attached to the nucleoside and the beta phosphate is cleaved, releasing pyrophosphate. For the compounds of the invention, the nucleoside will have at least one phosphate (the alpha phosphate), and will typically also have at least a second phosphate (the beta phosphate) in order to act as a good substrate for the polymerase enzyme. We have found that it is generally desirable for the substrate to have more than two phosphates, for example from 3 and 10 phosphates. In some cases, we have found that it is desirable to have more than three phosphates, for example from 4 to 10 phosphates, or from 4 to 8 phosphates. The compounds of the invention can have, for example, 2, 3, 4, 5, 6, 7, 8, 9, or 10 phosphates between the nucleoside and the remainder of the complex.

The small molecule compounds of the invention allow for precise control of the number of nucleoside polyphosphate moities and the number of fluorescent dye moieties in the compound. This control is not possible other approaches that have been described. For example, U.S. Pat. No. 7,462,452 entitled "Field Switch Sequencing" describes particles having multiple NP's attached to a particle having a dye. U.S Patent Application 2009-0208957A1 entitled "Alternate Labeling Strategies for Single Molecule Sequencing" describes particles to which multiple ligands are reversibly coupled. U.S. Patent Application No. 2010/0167299 entitled "Phospholink Nucleotides for Sequencing Applications" describes fluorescent beads having multiple nucleotides attached to their surfaces. The methods described in these patents generally result in an indeterminate number of dye or nucleotide groups on the particle. U.S. Patent Application No. 2010/0152424, entitled "Modular Nucleotide Compositions and Uses Therefor" describes producing multiple nucleotide compounds using non-covalent linking. The application describes how non-covalent linkage, e.g. to a protein such as streptavidin provides flexibility in the production of multiple nucleotide compounds. We have found, however that it can be extremely advantageous to make and use discrete "small molecule" compounds having a clearly defined number of nucleoside polyphosphates and a defined number of dye molecules. The use of small molecules is particularly useful in the reproducible production of kits for sequencing.

In some embodiments, the invention includes a compound of the structure:

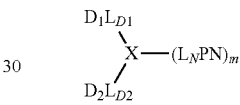

wherein D1 and D2 are each fluorescent dye moieties, $L_{D1}$ and $L_{D2}$ are each either direct bonds or linkers, N is a nucleoside moiety, and m is one or greater. These embodiments generally have two distinctly different fluorescent dye moities $D_1$ and $D_2$. In some embodiments, one of the fluorescent moieties is a FRET donor and the other is a FRET acceptor. We have found that while this structure has two dyes, with only one fluorescing, the use of a donor-acceptor combination allows for tailoring the absorption and emission characteristics of a set of dyes in order to produce a set that provides for good sequencing performance. The compounds of the invention generally have a branched rather than a linear configuration between the donor, the acceptor, and the element to which the donor/acceptor combination is attached. This configuration provides advantaged in synthesis, allowing for easily changing the donor and or acceptor to produce a family of related compounds. In addition, the branched configuration can be useful for controlling the lipophilicity of the polymerase enzyme substrates. For these embodiments, there can be one or more nucleoside polyphosphate moities. For example, the compound can have m=1, 2, 3, 4, 5, or 6 resulting in 1, 2, 3, 4, 5, or 6 nucleoside phosphate moieties. As described above, typically the nucleoside phosphate moities in a given compound will be of the same type.

In some embodiments the invention includes compounds of the structure:

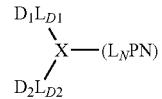

wherein D1 and D2 are each fluorescent dye moieties, $L_{D1}$ and $L_{D2}$ are each either direct bonds or linkers, and N is a nucleoside moiety. As described above, often one of the fluorescent dye moities is a FRET donor and the other is a FRET acceptor. In these embodiments there is only one nucleoside phosphate moiety. These compounds do not provide the increased nucleoside concentration described herein for the multiple nucleoside embodiments, but the compounds can take advantage of the having FRET dyes to control the absorption and emission profiles.

The invention includes compositions having a compound of the structure:

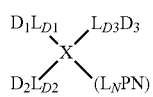

wherein $D_1$, $D_2$, and $D_3$ are each fluorescent dye moieties, $L_{D1}$, $L_{D2}$, and $L_{D3}$ are each either direct bonds or linkers. We have found, for example, that a compound of this structure can be particularly useful in single molecule nucleic acid sequencing where two of the fluorescent dye moieties comprise FRET donors and the other fluorescent dye moiety comprises a FRET acceptor. We have found that having more than one donor enhances the brightness from the acceptor dye. As with the compound directly above, this embodiment has only one nucleoside per compound.

The invention includes compositions comprising a compound of the structure

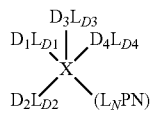

wherein $D_1$, $D_2$, $D_3$, and $D_4$ are each fluorescent dye moieties, $L_{D1}$, $L_{D2}$, $L_{D3}$, and $L_{D4}$ are each either direct bonds or linkers. In some cases, three of the fluorescent dye moieties comprise FRET donors, and one of the fluorescent dye moieties comprises a FRET acceptor. Here, each compound has only one nucleoside. In other embodiments more than one nucleoside polyphosphate can be used with a four dye, three donor configuration.

In a related aspect, the compounds of the invention include multi-dye constructs using the multifunctional cores described herein. For example, the core X is attached to 2, 3, 4, 5, 6, 7, 8, 9, 10, 11, 12, or more $DL_D$- moieties and is also attached to a molecule of interest such as a protein or nucleic acid.

We have found that in some cases, the chemical make-up of the core can be important for obtaining good performance, for example as a labeled polymerase enzyme substrate. We have found that in some cases, it is desirable that the core or scaffold X comprise a rigid component. For example, in some cases, the core comprises a tri-substituted six-membered aromatic ring such as a benzene or triazine. The aromatic core can be heterocyclic, containing, for example, one nitrogen (pyridine), two nitrogens (diazine), or preferably three nitrogens (triazine). The heterocyclic aromatic core can also comprise silicon, germanium, tin, phosphorous, or arsenic. The aromatic core is preferably substituted at the 1, 3, and 5 positions (or the 2, 4, and 6 positions). These substitution patterns result in the substituents radiating from the aromatic ring in a plane at an angle of 120 degrees from one another.

Examples of structures based on triazines that can be used in the enzyme substrates of the invention are shown in FIG. 1. FIG. 1A shows a core structures for the enzyme substrates of the invention based on a triazine trifunctional component, and having three piperidine moieties attached to the 2, 4, and 6 positions of the triazine through the piperidine nitrogen. Each piperidine has a substituent (indicated by an asterisk *) attached to its 4 position. The substituent is a fluorescent dye moiety (-LD), a nucleoside polyphosphate (-LPN) or a link to another multifunctional structure connected to two or more substituents. For X as described above where X has three linker sites, the triazine makes up the central core of the substrate. Where X has more than four substituent attached the triazine structure is linked to another multifunctional unit to which other fluorescent dye moieties (-LD) or nucleoside polyphosphate moities (-LPN) are connected. In some embodiments of the invention, multiple trifunctional triazine units are connected to produce cores having 4, 5, 6, 7, 8, 9, 10, 11, 12, or more components with dyes or nucleotides. Amine, ester, or amide groups can be used to connect the core structures to other portions of the enzyme substrate molecules. Amide groups provide for useful linkages in that they are stable, they tend to promote water solubility and they can be readily formed by the reaction of an amine with an activated ester. In FIG. 1B, each of the three substituents is connected through an —NH— linkage attached to the piperidine. In FIG. 1C, two substituents are connected via —NH— linkages and the third is connected through a carboxyl linkage, which could be, for example an amide linkage. FIG. 1C illustrates that in some cases having different functionality in an intermediate for the different substituents can assist in reactivity differentiation for controlling the attachment of different substituents to each of the three positions. In FIG. 1D, each of the substituents is connected through a carboxyl linkage.

FIG. 1E shows an alternate triazine based core structure having two piperidine groups attached to the triazine by an —NH— group at the 4 position and having one piperidine attached to the triazine through the piperidine nitrogen. FIG. 1F shows an alternative triazine based core structure having two piperidines attached by the piperidine nitrogen and having a third linking site through an —NHCH$_2$CO— linkage. The various embodiments described here are not meant to be limiting and the elements and linking groups can be combined to produce other embodiments.

Figure 2:
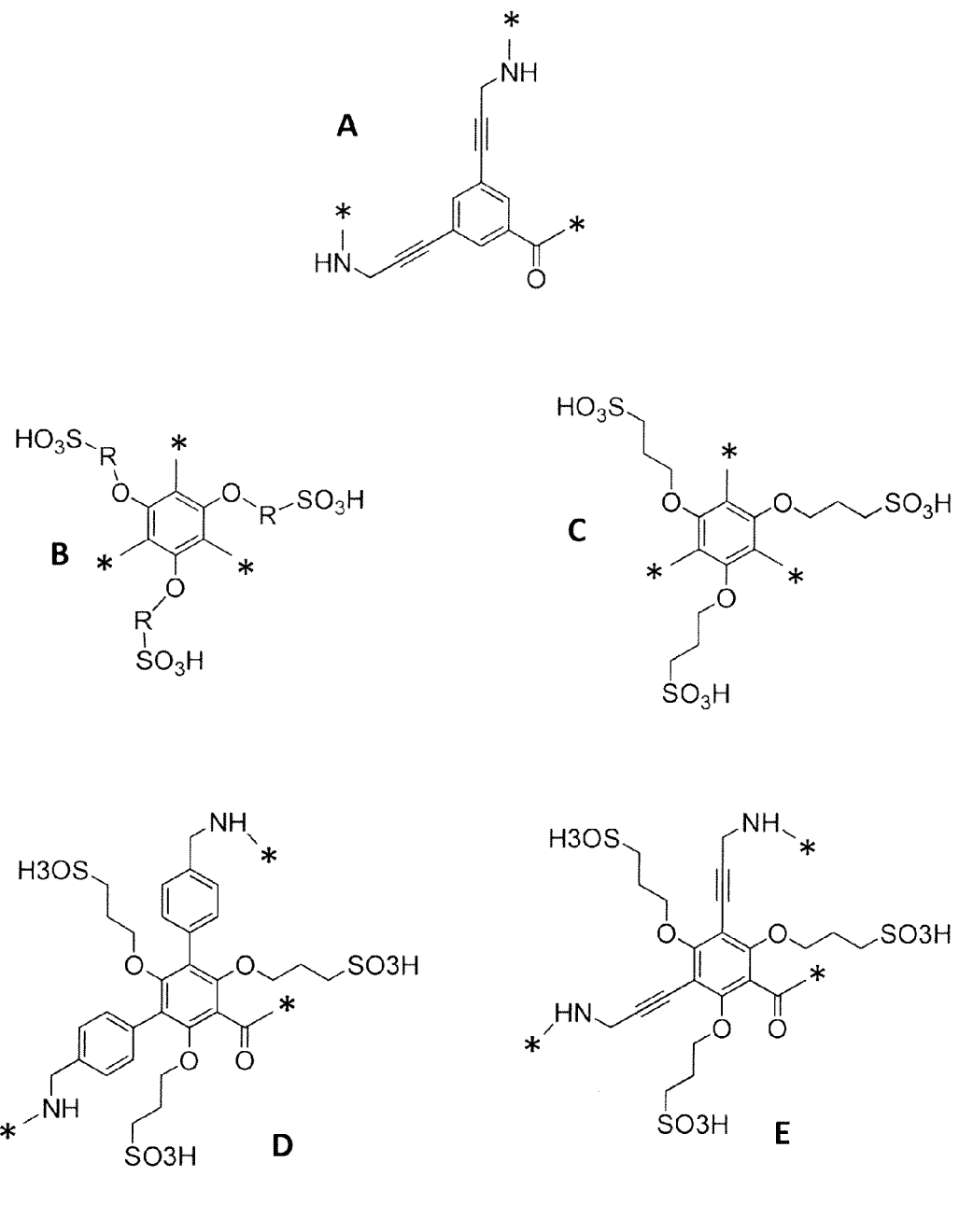
FIG. 2 shows representative benzene and substituted trihydroxy benzene based core units.

FIG. 2 shows several embodiments of trifunctional core units based on a tri-substituted benzene. FIG. 2A shows a core unit comprising a central benzene having two acetylene moieties and one carboxyl attached at the 1, 3, and 5 positions. Substituents are attached to the two —NH— groups and one carboxyl group. One preferred core is a trihydroxy benzene core as shown in FIG. 2B. It is generally desirable that the enzyme substrates of the invention are water soluble. Here, the hydroxy groups on the trihydroxy benzene are functionalized with sulfonate groups attached through a linker R. The sulfonate groups provide enhanced water solubility. Substituents are connected to the core unit at the 2, 4, and 6 positions. In some embodiments R comprises a linear or branched alkyl chain having, for example, 1 to 10 carbons. FIG. 2C shows a preferred core unit of FIG. 2B in which R comprises a linear alkyl chain having from 1 to 5 carbons (here the embodiment having 3 carbons). FIG. 2D shows a sulfonated trihydroxy benzene core unit having two 4-amino toluene groups and a carboxyl group attached at the 2, 4, and 6 positions. FIG. 2E shows a sulfonated trihydroxy benzene core unit with two acetylene methylene amine groups and one carboxylate attached at the 2, 4, and 6 positions.

Figure 3:
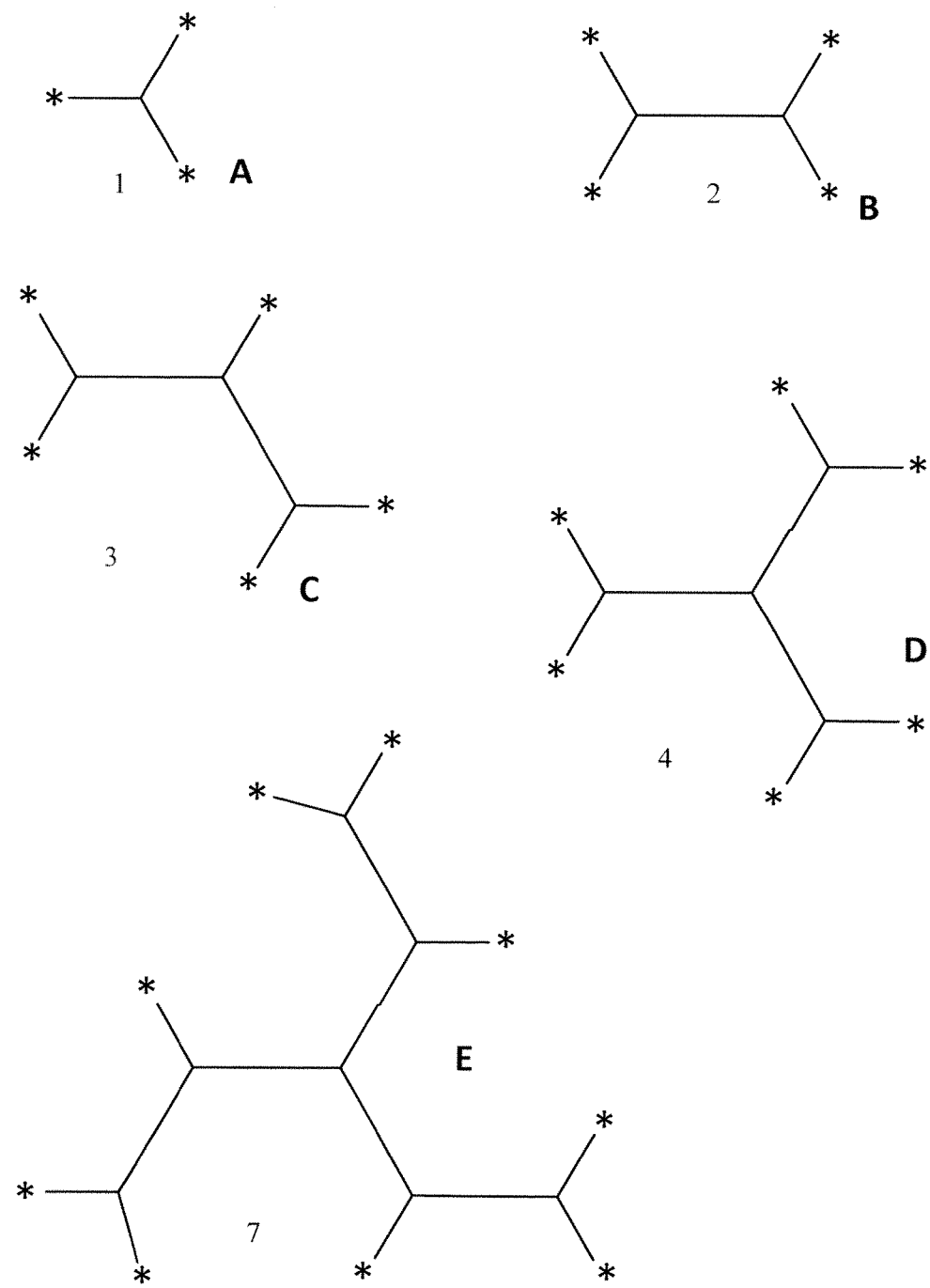
FIG. 3 illustrates how trifunctional core units can be used to produce multifunctional cores.

The tri-substituted aromatic core units of the invention can be used as tri-functional central cores for the fluorescent dye and nucleoside polyphosphate moities, or they can be combined to form cores having 4, 5, 6, 7, 8, 9, 10, 11, 12, or more linking sites. FIG. 3 illustrates how the trifunctional core units of the invention can be combined. FIG. 3A represents a single tri-functional core unit. In FIG. 3B two core units are combined to produce a core having four linking sites. In FIG. 3C three core units are combined to produce a core having five linking sites. In FIG. 3D three trifunctional core units are combined to produce a core having 6 linking sites. FIG. 3E illustrates how 6 core units can be combined to produce a core having 9 linking sites. In some preferred embodiments, the multiple core units are each of the same type, for example multiple triazine core units or multiple trihydroxy benzene core units.

Figure 4:
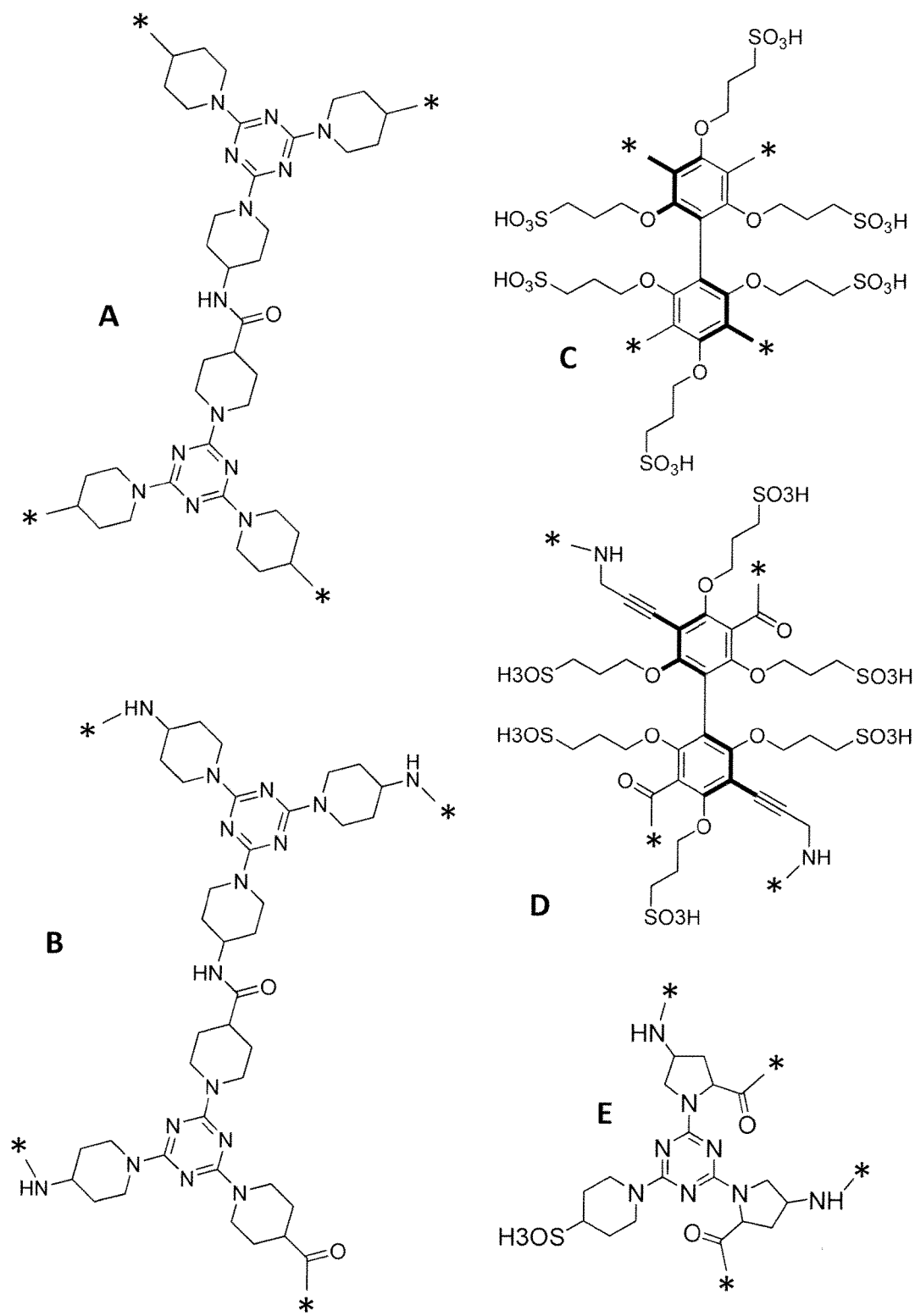
FIG. 4 shows representative tetrafunctional core units based on triazine or substituted trihydroxy benzene.

FIG. 4 provides examples of tetrafunctional cores of the invention. FIGS. 4A 4B show tetrafunctional cores based on trifunctional triazine core units linked by an amide group. In FIG. 4B, three piperidines have —NH— groups at their 4 positions for linking substituents, and one piperidine has a carboxyl group at its 4 position. FIGS. 4C and 4D each have two trihydroxy benzene core units with the benzenes directly connected through a C—C bond. For these structures, the lowest energy configuration has the two substituents on one benzene in a different plane from the two substituents on the other benzene. In FIG. 4D each benzene has one acetylene group and one carboxyl group attached through which substituents are attached. FIG. 4E shows a tetrafunctional core from a triazine core unit. The triazine has a sulfonated piperidine for providing enhanced water solubility and has two aminoproline groups. Each of the aminoproline groups has two positions for the attachment of substituents. These and other tetrafunctional cores are included in enzyme substrates having one fluorescent dye moiety and three nucleoside polyphosphate moieties, two fluorescent dye moieties and two nucleoside polyphosphate moieties, or three fluorescent dye moieties and one nucleoside polyphosphate moiety.

Figure 5:
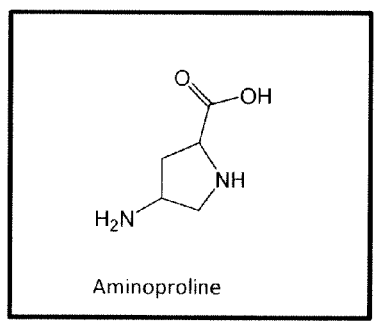
FIG. 5 has representative intermediates which can be used to produce multifunctional cores or scaffolds.
Figure 5:
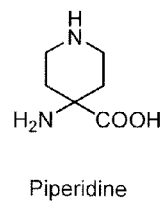
Figure 5:
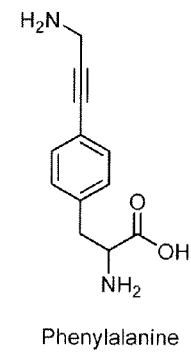
Figure 5:
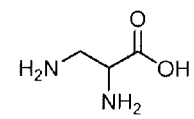
Figure 5:
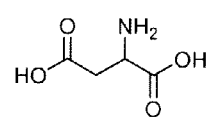
Figure 5:
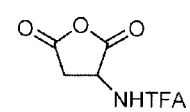
Figure 5:
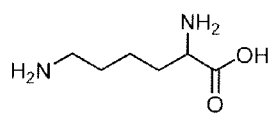
Figure 5:
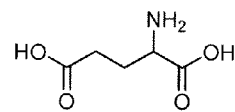
Figure 5:
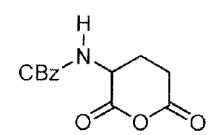
Figure 5:
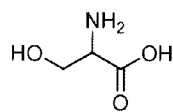
Figure 5:
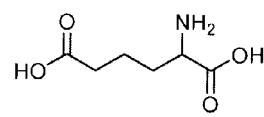
Figure 5:
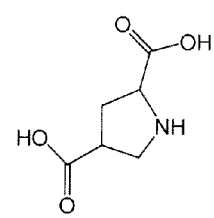
Figure 5:
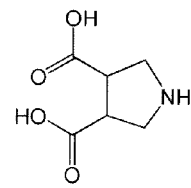
Figure 6:
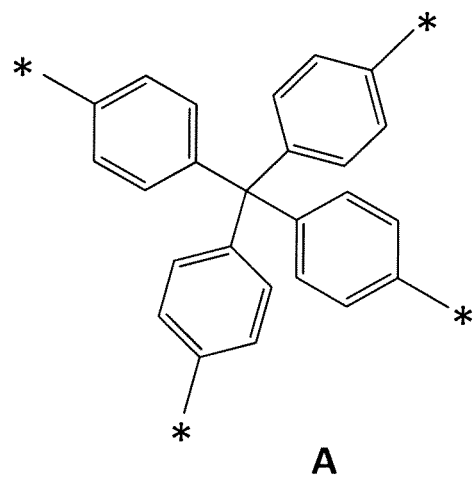
FIG. 6 shows two representative tetrafunctional core units.
Figure 6:
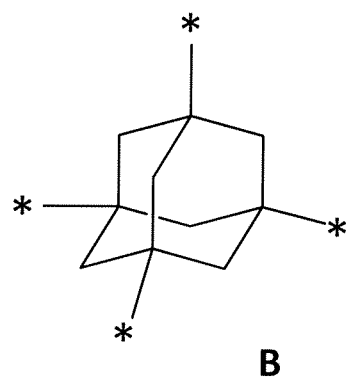

While cores comprising at least tri-substituted six-membered aromatic rings are preferred, other multifunctional units can be used in the enzyme substrates of the invention. These multifunctional units can be used in addition to or separately from the multifunctional aromatic core units. Any suitable small molecule having 3 or more linking sites can be used as core units to be assembled into cores, for example, those having 3, 4, 5, or 6 linking sites. FIG. 5 shows examples of suitable intermediates for tri-functional core units. For the proline derivatives, either the cis, the trans, or a mixture of cis and trans configurations can be used. FIG. 6 shows examples of structures for suitable tetrafunctional core units. One of the preferred core units for scaffolds of the invention comprises one or more aminoprolines. Aminoproline can be useful as a core unit as it provides more flexibility than an aromatic core unit, but more rigidity than an alkyl chain.

Another aspect of the invention is a composition comprising a compound that has multiple -D-P-N units attached to a multifunctional core, where D is a difunctional fluorescent dye moiety connected to both the multifunctional core and to the polyphosphate (P). P is a polyphosphate having 2 to 10 phosphates, and N is a nucleoside. The compound is useful as a substrate for a polymerase enzyme, for example in nucleic acid sequencing. The multifunctional core can have from 2 to about 20 or from 2 to about 10-D-P-N units. As for other compounds described herein, these compounds can provide for improved sequencing performance by having multiple fluorescent dye moieties and multiple nucleoside moieties within a single enzyme substrate molecule. The multiple dyes can be used to increase the brightness or alter the fluorescent absorption/emission properties of the substrate, and the multiple nucleotide phosphates can allow for increased nucleoside concentration for a given concentration of enzyme substrate molecule.

For the molecules of the invention, there can be linkers between the core and the fluorescent dye moiety and between the fluorescent dye moiety and the polyphosphate. Any suitable linker or a direct covalent bond can be used. The linker can be chosen to control the interaction between the substituents bonded to the core, to impart solubility, or to improve optical or enzymatic activity.

The invention includes compositions comprising a compound having the structure:

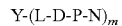

Y-(L-D-P-N)$_m$ wherein Y is a multifunctional core having m linking sites, L is either a direct bond or a linker, D is a fluorescent dye moiety, P is a polyphosphate having from 2 to 10 phosphates, and N is a nucleoside moiety, and m is greater than 2. The fluorescent dye moiety D is covalently connected to the polyphosphate either by a direct bond or through intermediate functional groups or a linker. For these structures, the dyes are difunctional. These molecules are organic small molecules connected through covalent bonds. The linker L can be any suitable linker including the linkers described herein. In some embodiments, the linker comprises a linear or branched alkyl chain with 2 to 20 carbons.

The core Y can be any suitable multifunctional liking group having a functionality from about 2 to about 20 or from about 2 to about 10. In some cases the core has three or more linking sites, in which case the core Y can comprise a core of the type X as described above. Thus, in some cases, the core comprises one or more tri-functional six-membered aromatic rings, such as benzene, substituted trihydroxy, or triazine rings.

Some compounds of the invention have a central dye molecule that acts as the core. The dye core has multiple linking sites to which multiple nucleoside polyphosphate (P-N) moieties are attached. The number of nucleoside phosphates attached is from 2 to about 20 or from 2 to about 8. The nucleoside polyphosphate moieties are attached either directly or through a linker as described herein. The invention includes composition comprising a compound having the structure:

D-(L-P-N)$_m$ wherein D is a fluorescent dye moiety having m linking sites, L is either a direct bond or a linker, P is a polyphosphate moiety having 2 to 10 phosphates, N is a nucleoside moiety, and m is from 2 to 8. In preferred embodiments, the fluorescent dye moiety comprises a cyanine dye such as a CY3 or Cy5 dye. For embodiments comprising a cyanine dye, the number of linked nucleoside polyphosphate moities is generally from 2 to 4, that is either 2, 3, or 4. The fluorescent dye moiety D can be a single dye or can be a core having multiple covalently connected dyes. The number of dyes in the core can be from 1 to about 12, from 1 to about 8, or can be 1, 2, 3, 4, 5, 6 or more dyes.

For any of the enzyme substrate molecules described herein it is generally desirable that the molecules be soluble in water. In order to enhance solubility, the compounds of the invention will often have attached ionic groups such as sulfonate groups. In some embodiments, the molecules of the invention have from 2 to about 40 sulfonate groups, or from about 4 to about 20 sulfonate groups. In some cases, the compound has from 2 to about 8 sulfonate groups per dye in the compound.

Some of the compositions of the invention are compounds having a central FRET acceptor dye moiety surrounded by two or more donor moities connected to the central FRET acceptor dye moiety through a multifunctional core unit X.

The multifunctional core units X each have at least one polyphosphate nucleoside (NP) attached through the polyphosphate. The various components will often have a linker between them. The linker provides covalent bonding, and can be used to control the spacing of the elements, the solubility and can also be used to enhance interaction with the polymerase enzyme. In some embodiments, such compounds have the structure:

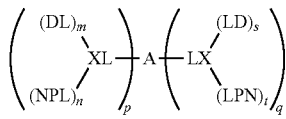

wherein X is a multifunctional linker, A is a FRET acceptor dye moiety, each D is a FRET donor each L is a direct bond or a linker, each N is a nucleoside, each P is a polyphosphate having from 2 to 10 phosphates, m, n, s, t, p, and q are each independently either 1, 2, or 3.

The central FRET acceptor is surrounded by donors attached to the core units X. We have found that for single molecule sequencing it can be advantageous to have more than one donor for each acceptor in a polymerase enzyme substrate. The number of donors can be from 2 to about 18. The number is typically from 2 to about 6, for example 2, 3, 4, 5, or 6. While each donor D can be a different dye, typically each D in the molecule will be the same. Typically A is a single acceptor dye, but in some cases A can have 2, 3, or 4 separate dye moieties. We have found that cyanine dyes, for example CY3, CY3.5, CY5, or CY5.5 dyes are generally good choices for the acceptor A. We have found the cyanine dyes to be good for single molecule sequencing as they can be made to have relatively high brightness, reasonable photostability, and relatively low levels of blinking. Preferred embodiments include symmetric structures in which there is an equal number of donors on each side of the acceptor and in which each D, X, N, and P are the same in the compound.

In some embodiments the compounds have the structure:

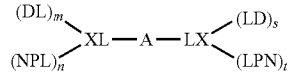

where D, L, P, X, A and N are defined as above and m, n, s, and t are from 1 to 3. The number of donors can be for example, 1, 2, 3, 4, 5, or 6, with the symmetric embodiments having 2, 4, or 6 donors generally preferred. In some preferred embodiments, m, n, s, and t are 1, resulting in a compound having two donors and two —PN units.

The core units X can be the same as those described above. For example, in some embodiments trifunctional core units comprising an trifunctional aromatic ring such as triazine or benzene are preferred. In some cases, where a core unit having more than three linking sites is used, a combination of an aromatic core unit such as those shown in FIGS. 1, 2, and 4 can be combined with one or two trifunctional core units such as those in FIG. 5 to produce a 4 or 5 functional core unit to be bound with the acceptor moiety. The linkers L can be any suitable linker including those described herein. Linkers having short linear alkyl chains are often preferred. Each of the ligands L can be different allowing for control of the optical, solvent, and enzymatic substrate properties of the molecules.

In some preferred embodiments, the acceptor moiety comprises a cyanine dye. As described above cyanine dyes have desirable optical properties, and their structures allow for the attachment to the core units described herein as well as to other substituents such as solubilizing substituents. Structures based, for example, on CY3, CY3.5, CY5 and CY5.5 dyes can be used.

Figure 7:
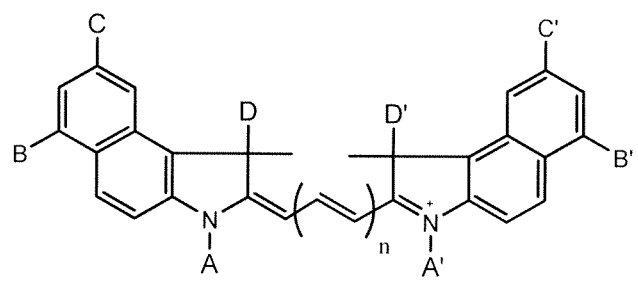
FIG. 7 shows cyanine dye core structures of the invention.
Figure 7:
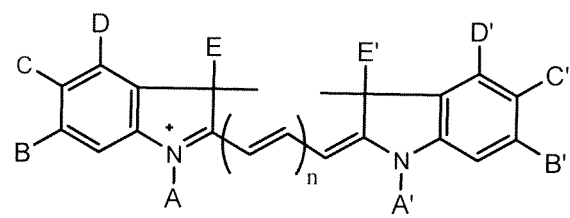

FIG. 7 shows exemplary acceptors for use in the core of the polymerase enzyme substrates of the invention. These molecules represent cyanine dyes, where n is generally either 1 or 2. For the structure shown in FIG. 7A, the positions A, B, C, D, A', B', C', and D' represent positions that can be readily functionalized, for example to connect to multifunctional core units of the invention or to connect to a solubilizing moiety. In FIG. 7B, such substitutions can be made, for example, at positions A, B, C, D, E, A', B', C', D', or E'. It is to be understood that the positions listed represent examples of suitable positions on these dyes, and that other suitable positions not specified here can also be used. In some cases symmetrical polymerase enzyme substrates are produced in which A and A', B and B', C and C', D and D', or E and E' are each attached to the same type of core unit X, and each core unit X is connected to at least one donor dye and at least one polyphosphate nucleoside. These connections can be through linkers. These symmetrical core dyes can each be connected to up to 6 such X units.

In some cases the cyanine dyes of FIG. 7A or 7B are each connected to 2 X units, and each X unit has one donor dye resulting in two donor dyes for one acceptor dye. In some cases, each dye is connected to 2 X units, and each X unit has two donor dyes resulting in four donor dyes for one acceptor dye. In some cases, each dye is connected to 2 X units, and each X unit has three donor dyes resulting in four donor dyes for one acceptor dye.

In some cases the cyanine dyes of FIG. 7A or 7B are each connected to 4 X units, and each X unit has one donor dye resulting in four donor dyes for one acceptor dye. In some cases, each dye is connected to 4 X units, and each X unit has two donor dyes resulting in eight donor dyes for one acceptor dye.

As discussed elsewhere herein, the attachment of solubilizing moieties to the dyes can improve their water solubility. In particular, charged groups such as carboxylate, sulfonate, or ammonium are substituted onto the dyes to increase solubility. In some cases, a sulfonate is attached directly to one or more of these positions or the sulfonate is attached through a short (1 to 6 carbon) alkyl chain. The substitution positions described herein, for example, can be used for the attachment of a solubilizing group if it is not being used for attachment to a core unit X. The core dyes of the invention will often have from 1 to about 8, or about 2 to about 6 solubilizing moities such as sulfonates or alkyl sulfonates. The core dyes of the invention will also generally each have from 1 to about 4 solubilizing moieties.

The dyes shown in FIG. 7 are individual FRET acceptor dyes. In some cases, the acceptor dye core can have 2, 3, or 4 FRET acceptor dyes, such as cyanine dyes linked together.

Dyes of use in forming any of the compounds of the invention belong to those dye classes generally known in the art, e.g., cyanine dyes. Exemplary cyanine dyes of use in the invention are set forth in Table 1. The dyes themselves are derivatized with a reactive functional group. Exemplary reactive functional groups are set forth herein. The reactive functional group on a dye is selected such that it participates with a reactive functional moiety on a scaffold, linker and/or polyphosphate moiety to form the scaffold-based dyes of the invention or a substructure thereof.

TABLE 1

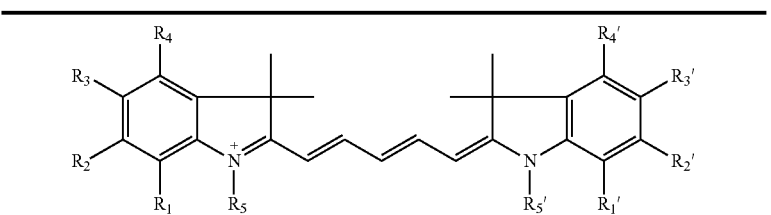

| Entry # | R1 | R2 | R3 | R4 | R5 | R1' | R2' | R3' | R4' | R5' | absorption |
|---|---|---|---|---|---|---|---|---|---|---|---|
| 1 | H | H | H | H | D | H | H | H | H | D | 642 nm |
| 2 | H | H | COOH | H | D | H | H | COOH | H | D | 650 nm |
| 3 | H | A | H | A | D | H | H | H | COOH | D | 642 nm |
| 4 | H | A | H | A | D | H | H | H | B | D | 641 nm |
| 5 | H | A | H | A | D | H | A | H | A | D | 640 nm |
| 6 | H | A | H | A | D | H | H | COOH | H | D | 648 nm |
| 7 | H | H | SO$_3$H | H | D | H | H | COOH | H | D | 650 nm |
| 8 | H | H | SO$_3$H | H | D | H | H | SO$_3$H | H | D | 649 nm |
| 9 | H | H | G | H | D | H | H | G | H | D | 671 nm |
| 10 | H | H | H | F | D | H | H | H | F | D | 650 nm |
| 11 | H | H | F | H | D | H | H | F | H | C | 671 nm |
| 12 | H | H | F | H | D | H | H | F | H | D | 672 nm |
| 13 | H | H | F | H | C | H | H | F | H | C | 671 nm |
| 14 | OCH$_3$ | H | F | H | D | OCH$_3$ | H | F | H | C | 690 nm |
| 15 | H | SO$_3$H | H | E | D | H | H | H | COOH | D | 637 nm |
| 16 | H | E | H | E | D | H | H | H | COOH | D | 638 nm |
| 17 | H | E | H | E | D | H | SO$_3$H | H | COOH | D | 640 nm |
| 18 | H | SO$_3$H | H | E | D | H | SO$_3$H | H | COOH | D | 640 nm |
| 19 | H | SO$_3$H | H | COOH | D | H | SO$_3$H | H | COOH | D | 641 nm |
| 20 | H | A | H | A | D | H | SO$_3$H | H | COOH | D | 641 nm |
| 21 | H | SO$_3$H | H | SO$_3$H | D | H | SO$_3$H | H | COOH | D | 648 nm |
| 22 | SO$_3$H | H | SO$_3$H | H | D | H | SO$_3$H | H | COOH | D | 650 nm |
| 23 | H | H | NH$_2$CH$_2$ | H | D | H | H | SO$_3$H | H | C | 648 nm |
| 24 | H | SO$_3$H | H | E | D | H | SO$_3$H | H | E | D | 640 nm |
| 25 | H | A | H | A | D | H | SO$_3$H | H | E | D | 640 nm |
| 26 | H | SO$_3$H | H | SO$_3$H | D | H | H | H | COOH | D | 648 nm |
| 27 | SO$_3$H | H | SO$_3$H | H | D | H | H | H | COOH | D | 650 nm |
| 28 | H | SO$_3$H | H | SO$_3$H | D | N | H | COOH | H | D | 653 nm |
| 29 | SO$_3$H | H | SO$_3$H | H | D | H | H | COOH | H | D | 658 nm |
| 30 | H | SO$_3$H | H | SO$_3$H | D | H | SO$_3$H | H | COOH | C | 651 nm |
| 31 | SO$_3$H | H | SO$_3$H | H | D | H | SO$_3$H | H | COOH | C | 653 nm |
| 32 | H | A | H | A | D | H | COOH | H | E | D | 641 nm |
| 33 | H | E | H | E | D | H | COOH | H | E | D | 639 nm |

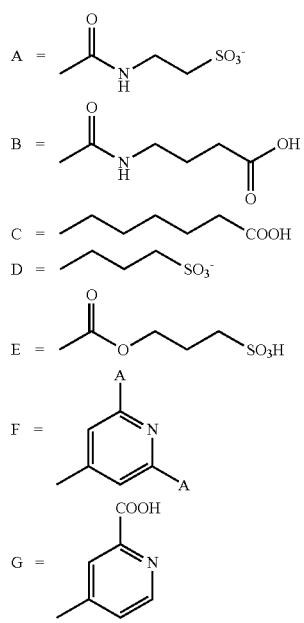

Further exemplary dyes of use in forming the compounds of the invention are shown in Table 2.

TABLE 2

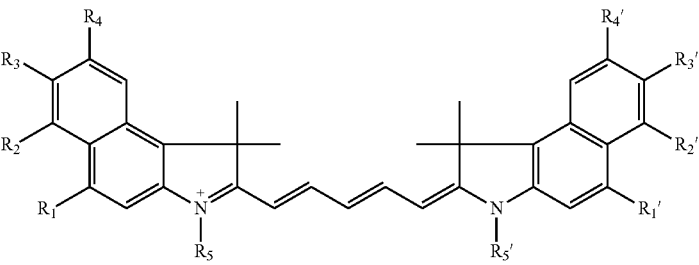

| Entry # | R1 | R2 | R3 | R4 | R5 | R1' | R2' | R3' | R4' | R5' | absorption |
|---|---|---|---|---|---|---|---|---|---|---|---|
| 1 | H | J | H | SO₃H | D | H | J | H | SO₃H | D | 674 nm |
| 2 | H | J | H | SO₃H | D | H | J | H | SO₃H | C | 674 nm |
| 3 | H | J | H | SO₃H | C | H | J | H | SO₃H | C | 675 nm |
| 4 | H | SO₃H | H | J | D | H | SO₃H | H | J | D | 675 nm |
| 5 | H | SO₃H | H | J | D | H | SO₃H | H | J | C | 675 nm |
| 6 | H | J | H | J | D | H | J | H | J | D | 675 nm |
| 7 | H | J | H | J | D | H | J | H | J | C | 676 nm |
| 8 | H | J | H | J | C | H | J | H | J | C | 677 nm |
| 9 | H | K | H | SO₃H | D | H | K | H | SO₃H | D | 675 nm |
| 10 | H | K | H | SO₃H | D | H | K | H | SO₃H | C | 676 nm |
| 11 | H | K | H | SO₃H | C | H | K | H | SO₃H | C | 676 nm |
| 12 | H | SO₃H | H | K | D | H | SO₃H | H | K | D | 675 nm |
| 13 | H | K | H | K | D | H | K | H | K | D | 677 nm |
| 14 | H | H | F | H | D | H | H | F | H | D | 691 nm |
| 15 | SO₃H | H | F | H | D | SO₃H | H | F | H | C | 689 nm |
| 16 | H | H | SO₃H | H | D | H | H | H | H | C | 682 nm |
| 17 | H | H | SO₃H | H | D | H | H | SO₃H | H | C | 686 nm |
| 18 | H | SO₃H | H | SO₃H | D | H | SO₃H | H | SO₃H | C | 677 nm |

A = 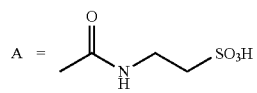

C = 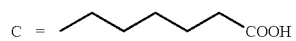

D = 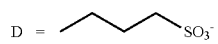

F = 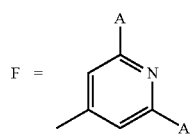

J = 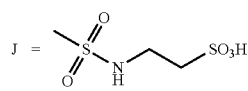

K = 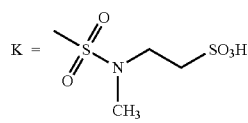

Further exemplary dyes that can be used in the scaffold-based dyes of the invention are set forth in Table 3 and Table 4.

TABLE 3

| Entry # | R1 | R2 | R3 | R4 | R5 | R1' | R2' | R3' | R4' | R5' | absorption |
|---|---|---|---|---|---|---|---|---|---|---|---|
| 1 | H | H | H | H | D | H | H | H | H | D | 546 nm |
| 2 | H | H | COOH | H | D | H | H | COOH | H | D | 557 nm |
| 3 | H | H | H | COOH | D | H | H | H | COOH | D | 546 nm |
| 4 | H | A | H | A | D | H | H | H | COOH | D | 546 nm |
| 5 | H | H | H | A | D | H | H | COOH | H | D | 551 nm |
| 6 | H | A | H | A | D | H | H | COOH | H | D | 551 nm |
| 7 | H | OCH₃ | H | H | D | H | H | H | COOH | D | 549 nm |
| 8 | H | H | SO₃H | H | D | H | H | COOH | H | D | 553 nm |
| 9 | H | H | COOH | H | D | H | H | COOH | H | D | 556 nm |
| 10 | H | COOH | H | COOH | D | H | COOH | H | COOH | D | 545 nm |
| 11 | H | COOH | H | COOH | D | H | A | H | A | C | 551 nm |
| 12 | H | A | H | A | D | H | COOH | H | COOH | D | 547 nm |
| 13 | H | COOH | H | COOH | D | H | H | SO₃H | H | C | 549 nm |
| 14 | SO₃H | H | F | H | D | SO₃H | H | F | H | D | 568 nm |
| 15 | H | H | H | F | D | H | H | H | F | C | 552 nm |
| 16 | H | H | H | F | D | H | F | H | F | D | 552 nm |
| 17 | OCH₃ | H | F | H | D | OCH₃ | H | F | H | C | 593 nm |
| 18 | H | H | SO₃H | H | D | H | H | SO₃H | H | D | 550 nm |
| 19 | SO₃H | H | SO₃H | H | D | H | H | SO₃H | H | C | 560 nm |
| 20 | H | SO₃H | H | SO₃H | D | H | H | SO₃H | H | C | 558 nm |
| 21 | H | H | SO₃H | H | D | H | H | SO₃H | H | C | 551 nm |
| 22 | H | H | H | H | D | H | H | SO₃H | H | C | 547 nm |
| 23 | H | H | SO₃H | H | D | H | H | H | H | C | 549 nm |
| 24 | H | H | H | H | C | H | H | H | H | C | 549 nm |
| 25 | H | H | H | H | CH₃ | H | H | H | H | C | 545 nm |
| 26 | H | H | H | H | CH₃ | H | H | H | H | CH₃ | 543 nm |
| 27 | H | H | SO₃H | H | C | H | H | SO₃H | H | C | 553 nm |
| 28 | H | H | H | H | CH₃ | H | H | SO₃H | H | C | 548 nm |
| 29 | H | H | NH₂CH₂ | H | D | H | H | COOH | H | C | 549 nm |
| 30 | H | E | H | E | D | H | SO₃H | H | COOH | D | 542 nm |
| 31 | H | E | H | E | D | H | E | H | E | D | 540 nm |
| 32 | H | SO₃H | H | COOH | D | H | SO₃H | H | COOH | D | 543 nm |
| 33 | H | SO₃H | H | E | D | H | SO₃H | H | COOH | D | 543 nm |
| 34 | H | A | H | A | D | H | SO₃H | H | COOH | D | 544 nm |
| 35 | H | SO₃H | H | E | D | H | SO₃H | H | E | D | 540 nm |
| 36 | H | A | H | A | D | H | SO₃H | H | E | D | 543 nm |
| 37 | H | SO₃H | H | SO₃H | D | H | H | H | COOH | D | 550 nm |
| 38 | SO₃H | H | SO₃H | H | D | H | H | H | COOH | D | 554 nm |

A = 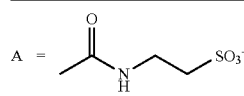

B = 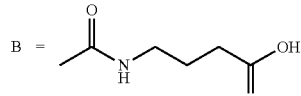

C = 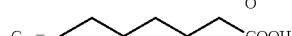

D = 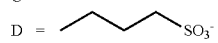

E = 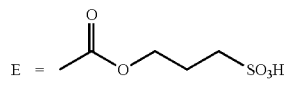

F = 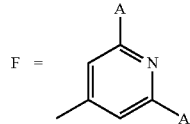

TABLE 3-continued

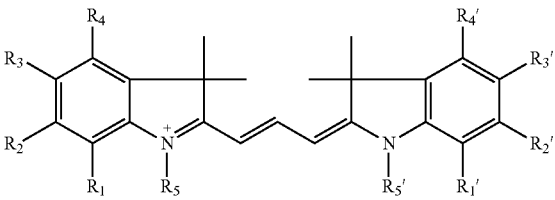

| Entry # | R1 | R2 | R3 | R4 | R5 | R1' | R2' | R3' | R4' | R5' | absorption |
|---|---|---|---|---|---|---|---|---|---|---|---|

G = 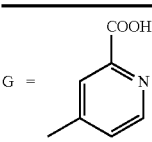

TABLE 4

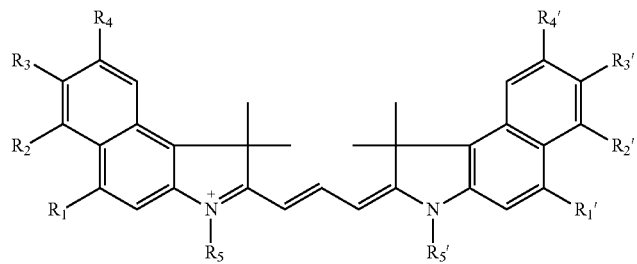

| Entry # | R1 | R2 | R3 | R4 | R5 | R1' | R2' | R3' | R4' | R5' | absorption |
|---|---|---|---|---|---|---|---|---|---|---|---|
| 1 | H | J | H | SO$_3$H | D | H | J | H | SO$_3$H | D | 579 nm |
| 2 | H | J | H | SO$_3$H | D | H | J | H | SO$_3$H | C | 579 nm |
| 3 | H | SO$_3$H | H | J | D | H | SO$_3$H | H | J | D | 581 nm |
| 4 | H | SO$_3$H | H | J | D | H | SO$_3$H | H | J | C | 581 nm |
| 5 | H | J | H | J | D | H | J | H | J | D | 579 nm |
| 6 | H | J | H | J | D | H | J | H | J | C | 580 nm |
| 7 | H | J | H | J | C | H | J | H | J | C | 581 nm |
| 8 | H | K | H | SO$_3$H | D | H | K | H | SO$_3$H | D | 580 nm |
| 9 | H | SO$_3$H | H | K | D | H | SO$_3$H | H | K | D | 578 nm |
| 10 | H | K | H | K | D | H | K | H | K | D | 580 nm |
| 11 | H | K | H | SO$_3$H | D | H | K | H | SO$_3$H | C | 580 nm |
| 12 | H | H | F | H | D | H | H | F | H | D | 602 nm |
| 13 | SO$_3$H | H | F | H | D | SO$_3$H | H | F | H | C | 595 nm |
| 14 | H | H | SO$_3$H | H | D | H | H | H | H | C | 587 nm |
| 15 | H | SO$_3$H | H | SO$_3$H | D | H | H | H | H | C | 582 nm |
| 16 | H | SO$_3$H | H | SO$_3$H | D | H | H | SO$_3$H | H | C | 584 nm |
| 17 | H | H | SO$_3$H | H | D | H | H | SO$_3$H | H | D | 587 nm |
| 18 | H | H | SO$_3$H | H | D | H | H | SO$_3$H | H | C | 587 nm |
| 19 | H | H | SO$_3$H | H | C | H | H | SO$_3$H | H | C | 590 nm |
| 20 | H | H | NH$_2$CH$_2$ | H | D | H | H | SO$_3$H | H | C | 585 nm |
| 21 | H | SO$_3$H | H | SO$_3$H | D | H | SO$_3$H | H | SO$_3$H | C | 581 nm |
| 22 | H | SO$_3$H | H | SO$_3$H | D | H | SO$_3$H | H | SO$_3$H | D | 581 nm |
| 23 | SO$_3$H | H | COOH | H | D | SO$_3$H | H | COOH | H | D | 590 nm |

A = 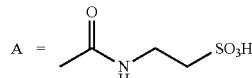

C = 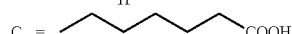

D = 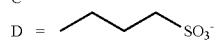

F = 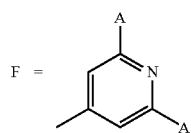

TABLE 4-continued

[Chemical structure diagram of a cyanine dye with substituents R1, R2, R3, R4, R5 on left naphthalene/indoline system and R1', R2', R3', R4', R5' on right system, connected by a trimethine bridge]

Entry # | R1 | R2 | R3 | R4 | R5 | R1' | R2' | R3' | R4' | R5' | absorption

J = [structure: -S(=O)₂-NH-CH₂CH₂-SO₃H]

K = [structure: -S(=O)₂-N(CH₃)-CH₂CH₂-SO₃H]

These and additional cyanine dyes of use in practicing the instant invention are set forth in commonly owned U.S. Provisional Patent Application 61/377,048 filed Aug. 25, 2010, U.S. Provisional Patent Application 61/377,038 filed Aug. 25, 2010, U.S. Provisional Patent Application 61/377,004 filed Aug. 25, 2010, and U.S. Provisional Patent Application 61/377,031 filed Aug. 25, 2010. The disclosure of each of these applications is incorporated herein by reference in its entirety for all purposes.

Exemplary fluorophores that can be incorporated into a polymerase enzyme substrate of the invention include those set forth in Table 5.

TABLE 5

Exemplary Dyes of use in Scaffold-based Dyes and in Donor-Acceptor Pairs 4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
coumarin
    7-amino-4-methylcoumarin (AMC, Coumarin 120)
    7-amino-4-trifluoromethylcouluarin (Coumarin 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate
erythrosin and derivatives:
    erythrosin B
    erythrosin isothiocyanate

TABLE 5-continued

Exemplary Dyes of use in Scaffold-based Dyes and in Donor-Acceptor Pairs ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
    pyrene butyrate
    succinimidyl 1-pyrene butyrate
quantum dots
Reactive Red 4 (Cibacron™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
terbium chelate derivatives
Black Hole Quenchers™

Any of the dyes in Tables 1-5 can be combined in a scaffold-based polymerase enzyme substrate of the invention in any combination.

There is a great deal of practical guidance available in the literature for functionalizing dyes for conjugation to other moieties and for selecting appropriate donor-acceptor pairs for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties for choosing reporter-quencher pairs (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via common reactive groups that can be added to a nucleic acid, as exemplified by the following references: Haugland (supra); Ullman et al., U.S. Pat. No. 3,996,345; Khanna et al., U.S. Pat. No. 4,351,760. Thus, it is well within the abilities of those of skill in the art to choose an energy exchange pair for a particular application and to conjugate the members of this pair to a probe molecule, such as, for example, a nucleic acid, peptide or other polymer.

To enable the coupling of a fluorescent label with a group of complementary reactivity on a carrier molecule, a reactive derivative of the fluorophore is prepared. For example, Reedy et al. (U.S. Pat. No. 6,331,632) describe cyanine dyes that are functionalized at a nitrogen atom of a heteroaryl moiety with hydrocarbon linker terminating in a hydroxyl moiety. The hydroxyl moiety is converted to the corresponding phosphoramidite, providing a reagent for conjugating the cyanine dye to a nucleic acid. Waggoner (U.S. Pat. No. 5,627,027) has prepared derivatives of cyanine and related dyes that include a reactive functional group through which the dye is conjugated to another species. The compounds set forth in Ohno et al. (U.S. Pat. No. 5,106,990) include cyanine dyes that have a $C_1$-$C_5$ alkyl linker terminated with a sulfonic acid, a carboxyl or a hydroxyl group. Randall et al. (U.S. Pat. Nos. 6,197,956; 6,114,350; 6,224,644; and 6,437,141) disclose cyanine dyes with a linker arm appended to an heteroaryl nitrogen atom. The linkers include a thiol, amine or hydroxyl group, or a protected analogue of these residues. Additional linker arm-cyanine dyes are disclosed by Brush et al. (U.S. Pat. Nos. 5,808,044; 5,986,086). One hydroxyl moiety is converted to the corresponding phosphoramidite and the other is protected as a dimethoxytrityl ether.

As will be apparent to those of skill in the art the methods set forth above are equally applicable to the coupling to a nucleic acid of groups other than the fluorescent compounds of the invention, e.g., quenchers, intercalating agents, hybridization enhancing moieties, minor groove binders, alkylating agents, cleaving agents, etc.

Polyvalent scaffolds, which can be derivatized with dyes according to the invention are generally known in the art and include linear (e.g., polyamino acids, polysaccharides) and branched (e.g., dendrimeric) species. In exemplary embodiments, the scaffold of use in the compounds of the invention, X, is a residue derived from a member selected from perylene, piperidine, phenylalanine, diaminopropanoic acid, aspartic acid, lysine, glutamic acid, serine, aminoadipic acid, 3,5-dihydroxybenzoic acid, 2-amino-4-hydroxy-butyric acid, 4-(1-amino-1-carboxyethyl)-benzoic acid, piperazine-2-carboxylic acid, 4-[4,6-bis-(piperidin-4-ylamino)-[1,3,5]triazin-2-ylamino]-cyclohexanecarboxylic acid and 3-amino-3-[4-(3-amino-prop-1-ynyl)-phenyl]-propionic acid, and trans-4-amino-cyclohexanecarboxylic acid.

Other exemplary scaffolds of use in the invention include:

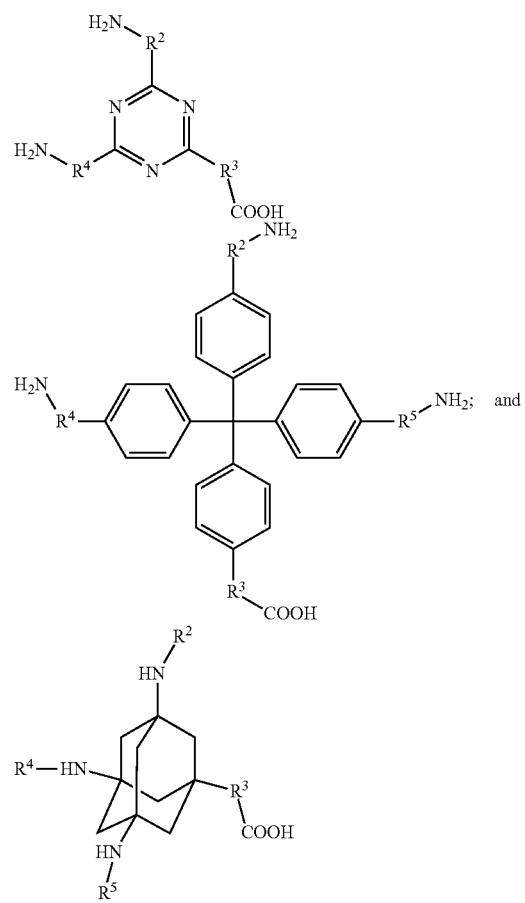

wherein $R^2$, $R^3$, $R^4$ and $R^5$ are members selected from "alkyl group substituents," "dyes," e.g., cyanine dyes, "dye-nucleic acid cassettes," and "aryl group substituents," "linkers," and "adaptors.". In exemplary embodiments, these linker groups are independently selected from substituted or unsubstituted alkyl and substituted or unsubstituted heteroalkyl moieties. In an exemplary embodiment, the $NH_2$ moieties are derivatized with a dye-nucleic acid or a linker-dye-nucleic acid cassette. In the third structure above, the R radicals optionally represent a dye, a dye-nucleic acid cassette or a dye-linker-nucleic acid construct.

In various embodiments, a member selected from X and $R^1$ is a residue derived from a moiety having the formula:

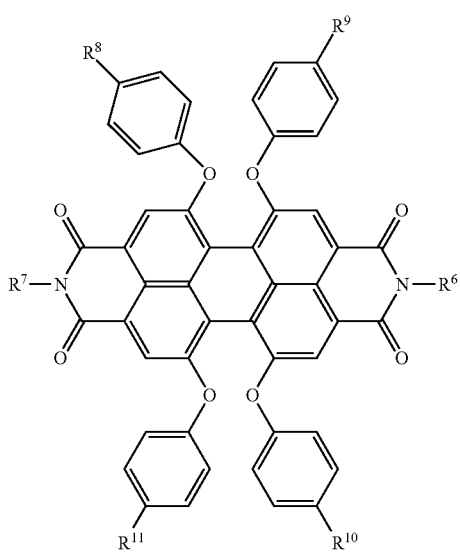

wherein $R^6$ and $R^7$ are independently substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted cycloalkyl, or a polyphosphate substituted with a nucleic acid. $R^8$, $R^9$, $R^{10}$ and $R^{11}$ are independently $CO_2H$, $SO_3H$ or $SO_2NR^{12}R^{13}$. The symbols $R^{12}$ and $R^{13}$ independently represent substituted or unsubstituted alkyl, substituted or unsubstituted heteroalkyl, substituted or unsubstituted aryl, substituted or unsubstituted heteroaryl, substituted or unsubstituted heterocycloalkyl or substituted or unsubstituted cycloalkyl.

In an exemplary embodiment, at least one of $R^6$, $R^7$, $R^8$, $R^9$, $R^{10}$, $R^{11}$ and $R^{12}$ and $R^{13}$ is a moiety having the formula:

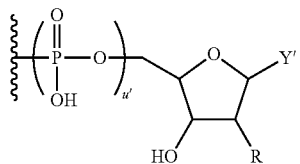

wherein Y' is a nucleobase; u' is selected from the integers 1, 2, 3, 4, 5, 6, 7, 8, or greater; and R is either H or OH.

The compounds of the invention can be prepared as a single isomer or a mixture of isomers, including, for example cis-isomers, trans-isomers, diastereomers and stereoisomers. In a preferred embodiment, the compounds are prepared as substantially a single isomer. Isomerically pure compounds are prepared by using synthetic intermediates that are isomerically pure in combination with reactions that either leave the stereochemistry at a chiral center unchanged or result in its complete inversion. Alternatively, the final product or intermediates along the synthetic route can be resolved into a single isomer. Techniques for inverting or leaving unchanged a particular stereocenter, and those for resolving mixtures of stereoisomers are well known in the art and it is well within the ability of one of skill in the art to choose an appropriate resolution or synthetic method for a particular situation. See, generally, Furniss et al. (eds.), VOGEL'S ENCYCLOPEDIA OF PRACTICAL ORGANIC CHEMISTRY 5TH ED., Longman Scientific and Technical Ltd., Essex, 1991, pp. 809-816; and Heller, Acc. Chem. Res. 23: 128 (1990).

Exemplary synthetic routes to exemplary scaffold-based dye moieties of the invention are set forth in the figures and examples appended hereto.

FIGS. 8 through 25 show structures of various embodiments of the invention.

Figure 8:
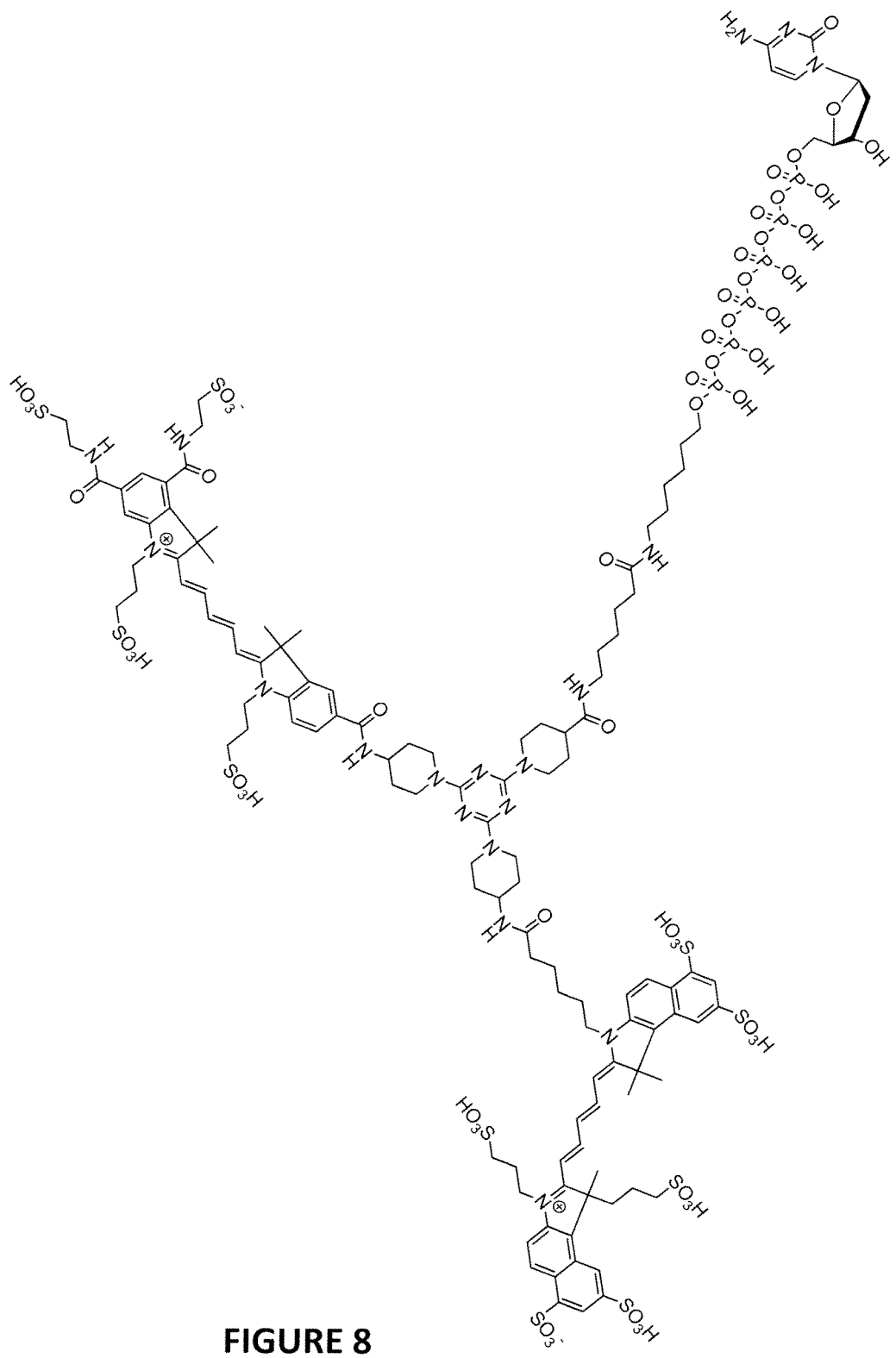
FIG. 8 displays representative structures of a scaffold-based dye nucleotide of the invention based on a triazine scaffold.

FIG. 8 shows a polymerase enzyme substrate of the invention having a trifunctional triazine piperidine core with two cyanine dyes and one nucleoside polyphosphate. The polyphosphate has 6 phosphates. One of the cyanine dyes is a FRET donor and the other is a FRET acceptor. The nucleoside polyphosphate is attached to the core through a linker having alkyl units and amide bonds.

Figure 9:
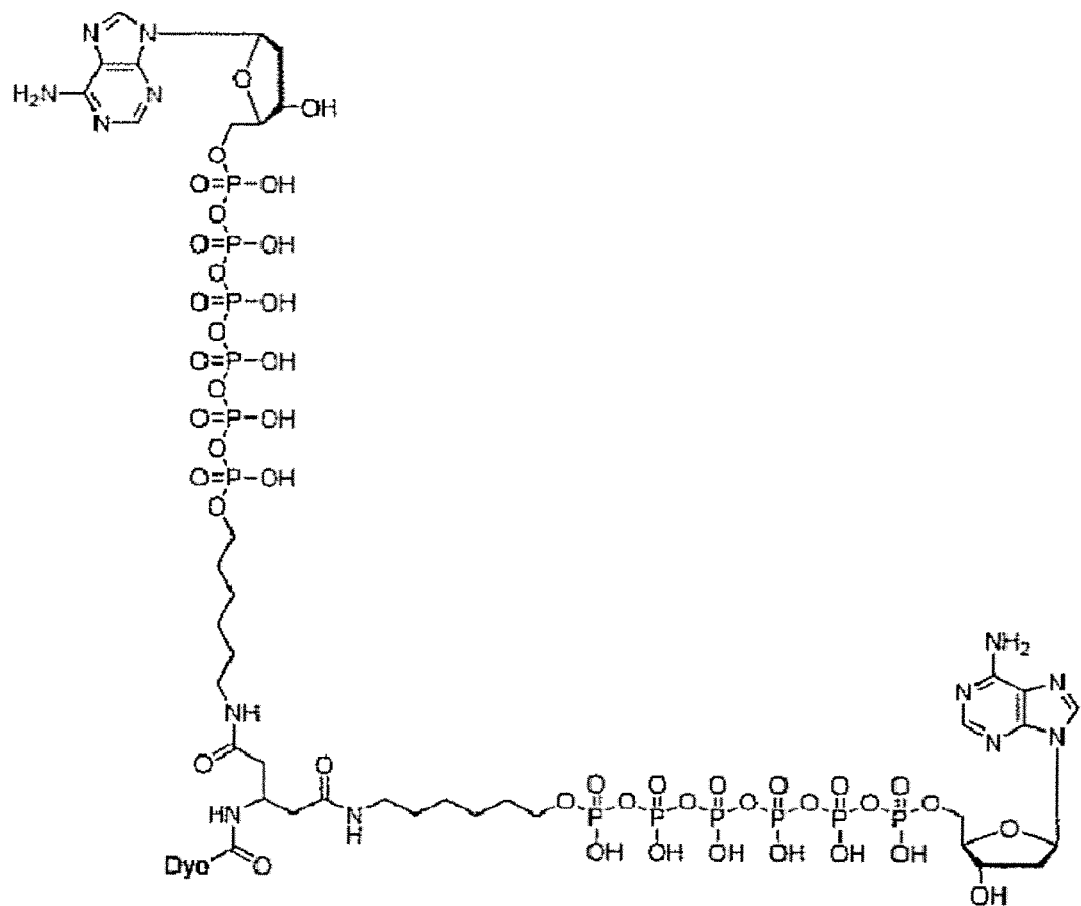
FIG. 9 displays an exemplary polymerase enzyme substrate of the invention having two nucleoside polyphosphates and one fluorescent dye on a branched amino acid core.
Figure 10:
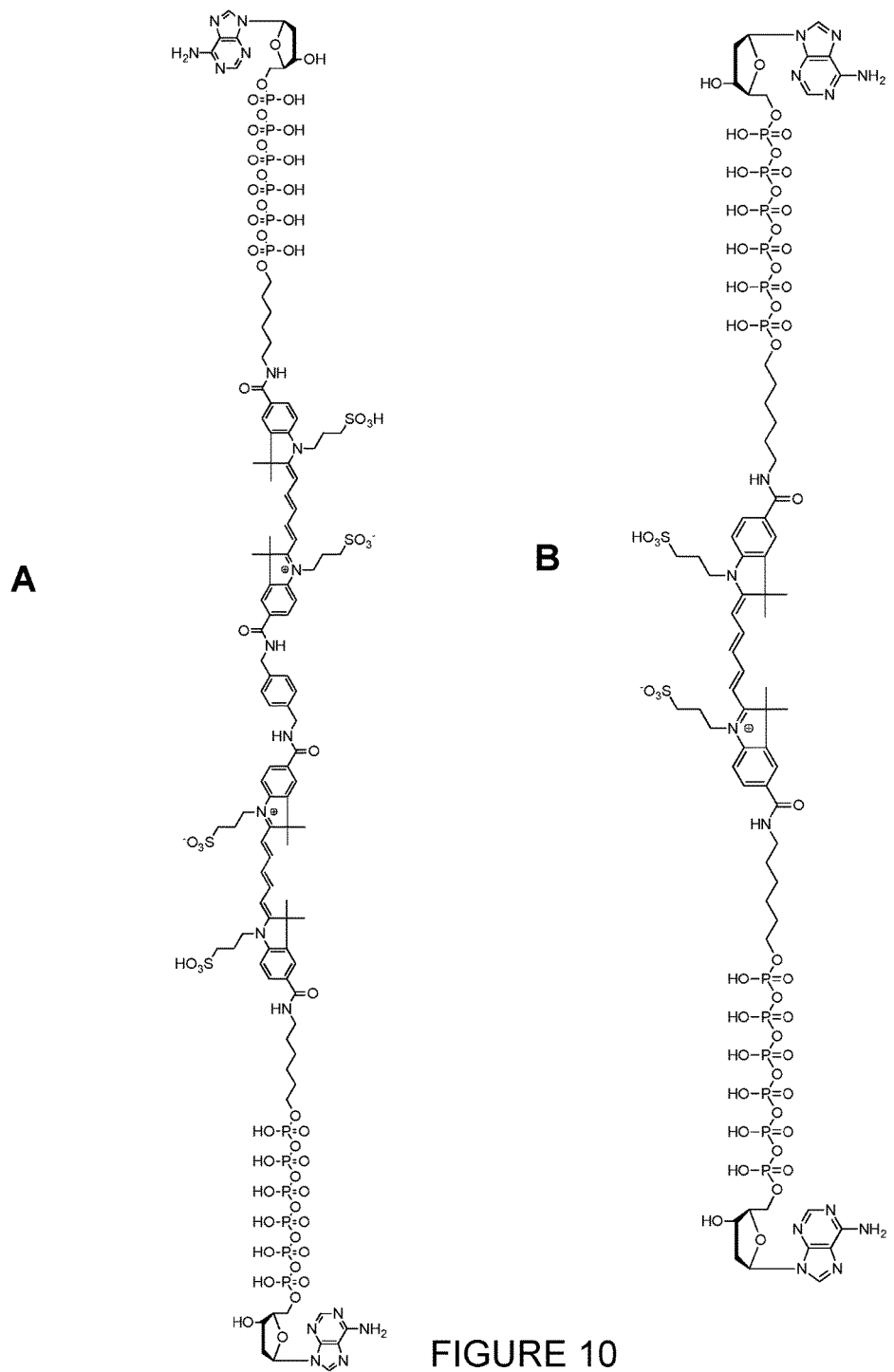
FIG. 10 displays exemplary polymerase enzyme substrates having a multifunctional dye at the core. In 10A, the dye core comprises two linked cyanine dyes. In 10B the core comprises a single cyanine dye.

FIG. 9 shows a polymerase enzyme substrate of the invention with a trifunctional core having two nucleoside polyphosphates and one dye. The nucleosides comprise adenine. The nucleoside polyphosphates are attached to the core through a linear alkyl linker.

FIG. 10A shows a polymerase enzyme substrate of the invention with a difunctional dye at the core and having two nucleoside polyphosphate moieties. The dye core comprises two cyanine dyes linked through an amide bond. The polyphosphates are linked to the dye core through a linear alkyl linker. The polymerase enzyme substrate of 10B has a single cyanine dye at the core attached to two nucleoside polyphosphates connected through linear alkyl linkers.

Figure 11:
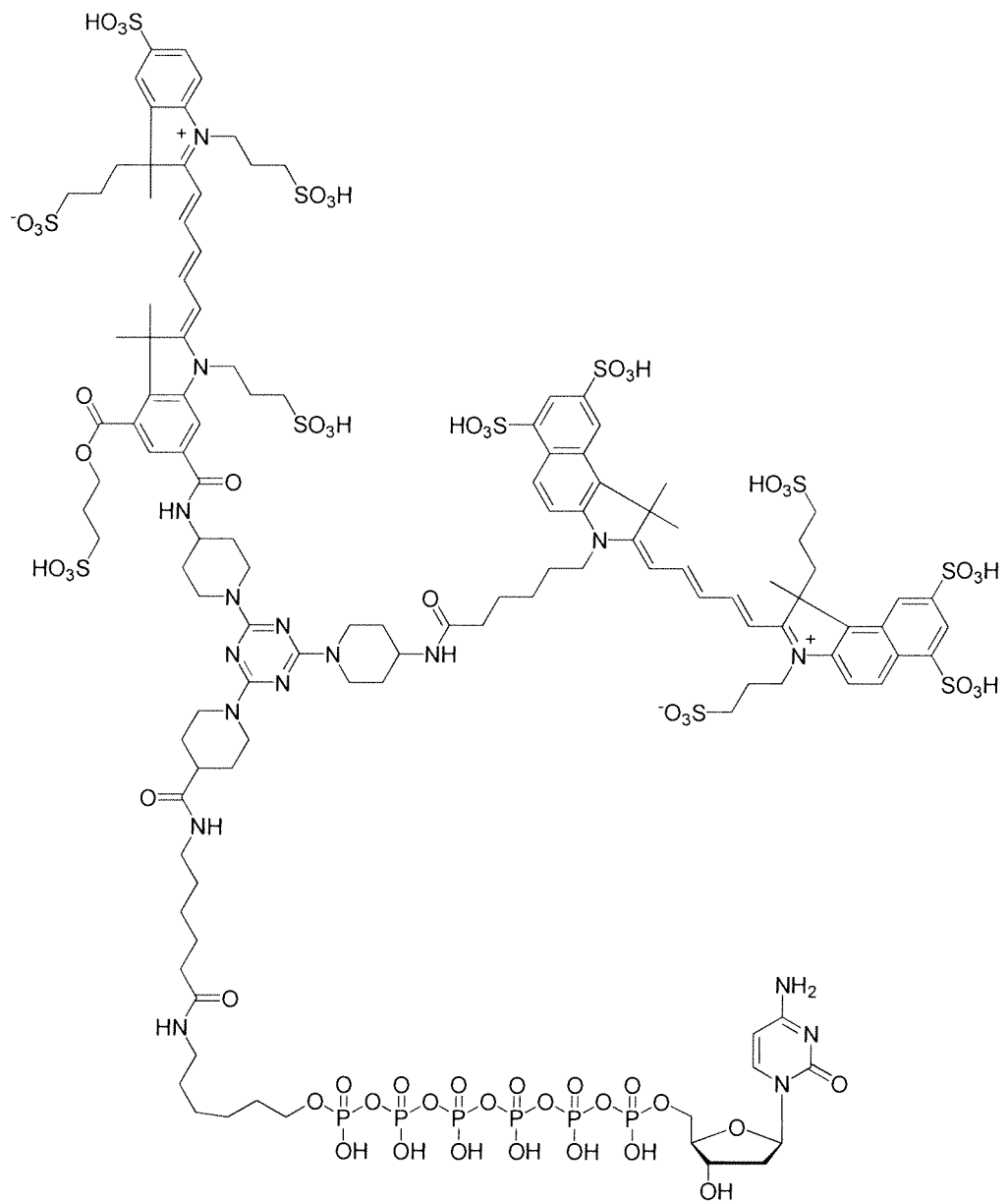
FIG. 11 shows a polymerase enzyme substrate of the invention having a triazine-piperidine core and having two cyanine dyes and one nucleoside polyphosphate in which one dye is FRET donor and the other is a FRET acceptor.

FIG. 11 shows a polymerase enzyme substrate of the invention with a triazine piperidine core attached to two cyanine dyes and to one nucleoside polyphosphate. One of the dyes is attached to the core directly through a an amide linkage, the other dye is attached through an alkyl linker.

Figure 12:
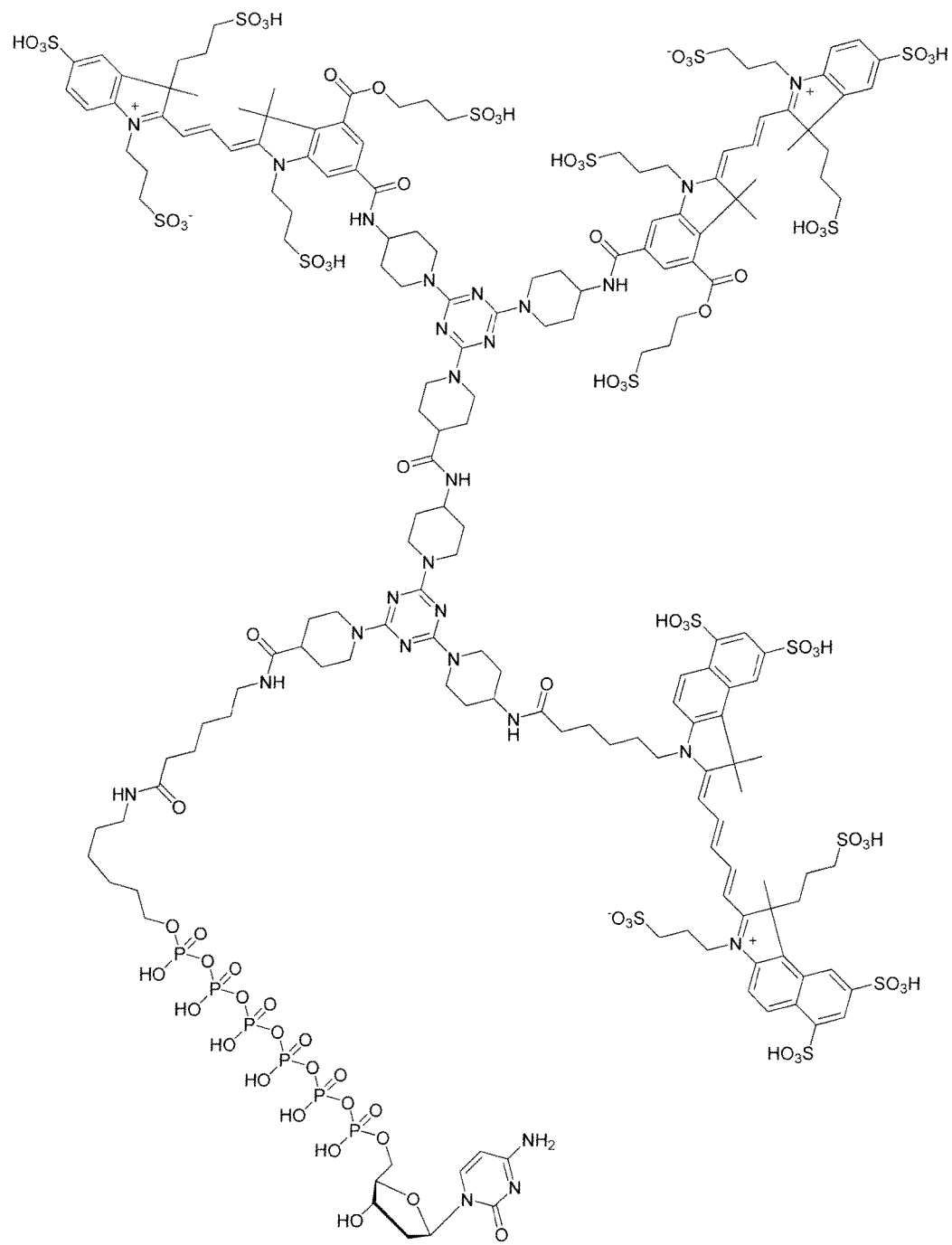
FIG. 12 shows a polymerase enzyme substrate of the invention having a tetrafunctional core comprising two triazine-piperidine units. The substrate has two FRET donor dyes, one FRET acceptor dye, and one nucleoside polyphosphate moiety.

FIG. 12 shows a polymerase enzyme substrate of the invention with a core comprising two triazine piperidine core units linked through an amide bond. Two of the dyes are FRET donors, and one of the dyes is a FRET acceptor. Two of the dyes are attached to the core through amide linkages. One of the dyes is attached through an alkyl linker.

Figure 13:
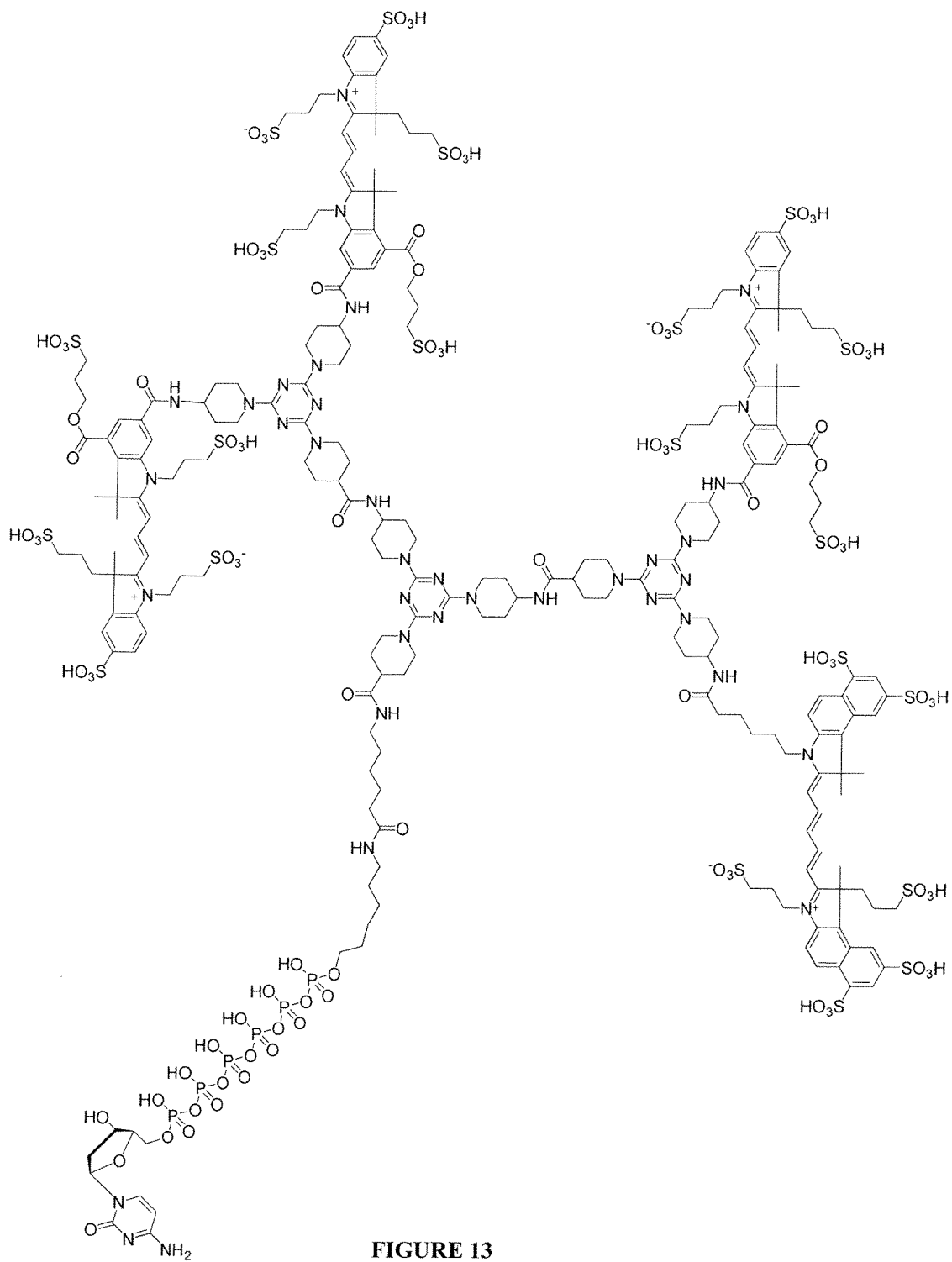
FIG. 13 shows a polymerase enzyme substrate of the invention with a pentafunctional core comprising three triazine piperidine core units. The substrate has three FRET donor dyes, one FRET acceptor dye, and one nucleoside polyphosphate.

FIG. 13 shows a polymerase enzyme substrate of the invention with a core comprising three triazine piperidine core units linked to produce a pentafunctional core. The molecule has three FRET donors, one FRET acceptor, and a nucleoside polyphosphate attached to the core. Three of the dyes are attached through an amide bond, one of the dyes is attached trough a linear alkyl linker.

Figure 14:
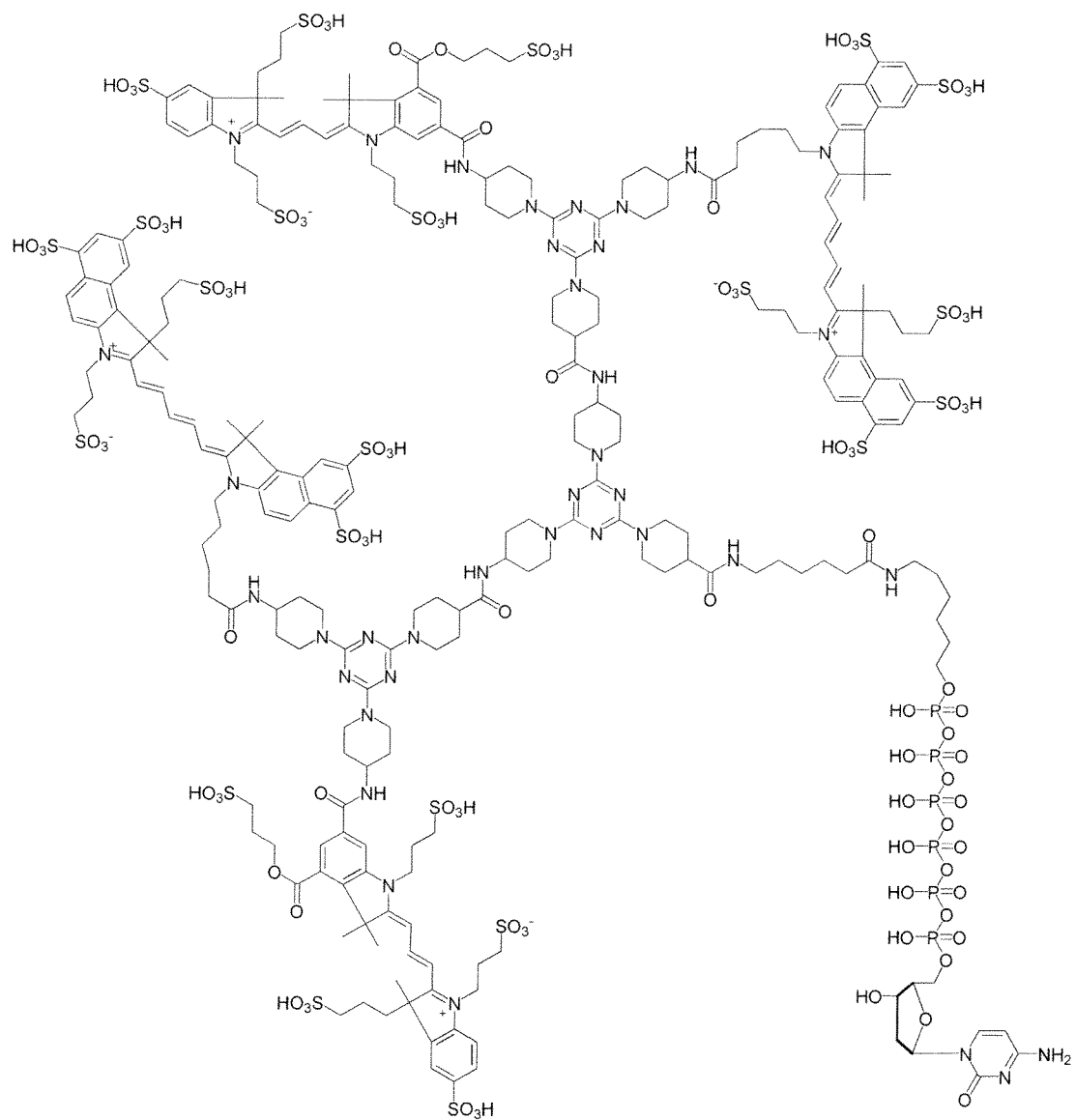
FIG. 14 shows a polymerase enzyme substrate of the invention with a pentafunctional core comprising three triazine piperidine core units. The substrate has two FRET donors, two FRET acceptors, and one nucleoside polyphosphate.
Figure 15:
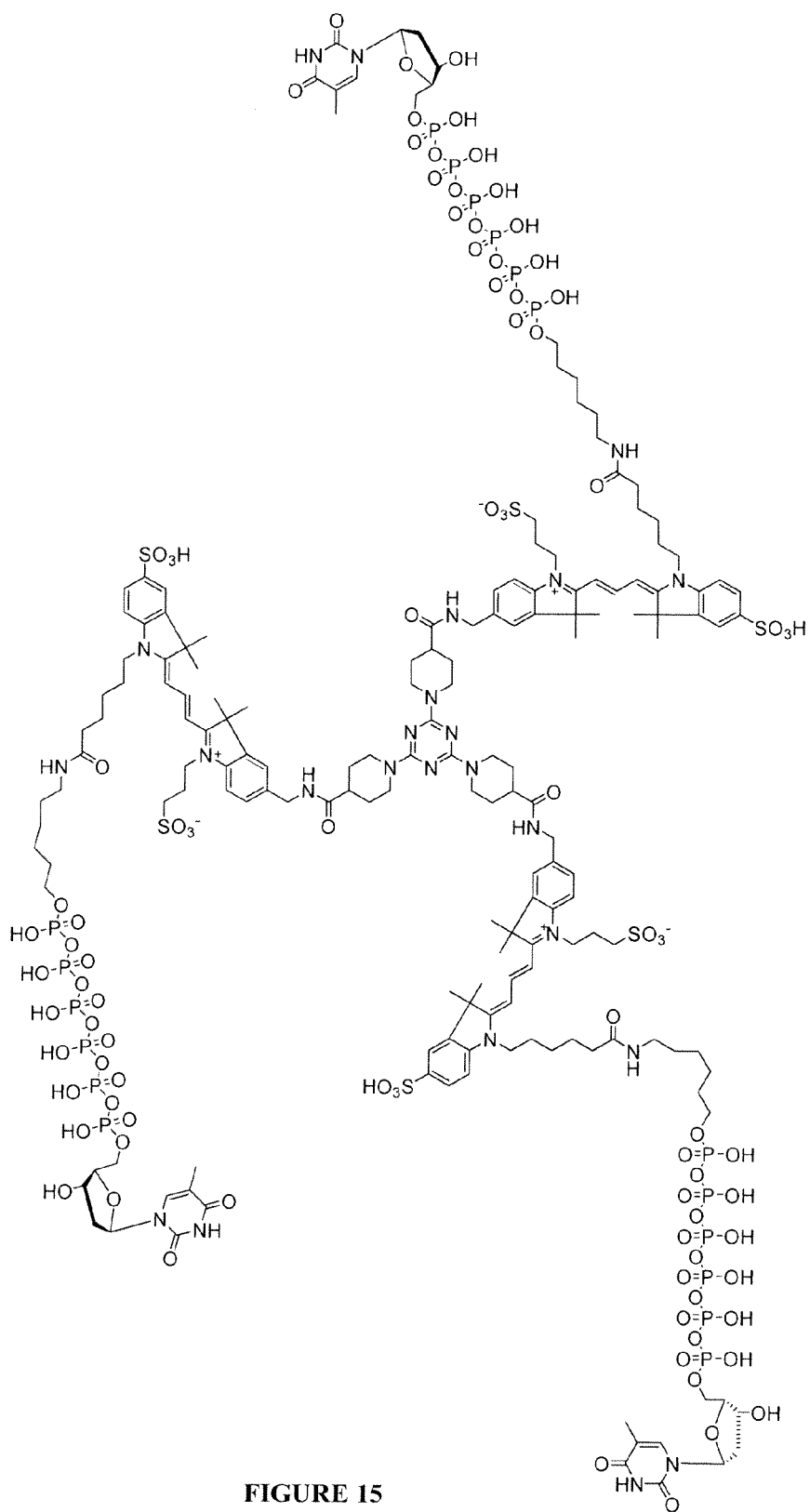
FIG. 15 shows a polymerase enzyme substrate of the invention having a trifunctional triazine-piperidine core with three dye-linker-polyphosphate-nucleoside moieties.
Figure 16:
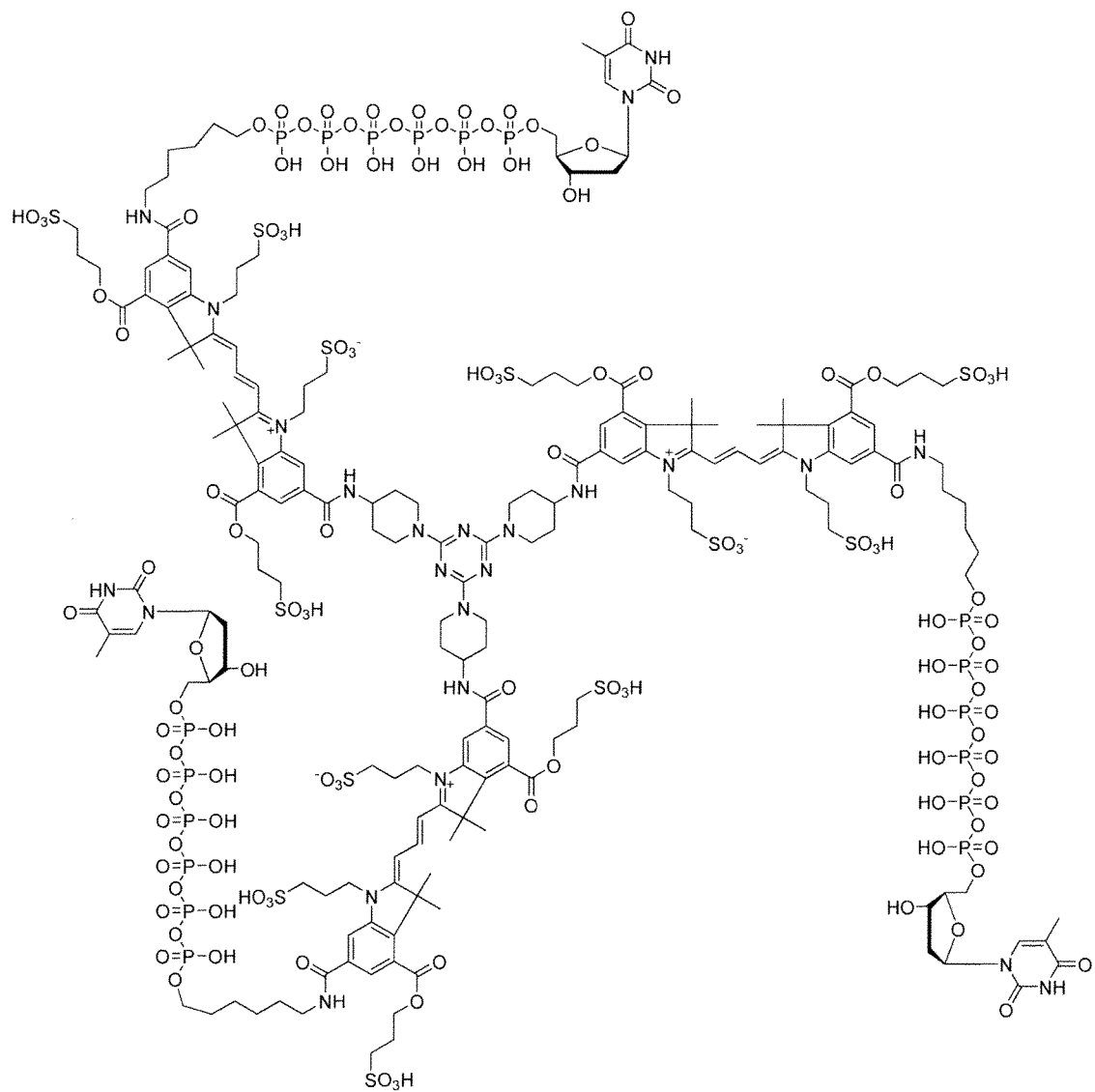
FIG. 16 shows another polymerase enzyme substrate of the invention having a trifunctional triazine-piperidine core with three dye-linker-polyphosphate-nucleoside moieties.
Figure 17:
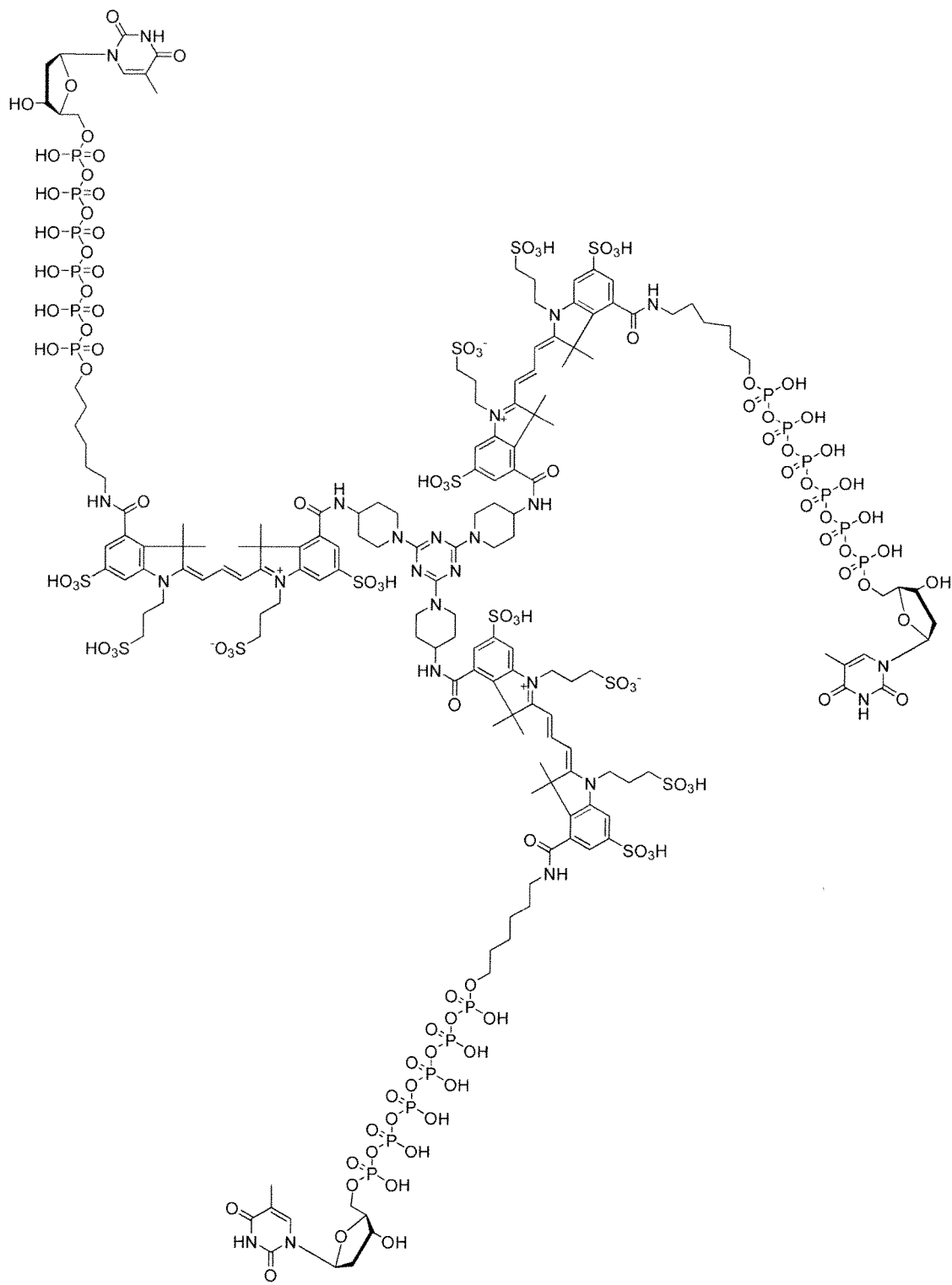
FIG. 17 shows another polymerase enzyme substrate of the invention having a trifunctional triazine-piperidine core with three dye-linker-polyphosphate-nucleoside moieties.
Figure 18:
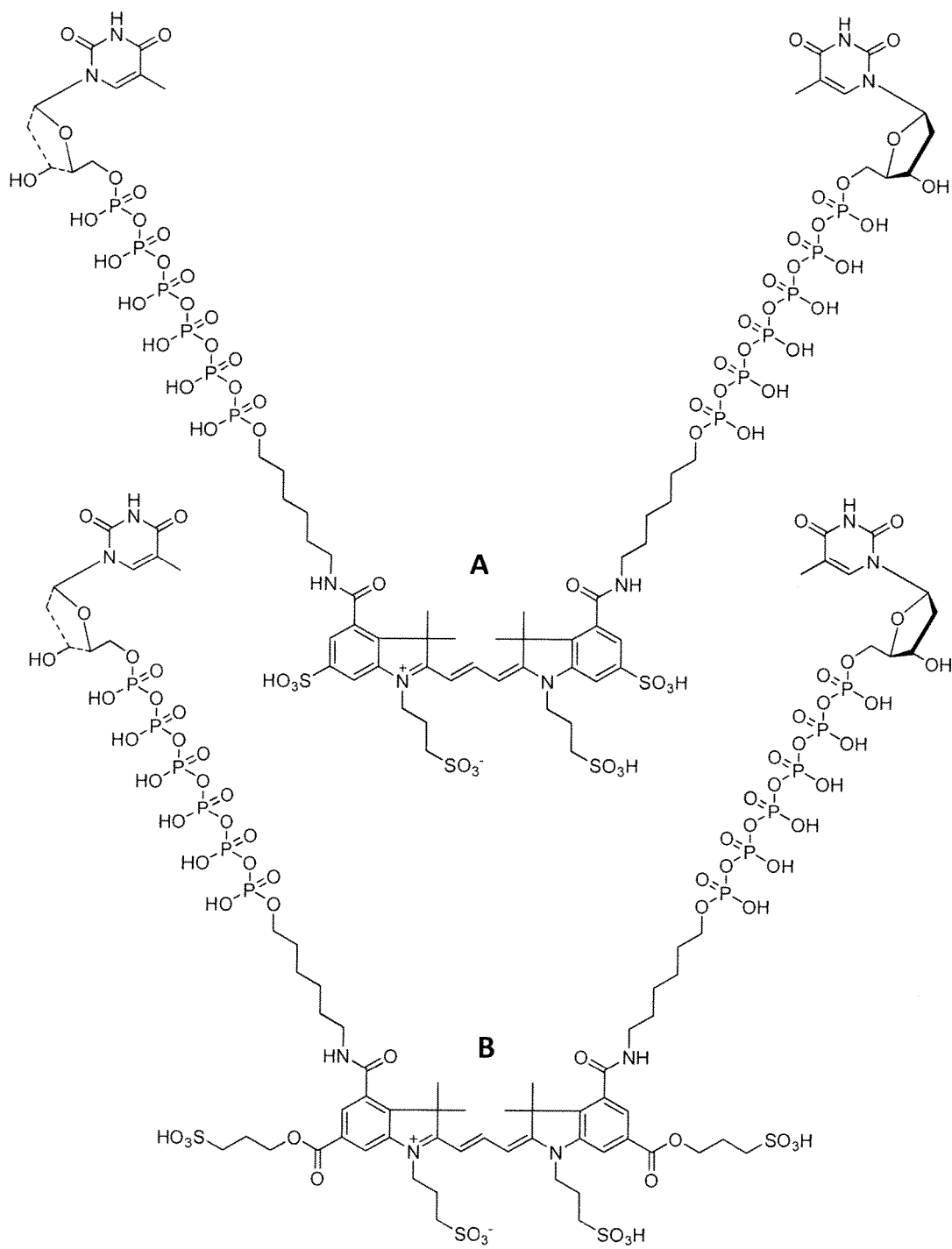
FIG. 18 shows two representative polymerase enzyme substrates of the invention having a cyanine core and two nucleoside phosphate moieties.
Figure 19:
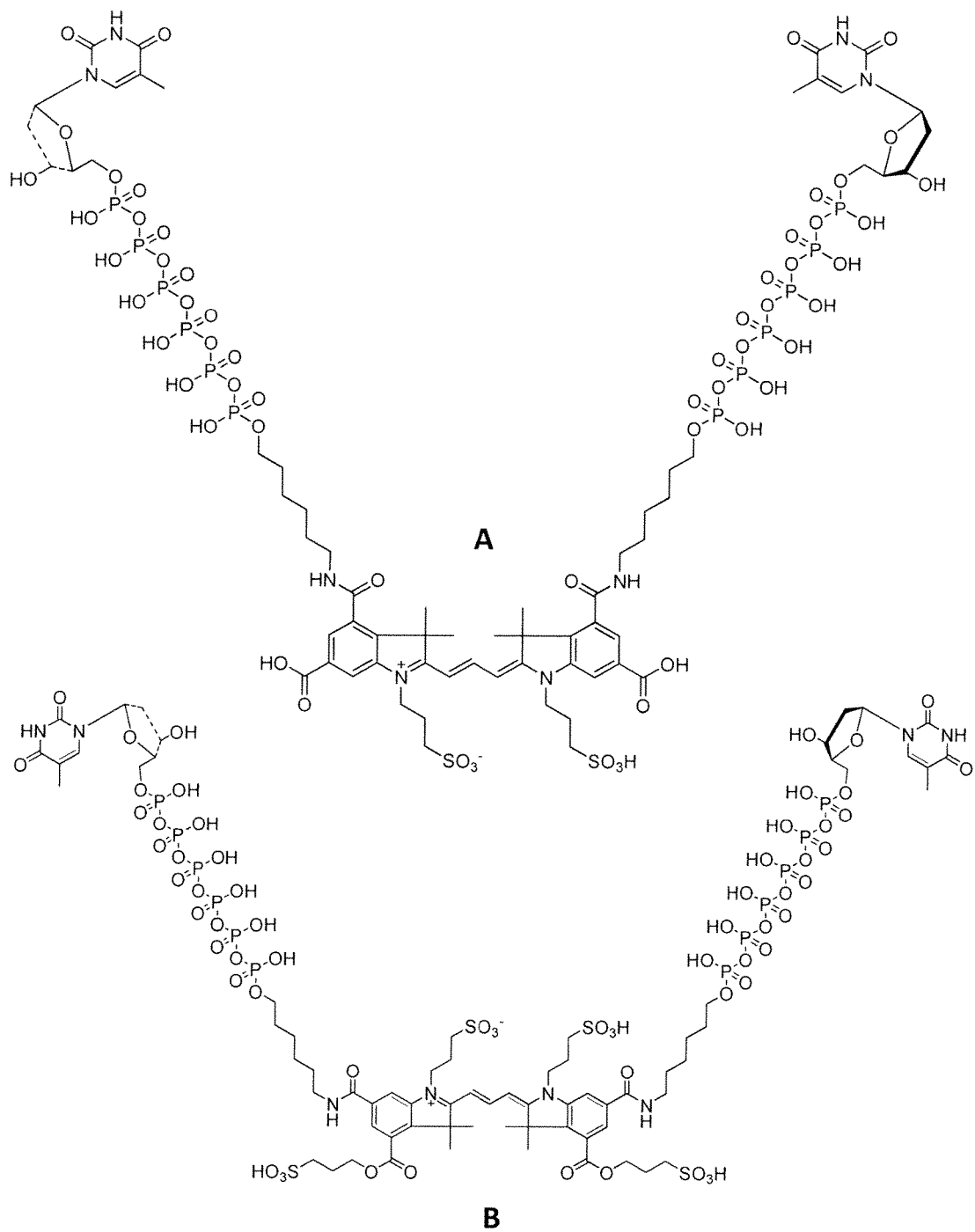
FIG. 19 shows two representative polymerase enzyme substrates of the invention having a cyanine core and two nucleoside phosphate moieties.
Figure 20:
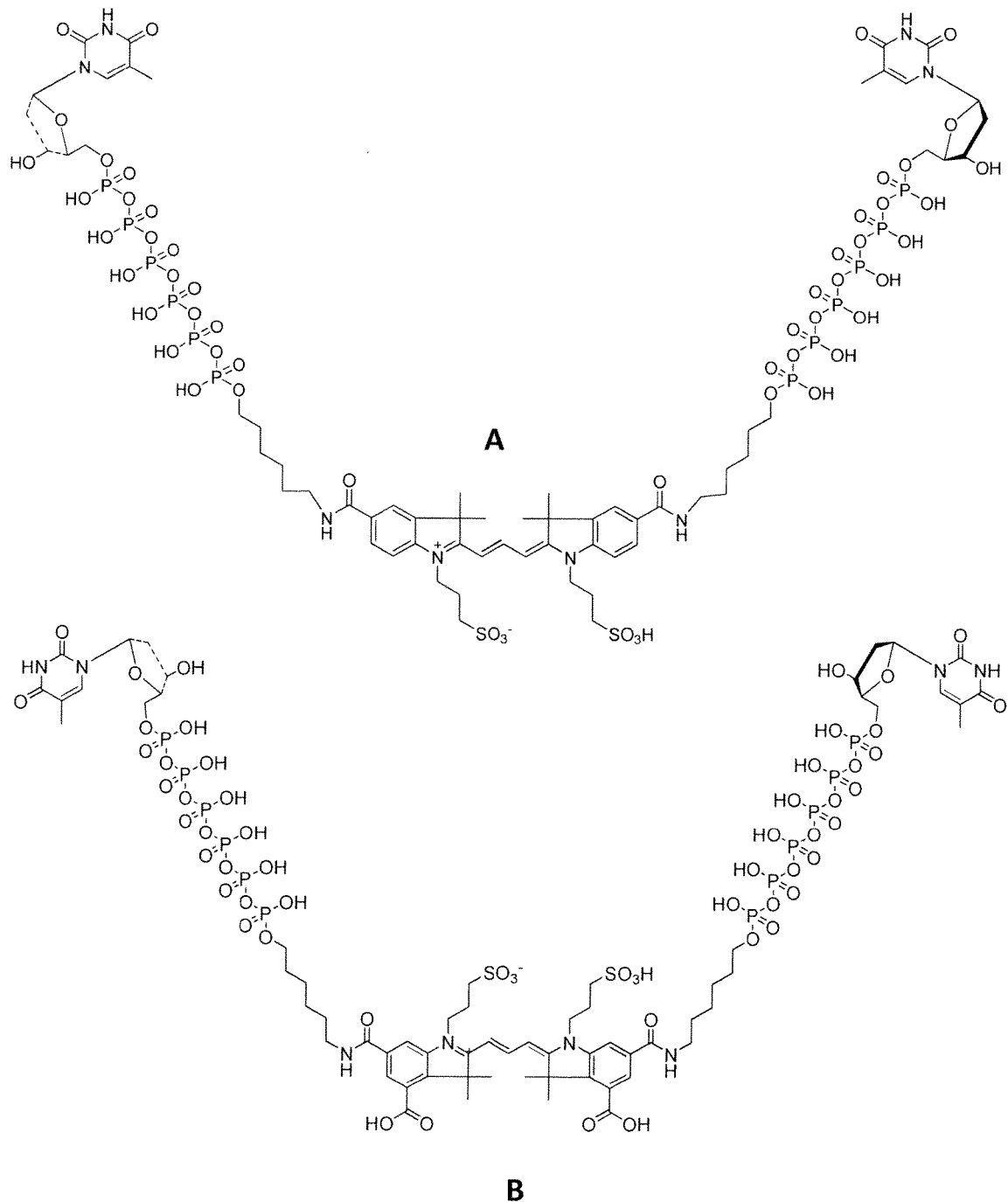
FIG. 20 shows two representative polymerase enzyme substrates of the invention having a cyanine core and two nucleoside phosphate moieties.
Figure 21:
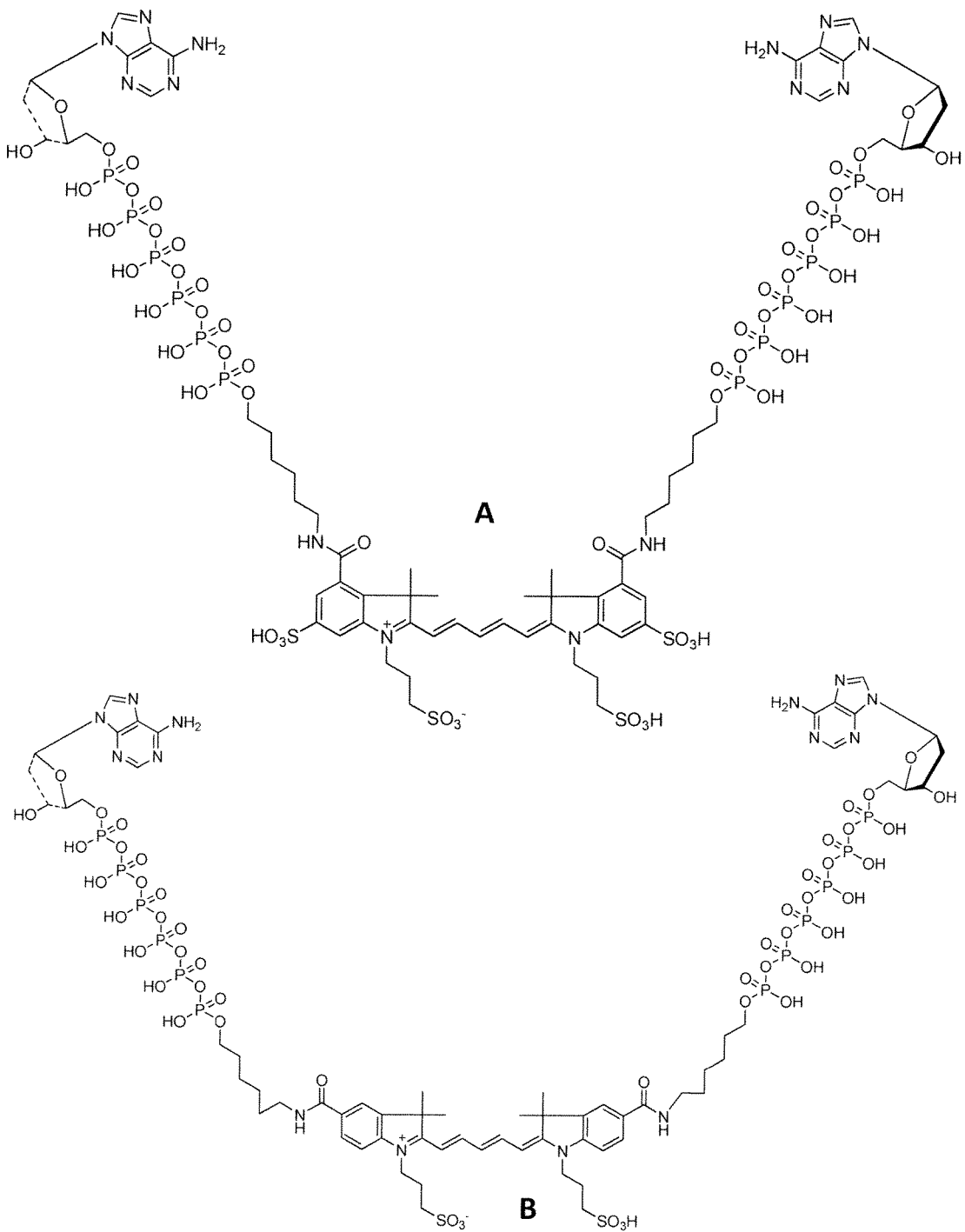
FIG. 21 shows two representative polymerase enzyme substrates of the invention having a cyanine core and two nucleoside phosphate moieties.
Figure 22:
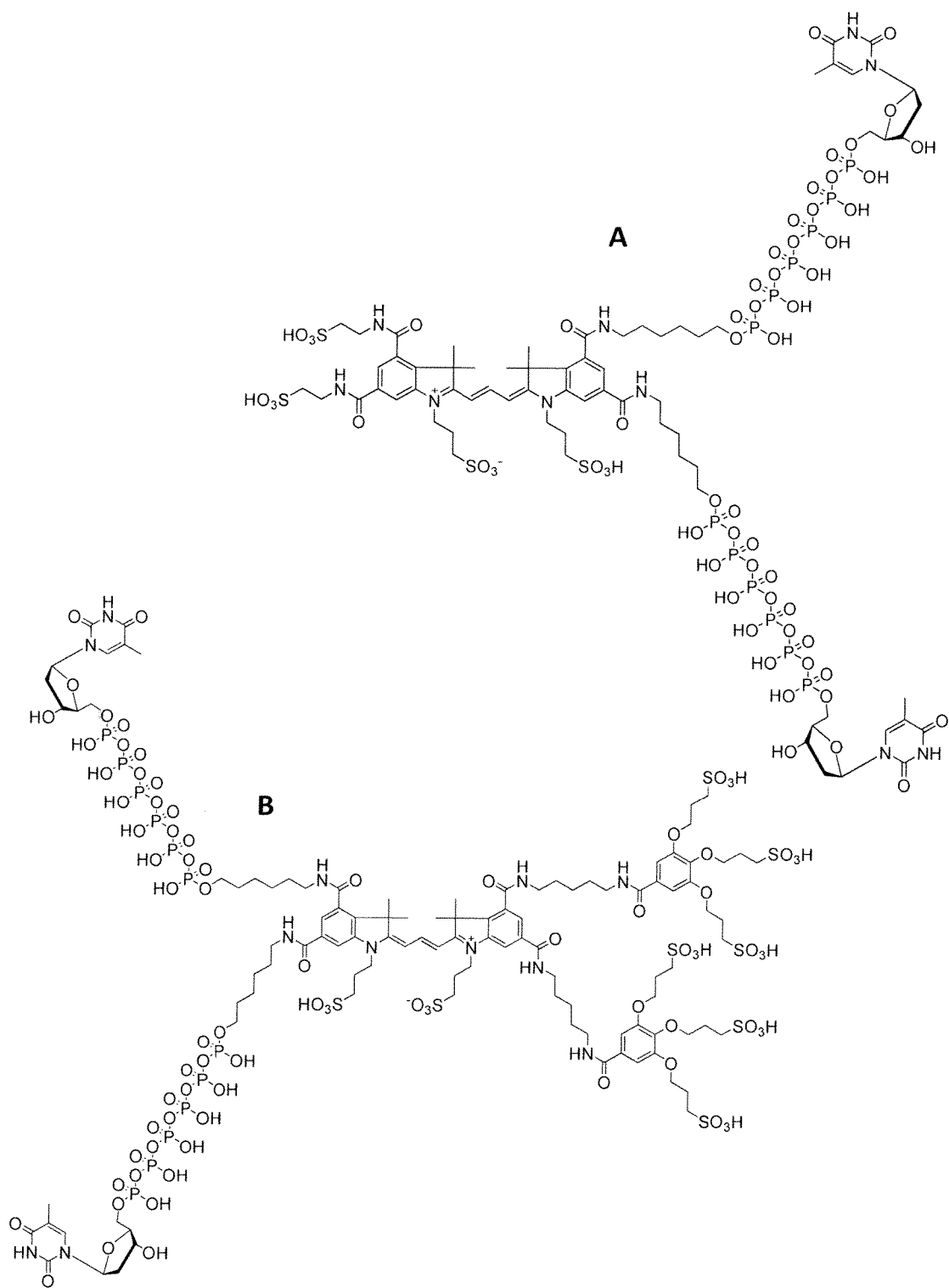
FIG. 22 shows two representative polymerase enzyme substrates of the invention having a cyanine core and two nucleoside phosphate moieties.

FIG. 14 shows a polymerase enzyme substrate of the invention with a core comprising three triazine piperidine core units linked to produce a pentafunctional core. Attached to the core are two FRET donor dyes, two FRET acceptor dyes, and a nucleoside polyphosphate where the polyphosphate comprises six phosphates.

FIGS. 15-18 shows a polymerase enzyme substrate of the invention with a triazine piperidine trifunctional core having three dye-linker-phosphate-nucleoside moieties. Each of the dyes are cyanine dyes.

FIG. 18-22 shows a polymerase enzyme substrates of the invention with a core comprising a cyanine dye, each with two linker-polyphosphate-nucleoside moieties attached. In FIG. 21A and FIG. 21B the linker nucleoside polyphosphate moities are each attached to the same ring in the cyanine dye structure. The enzyme substrate of 21B has multiple (6) sulfonate groups attached to the opposite end of the cyanine dye from the attachment point of the dyes. The sulfonate groups can aid in increasing the water solubility of the molecule.

Figure 23:
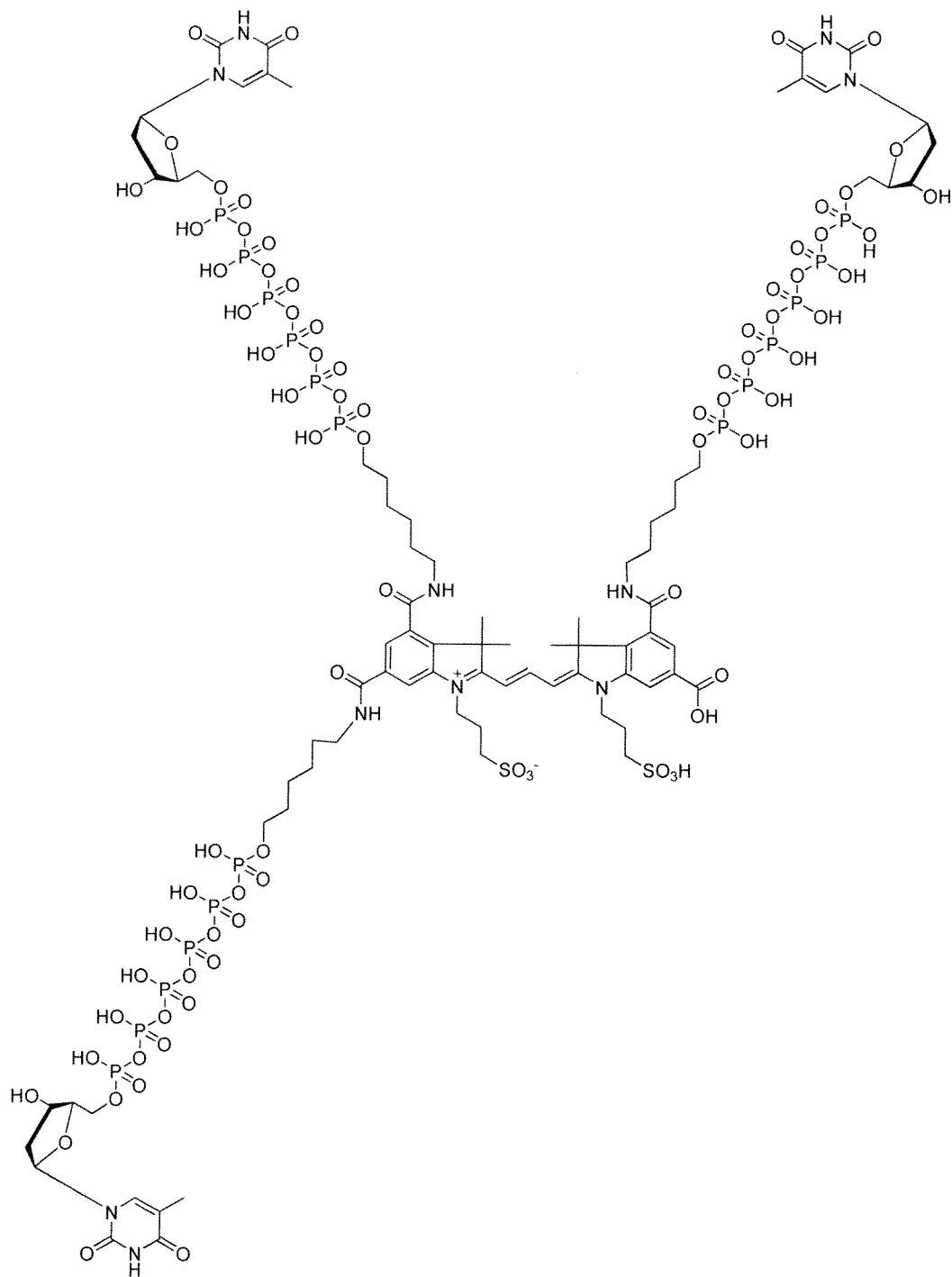
FIG. 23 shows a representative polymerase enzyme substrates of the invention having a cyanine core and three nucleoside phosphate moieties.
Figure 24:
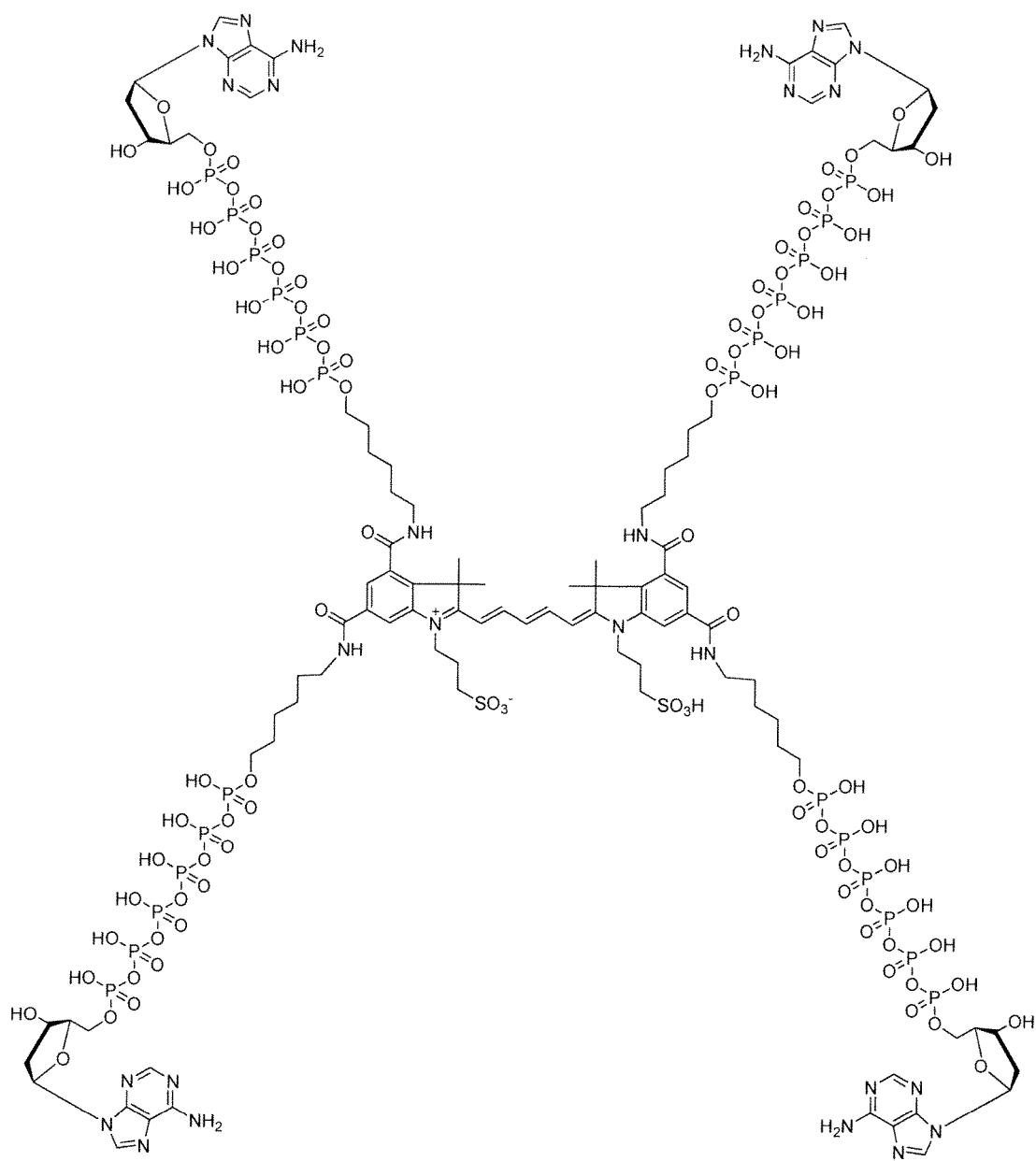
FIG. 24 shows a representative polymerase enzyme substrates of the invention having a cyanine core and four nucleoside phosphate moieties.
Figure 25:
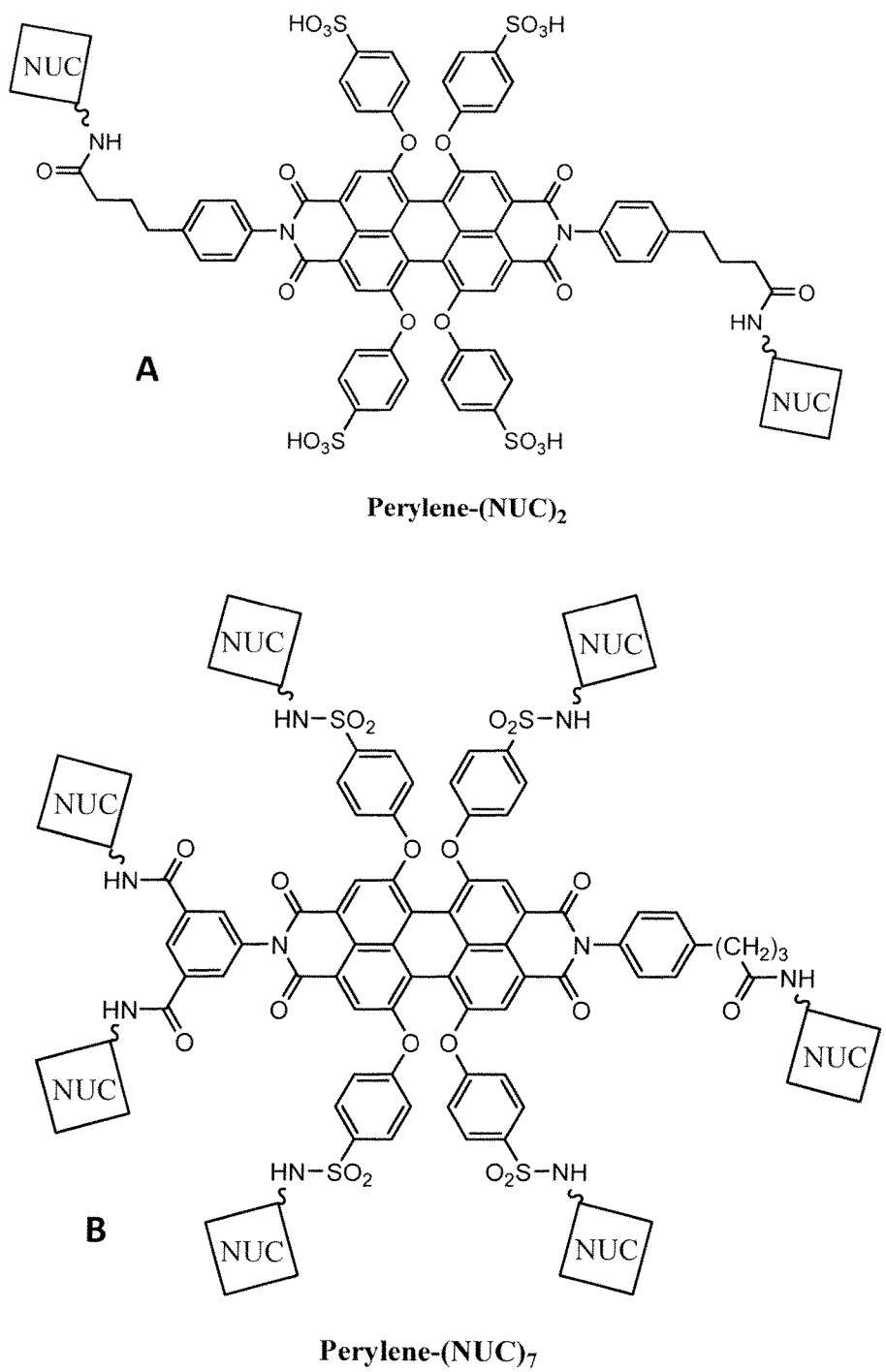
FIG. 25 shows representative polymerase enzyme substrates of the invention having a perylene dye core.

FIG. 23 shows a polymerase enzyme substrate of the invention with a cyanine dye core having three linker-polyphosphate-nucleoside moieties FIG. 24 shows a polymerase enzyme substrate of the invention with a cyanine dye core having four linker-polyphosphate-nucleoside moieties FIG. 25 shows polymerase enzyme substrates of the invention having a perylene dye core. In FIG. 25A, the perylene dye core has two polyphosphate nucleoside (NUC) moieties. In FIG. 25B, the perylene dye core has eight polyphosphate nucleoside (NUC) moieties.

Figure 26:
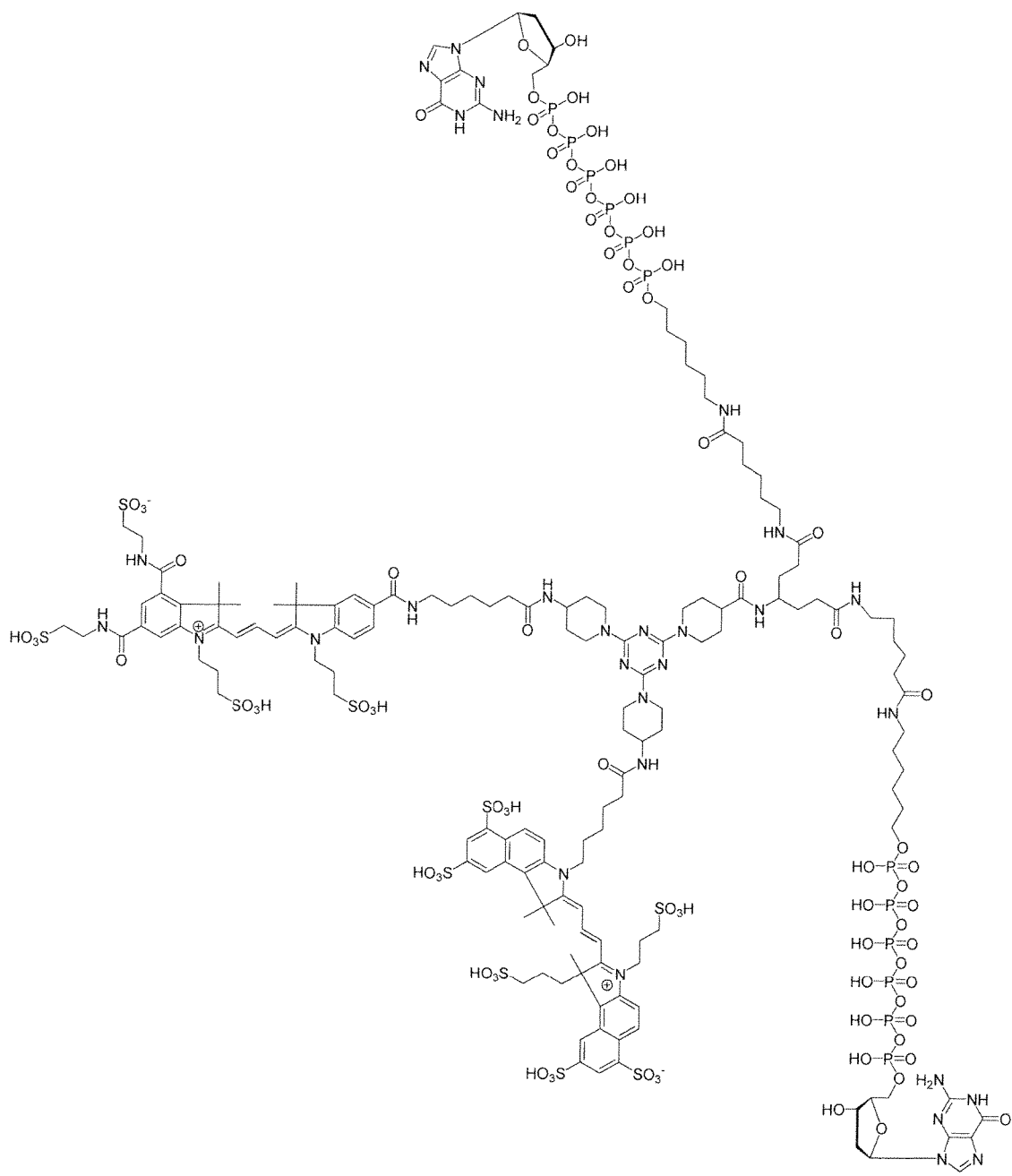
FIG. 26 shows representative polymerase enzyme substrates of the invention having two fluorescent dyes and two nucleoside phosphate units.
Figure 27A:
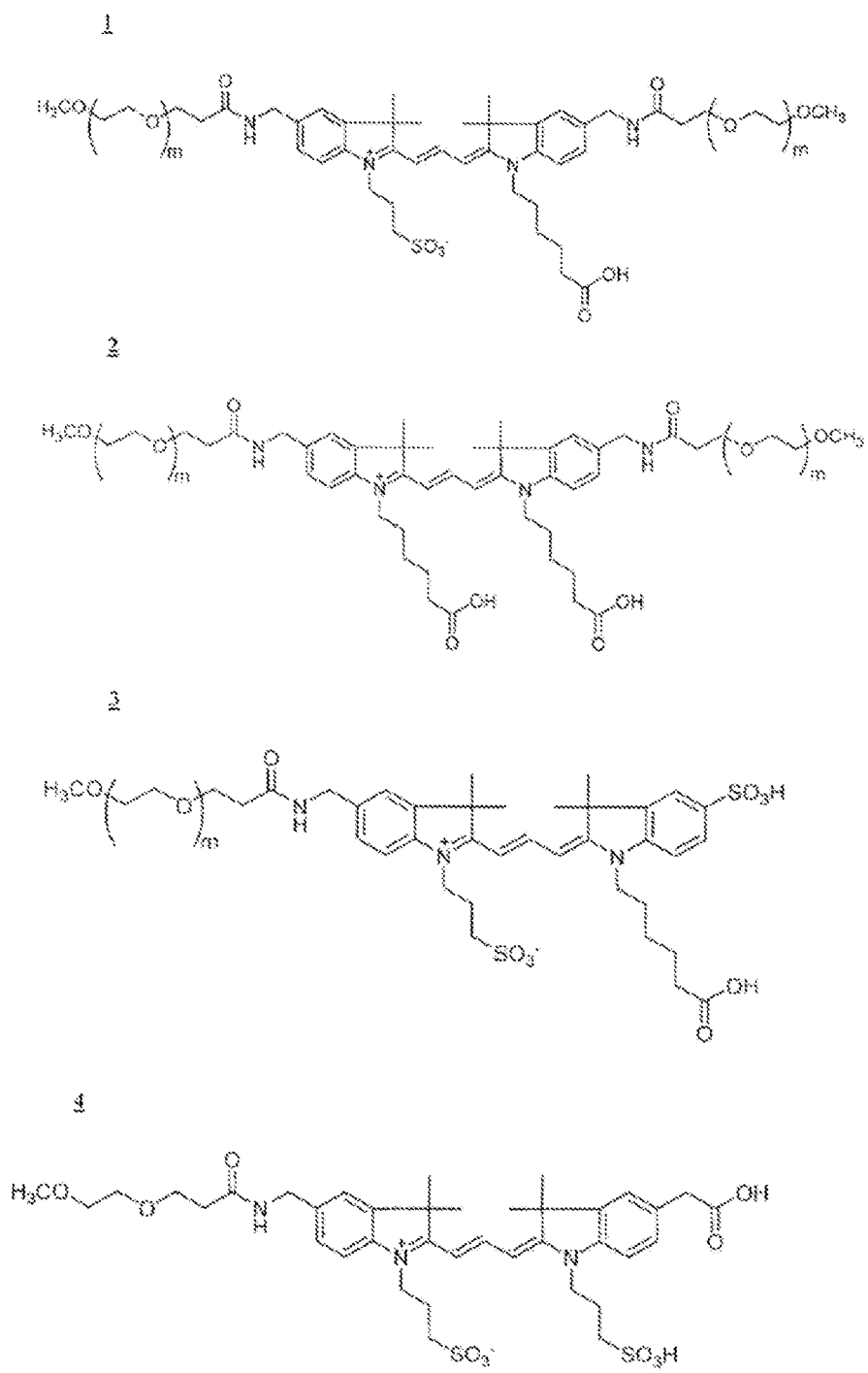
FIG. 27(a), FIG. 27(b) FIGS. 27(c) and 27(d) show structures of exemplary precursors of the dye components of the conjugates of the invention. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 27B:
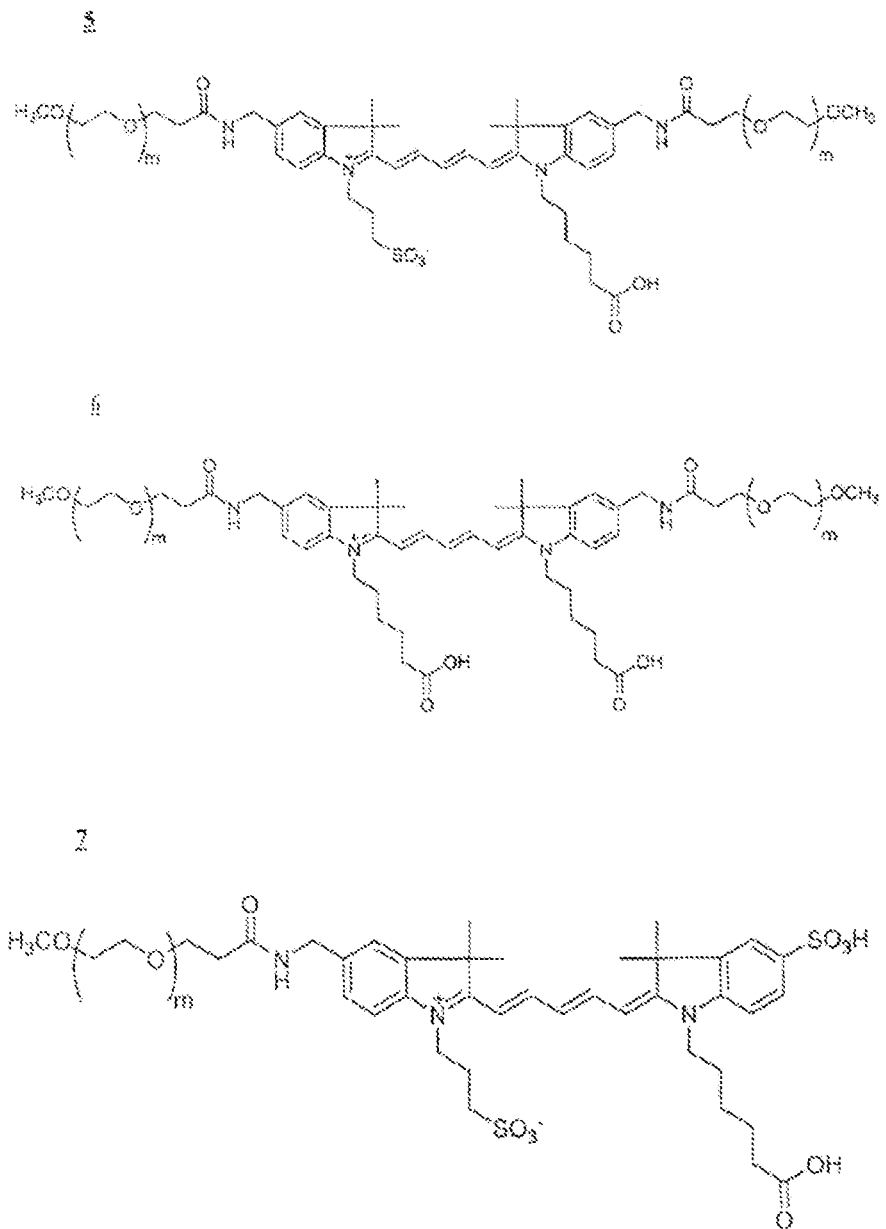
Figure 27C:
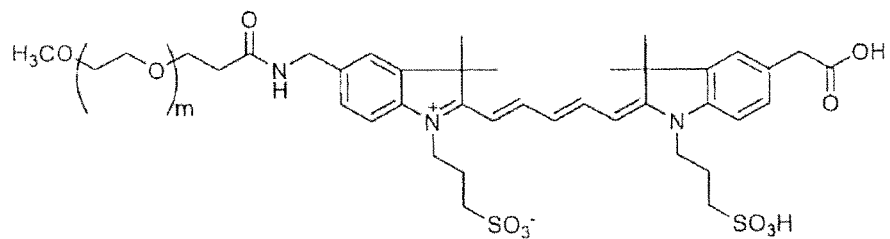
Figure 27C:
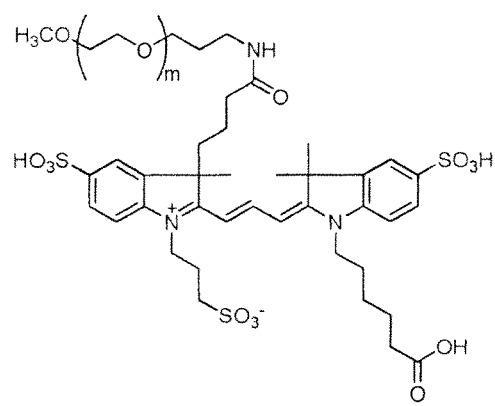
Figure 27C:
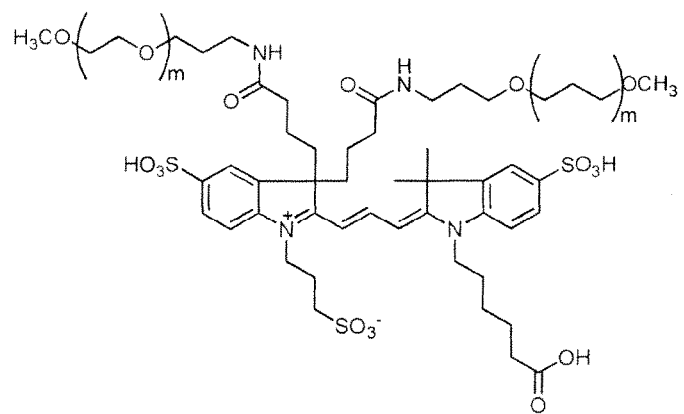
Figure 27D:
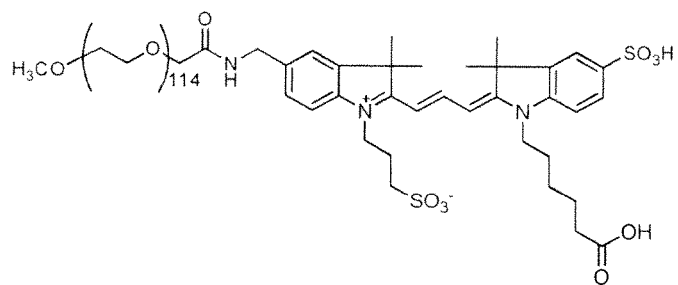
Figure 27D:
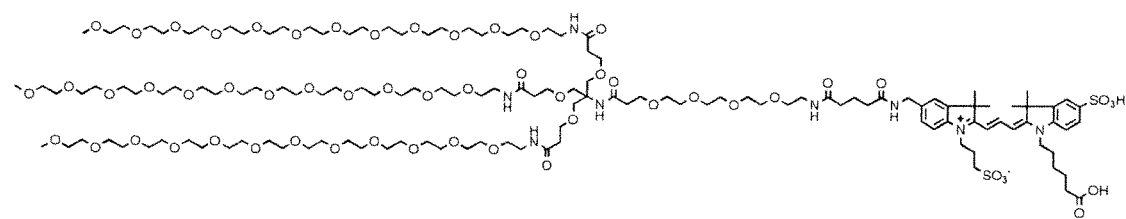
Figure 28A:
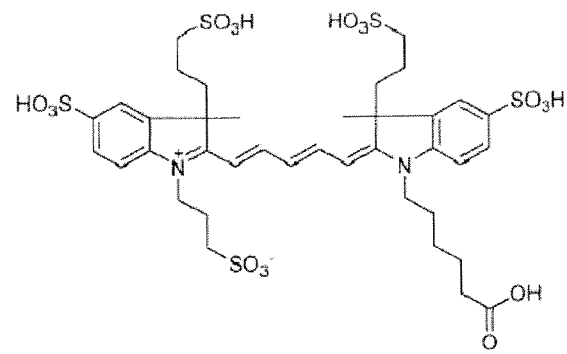
FIG. 28(a), FIG. 28(b) and FIG. 28(c) show structures of exemplary precursors of the dye components of the conjugates of the invention. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 28A:
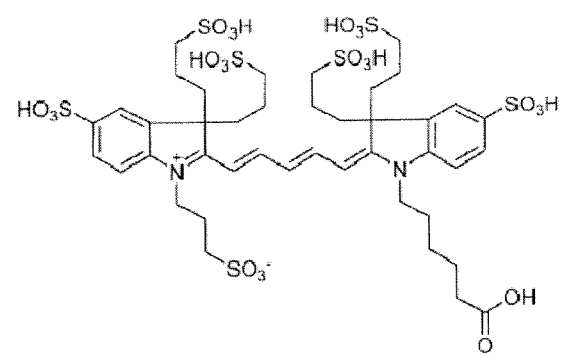
Figure 28A:
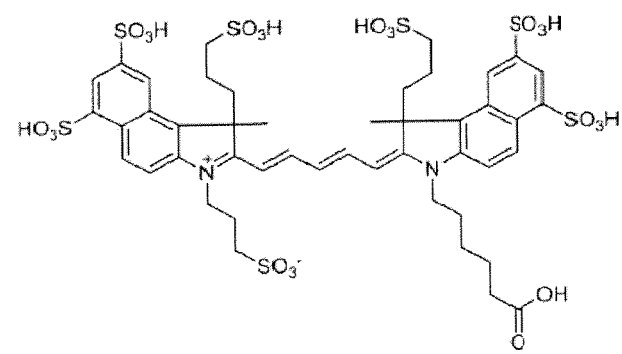
Figure 28B:
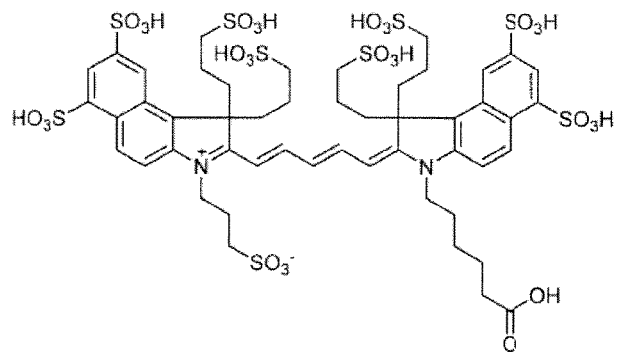
Figure 28B:
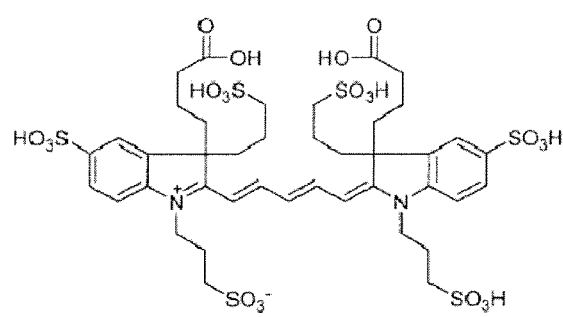
Figure 28B:
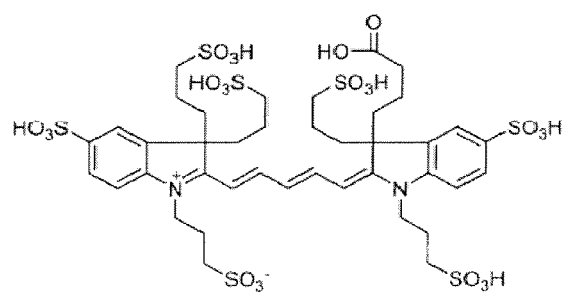
Figure 28C:
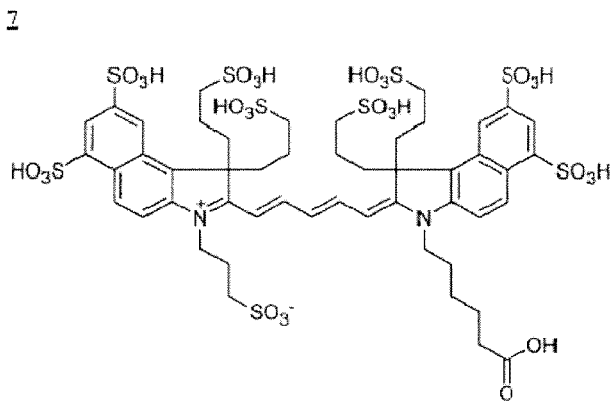
Figure 28C:
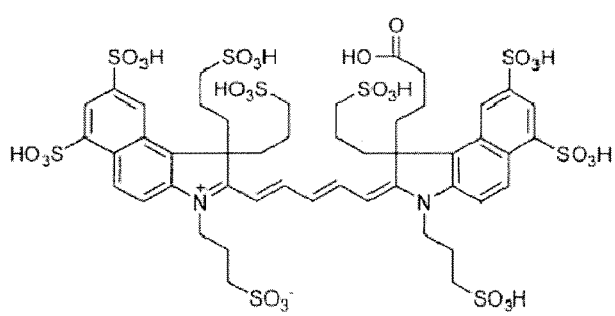
Figure 28C:
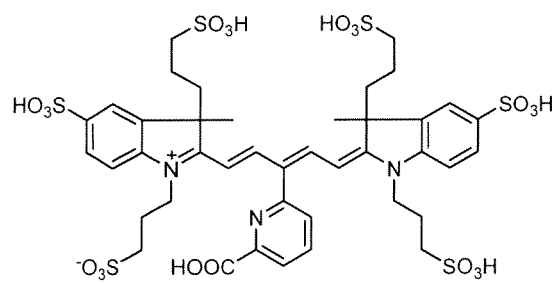
Figure 28C:
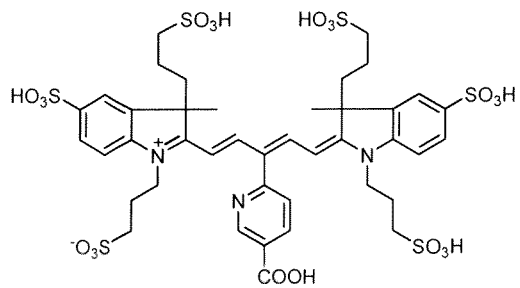
Figure 29A:
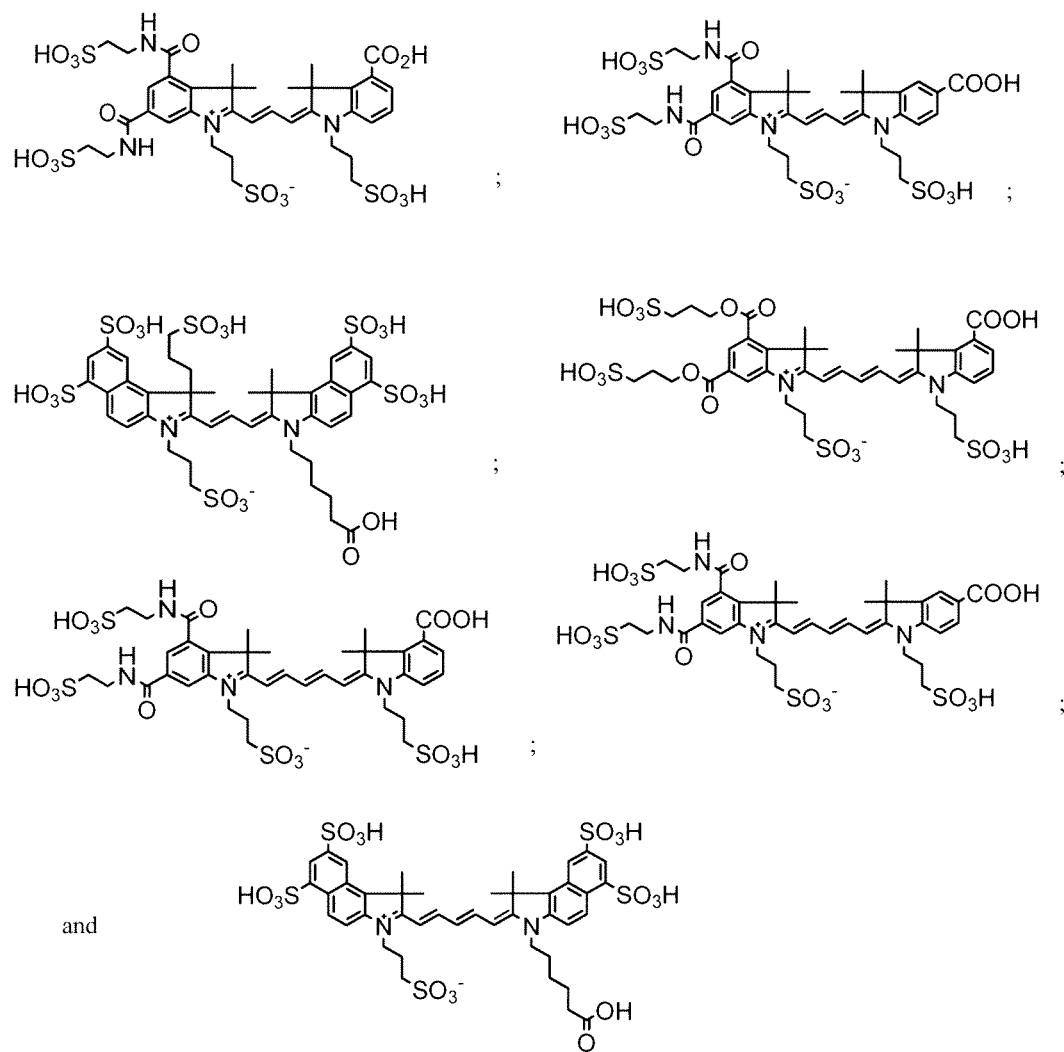
FIG. 29(a) and FIG. 29(b) show structures of exemplary precursors of the dye components of the conjugates of the invention. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 29B:
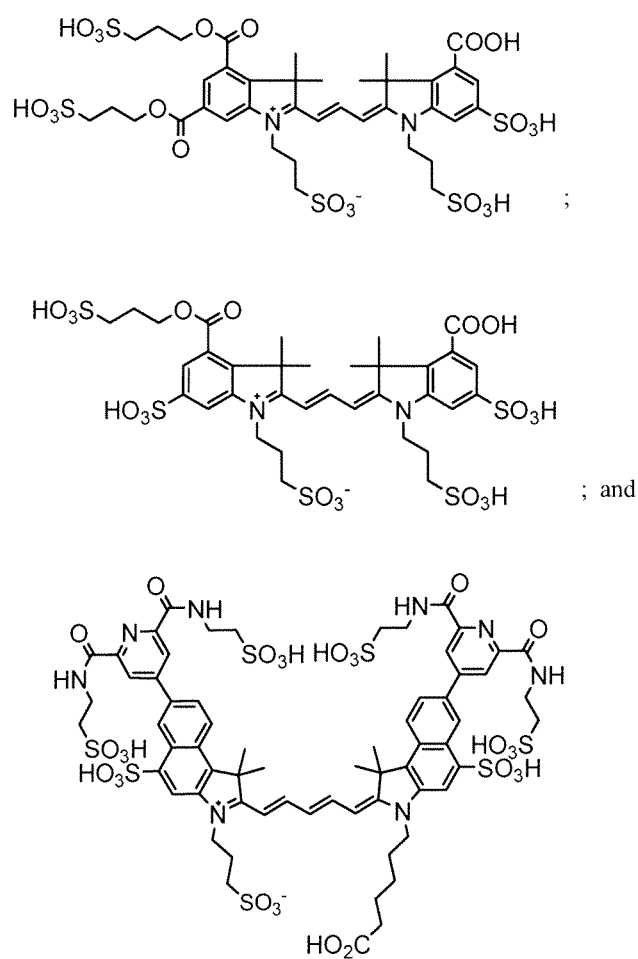
Figure 30A:
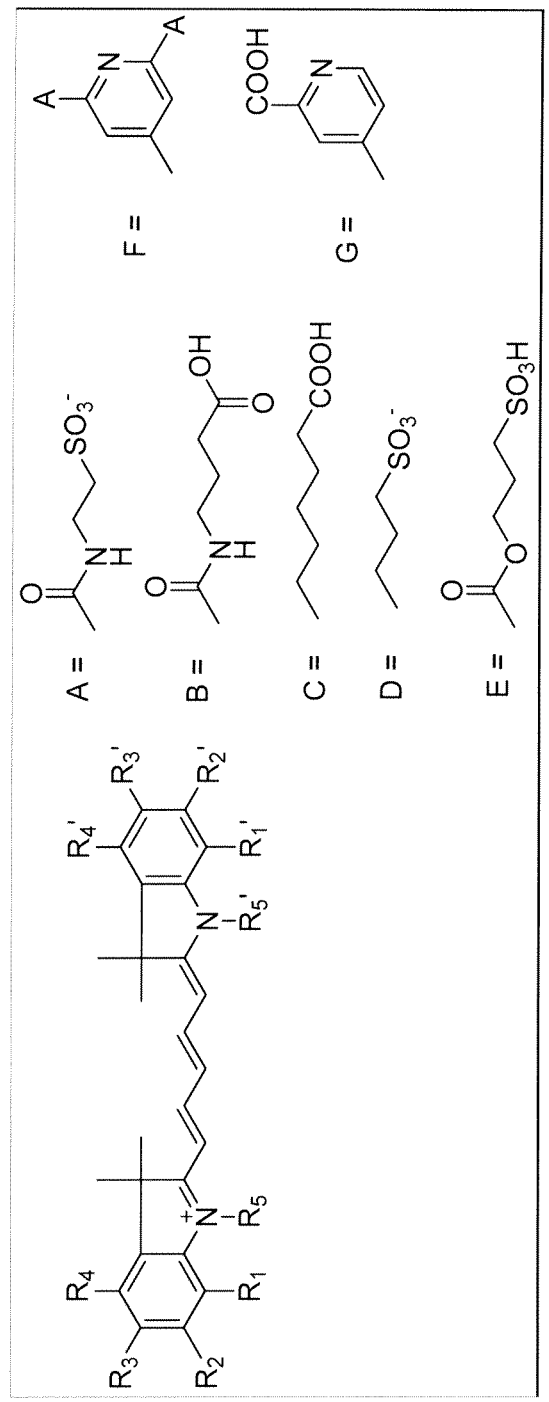
FIG. 30(a) is a generic structure of exemplary precursors of the dye components of the conjugates of the invention and of substituents on these precursors. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 31A:
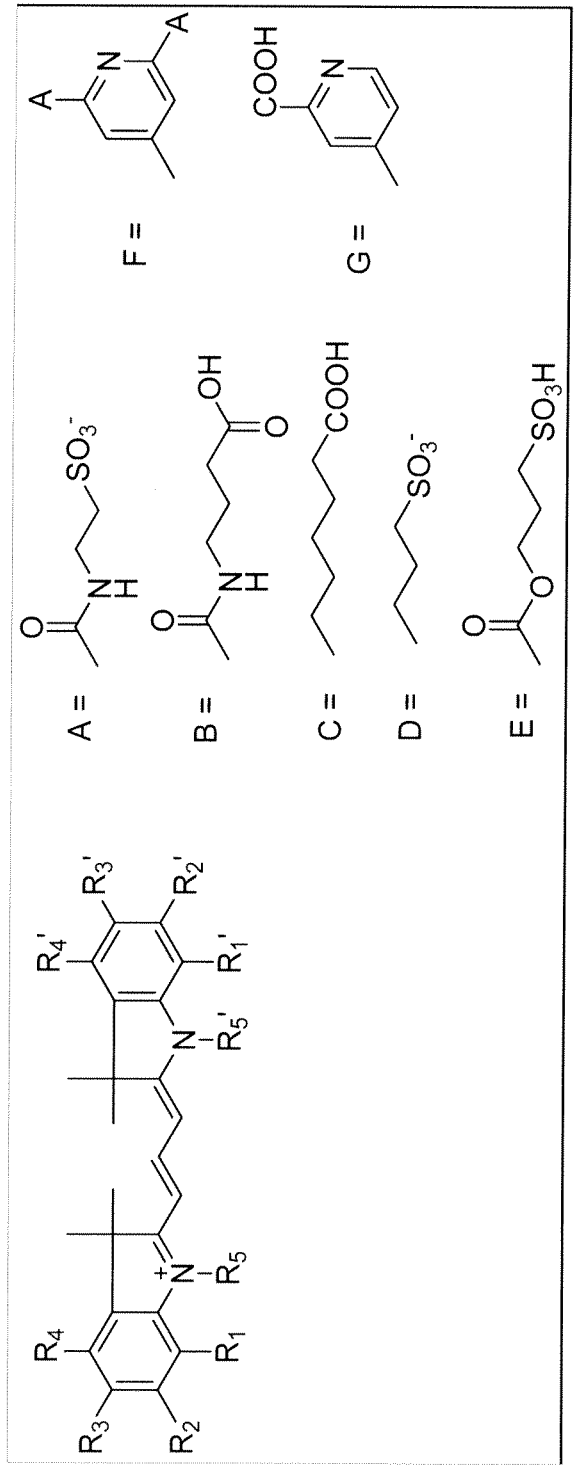
FIG. 31(a) is a generic structure of exemplary precursors of the dye components of the conjugates of the invention and of substituents on these precursors. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 32A:
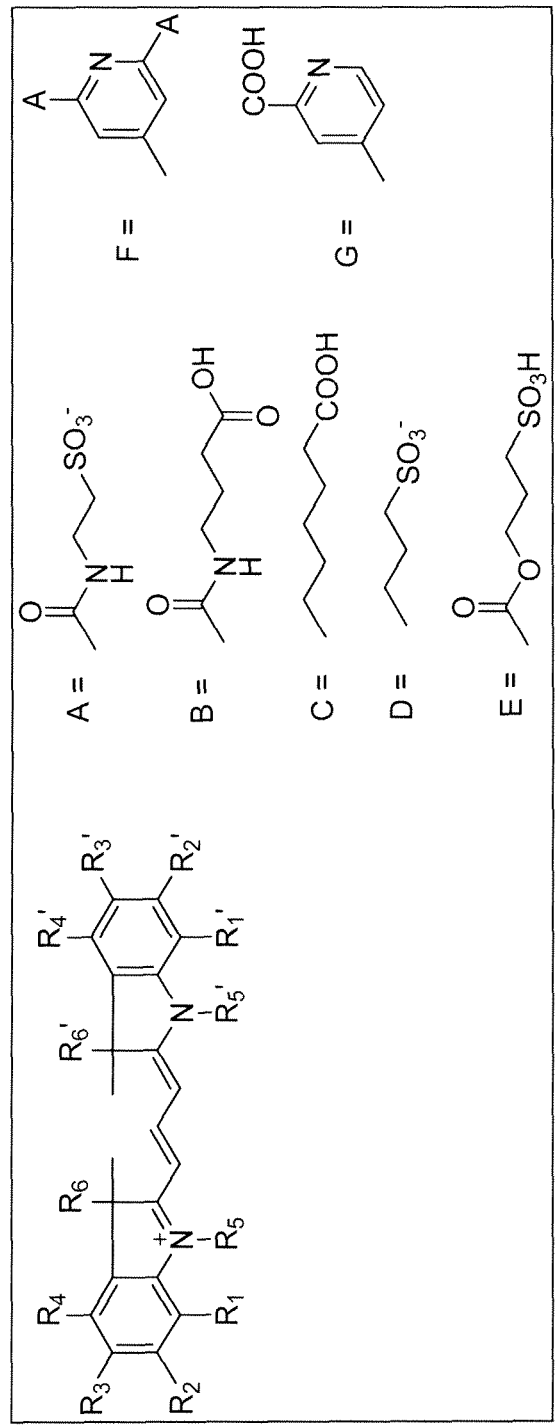
FIG. 32(a) is a generic structure of exemplary precursors of the dye components of the conjugates of the invention and of substituents on these precursors. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 33A:
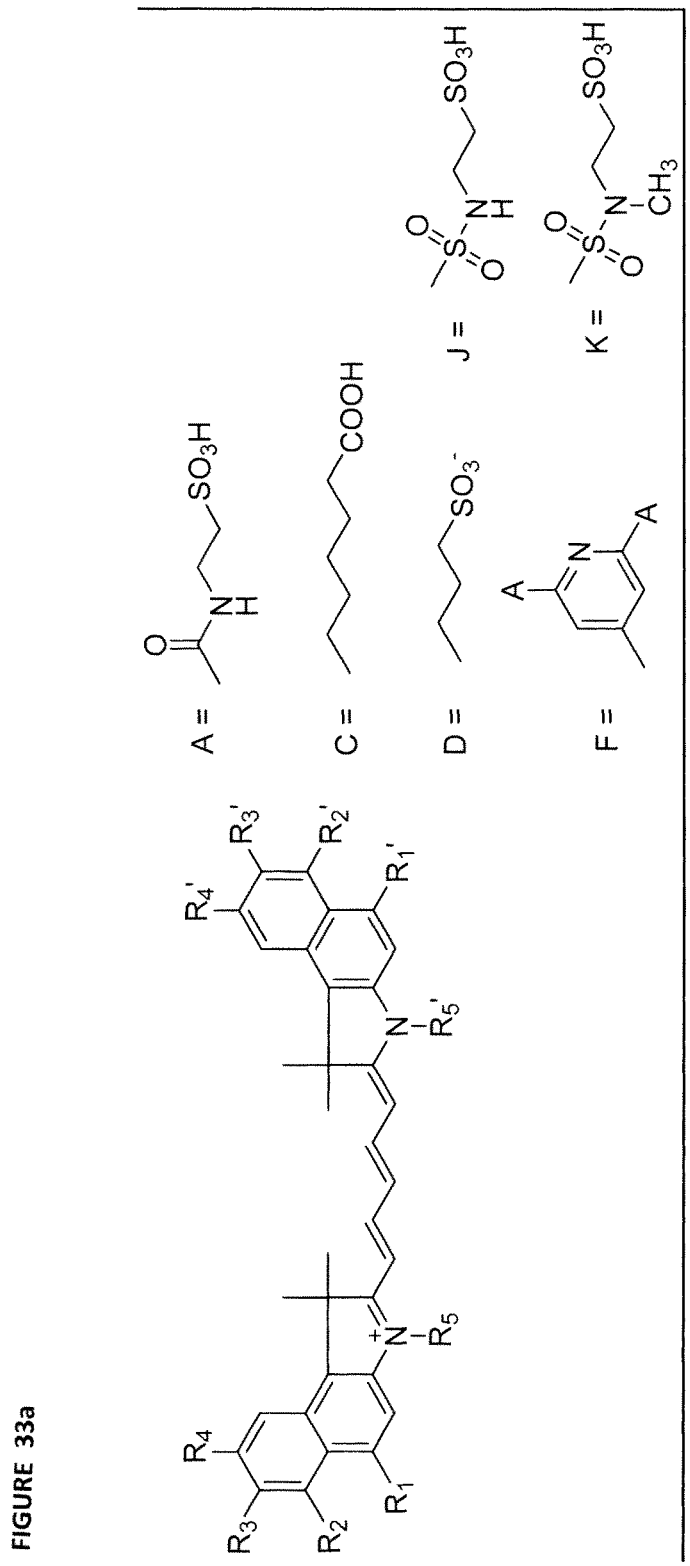
FIG. 33(a) is a generic structure of exemplary precursors of the dye components of the conjugates of the invention and of substituents on these precursors. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 34A:
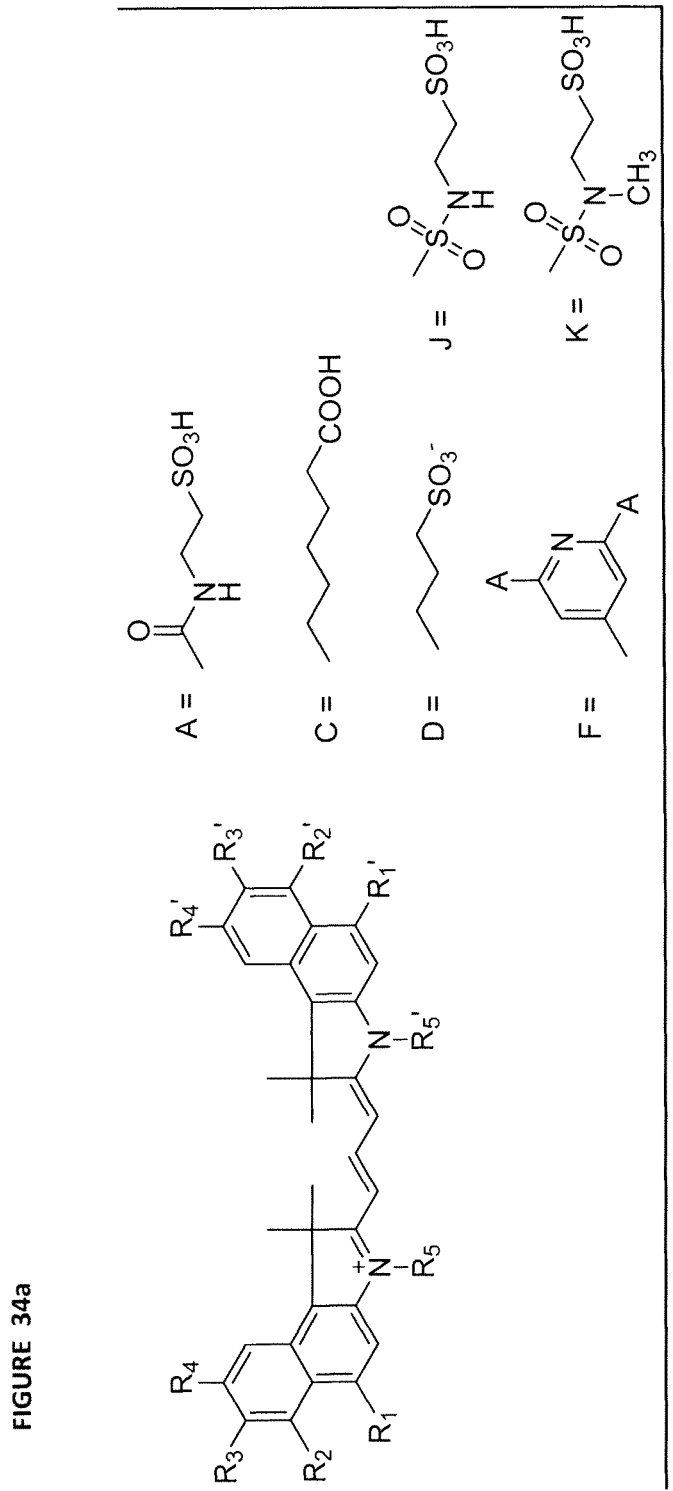
FIG. 34(a) is a generic structure of exemplary precursors of the dye components of the conjugates of the invention and of substituents on these precursors. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 35A:
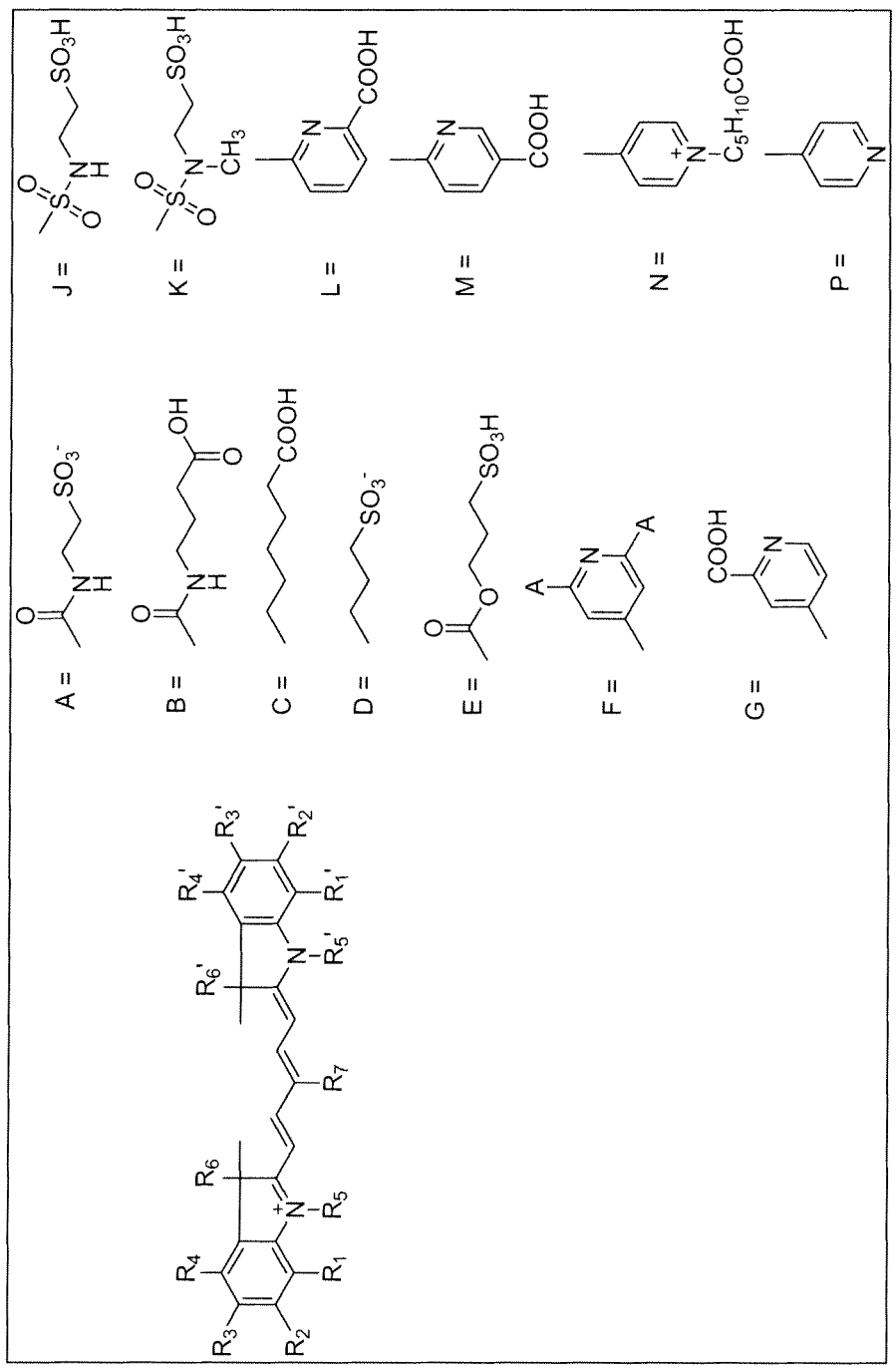
FIG. 35(a) is a generic structure of exemplary precursors of the dye components of the conjugates of the invention and of substituents on these precursors. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 36A:
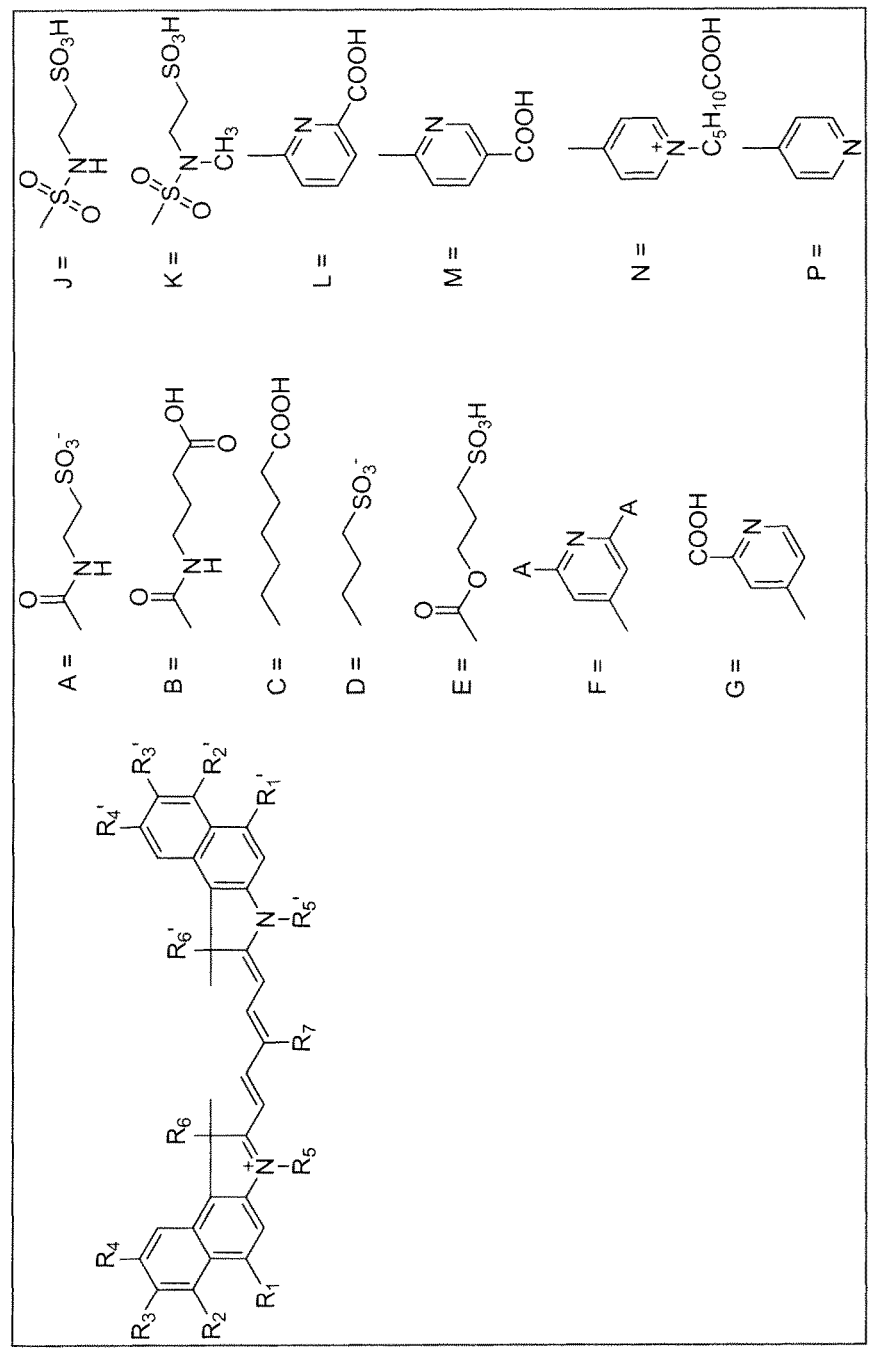
FIG. 36(a) is a generic structure of exemplary precursors of the dye components of the conjugates of the invention and of substituents on these precursors. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 37A:
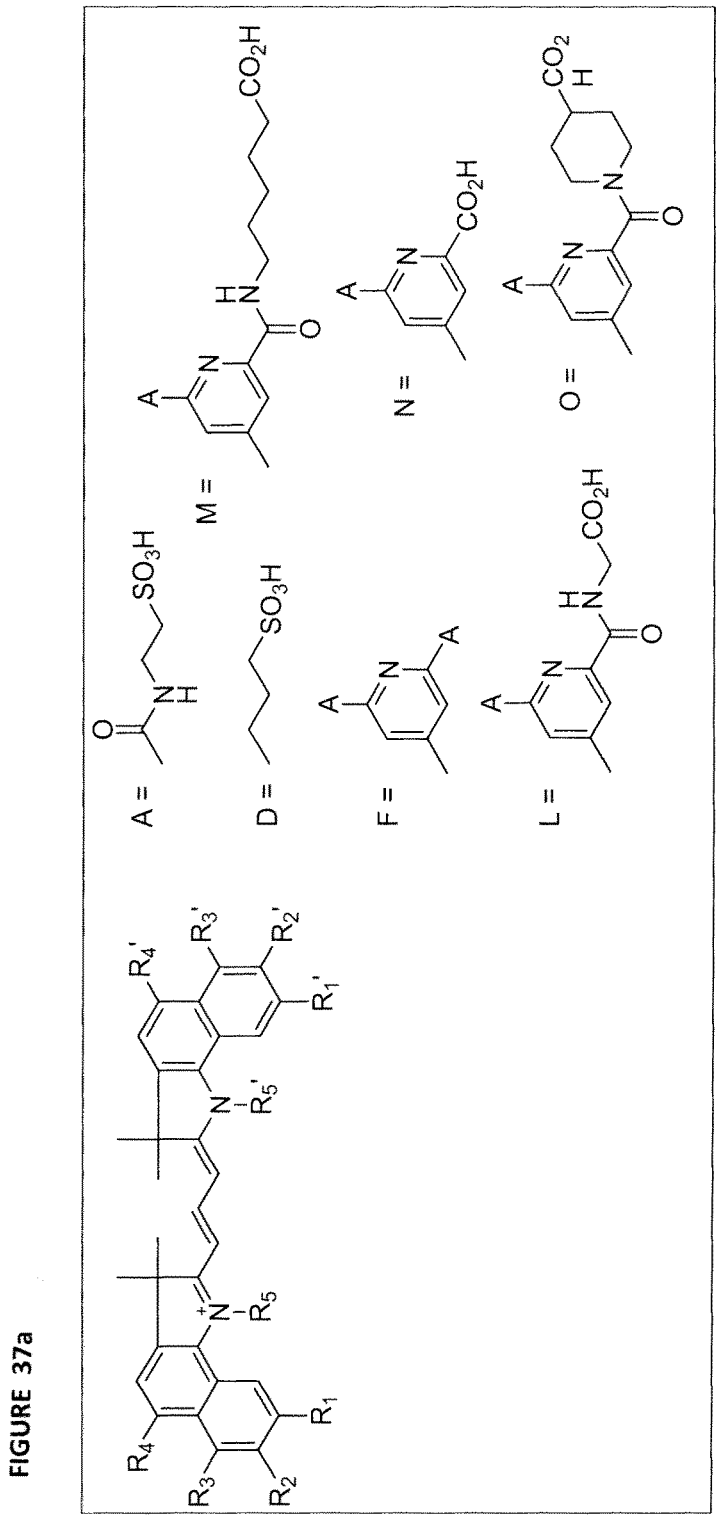
FIG. 37(a) is a generic structure of exemplary precursors of the dye components of the conjugates of the invention and of substituents on these precursors. Once incoporated into a conjugate of the invention, the conjugated dyes can be further conjugated to one or more additional species, e.g., a polyvalent scaffold (e.g., into a FRET pair), conjugated to a nucleic acid or to a linker.
Figure 38:
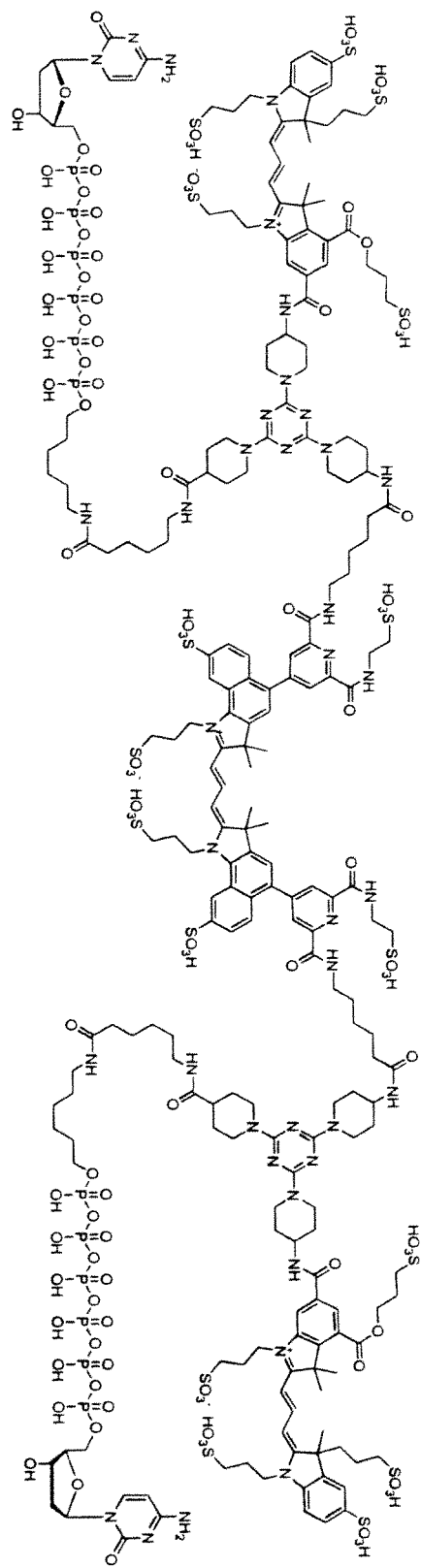
FIG. 38 displays a structure of an exemplary polyvalent dye nucleic acid (polyphosphate) conjugates of the invention.

FIG. 26 shows a polymerase enzyme substrate of the invention having two dyes and two nucleoside phosphate moieties. One of the dyes is a FRET donor and the other dye is a FRET acceptor. As is typical, the two nucleoside phosphate moities are the same. The molecule has a triazine-piperidine core unit which is attached to an aliphatic trifunctional core unit to produce a tetrafunctional core. The aliphatic trifunctional core unit can be incorporated using a 3-amino adipic acid precursor.

Reactive Functional Groups

The compounds of the invention are generally constructed using reactive functional groups. Exemplary species include a reactive functional group attached directly to the core nucleus (e.g., aryl ring) or to a linker attached to a component (e.g., aryl ring) of the core. When the reactive group is attached to a substituted or unsubstituted alkyl or substituted or unsubstituted heteroalkyl linker moiety, the reactive group is preferably located at a terminal position of the alkyl or heteroalkyl chain. Reactive groups and classes of reactions useful in practicing the present invention are generally those that are well known in the art of bioconjugate chemistry. Currently favored classes of reactions available with reactive groups to produce compounds of the invention the are those proceeding under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups include, for example:

(a) carboxyl groups and derivatives thereof including, but not limited to activated esters, e.g., N-hydroxysuccinimide esters, N-hydroxyphthalimide esters, N-hydroxybenztriazole esters, acid halides, acyl imidazoles, thioesters, p-nitrophenyl esters, alkyl, alkenyl, alkynyl and aromatic esters, activating groups used in peptide synthesis and acid halides;

(b) hydroxyl groups, which can be converted to esters, sulfonates, phosphoramidites, ethers, aldehydes, etc.

(c) haloalkyl groups, wherein the halide can be displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups, which are capable of participating in Diels-Alder reactions such as, for example, maleimido groups;

(e) aldehyde or ketone groups, allowing derivatization via formation of carbonyl derivatives, e.g., imines, hydrazones, semicarbazones or oximes, or via such mechanisms as Grignard addition or alkyllithium addition;

(f) sulfonyl halide groups for reaction with amines, for example, to form sulfonamides;

(g) thiol groups, which can be converted to disulfides or reacted with acyl halides, for example;

(h) amine or sulfhydryl groups, which can be, for example, acylated, alkylated or oxidized;

(i) alkenes, which can undergo, for example, cycloadditions, acylation, Michael addition, etc;

(j) epoxides, which can react with, for example, amines and hydroxyl compounds; and (k) phosphoramidites and other standard functional groups useful in nucleic acid synthesis.

The reactive functional groups can be chosen such that they do not participate in, or interfere with, the reactions necessary to assemble or utilize a cyanine analogue. Alternatively, a reactive functional group can be protected from participating in the reaction by the presence of a protecting group. Those of skill in the art understand how to protect a particular functional group such that it does not interfere with a chosen set of reaction conditions. Such protecting groups can be used to produce compounds of the invention with different substituents, e.g. fluorescent dye moieties and nucleoside phosphate moieties linked to the same core. For examples of useful protecting groups, see, for example, Greene et al., PROTECTIVE GROUPS IN ORGANIC SYNTHESIS, John Wiley & Sons, New York, 1991.

Polyphosphate Analogues

In an exemplary embodiment, the present invention is generally directed to compositions that comprise compounds analogous to nucleotides, and which, in various aspects are readily processible by nucleic acid processing enzymes, such as polymerases. In addition to the unexpectedly advantageous features imparted to the compounds by incorporation of dyes of novel structures, the compounds of the invention generally benefit from one or more advantages of greater stability to undesired enzymatic or other cleavage or non-specific degradation. Exemplary compounds of the invention have efficiencies for their incorporation into a growing nucleic acid chain that are better than, or at least comparable to, triphosphate, tetraphosphate or pentaphosphate analogs.

In various embodiments, the invention provides polyphosphate analogs of the cyanine dyes of the invention. As used herein, the term "scaffold" and the term "core" are used synonymously. In various embodiments, the polyphosphate analogs are polyphosphate analogue of a nucleic acid. An exemplary compound according to this motif has the general structure:

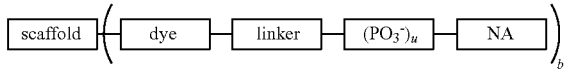

in which N is a nucleoside, and the indices b and u are integers independently selected from 2, 3, 4, 5, 6, 7, 8, 9, 10 or greater.

In an exemplary embodiment, the polyphosphate analogue of the invention has the general structure:

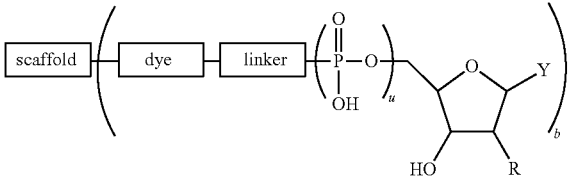

in which Y is a naturally occurring or non-natural nucleobase and R is either H or OH. As will be appreciated by those of skill in the art, a linker can also be present between the scaffold and the dye moiety, or it can be present instead of the linker between the dye and the polyphosphate moiety.

In various embodiments, the polyphosphate analogue of the invention has the general structure:

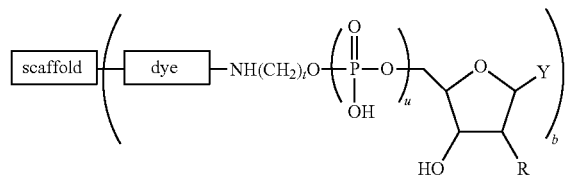

in which t is an integer selected from 1-40, more particularly, 1, 2, 3, 4, 5, 6, 7, 8, 9, 10, 11, 12, 13, 14, 15, 16, 17, 18, 19 and 20. Y, b and u are generally as discussed herein. R is either H or OH.

In another embodiment, the scaffold is itself a dye moiety. In various embodiments according to this motif, the dye acts as the scaffold or core connected to the nucleoside phosphate. Exemplary structures according to this motif include:

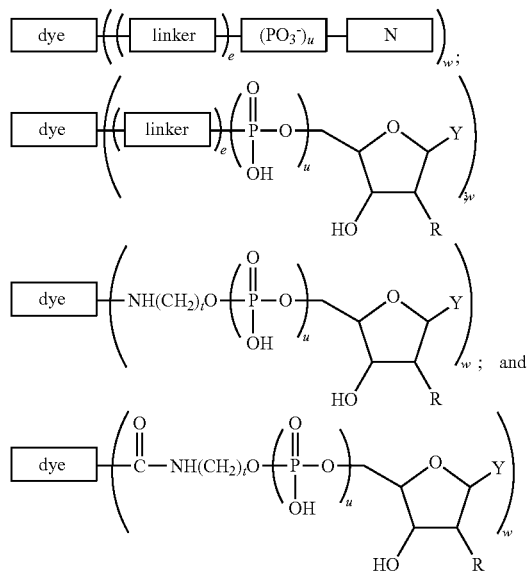

In the formulae above, the indices t, w, e, and u are generally as discussed herein and R is either H or OH.

In various embodiments, the dye is a conjugate formed by the covalent conjugation of a first dye moiety to a second dye moiety through a first reactive functional group on the first dye moiety and a second reactive functional group on the second dye moiety.

Exemplary linkers of use in compound of the invention are further described in co-owned U.S. patent application entitled "Phospholinked Dye Analogs With An Amino Acid Linker", bearing Attorney Docket No. 067191-5039-US, filed Aug. 25, 2011, the disclosure of which is incorporated in its entirety herein by reference for all purposes. Additional peptide linkers are set forth in co-owned U.S. Patent Application Publication No. 2009/0233302, the disclosure of which is incorporated in its entirety herein by reference for all purposes.

In an exemplary embodiment, the scaffold-based dye in the figures above comprises multiple cyanine dyes bound the polyvalent scaffold. Alternatively, the cyanine dye itself may serve as the amplifier for the nucleic acid (or other carrier molecule). Examples of cyanine dyes appropriate for incorporation into the compounds of the invention are known in the art. Specific examples of cyanine dyes of use in the invention are described in commonly owned U.S. patent application entitled "Cyanine Dyes", bearing Attorney Docket No. 067191-5037-US, filed Aug. 25, 2011, U.S. patent application entitled "Cyanine Dyes", bearing Attorney Docket No. 067191-5037-US01, filed Aug. 25, 2011, and U.S. patent application entitled "Cyanine Dyes", bearing Attorney Docket No. 067191-5038-US, filed Aug. 25, 2011, the disclosures of which are incorporated their entirety herein by reference for all purposes. The scaffold-based dyes of the invention can include FET or FRET pairs. In an exemplary embodiment, the scaffold-based composition includes a Cy3, CY3.5, CY5, or CY5.5 type of dyes attached to a common polyvalent scaffold. In various embodiments, The molecules of the invention include an adaptor moiety as set forth in commonly owned U.S. patent application entitled "Molecular Adaptors For Dye Conjugates", bearing Attorney Docket No. 067191-5041-US, filed Aug. 25, 2011, the disclosure of which is incorporated in its entirety herein by reference for all purposes.

Linkers

As used herein, the term "linker," refers to a constituent of a conjugate between various units within the molecules of the invention as described above including the link between a scaffold or core and a fluorescent dye moiety or a nucleoside polyphosphate moiety. For example, a linker can be interposed between a cyanine dye and a core or nucleoside polyphosphate moiety. An exemplary linker can be a component of the cyanine dye, the polyvalent scaffold, the carrier molecule or it is a reactive cross-linking species that reacts with both the carrier molecule and the cyanine dye. The linker groups can be hydrophilic (e.g., tetraethylene glycol, hexaethylene glycol, polyethylene glycol) or they can be hydrophobic (e.g., hexane, decane, etc.). Exemplary linkers include substituted or unsubstituted $C_6$-$C_{30}$ alkyl groups, polyols (e.g., glycerol), polyethers (e.g., poly(ethyleneglycol)), polyamines, amino acids (e.g., polyaminoacids), peptides, saccharides (e.g., polysaccharides) and combinations thereof.

In various embodiments, the linker is rigid. For example, linkers of use in the scaffold-based dyes of the invention include one or more proline, pyrrolidine, or alkynyl moiety within their structure. An exemplary rigid linker is a polyproline including 1, 2, 3, 4, 5, 6, 7, 8, 9, 10, 11, 12, or more proline residues.

As noted previously, the elongated phosphorus containing chain, e.g., containing four or more phosphorus atoms in a linear configuration, is believed to impart an advantage to the compounds of the invention of use in nucleic acid sequencing by placing labeling molecules that may be foreign to nucleotide processing enzymes, e.g., DNA polymerases, away from the relevant portion of the analog and/or away from the active site of the enzyme. In addition to providing such distance through the phosphorus containing chain, additional linker molecules may be used to provide additional distance between the nucleoside portion of the analog, and the label group. In particular, while the label group may be directly coupled to the terminal phosphorus atom of the analog structure, in alternative aspects, it may additionally include a linker molecule to provide the coupling through, e.g., an alkylphosphonate linkage.

In an exemplary embodiment in which the compound of the invention is a dual-labeled polymerase enzyme substrate, the linker joins donor and/or acceptor moieties and other groups to one or more nucleoside polyphosphate moities.

In certain embodiments, it is advantageous to have the donor and/or acceptor moieties attached to the molecule by a group that provides flexibility and distances the linked species from the carrier molecule. Using linker groups, the properties of the donor and/or acceptor moiety are modulated. Properties that are usefully controlled include, for example, hydrophobicity, hydrophilicity, surface-activity, the distance of the quencher and/or cyanine dye of the invention moiety from the other probe components (e.g., carrier molecule) and the distance of the quencher from the cyanine dye of the invention.

A wide variety of linkers and linker chemistries are known in the art of synthetic chemistry may be employed in coupling the labeling group to the analogs of the invention. For example, such linkers may include organic linkers such as alkane or alkene, alkynyl linkers of from about $C_2$ to about $C_{20}$, or longer, polyethyleneglycol (PEG) linkers, aryl, heterocyclic, saturated or unsaturated aliphatic structures comprised of single or connected rings, amino acid linkers, peptide linkers, nucleic acid linkers, PNA, LNAs, or the like or phosphate or phosphonate group containing linkers. In preferred aspects, alkyl, e.g., alkane, alkene, alkyne alkoxy or alkenyl, or ethylene glycol linkers are used. Some examples of linkers are described in Published U.S. Patent Application No. 2004/0241716, which is incorporated herein by reference in its entirety for all purposes. Additionally, such linkers may be selectively cleavable linkers, e.g., photo- or chemically cleavable linkers or the like.

In various embodiments, the linker serves to enhance the interaction between a polymerase enzyme substrate of the invention and the DNA polymerase. The linker can enhance the interaction through electrostatic, hydrophobic, or steric interactions. In an exemplary embodiment in which a molecule comprising the linker is utilized in a single molecule nucleic acid sequencing technique, the linker enhances the interaction between the substrate molecule and the DNA polymerase, thereby lowering the $K_m$ of the sequencing reaction and influencing the 2-slow step to achieve optimized residence time of the conjugate on the polymerase andenzyme kinetics. In examples of this embodiment, the linker is an amino acid or peptide. In various embodiments, the linker-polyphosphate-nucleoside (L-P-N) has the formula below:

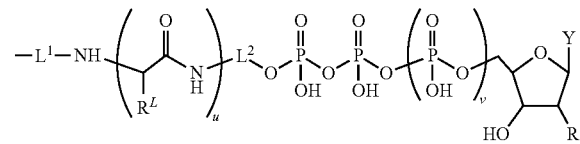

in which $L^1$ and $L^2$ are independently selected linkers, e.g., substituted or unsubstituted alkyl or substituted or unsubstituted heteroalkyl. The index u is an integer selected from 1, 2, 3, 4, 5, 6, 7, 8, 9, 10, 11, and 12. Each u amino acid residue is independently selected from naturally occurring or unnatural amino acids. $R^L$ is H or is an amino acid side-chain (e.g., $NH_2$, SH, COOH). The index v is an integer selected from 0, 1, 2, 3, 4, 5, and 6. R is either H or OH. In an exemplary embodiment, the amino acid/peptide is lysine or an oligomer or polymer including or composed solely of lysine. An exemplary linker is one in which u is an integer selected from 1, 2, 3 and 4 or higher. In various embodiments, the amino acid/peptide is glutamic acid or an oligomer or polymer including or composed solely of glutamic acid. An exemplary linker is one in which u is an integer selected from 1, 2, 3 and 4 or higher. This linker can connect the nucleoside polyphosphate, for example, to a multifunctional core or to a dye moiety.

Exemplary linkers of use in this embodiment are further described in co-owned U.S. Provisional Application No. 61/377,031, filed Aug. 25, 2010, the disclosure of which is incorporated in its entirety herein by reference for all purposes. Additional peptide linkers are set forth in co-owned U.S. Patent Application Publication No. 20090233302, the disclosure of which is incorporated in its entirety herein by reference for all purposes.

In an exemplary embodiment, the linker serves to distance a fluorescent dye and a nucleoside to which it is attached. Linkers with this characteristic have several uses. For example, a cyanine dye of the invention held too closely to the nucleoside may interact with a protein (e.g., DNA polymerase) in a detrimental fashion, or it may not interact with a quencher group, or it may interact with another component of an analysis with too low of an affinity. For example, when a cyanine dye of the invention is itself sterically demanding, the interaction leading to quenching can be undesirably weakened, or it may not occur at all, due to a sterically induced hindering of the approach of the two components.

When the construct comprising the cyanine dye is immobilized by attachment to, for example, a solid support, the construct can also include a linker moiety placed between the reactive group of the solid support and the cyanine analogue, or other probe component bound to the solid support.

In yet a further embodiment, a linker group used in the polymerase enzyme substrates of the invention is provided with a group that can be cleaved to release a bound moiety, e.g., a scaffold-based dye of the invention, dye moiety, carrier molecule, quencher, minor groove binder, intercalating moiety, and the like from the polymeric component. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. mmunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and heterobifunctional) linker arms is commercially available from suppliers such as Pierce. Exemplary cleaveable groups are those cleaved by light, e.g., nitrobenzyl derivatives, phenacyl groups, benzoin esters; hydrolysis, e.g., esters, carbonates; changes in pH, etc.

In various embodiments according to the figures set forth above, the scaffold or core comprises a perylene moiety. There are a number of positions on perylene that allow for attachment of substituents. Exemplary structures according to this embodiment include those set forth in FIG. 24, in which the radical NUC represents a dye-polyphosphate-nucleoside moiety. FIG. 24 shows one structure having two a dye-polyphosphate-nucleoside moieties and another having seven dye-polyphosphate moieties. Similar structures having 3, 4, 5, 6, 8 or more can also be used in the invention.

Branched Multi-Dye Constructs

While many of the compositions of the invention are suitable as substrates for polymerase enzymes, some aspects of the invention are directed to multi-dye constructs that are not enzyme substrates. For example, some compounds of the invention can be used for multi-dye constructs for nucleic acid probes. One aspect of the invention is a compound having a multifunctional core and having at least one FRET donor and at least one FRET acceptor attached to the core. For example, any of the trifunctional core units described herein can have one FRET donor and one FRET acceptor attached to it with the third linkage being to a molecule of interest such as a protein or a nucleic acid. The core units for such multi-dye constructs can comprise tri-functional six-membered aromatic rings including triazine and benzene rings as described in more detail above. The multi-dye constructs of the invention result in a branched relationship between the molecule of interest, donor, and acceptor rather than a linear relationship between molecule of interest-donor-acceptor as is commonly used.

In some embodiments the multi-dye constructs of the invention comprise a multifunctional core covalently bound to a molecule of interest, and having more than one FRET donor, more than one FRET acceptor, or having both more than one FRET donor and more than one FRET acceptor. The molecule of interest for the multi-acceptor/multi-donor constructs can be proteins or nucleic acids.

For example, the multi-dye constructs include those that correspond to the structures disclosed in this application where one of the linking sites on the core X is attached to a molecule of interest, and the other sites on the core X are attached to fluorescent dye moieties. These molecules can have the structure:

wherein X is a multivalent core as described herein, L is a linker, D is a fluorescent dye moiety, and M is the molecule of interest which can be, for example, a protein or nucleic acid.

The fluorophores of the invention are of use in single molecule DNA sequencing assays. Of particular note in this context is the ability provided by the invention to design fluorophores with selected absorbance and emission properties including wavelength and intensity. The compounds of the invention provide for very versatile assay design. For example, according to the present invention a series of fluorophores of use in an assay are readily designed to have selected absorbance and emission wavelengths and emission intensities, allowing multiple fluorophores with the same or different excitation/emission profiles to be utilized and distinguished in an assay. In exemplary embodiments, use of compounds of the invention in a multifluorophore assay, e.g., single molecule DNA sequencing, enhances assay performance by at least about 10%, at least about 20% or at least about 30% over a similar assay using currently available fluorophores.

When the dye of the invention is a FRET dye, in exemplary embodiments, significantly lower laser power can be used to excite the dye, mitigating photodamage to the polymerase.

Probes

The multi-dye constructs of the invention can be used to provide improved probes. The invention provides probes having multiple cyanine dyes conjugated to a carrier molecule, for example, a target species (e.g., receptor, enzyme, etc.) a ligand for a target species (e.g., nucleic acid, peptide, etc.), a small molecule (e.g., drug, pesticide, etc.), a solid support and the like. The probes can be used for in vitro and in vivo applications.

In an exemplary embodiment, the probe is a nucleic acid probe, e.g., a dual labeled nucleic acid probe for PCR or other applications.

Chemical synthesis of nucleic acid derivatives attached to the scaffold-based dyes of the invention can be automated and performed by coupling nucleosides through phosphorus-containing covalent linkages. The most commonly used oligonucleotide synthesis method involved reacting a nucleoside with a protected cyanoethyl phosphoramidite monomer in the presence of a weak acid. The coupling step is followed by oxidation of the resulting phosphite linkage. Finally, the cyanoethyl protecting group is removed and the nucleic acid is cleaved from the solid support on which it was synthesized. The labels of the present invention can be incorporated during oligonucleotide synthesis using a mono- or bis-phosphoramidite derivative of the fluorescent compound of the invention. Alternatively, the label can be introduced by combining a compound of the invention that includes a reactive functional group with the nucleic acid under appropriate conditions to couple the compound to the nucleic acid. In yet another embodiment, the fluorescent compound is attached to a solid support through a linker arm, such as a substituted or unsubstituted alkyl, substituted or unsubstituted heteroalkyl or a nucleic acid residue. Synthesis proceeds with the fluorescent moiety already in place on the growing nucleic acid chain.

Enzymatic methods of synthesis involve the use of fluorescent-labeled nucleic acids in conjunction with a nucleic acid template, a primer and an enzyme. Efficient enzymatic incorporation of a fluorescent-labeled nucleic acid is facilitated by selection of reaction partners that do not adversely affect the enzymes ability to couple the partners.

In those embodiments of the invention in which the cyanine-based fluorescent compound of the invention is attached to a nucleic acid, the carrier molecule is produced by either synthetic (solid phase, liquid phase or a combination) or enzymatically or by a combination of these processes.

Another synthetic strategy for the preparation of oligonucleotides is the H-phosphonate method (B. Froehier and M. Matteucci, *Tetrahedron Lett.*, vol 27, p 469-472, 1986). This method utilizes activated nucleoside H-phosphonate monomers rather than phosphoramidites to create the phosphate internucleotide linkage. In contrast to the phosphoramidite method, the resulting phosphonate linkage does not require oxidation every cycle but instead only a single oxidation step at the end of chain assembly. The H-phosphonate method may also be used to conjugate reporters and dyes to synthetic oligonucleotide chains (N. Sinha and R. Cook, *Nucleic Acids Research*, Vol 16, p. 2659, 1988).

Small Molecule Probes

The multi-dye constructs of the invention can be used as components of small molecule probes. In a preferred design, a small molecule probe includes a multi-dye probe of the invention and a second species that alters the luminescent properties of the dyes, e.g., a quencher of fluorescence. In an exemplary embodiment, an agent, such as an enzyme cleaves the cyanine dye, the quencher or both from the small molecule generating fluorescence in the system under investigation (see, for example, Zlokarnik et al., *Science* 279: 84-88 (1998)).

Nucleic Acid Capture Probes

In one embodiment, an immobilized nucleic acid comprising a multi-dye constructs of the invention is used as a capture probe. The nucleic acid probe can be used in solution phase or it can be attached to a solid support. The immobilized probes can be attached directly to the solid support or through a linker arm between the support and the cyanine dye or between the support and a nucleic acid residue. Preferably, the probe is attached to the solid support by a linker (i.e., spacer arm, supra). The linker serves to distance the probe from the solid support. The linker is most preferably from about 5 to about 30 atoms in length, more preferably from about 10 to about 50 atoms in length. Exemplary attachment points include the 3'- or 5'-terminal nucleotide of the probe as well as other accessible sites discussed herein.

In view of the well-developed body of literature concerning the conjugation of small molecules to nucleic acids, many other methods of attaching donor/acceptor pairs to nucleic acids will be apparent to those of skill in the art.

There are many linking moieties and methodologies for attaching groups to the 5'- or 3'-termini of nucleic acids, as exemplified by the following references: Eckstein, editor, Nucleic acids and Analogues: A Practical Approach (IRL Press, Oxford, 1991); Zuckerman et al., *Nucleic Acids Research*, 15: 5305-5321 (1987) (3'-thiol group on nucleic acid); Sharma et al., *Nucleic Acids Research*, 19: 3019 (1991) (3'-sulfhydryl); Giusti et al., *PCR Methods and Applications*, 2: 223-227 (1993) and Fung et al., U.S. Pat. No. 4,757,141 (5'-phosphoamino group via Aminolink™ II available from P.E. Biosystems, CA.) Stabinsky, U.S. Pat. No. 4,739,044 (3-aminoalkylphosphoryl group); Agrawal et al., *Tetrahedron Letters*, 31: 1543-1546 (1990) (attachment via phosphoramidate linkages); Sproat et al., *Nucleic Acids Research*, 15: 4837 (1987) (5-mercapto group); Nelson et al., *Nucleic Acids Research*, 17: 7187-7194 (1989) (3'-amino group), and the like.

When the nucleic acids are synthesized utilizing an automated nucleic acid synthesizer, the donor and acceptor moieties can be introduced during automated synthesis. Alternatively, one or more of these moieties can be introduced either before or after the automated synthesis procedure has commenced. For example, donor and/or acceptor groups can be introduced at the 3'-terminus using a solid support modified with the desired group(s). Additionally, donor and/or acceptor groups can be introduced at the 5'-terminus by, for example a derivative of the group that includes a phosphoramidite. In another exemplary embodiment, one or more of the donor and/or acceptor groups is introduced after the automated synthesis is complete.

Peptide Probes

Peptides, proteins and peptide nucleic acids that are labeled with a multi-dye construct of the invention can be used in both in vivo and in vitro enzymatic assays.

In some cases the peptide construct is exists in at least one conformation that allows donor-acceptor energy transfer between a multi-dye construct of the invention and a quencher when the fluorophore is excited.

Solid Support Immobilized Cyanine Dye Analogues

The multi-dye constructs of the invention can be immobilized on substantially any polymer, biomolecule, or solid or semi-solid material having any useful configuration. Moreover, any conjugate comprising one or more cyanine dye of the invention can be similarly immobilized. When the support is a solid or semi-solid, examples of preferred types of supports for immobilization of the nucleic acid probe include, but are not limited to, controlled pore glass, glass plates, polystyrene, avidin coated polystyrene beads, cellulose, nylon, acrylamide gel and activated dextran. These solid supports are preferred because of their chemical stability, ease of functionalization and well-defined surface area. Solid supports such as, controlled pore glass (CPG, 500 Å, 1000 Å) and non-swelling high cross-linked polystyrene (1000 Å) are particularly preferred.

According to the present invention, the surface of a solid support is functionalized with a cyanine dye of the invention or a species to which a multi-dye construct of the invention is conjugated. For clarity of illustration, the following discussion focuses on attaching a reactive cyanine dye of the invention to a solid support. The following discussion is also broadly relevant to attaching to a solid support a species that includes within its structure a cyanine dye of the invention.

The multi-dye construct of the invention are preferably attached to a solid support by forming a bond between a reactive group on the multi-dye construct and a reactive group on the surface of the solid support, thereby derivatizing the solid support with one or more cyanine dye of the invention. Alternatively, the reactive group on the multi-dye construct coupled with a reactive group on a linker arm attached to the solid support. The bond between the solid support and the multi-dye construct is preferably a covalent bond, although ionic, dative and other such bonds are useful as well. Reactive groups which can be used in practicing the present invention are discussed in detail above and include, for example, amines, hydroxyl groups, carboxylic acids, carboxylic acid derivatives, alkenes, sulfhydryls, siloxanes, etc.

A large number of solid supports appropriate for practicing the present invention are available commercially and include, for example, peptide synthesis resins, both with and without attached amino acids and/or peptides (e.g., alkoxybenzyl alcohol resin, aminomethyl resin, aminopolystyrene resin, benzhydrylamine resin, etc. (Bachem)), functionalized controlled pore glass (BioSearch Technologies, Inc.), ion exchange media (Aldrich), functionalized membranes (e.g., —COOH membranes; Asahi Chemical Co., Asahi Glass Co., and Tokuyama Soda Co.), and the like.

Microarrays

The present invention also provides microarrays including immobilized multi-dye constructs of the invention and compounds (e.g., peptides, nucleic acids, bioactive agents, etc.) functionalized with multi-dye constructs of the invention. Moreover, the invention provides methods of interrogating microarrays using probes that are functionalized with multi-dye constructs of the invention. The immobilized species and the probes are selected from substantially any type of molecule, including, but not limited to, small molecules, peptides, enzymes nucleic acids and the like.

Nucleic acid microarrays consisting of a multitude of immobilized nucleic acids are revolutionary tools for the generation of genomic information, see, Debouck et al., in supplement to *Nature Genetics*, 21:48-50 (1999). The discussion that follows focuses on the use of a multi-dye construct of the invention in conjunction with nucleic acid microarrays. This focus is intended to be illustrative and does not limit the scope of materials with which this aspect of the present invention can be practiced. See, Lehrach, et al., HYBRIDIZATION FINGERPRINTING IN GENOME MAPPING AND SEQUENCING, GENOME ANALYSIS, Vol. 1, Davies et al, Eds., Cold Springs Harbor Press, pp. 39-81 (1990), Pirrung et al. (U.S. Pat. No. 5,143,854, issued 1992), and also by Fodor et al., (*Science*, 251: 767-773 (1991), Southern et al. (*Genomics*, 13: 1008-1017 (1992), Khrapko, et al., *DNA Sequence*, 1: 375-388 (1991), Kleinfield et al., *J. Neurosci.* 8:4098-120 (1998)), Kumar et al., *Langmuir* 10:1498-511 (1994), Xia, Y., *J. Am. Chem. Soc.* 117:3274-75 (1995), Hickman et al., *J. Vac. Sci. Technol.* 12:607-16 (1994), Mrkish et al. *Ann. Rev. Biophys. Biomol. Struct.* 25:55-78 (1996).

The Methods

In addition to the compounds of the invention, there are also provided an array of methods utilizing the compounds. The following discussion is intended to be illustrative of the type and scope of methods with which the compounds of the invention can be practiced and should not be interpreted as being either exhaustive or limiting.

Nucleic Acid Sequencing

In another aspect, the present invention provides a method for nucleic acid sequencing using one or more compounds of the invention. In various embodiments, the compounds of the method find use in methods for single molecule nucleic acid sequencing. Significant interest in the sequencing of single DNA molecules dates to 1989 when Keller and colleagues began experimenting with "sequencing by degradation." In their experiments, isolated fully-labeled DNA molecules are degraded by an exonuclease, and individual labeled bases are detected as they are sequentially cleaved from the DNA (Jett, J. H. et al., *J. Biomol. Struct. Dynamics*, 7, 301-309 (1989); Stephan, J. et al., *J Biotechnol.*, 86, 255-267 (2001); Werner, J H. et al., *J. Biotechnol.*, 102, 1-14 (2003)). This approach was ultimately compromised by poor DNA solubility caused by the densely-packed dye labels. More recently, alternative single-molecule approaches have been investigated, including "sequencing by synthesis," where bases are detected one at a time as they are sequentially incorporated into DNA by a polymerase (Braslavsky, I. et al., *Proc. Natl. Acad. Sci. USA*, 100, 3960-3964 (2003); Levene, M. J. et al., *Science*, 299, 682-686 (2003); Metzker, M. L., *Genome Res.*, 15, 1767-1776 (2005)); and nanopore sequencing where electrical signals are detected while single DNA molecules pass through protein or solid-state nanopores (Akeson, M. et al., *Biophys. J.*, 77, 3227-3233 (1999); Lagerqvist, J. et al., *Nano Lett.*, 6, 779-782 (2006); Rhee, K. J. et al., Annals of emergency medicine, 13, 916-923 (1984)). So far, only sequencing by synthesis has been successful. In the method of Quake and colleagues (Braslavsky, I. et al., *Proc. Natl. Acad. Sci. USA*, 100, 3960-3964 (2003)), base-labeled nucleotide triphosphates (dNTPs) are incorporated into DNA immobilized on a microscope coverglass. Each type of dNTP is applied separately in a fluidics cycle, and incorporated bases are imaged on the surface after washing away the excess of free nucleotides. While the obtained sequence reads are short, high sequencing rates can potentially be achieved by analyzing billions of different, individual molecules in parallel with applications in re-sequencing and gene expression profiling.

To obtain long single-molecule reads, potentially tens of kilobases, sequencing-by-synthesis approaches using phosphate-labeled nucleotides have been developed (Levene, M. J. et al., *Science*, 299, 682-686 (2003)). These nucleotides are labeled with a fluorophore on the terminal phosphate instead of on the base. Labeled nucleotides are detected while bound to polymerase during the catalytic reaction. The label is released with pyrophosphate as the nucleotide is incorporated into DNA. An advantage is that the DNA remains label-free and fully soluble. Individual polymerase enzymes immobilized on a clear substrate are monitored in real time to detect the sequence of incorporated nucleotides. In order to achieve long reads, the polymerase, but not the DNA, can be attached to the clear substrate. Polymerase attachment facilitates detection because it keeps the active site at a single position on the clear substrate surface. In the alternative format, with the polymerase in solution and the DNA attached, the enzyme active site would be a moving target for detection, diffusing up to several microns from the DNA attachment point as the primer strand is extended from long templates.

U.S. Pat. No. 6,255,083, issued to Williams and incorporated herein by reference, discloses a single molecule sequencing method on a solid support. The solid support is optionally housed in a flow chamber having an inlet and outlet to allow for renewal of reactants that flow past the immobilized polymerases. The flow chamber can be made of plastic or glass and should either be open or transparent in the plane viewed by the microscope or optical reader.

In accordance with one embodiment of the methods of invention, the compounds described herein are used in analyzing nucleic acid sequences using a template dependent polymerization reaction to monitor the template dependent incorporation of specific analogs into a synthesized nucleic acid strand, and thus determine the sequence of nucleotides present in the template nucleic acid strand. In particular, a polymerase enzyme is complexed with the template strand in the presence of one or more nucleotides and/or one or more nucleotide analogs of the invention. In preferred aspects, only the labeled analogs of the invention are present representing analogous compounds to each of the four natural nucleotides, A, T, G and C. When a particular base in the template strand is encountered by the polymerase during the polymerization reaction, it complexes with an available analog that is complementary to such nucleotide, and incorporates that analog into the nascent and growing nucleic acid strand, cleaving between the α and β phosphorus atoms in the analog, and consequently releasing the labeling group (or a portion thereof). The incorporation event is detected, either by virtue of a sufficiently long presence of the analog in the complex, or by virtue of release of the label group into the surrounding medium. Where different labeling groups are used for each of the types of analogs, e.g., A, T, G or C, identification of a label of an incorporated analog allows identification of that analog and consequently, determination of the complementary nucleotide in the template strand being processed at that time. Sequential reaction and monitoring permits a real-time monitoring of the polymerization reaction and determination of the sequence of the template nucleic acid. As noted above, in particularly preferred aspects, the polymerase enzyme/template complex is provided immobilized within an optical confinement that permits observation of an individual complex, e.g., a zero mode waveguide. In addition to their use in sequencing, the polymerase enzyme substrates of the invention are also equally useful in a variety of other genotyping analyses, e.g., SNP genotyping use single base extension methods, real time monitoring of amplification, e.g., RT-PCR methods, and the like.

An exemplary single molecule DNA sequencing technique uses the signal from a fluorescent dye to detect the presence of a nucleotide within the illuminated volume of a zero mode wave guide. Ideally, the signal comes from only those molecules bound and incorporated by the DNA polymerase. In practice, any molecule that diffuses into the illuminated volume and remains long enough to be recorded by the camera is counted as a signal, regarding of whether that signal was actually the result of an incorporation event. See e.g., Eid et al., "*Real-Time Sequencing from Single Polymerase Molecules*", Science Express 2008, 323(5910), 133-138.

In an exemplary embodiment, the present invention provides for the use of a first and a second dye incorporated into the scaffold-based structure of the dyes of the invention. The second dye emits at a wavelength different from that of the first dye. Exemplary second dyes are environmentally sensitive, and not fluorescent when solubilized in water. However, upon binding to the DNA polymerase, the dye would fluoresce. In this embodiment, each true nucleotide incorporation event would be accompanied by a signal from the first dye and a signal from the second dye, the second signal serves as confirmation that the incorporation event occurred. Accordingly, the present method provides for a more accurate assay by decreasing the relevance of signals due merely to a dye "sticking" within the wave guide at a position recordable by the camera.

Environmentally sensitive dyes are known in the art. An exemplary dye of use in the current invention is Dapoxyl® (Molecular Probes).

In another exemplary embodiment, the second dye serves as an additional signal serving to augment the signal of a dye analog with weak signal. More than two dyes can be incorporated into the scaffold-based dyes of the invention, e.g., 2, 3, 4, 5, 6, 7 or more dyes.

The following discussion is generally relevant to the assays described herein. This discussion is intended to illustrate the invention by reference to certain exemplary embodiments and should not be interpreted as limiting the scope of probes and assay types in which the compounds of the invention find use. Other assay formats utilizing the compounds of the invention will be apparent to those of skill in the art.

Kits

In another aspect, the present invention provides kits containing one or more of the polymerase enzyme substrates of the invention. In one embodiment, a kit includes four labeled nucleotide analogs, each corresponding to A, G, C, T, or A G, C, U, wherein at least one of which is a polymerase enzyme substrate of the invention. In another embodiment, a kit includes four labeled nucleotide analogs, each corresponding to A, G, C, T, or A G, C, U, wherein at least two of which is a polymerase enzyme substrate of the invention. Other formats for kits will be apparent to those of skill in the art and are within the scope of the present invention.

The materials and methods of the present invention are further illustrated by the examples that follow. These examples are offered to illustrate, but not to limit the claimed invention.

The following examples are provided by way of illustration only and not by way of limitation. Those of skill in the art will readily recognize a variety of non-critical parameters that could be changed or modified to yield essentially similar results.

EXAMPLES

Example 1

Synthesis of Scaffolds

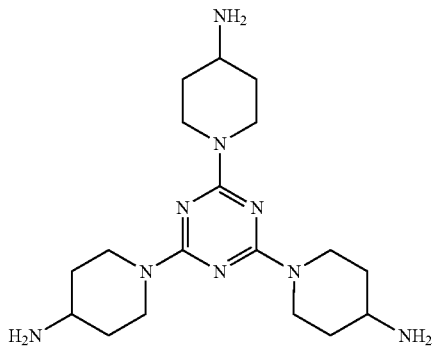
T1

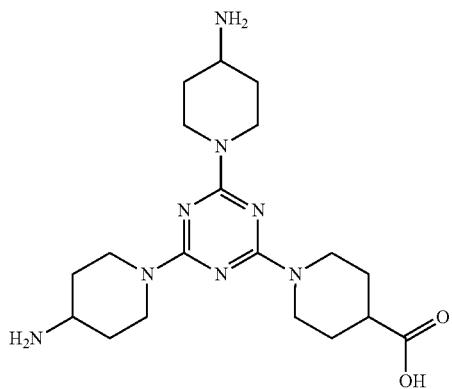
T2

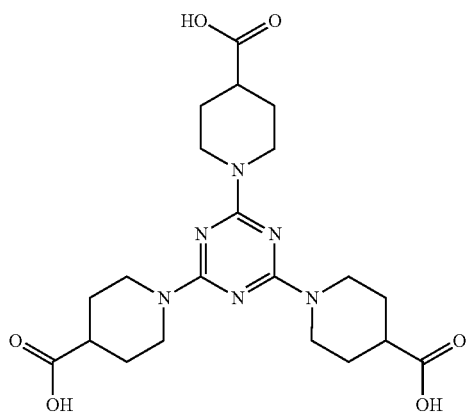
T3

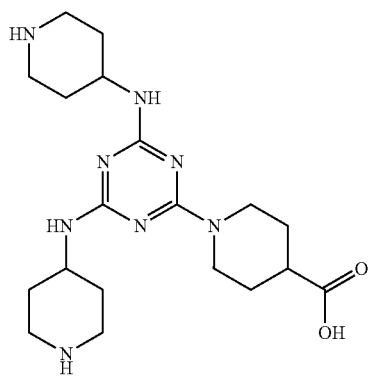
T4

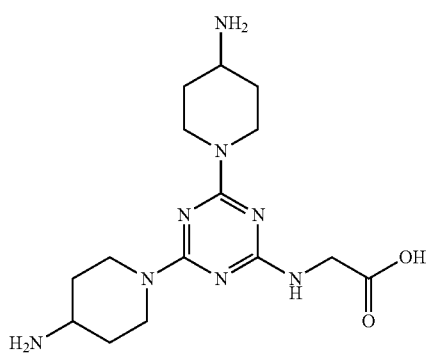
T5

T6

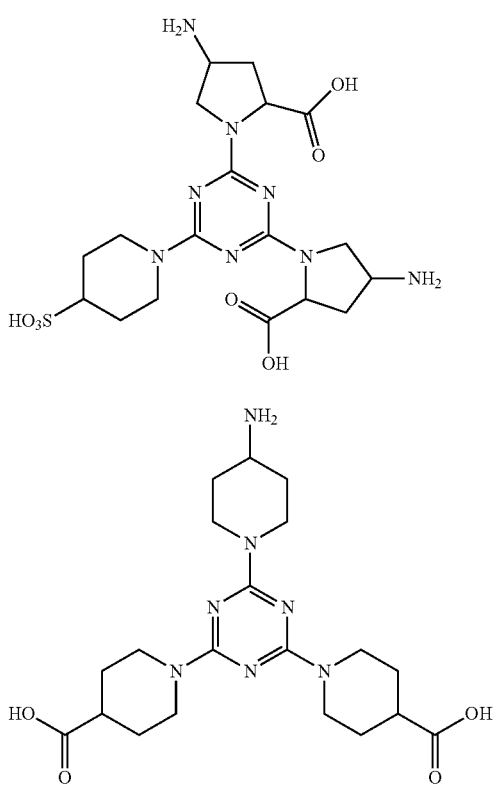

T7

S1

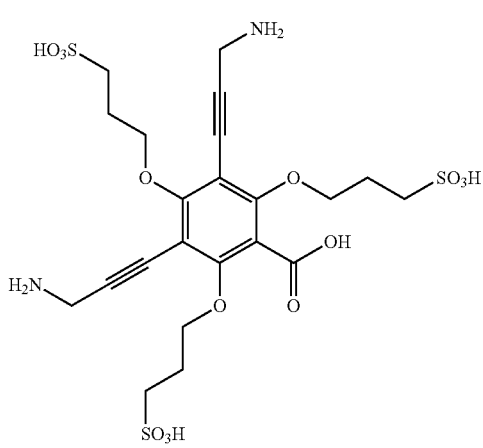

S3

S6

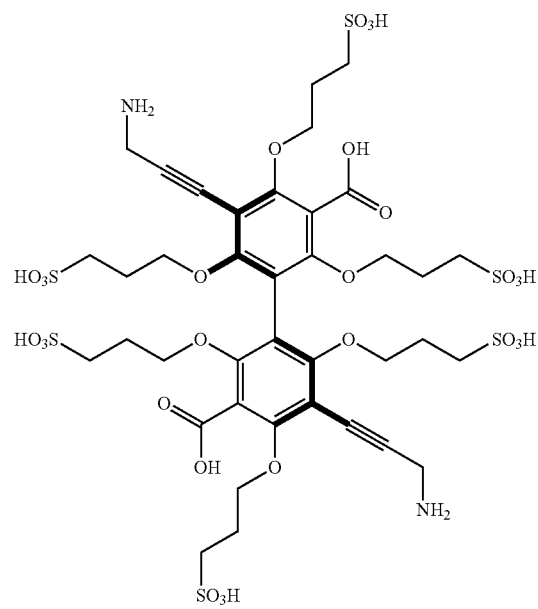

S7

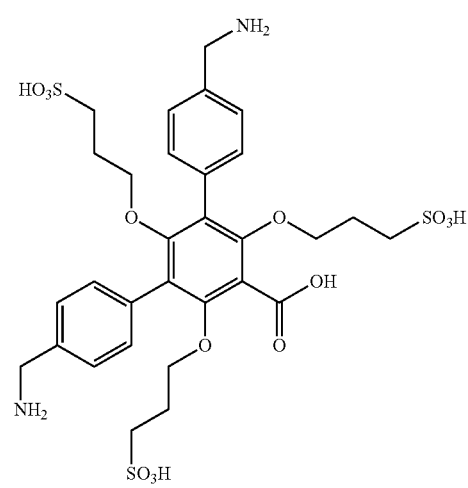

1.1 Synthesis of T2 Triazine Scaffold

Cyanuric chloride was reacted with 4-(N-Boc-amino) piperidine to give a bisamino substituted triazine 1b that was further reacted with ethyl isonipecotate to give the N-Boc protected T2 ethyl ester 1c. The ester was hydrolyzed and the amino groups were deprotected to yield the diaminoacid T2 1d. TFA-NHS was then used to prepare the N-TFA protected T2 NHS ester 1e.

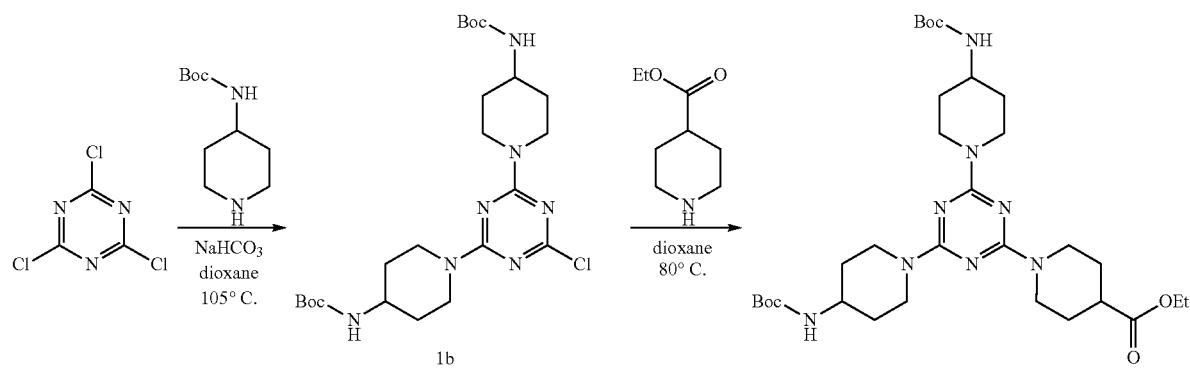
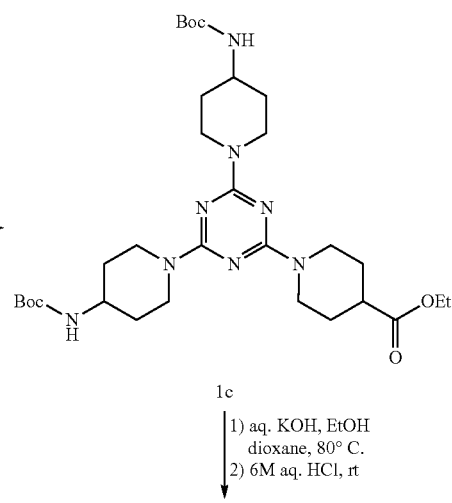
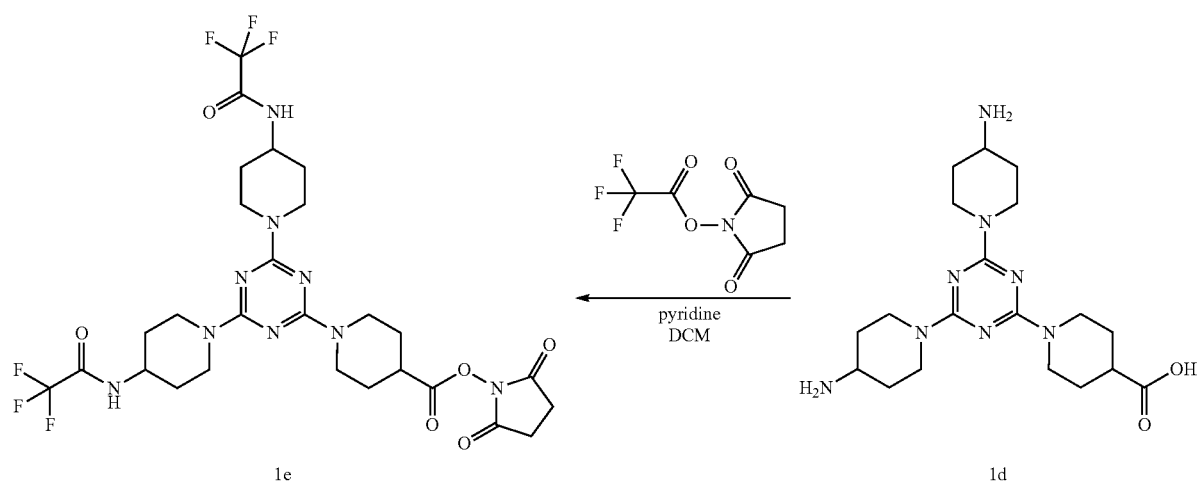
1.2 Synthesis of T3 Triazine Scaffold
Cyanuric chloride was reacted with the excess of ethyl isonipecotate to give the triester 1f, which was hydrolyzed to give the triacid 1g.
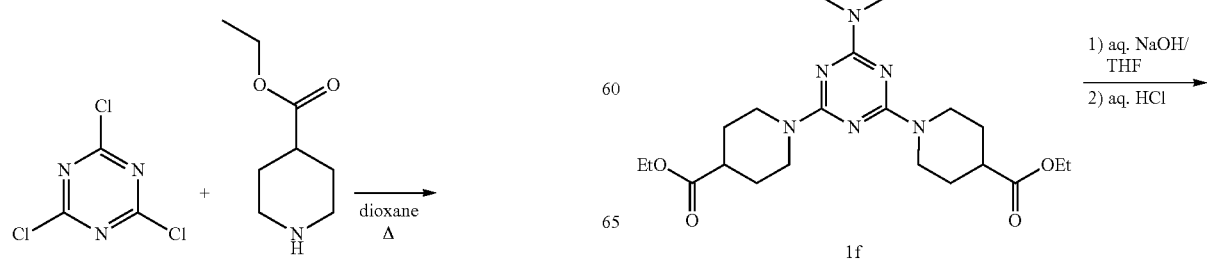

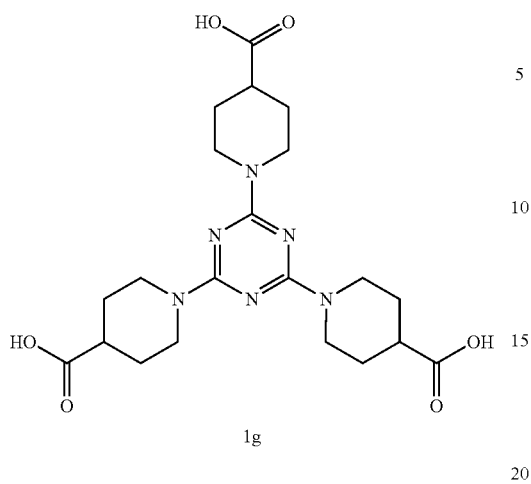
1g
1.3 Synthesis of T2 Triazine Linker Nucleotides
The N-TFA protected T2 NHS ester was reacted with an amino functionalized linker nucleotide and the purified product was deprotected to give the T2 triazine linker nucleotide.
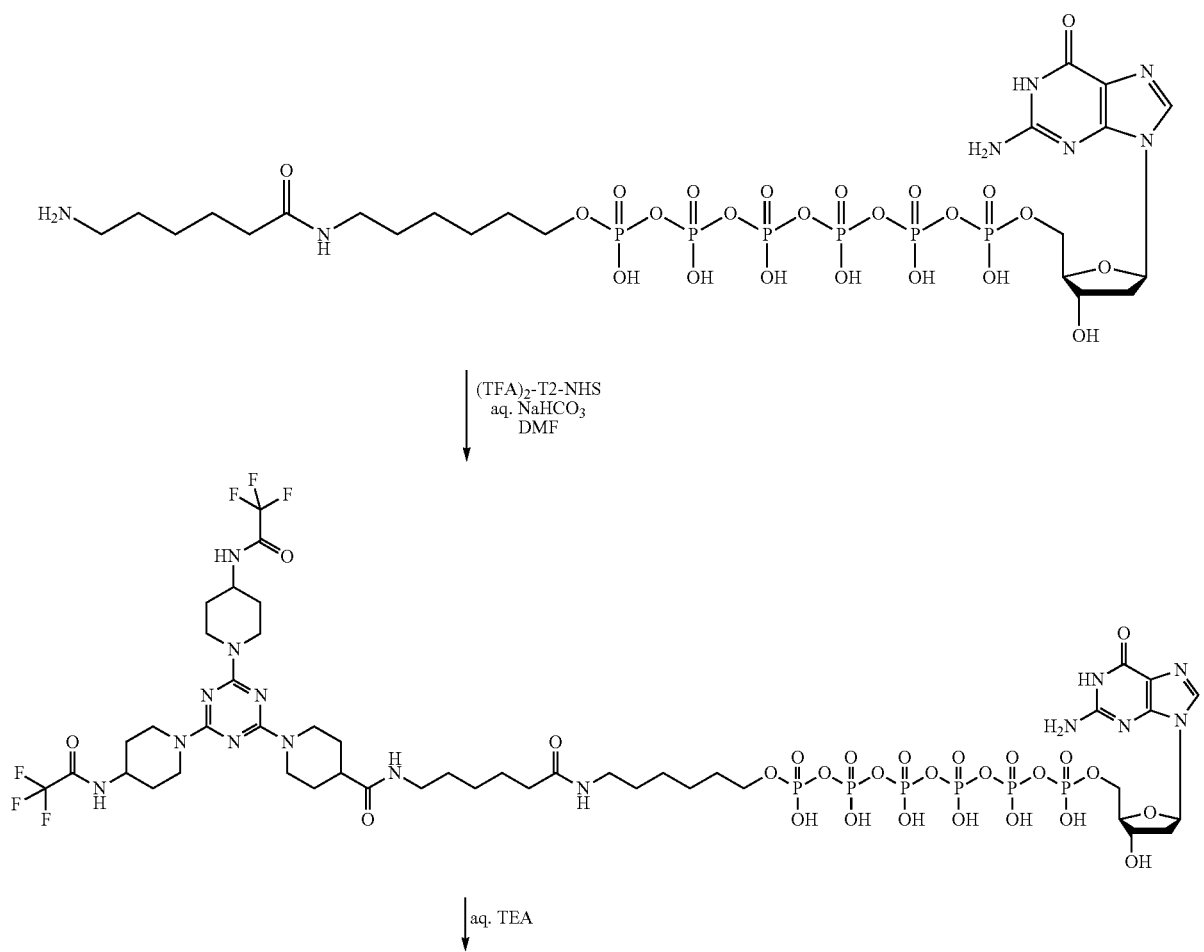

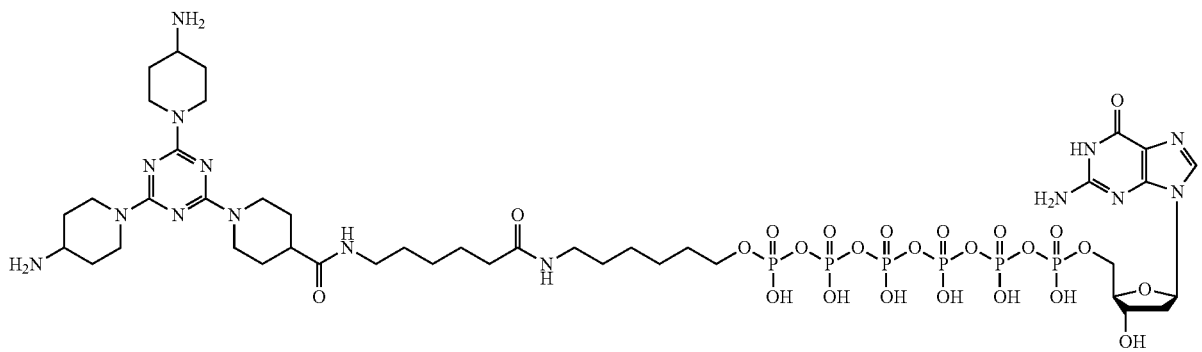
Alternatively the N-TFA protected T2 NHS ester was coupled with an amino acid (AA) extension and the purified acid (TFA)$_2$-T2-AA-OH was then activated. The resulting NHS ester was reacted with an amino functionalized linker nucleotide and the purified product was deprotected to give the T2 linker nucleotide.
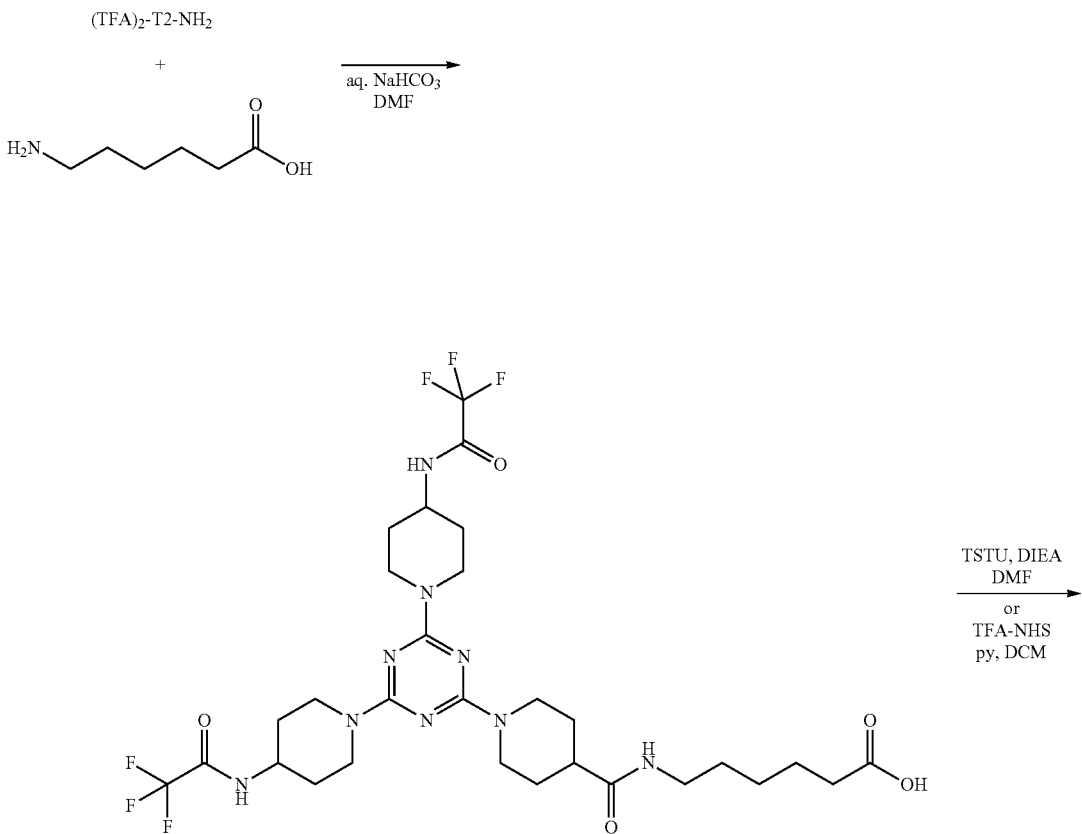

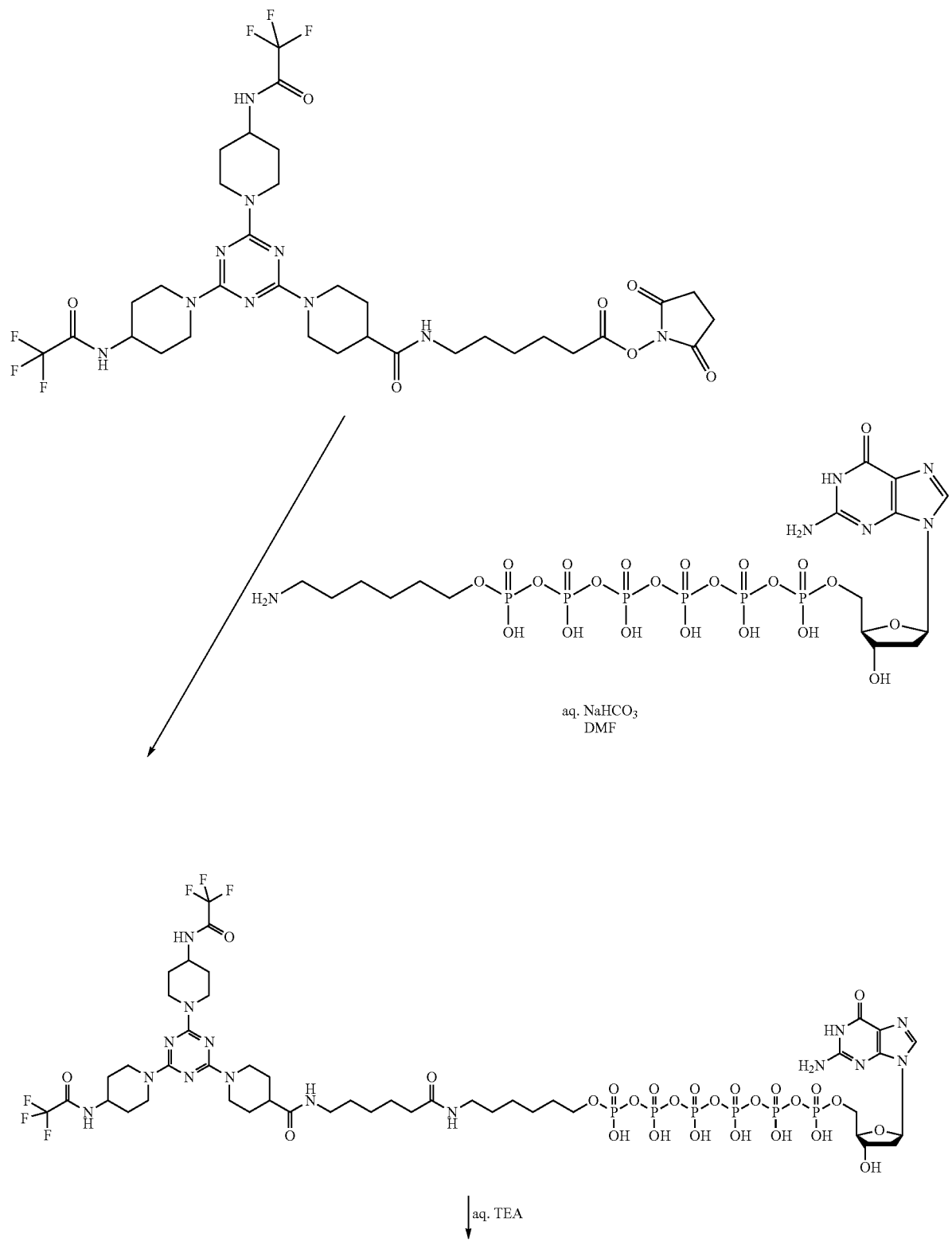

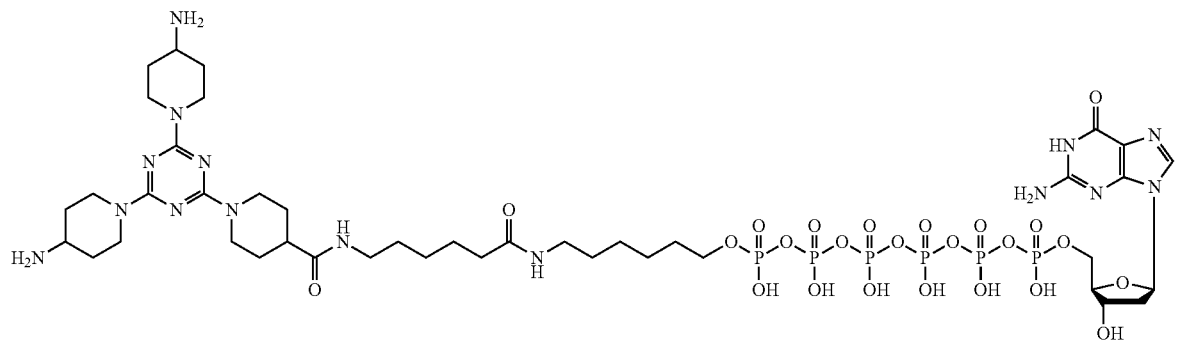

1.4 Synthesis of T2 Double-Dye and FRET Nucleotide Analogs

The T2 linker nucleotide was reacted with an excess of the dye NHS ester to give the T2 double-dye nucleotide analog. In a similar manner, an excess of both the donor and acceptor dye was used to prepare T2 FRET nucleotide analog which was separated from the two T2 double-dye side-products. Alternatively the donor and the acceptor dye NHS esters were coupled to the T2 linker nucleotide stepwise, where the first dye containing intermediate was purified before it was reacted with the second dye.

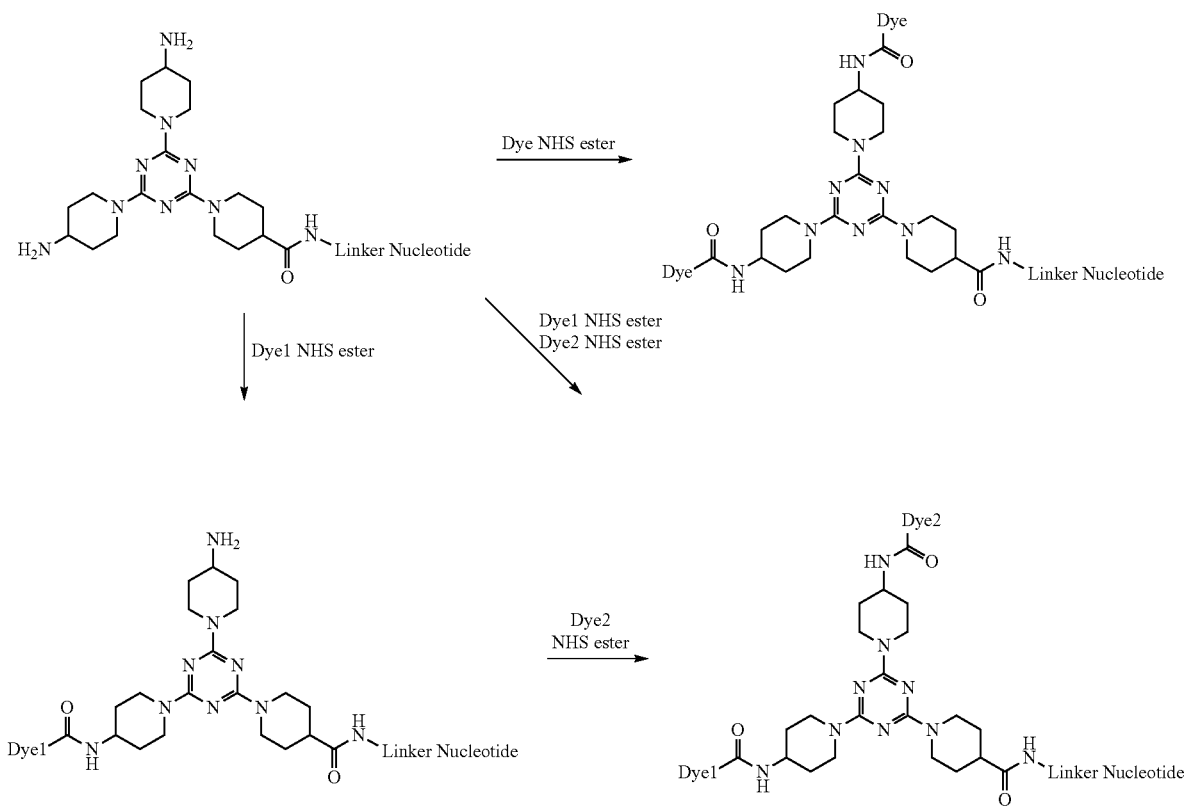

1.5 Alternative Synthesis of T2 Triazine Nucleotide Analogs

Alternatively the donor and the acceptor dye NHS esters were coupled to the T2 diaminoacid, where the first dye containing intermediate was purified before it was reacted with the second dye. The resulting carboxylic acid was activated using CDI/NHS, CDI/BOSu, or TSTU and reacted with the amino-terminated linker nucleotide to give the multi dye T2 triazine nucleotide analog.

1.6 Synthesis of S3 and S6 Scaffolds

Methyl 2,4,6-trihydroxybenzoate was alkylated with an excess of 1,3-propane sulfone. The resulting trisulfonate 1h was iodinated using iodine and periodic acid in acetic acid to give the diiodobenzoic acid derivative ii as well as a biphenyl side-product 1j that originated from dimerization of the monoiodo intermediate. Sonogashira couplings of the iodinated products with N-Boc-propargylamine yielded the protected S3 (1l) and S6 (1k) scaffolds.

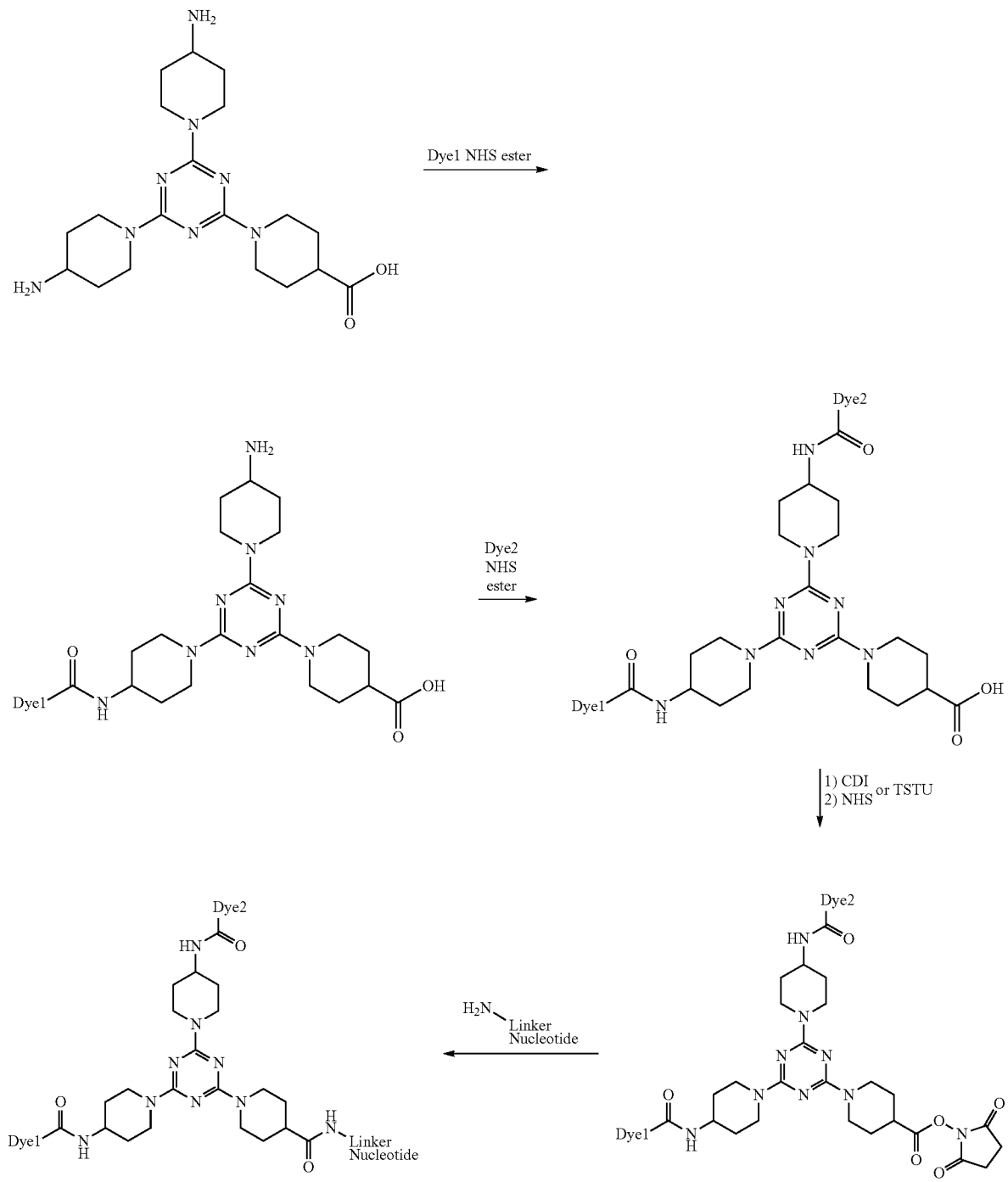

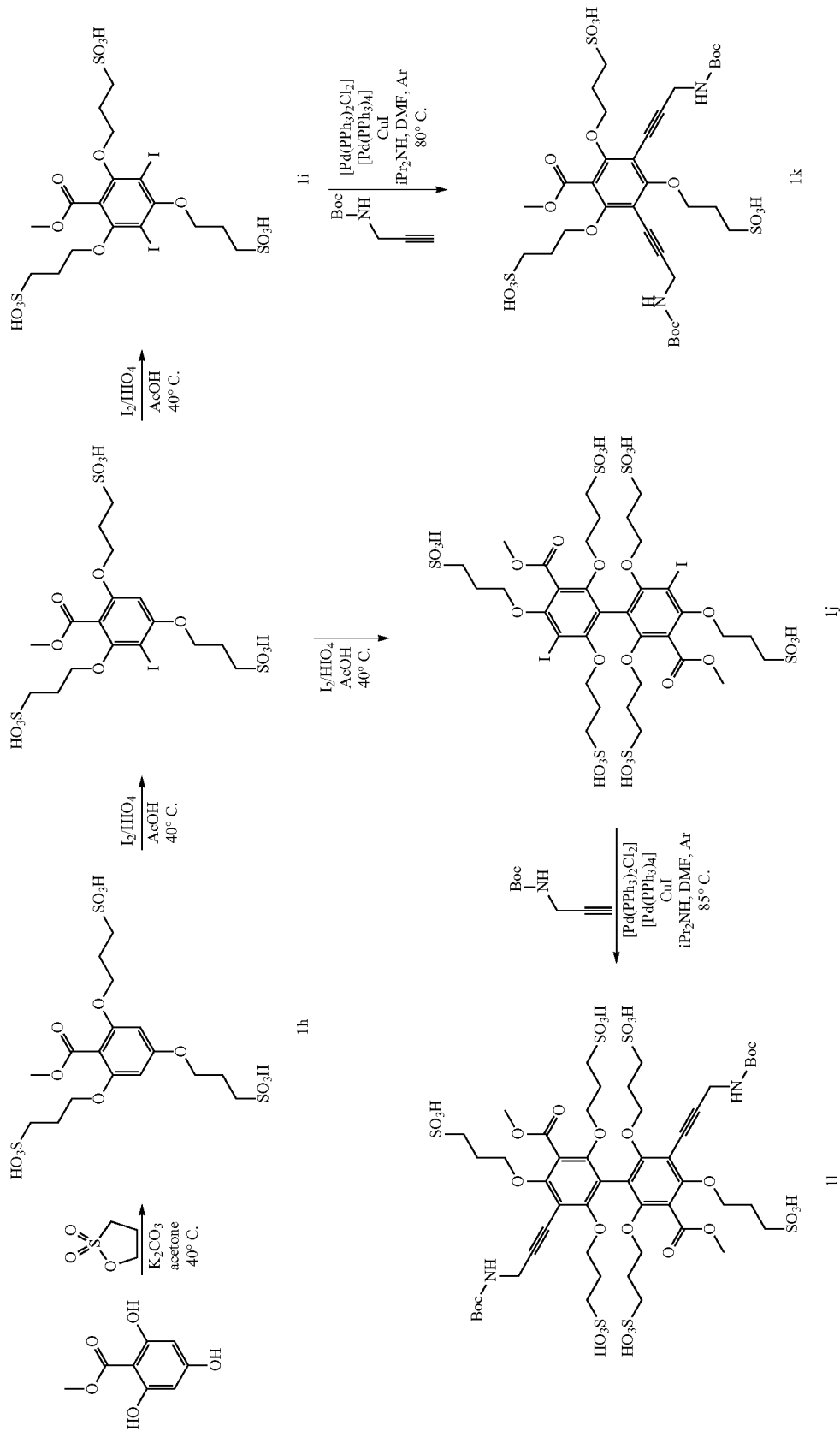

The carboxy moiety of S3 or S6 scaffolds can be extended using aminocaproic acid.

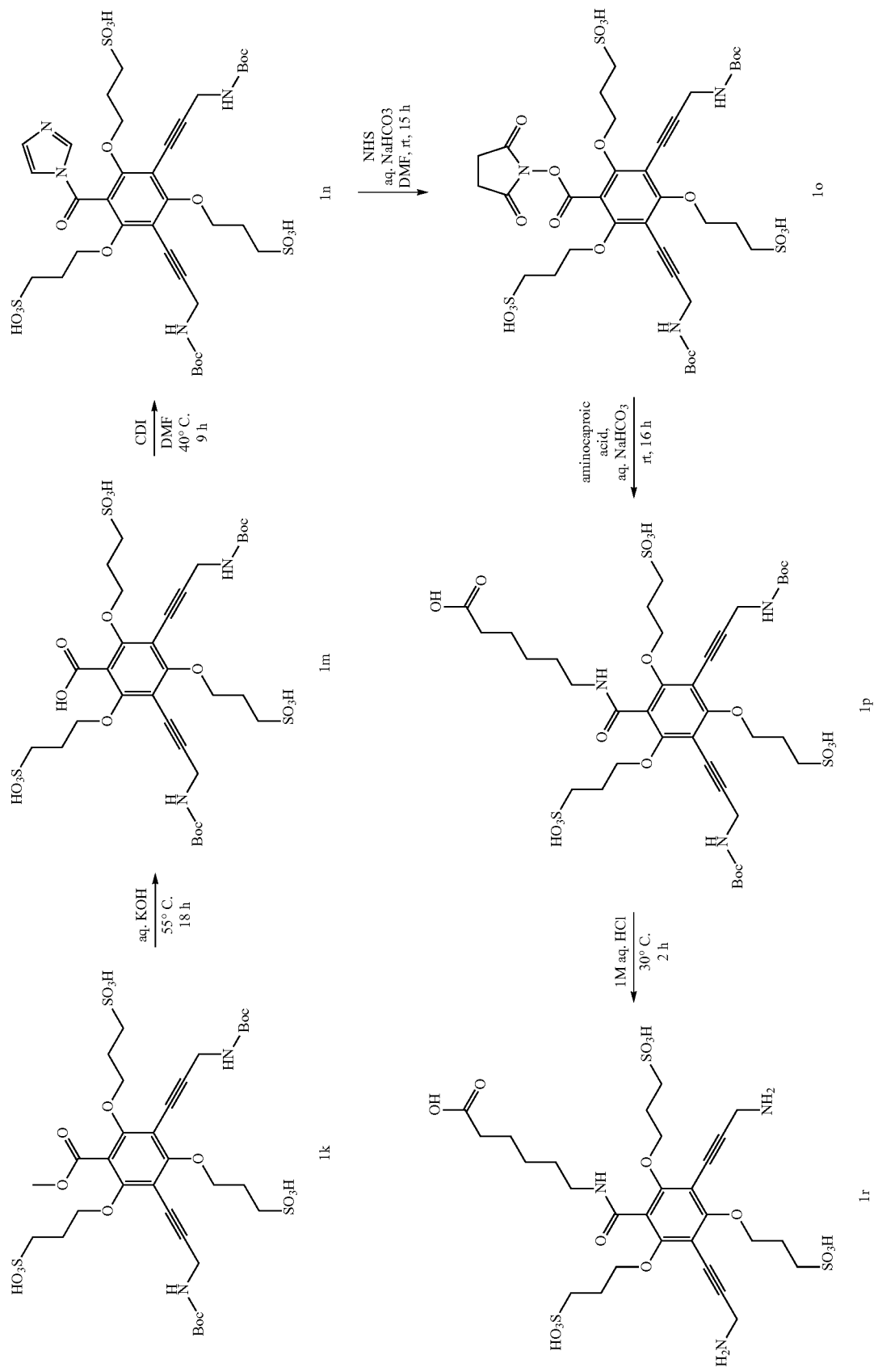

Example 2

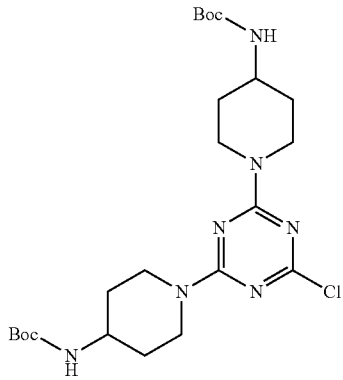

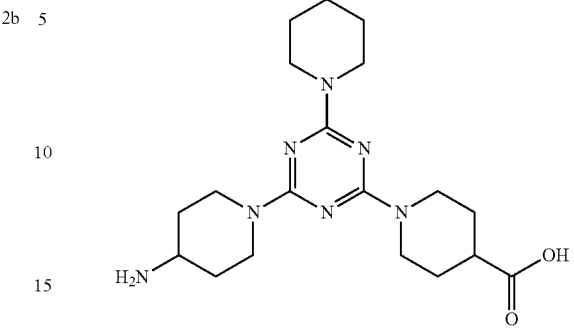

2.1 Synthesis of tert-butyl 1,1'-(6-chloro-1,3,5-triazine-2,4-diyl)bis(piperidine-4,1-diyl)dicarbamate (2b)

A mixture of cyanuric chloride (738 mg, 4.00 mmol, 1.0 eq), 4-(N-Boc-amino)-piperidine (1602 mg, 8.00 mmol, 2.0 eq), NaHCO$_3$ (672 mg, 8.00 mmol, 2.0 eq) in dioxane (5.0 ml) was heated to 105° C. for 1 h. After cooling to rt, the mixture was suspended in water, sonicated, and the crude product was separated by filtration. The solid was suspended in methanol (20 ml), sonicated, filtered to give 2b (1550 mg, 76% yield) as a white solid. LCMS: Calculated Mass 511.3, Observed Mass 569.8 (M+AcO$^-$).

2.3 Synthesis of 1-(4,6-bis(4-aminopiperidin-1-yl)-1,3,5-triazin-2-yl)piperidine-4-carboxylic acid (1d)

A mixture of 2c (1005 mg, 1.59 mmol, 1.00 eq), aq. KOH (1 M, 5.05 ml, 5.05 mmol, 3.18 eq), ethanol (10 ml), and dioxane (10 ml) was heated to 80° C. for 2 h, concentrated in vacuo, and dried in HV. The residue was dissolved in aq. HCl (6 M, 10.0 ml), stirred at rt for 1 h, and the solution was concentrated in vacuo. Water (10 ml) and triethylamine (4 ml) added, concentrated in vacuo. The product was purified by reverse phase HPLC (Waters Xterra C18 RP 30×100 column, 0-10% AcN in 0.1 M TEAB, Akta Purifier) to give 2d (605 mg, 94% yield) as a white solid. LCMS: Calculated Mass 404.3, Observed Masses 403.3 (M$^-$); 462.8 (M+AcO$^-$).

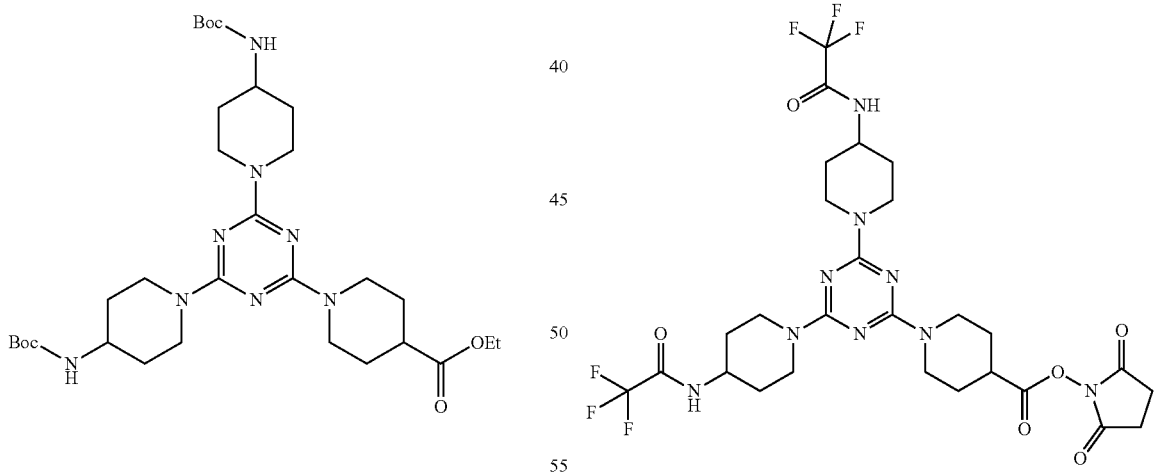

2.2 Synthesis of ethyl 1-(4,6-bis(4-(tert-butoxycarbonylamino)piperidin-1-yl)-1,3,5-triazin-2-yl)piperidine-4-carboxylate (1c)

A mixture of 2b (1039 mg, 1.03 mmol, 1.00 eq) and ethyl isonipecotate (937 µl, 957 mg, 6.09 mmol, 3.00 eq) in dioxane (7.5 ml) was heated to 80° C. for 1 h. The mixture was concentrated in vacuo, the product was crystallized from hot methanol to give 2c (1072 mg, 84% yield) as a white solid. LCMS: Calculated Mass 632.4, Observed Masses 630.7 (M$^-$); 690.8 (M+AcO$^-$).

2.4 Synthesis of 2,5-Dioxopyrrolidin-1-yl 1-(4,6-bis(4-(2,2,2-trifluoroacetamido)piperidin-1-yl)-1,3,5-triazin-2-yl)piperidine-4-carboxylate (2e)

TFA-NHS (553 mg, 2.62 mmol, 10.0 eq) was added to a suspension of 2d (106 mg, 0.262 mmol, 1.0 eq) in pyridine (1 ml) and DCM (0.5 ml). The mixture was stirred at rt in a closed 40 ml vial for 2 h, diluted with DCM (50 ml), and washed with water (3×50 ml). The organic layers were dried (Na$_2$SO$_4$), concentrated, the residue was coevaporated with toluene (20 ml) and dried in HV to yield 2e (170 mg, 93% yield) as a white solid. LCMS: Calculated Mass 693.3, Observed Masses 692.1 (M⁻); 752.0 (M+AcO⁻). *Procedure from Tet. Lett. 43,*

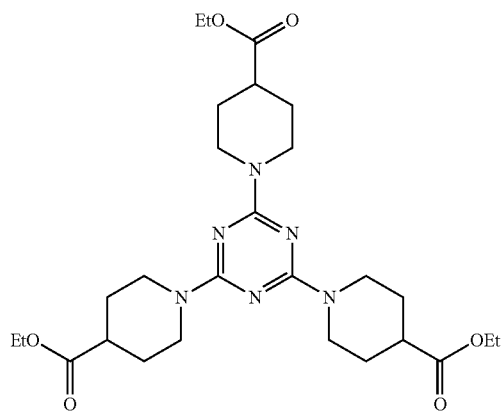

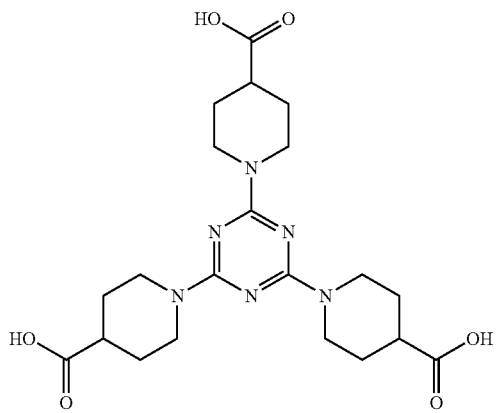

2.6 1,1',1''-(1,3,5-Triazine-2,4,6-triyl)tripiperidine-4-carboxylic acid (1g)

2.5 Synthesis of triethyl 1,1',1''-(1,3,5-triazine-2,4,6-triyl)tripiperidine-4-carboxylate (2f)

Ethyl isonipecotate (4.62 ml, 4.72 g, 30.00 mmol, 6.0 eq) was added to a solution of cyanuric chloride (922 mg, 5.00 mmol, 1.0 eq) in anhydrous THF (20 ml) at rt. Exothermic reaction occurred and a white suspension formed. The mixture was stirred at 50° C. for 14 h. After cooling to rt the voluminous white solid (ethyl isonipecotate salt) was filtered, washed with ether, and the filtrate containing the crude product was concentrated in vacuo. The product was purified by column chromatography on silica (40 g, 0-30% AcOEt in DCM, ISCO CombiFlash Rf) to yield 2f (2.44 g, 89% yield) as a white solid.

Aqueous NaOH (1 M, 9.2 ml, 5 eq) was added to a solution of 2f (1.00 g, 1.83 mmol, 1.0 eq) in a mixture of THF (20 ml) and ethanol (7 ml). The mixture was stirred at 55° C. for 16 h, concentrated in vacuo, dissolved in excess of 1 M aq. HCl, concentrated in vacuo and dried in HV. The crude product was dissolved in water and the solution was carefully neutralized with 1 M aq. NaOH until white solid was precipitating. The solid was filtered, washed with water, dried in HV to give product 2g (634 mg, 75% yield) as an off-white solid. LCMS: Calculated Mass 462.2; Observed Mass 461.3 (M⁻).

Example 3

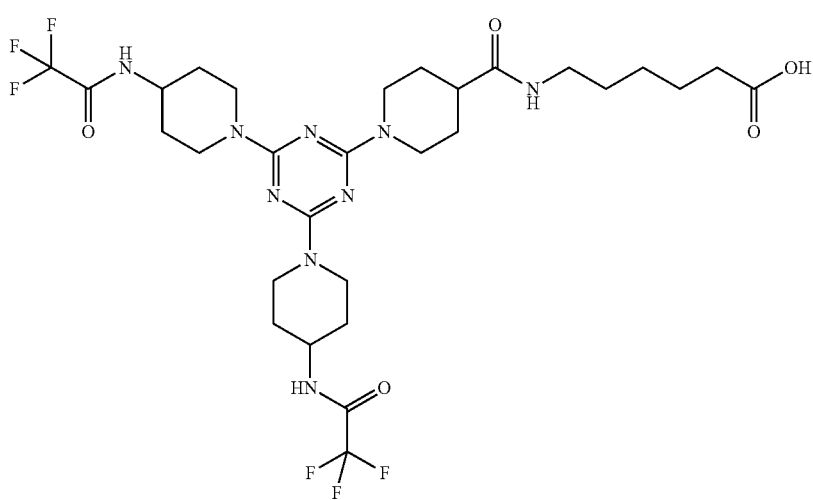

3.1 Synthesis of (TFA)₂-T2-X—COOH=6-(1-(4,6-bis(4-(2,2,2-trifluoroacetamido)piperidin-1-yl)-1,3,5-triazin-2-yl)piperidine-4-carboxamido)hexanoic acid (3a)

A solution of 6-aminocaproic acid (11.3 mg, 86.51 μmol, 3.0 eq) in aq. sodium bicarbonate buffer (1 ml, 0.1 M, pH 8.3) was added to a chilled solution of (TFA)₂-T2 NHS ester (20.0 mg, 28.84 μmol, 1.0 eq) in anhydrous DMF (4 ml). After complete mixing, the solution was kept at room temperature for 72 h. The product was purified by reverse phase HPLC (Waters XTerra C18 RP 30×100, 0-55% AcN in 0.1 M TEAB, Akta Purifier) to give 3a (12.0 mg, 51% yield) as a white solid. LCMS: Calculated Mass 709.3; Observed Mass 708.3 (M⁻).

3.3 Synthesis of (NH₂)₂-T2-14C-dG6P (3c)

A solution of (TFA)₂-T2-X—CO—NHS (10.0 mg, 12.40 μmol, 1.0 eq) in anhydrous DMF (1000 μl) and DMSO (2000 μl) was added to a solution of NH₂-6C-dG6P (200 μl, 61.0 mM, 12.21 μmol, 1.0 eq) in aq. sodium bicarbonate buffer (500 μl, 0.1 M, pH 8.3). After complete mixing, the solution was kept in dark at room temperature for 50 h. (TFA)₂-T2-14C-dG6P was purified by a reverse phase HPLC (Waters XTerra C18 RP 19×100, 0-51% AcN in 0.1 M TEAB, Akta Purifier). The intermediate was deprotected

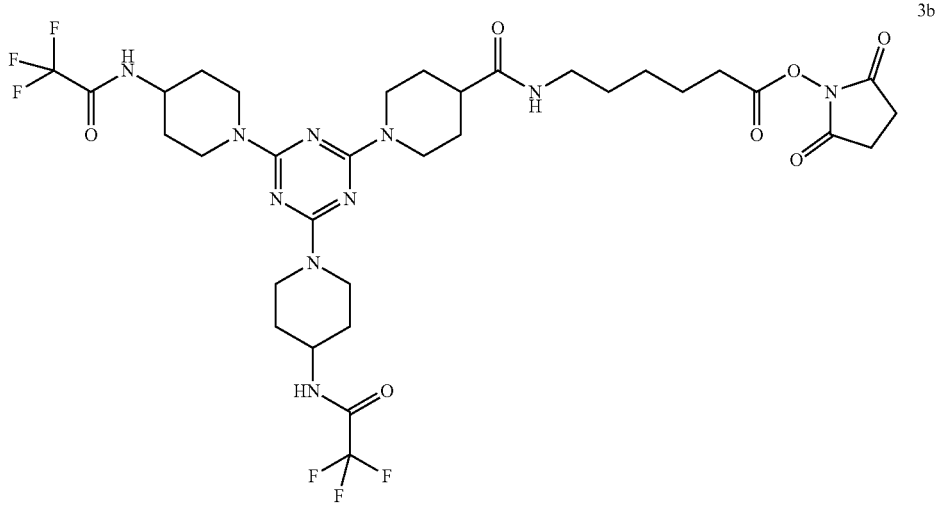 [SMILES: O=C(CCCCCNC(=O)C1CCN(c2nc(N3CCC(NC(=O)C(F)(F)F)CC3)nc(N3CCC(NC(=O)C(F)(F)F)CC3)n2)CC1)ON1C(=O)CCC1=O]

3b

3.2 Synthesis of (TFA)₂-T2-X—CO—NHS (3b)

TSTU (8.8 mg, 29.2 μmol, 2.3 eq) was added to a soln. of 3a (10.3 mg, 12.7 μmol, 1.0 eq) in DMF (1000 μl). DIEA (6.6 μl, 38.1 μmol, 3.0 eq) was added and the reaction mixture was kept at rt for 5 h. The solution was used without purification for the next step as a DMF soln. of (TFA)₂-T2-X—CO—NHS. LCMS: Calculated Mass 806.3. Observed Masses 805.1 (M⁻), 864.8 (M+AcO⁻).

using aq. ammonia (10 ml, 3 M, 15 h at rt). The product was purified by reverse phase HPLC (Waters XTerra Ct18 RP 19×100, 0-30% AcN in 0.1 M TEAB, Akta Purifier) to give 3c (9.77 μmol, 79% yield, 48.9 mM, 200 μl). LCMS: Calculated Mass 1345.3; Observed Masses 1344.0 (M⁻), 671.7 (M²⁻/2).

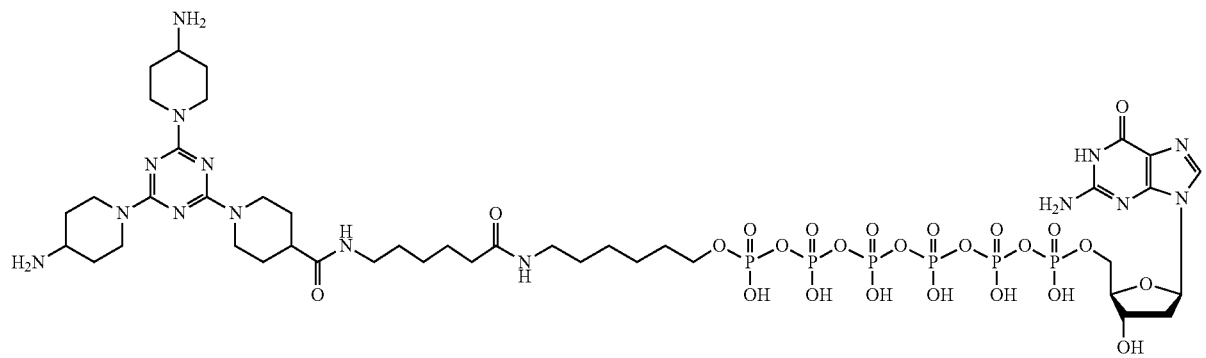

3c

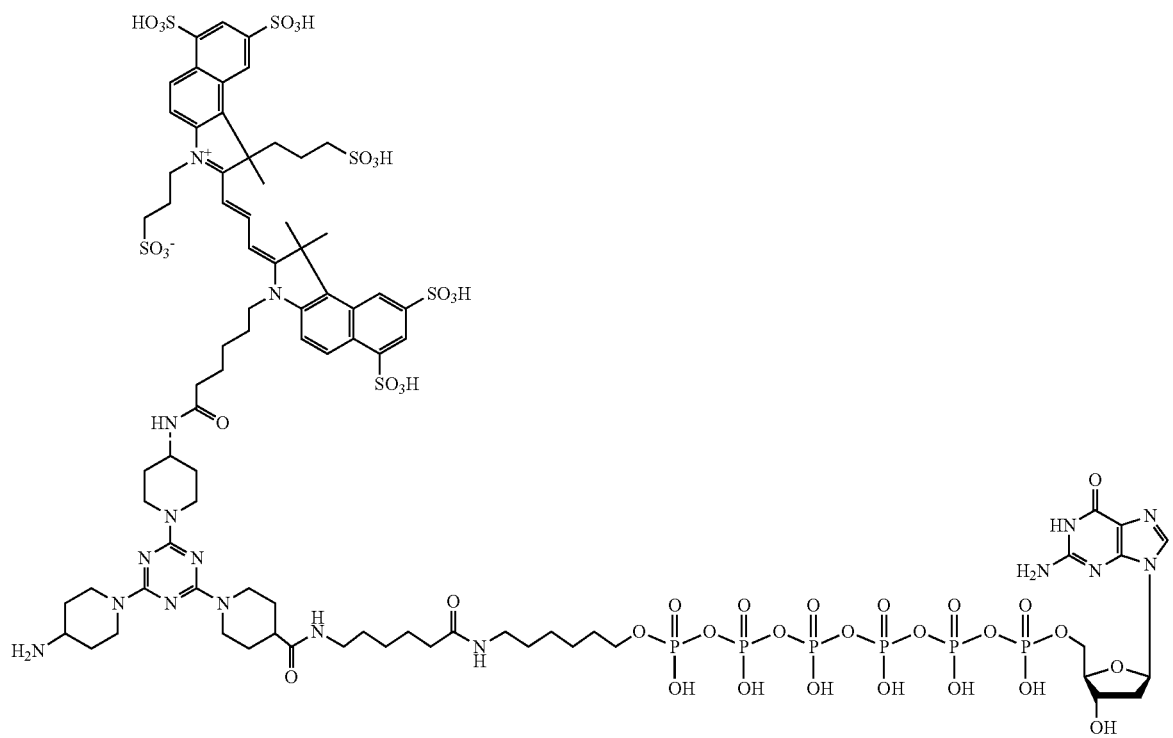

3d 3.4 Synthesis of (NH$_2$,cyanine)-T2-14C-dG6P (3d)

A solution of cyanine NHS ester (1.7 mg, 1.00 μmol, 1.0 eq) in anhydrous DMF (40.0 μl) was added to a chilled solution of (NH$_2$)$_2$-T2-14C-dG6P (1.00 μmol, 1.0 eq) in aq. sodium bicarbonate buffer (53.5 μl, 0.1 M, pH 8.3). After complete mixing, the solution was kept in dark at room temperature for 40 h. The product was purified by reverse phase HPLC (Waters XTerra C18 RP 19×100, 0-30% AcN in 0.1 M TEAB, Akta Purifier) to give 3d (0.405 μmol, 41% yield, 2.7 mM solution in 0.1 M aq. bicarbonate buffer, 150 μl).

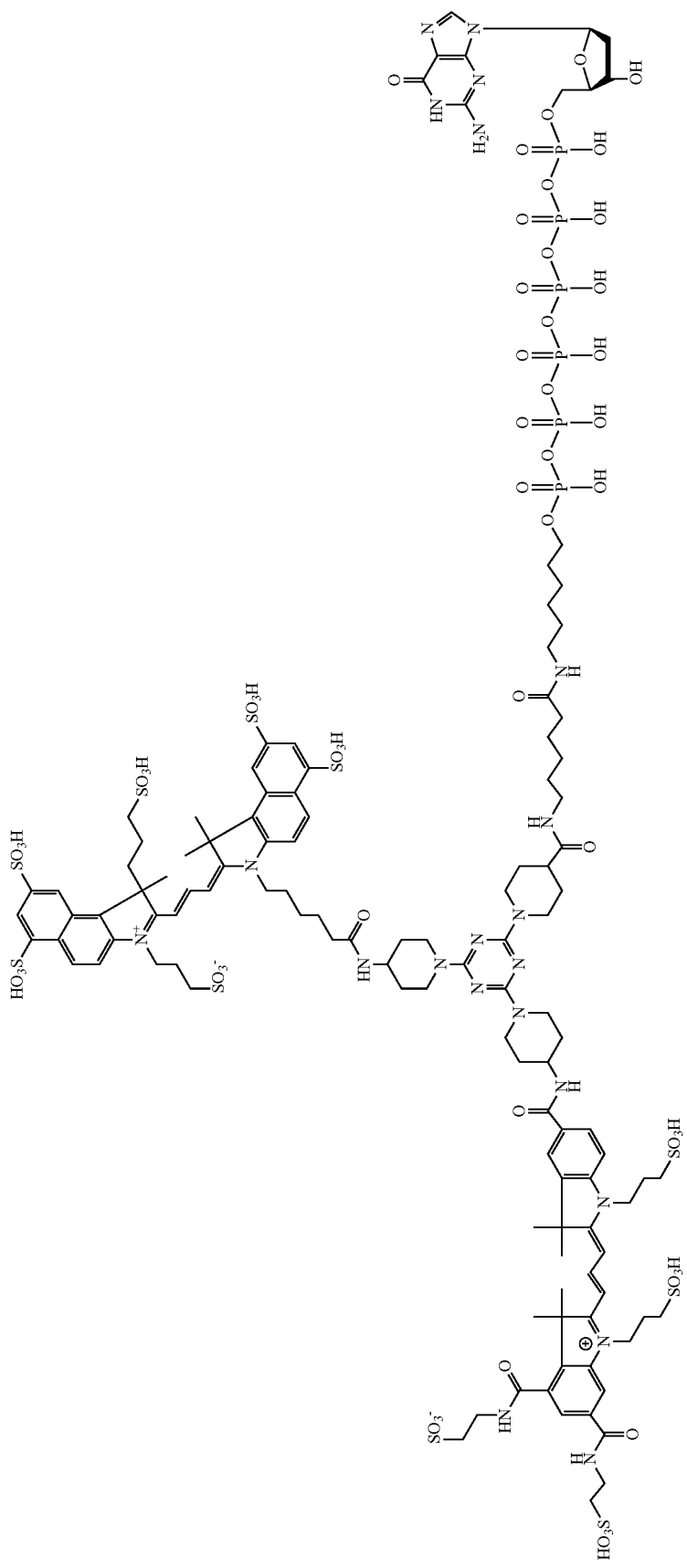

3.5 Synthesis of 3e

A solution of cyanine dye NHS ester (1.5 mg, 1.137 µmol, 5.6 eq) in anhydrous DMF (75.0 µl) was added to a chilled solution of (NH$_2$,PB594)-T2-14C-dG6P (75.0 µl, 2.7 mM, 0.203 µmol, 1.0 eq, 3d) in aq. bicarbonate buffer (75.0 µl, 0.1 M, pH 8.3). After complete mixing, the solution was kept in dark at room temperature for 45 h. The product was purified by ion exchange chromatography on Q sepharose FF (GE, 0.05-1.5 M TEAB with 20% AcN, Akta Purifier) followed by a reverse phase HPLC (Waters XTerra C18 RP 19×100, 0-33% AcN in 0.1 M TEAB, Akta Purifier) to give 3e (88 nmol, 44% yield, 884 µM, 100 µl).

Example 4

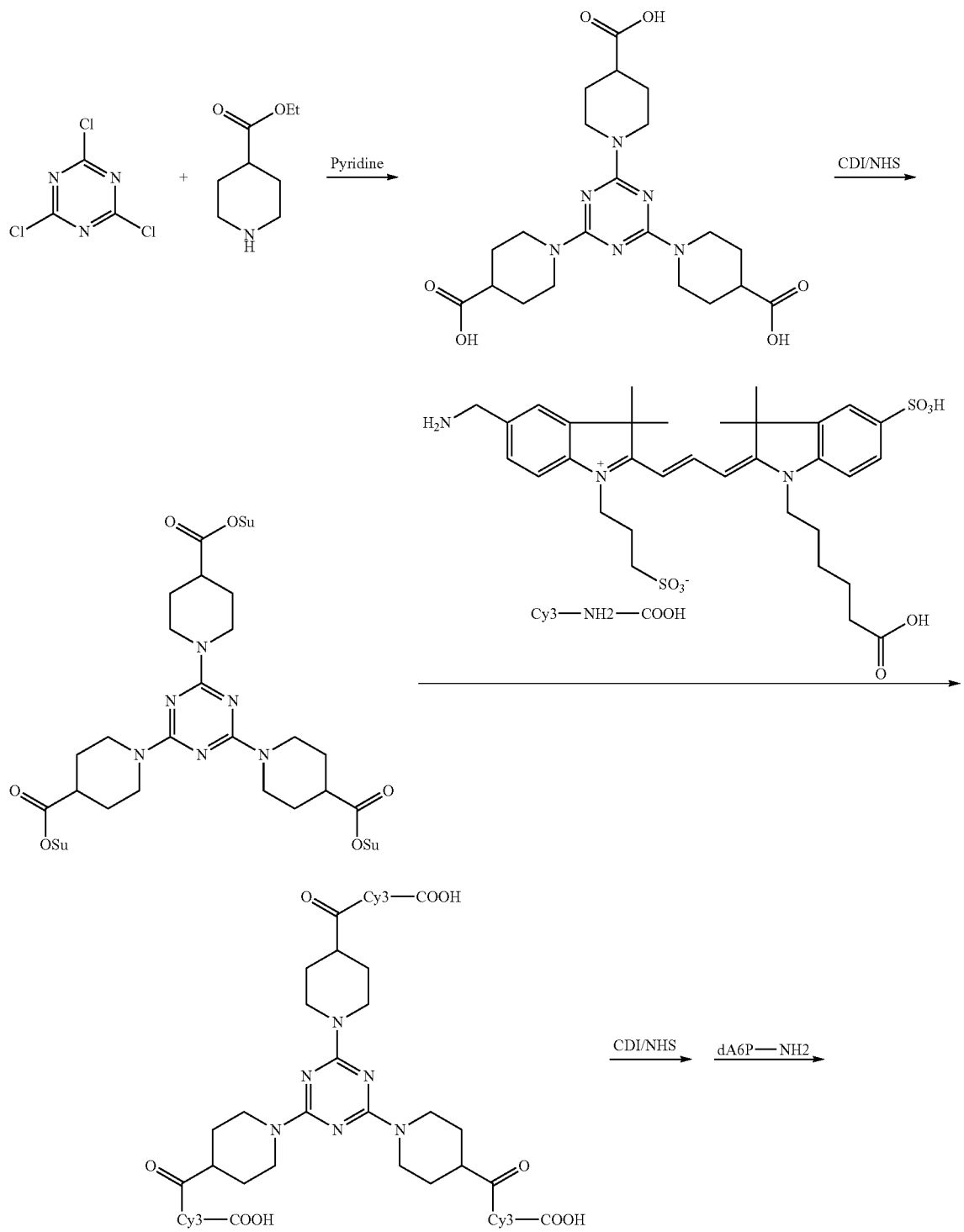

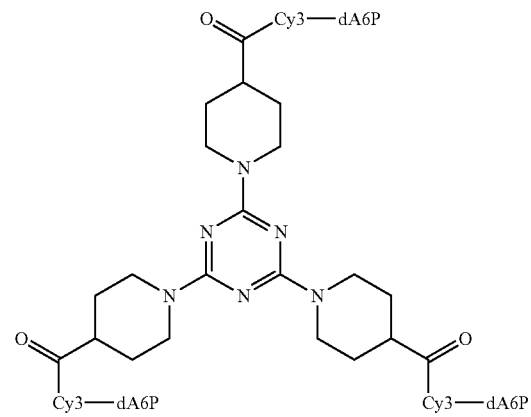
4a
4.1 Synthesis of 4a
The schematic shown above provides a synthetic route to producing the compound 4a having a triazine with three piperidine groups as the core, and having three Cy3-dA6P substituents connected to the core. dA6P has a polyphosphate with 6 phosphates and a deoxy nucleoside having the base adenine (A).
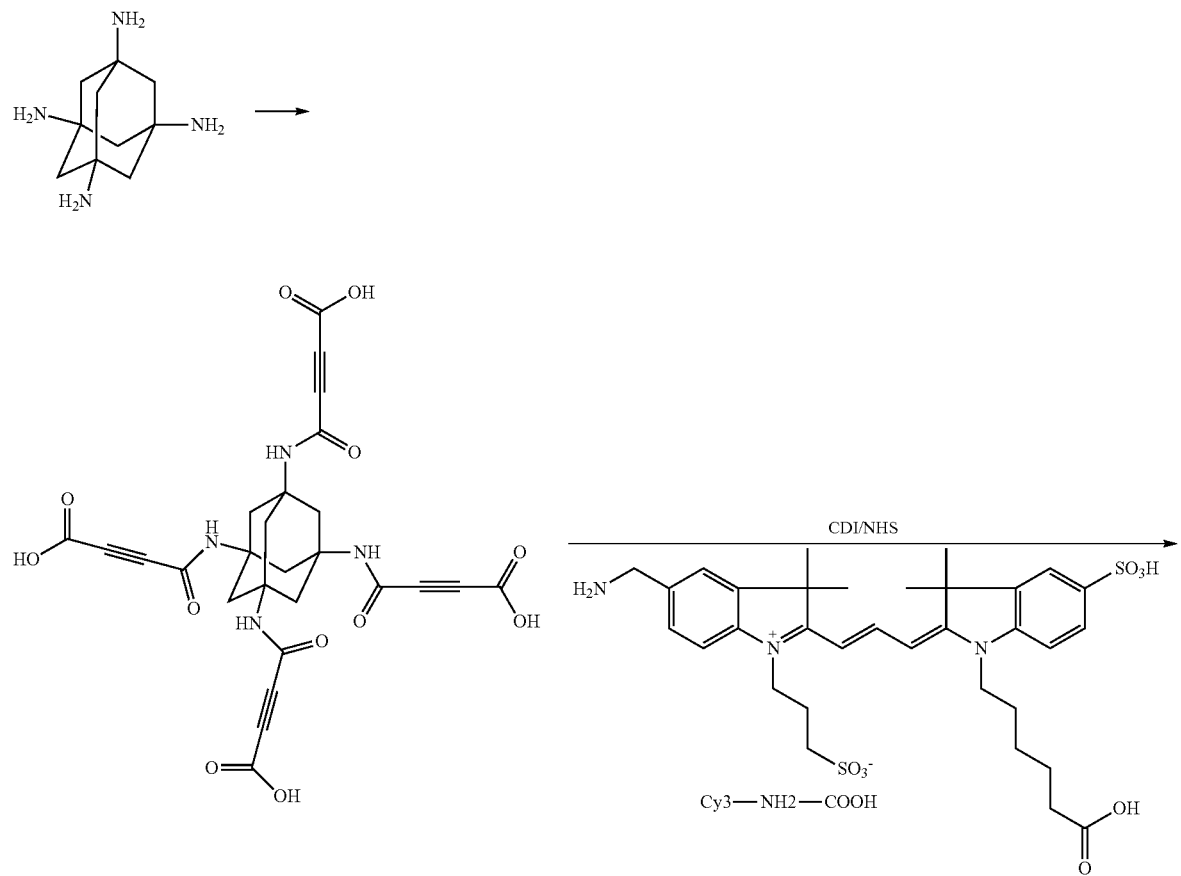

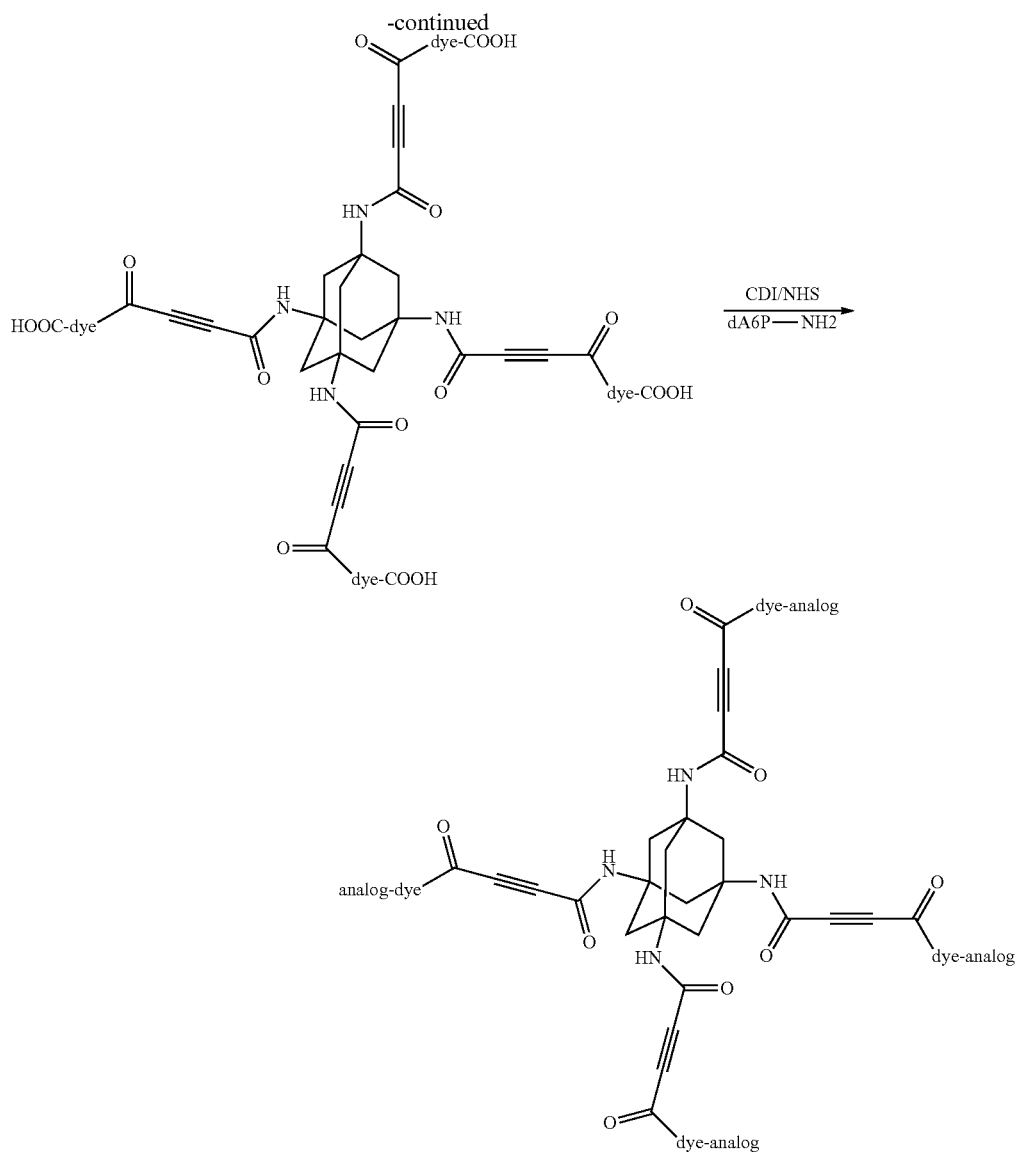
4.1 Synthesis of 4b
The schematic shown above provides a synthetic route to producing the compound 4b having an adamantane core and having four dye-polyphosphate nucleosides. The term analog as used in the figure above refers to the nucleoside polyphosphate dA6P having six phosphates and a nucleoside comprising the base adenine.
Example 5
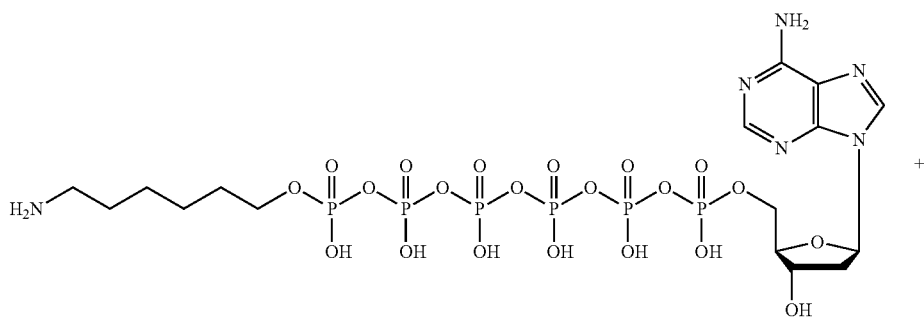

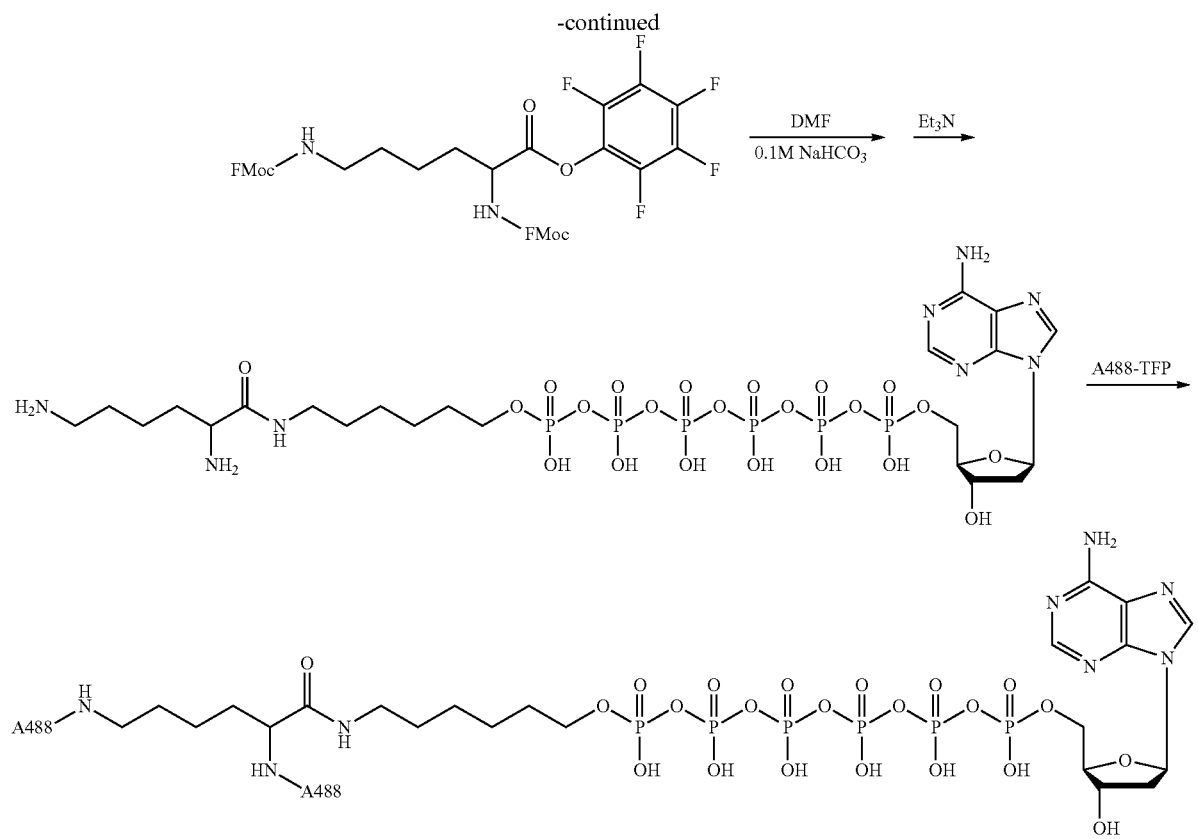
Synthesis of 5a
The schematic shown above provides a synthetic route to producing the compound 5a having a trifunctional core attached to two dye moieties (A488) and to one deoxy nucleoside polyphosphate having six phosphates and the nucleobase adenine.
Example 6
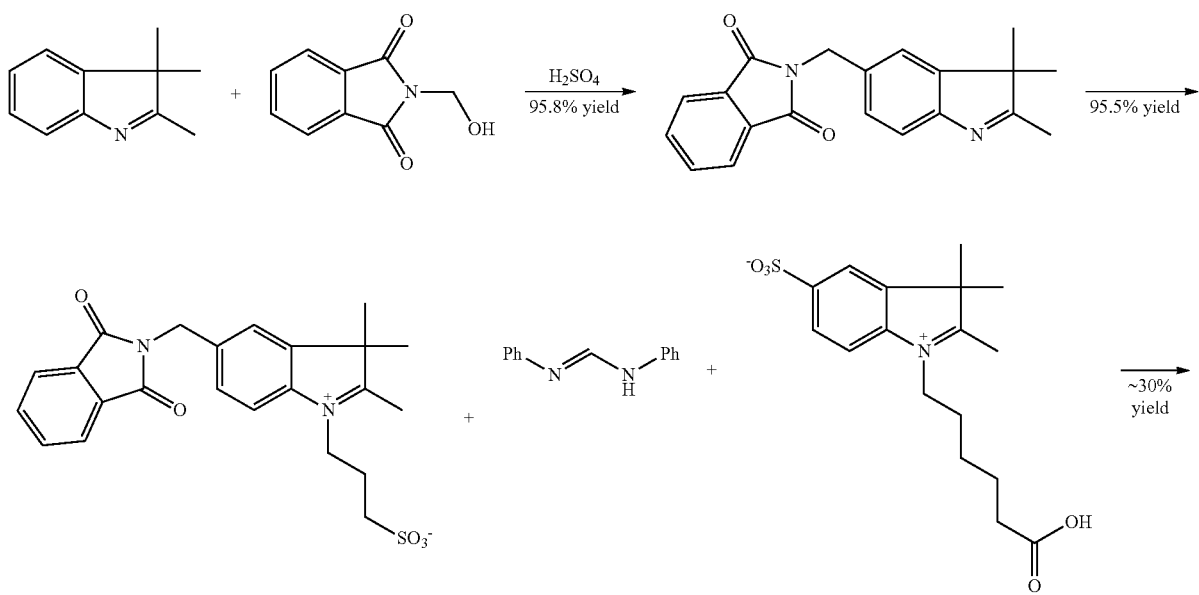

-continued
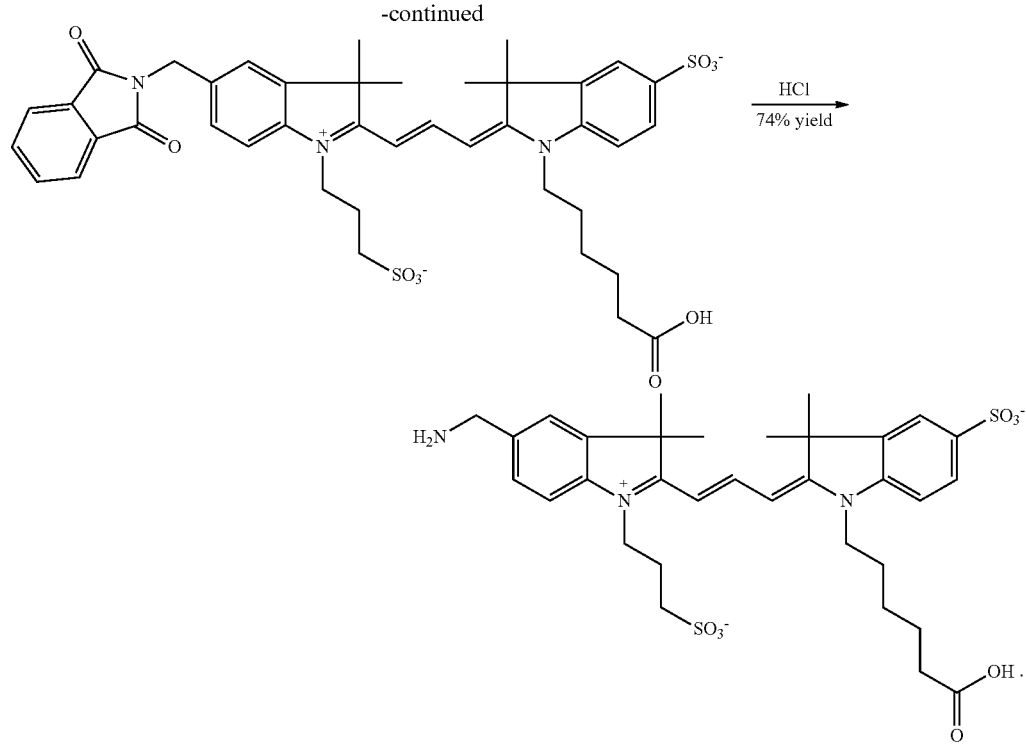
6a
Synthesis of 6a
The schematic shown above provides a synthetic route to producing the cyanine dye 6a.
Example 7
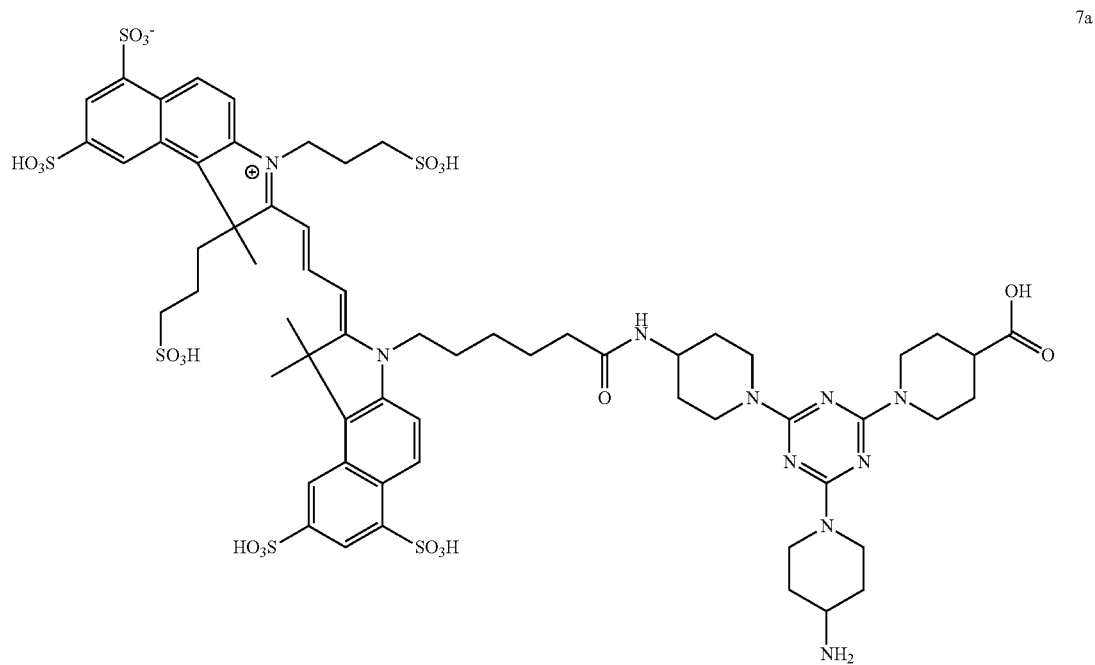
7a

7.1 Synthesis of (Dye1,NH$_2$)-T2-COOH (7a)

A 100 mM solution of (NH$_2$)$_2$-T2-COOH (15.4 mg, 38.1 Mmol, 3.00 eq) in aq. NaHCO$_3$ (0.2 M, 381 µl) was added to a chilled solution of Dye1 NHS ester (21.5 mg, 12.7 µmol, 1.00 eq) in anhydrous DMA (635 µl). After complete mixing the solution was kept in dark at rt for 16 h. The product was purified by a reverse phase HPLC (Waters XTerra C18 RP 30×100, 0-24% AcN in 0.1 M TEAB, Akta Purifier) to give 7a. (22.3 mg, 83% yield, DIEA salt). LCMS: Calculated Mass 1478.4, Observed Mass 738.8 (M$^{2-}$/2).

7.2 Synthesis of (Dye1,Dye2)-T2-COOH (7b)

A solution of Dye2 NHS ester (16.4 mg, 11.5 µmol, 1.28 eq) in anhydrous DMA (574 µl) was added to a chilled solution of 7a DIEA salt (19.1 mg, 9.0 µmol, 1.00 eq) in aq. NaHCO$_3$ (0.2 M, 287 µl). After complete mixing the solution was kept in dark at 40° C. overnight. The product was purified by ion exchange chromatography on Q sepharose FF (GE, 0.05-1.5 M TEAB with 20% AcN, Akta Purifier) followed by a reverse phase HPLC (Waters XTerra C18 RP 30×100, 0-28% AcN in 0.1 M TEAB, Akta Purifier) to give 7b (23.5 mg, 79% yield, TEA salt). LCMS: Calculated Mass 2491.6, Observed Mass 830.2 (M$^{3-}$/3).

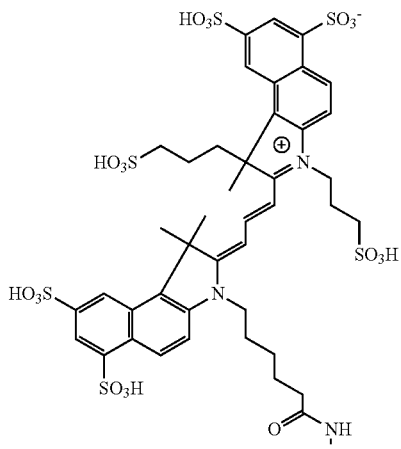

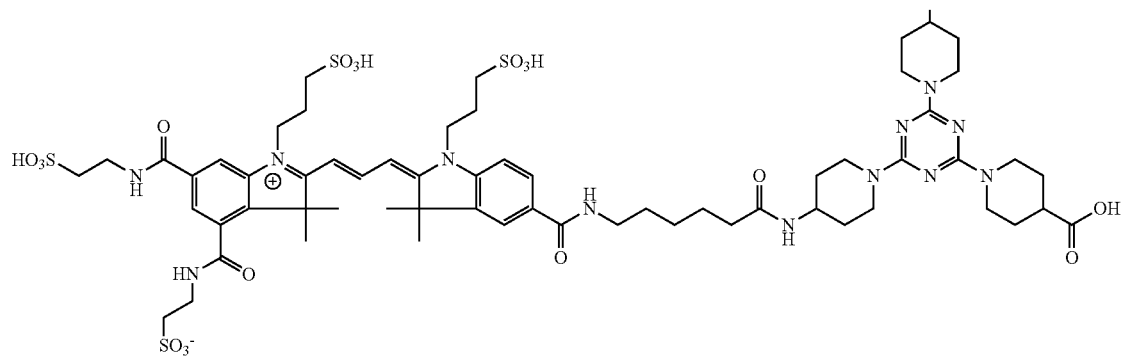

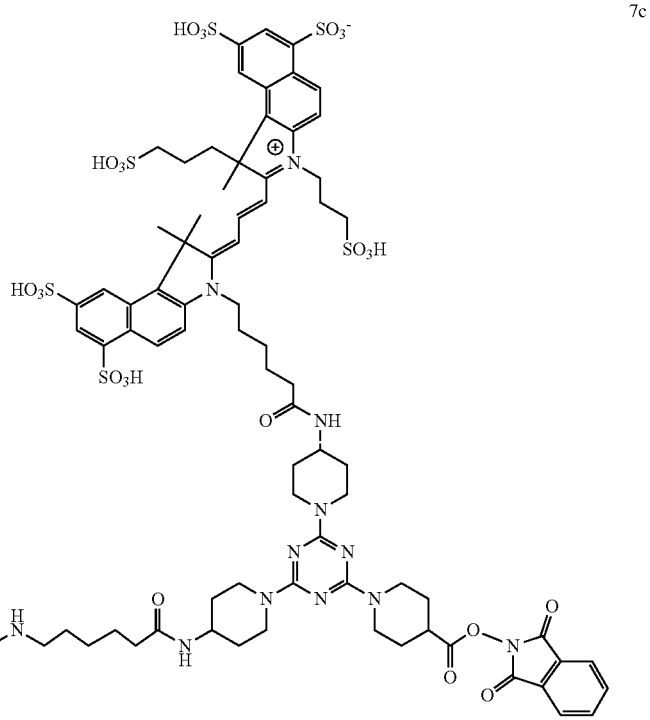

7c

7.3 Synthesis of activated ester (Dye1,Dye2)-T2-CO—BOSu (7c)

Carbonyldiimidazole (17.3 mg, 10.7 μmol, 15.00 eq) was added to a solution of 7b (23.5 mg, 7.10 mol, 1.00 eq) in anhydrous DMF (200 μl) and the mixture was kept at rt in dark for 5 h. N-Hydroxyphthalimide (29.0 mg, 17.8 μmol, 25.00 eq) was added and after complete mixing the mixture was kept at rt in dark for 16 h. Ethyl acetate (1.5 ml) was added to the reaction mixture and the precipitated solid was separated by centrifuge. The solid was triturated with ethyl acetate (2×1.5 ml) and dried in HV to give 7c (26 mg, quant. yield). LCMS: Calculated Mass 2636.6, Observed Mass 878.2 ($M^{3-}/3$).

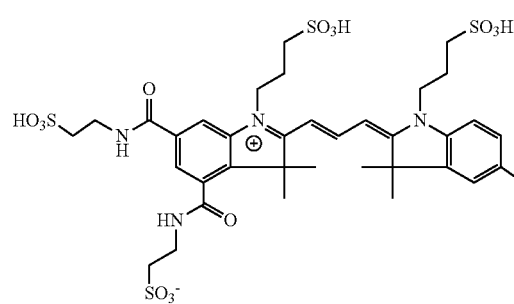

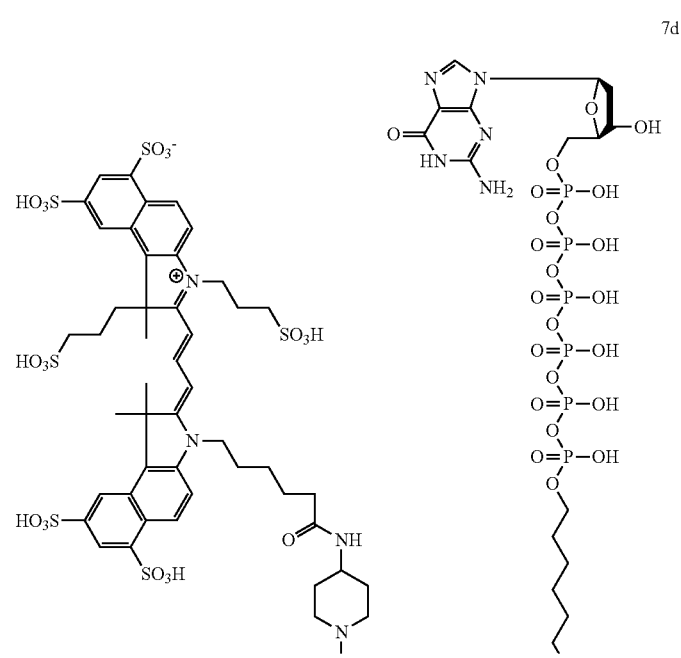

7d

-continued

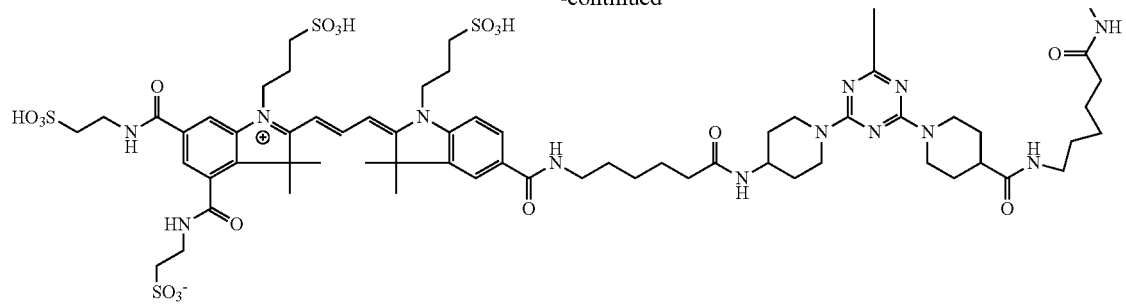

7.4 Synthesis of (Dye1,Dye2)-T2-14C-dG6P (7d)

A solution of 7c (43.5 mg, 12.61 mol, 1.00 eq) in anhydrous DMA (630 μl) was added to a chilled solution of NH$_2$-14C-dG6P (236 μl, 107 mM, 25.22 μmol, 2.00 eq, DIEA salt) in aq. NaHCO$_3$ buffer (118 μl, 0.4 M). After complete mixing the solution was kept in dark at 40° C. for 16 h. The product was purified by ion exchange chromatography on Q sepharose FF (GE, 0.05-1.5 M TEAB with 20% AcN, Akta Purifier) followed by a reverse phase HPLC (Waters XTerra C18 RP 30×100, 0-25% AcN in 0.1 M TEAB, Akta Purifier) to give 7d (34.5 mg, 7.11 μmol, 56% yield). LCMS: Calculated Mass 3432.7, Observed Mass 1143.5 ($M^{3-}/3$).

Example 8

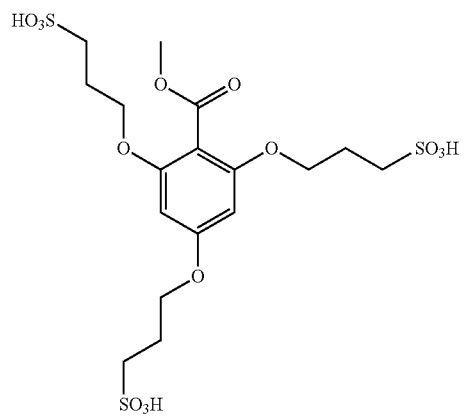

8.1 Synthesis of methyl 2,4,6-tris(3-sulfopropoxy)benzoate (8a)

1,3-Propane sulfone (3.54 ml, 4.93 g, 40.0 mmol, 10.00 eq) was added to a mixture of methyl 2,4,6-trihydroxybenzoate (737 mg, 4.00 mmol, 1.00 eq), potassium carbonate (8.29 g, 60.0 mmol, 15.00 eq), and acetone (20 ml). The mixture was stirred under Ar at 40° C. for 5 d. The solid was separated by filtration and washed with acetone. The product was purified by reverse phase HPLC (Waters Xterra C18 RP 30×100 column, 0-18% AcN in 0.1 M TEAB, Akta Purifier) to give 8a (2.21 g, 65% yield) as a colorless oil. LCMS: Calculated Mass 550.1, Observed Mass 549.1 (M$^-$).

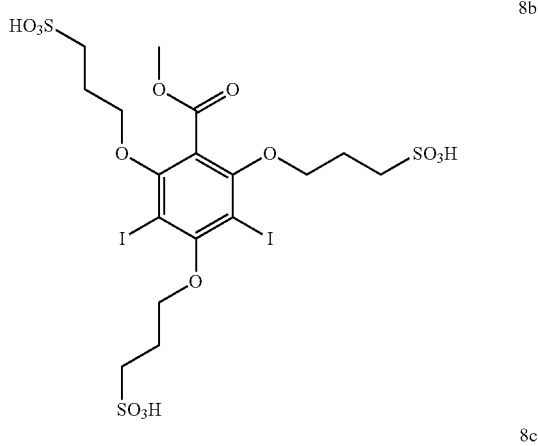

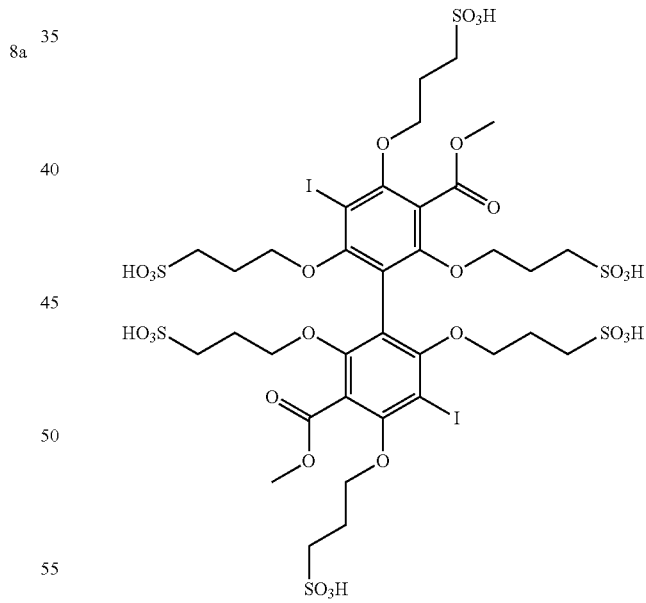

8.2 Synthesis of methyl 3,5-diiodo-2,4,6-tris(3-sulfopropoxy)benzoate (8b) and dimethyl 3',5-diiodo-5'-propionyl-2,2',4,4',6,6'-hexakis(3-sulfopropoxy)biphenyl-3-carboxylate (8c)

A mixture of 8a (1883 mg, 2.20 mmol, 1.00 eq), iodine (839 mg, 3.31 mmol, 1.50 eq), periodic acid (251 mg, 1.10 mmol, 0.50 eq), and acetic acid (20 ml) was stirred and heated to 55° C. for 3.5 h. After cooling to rt the mixture was concentrated in vacuo, coevaporated with water and ethyl acetate to remove the excess of iodine. The residue was neutralized with triethylamine and purified by reverse phase HPLC (Waters Xterra C18 RP 50×100 column, 0-20% AcN in 0.1 M TEAB, Akta Purifier) to give 8b (1944 mg, 80% yield) and 8c (197 mg, 9% yield) as a colorless oils. LCMS: 8b Calculated Mass 801.8, Observed Mass 800.9 (M⁻); 8c Calculated Mass 1349.9, Observed Mass 674.1 (M²⁻/2).

8d

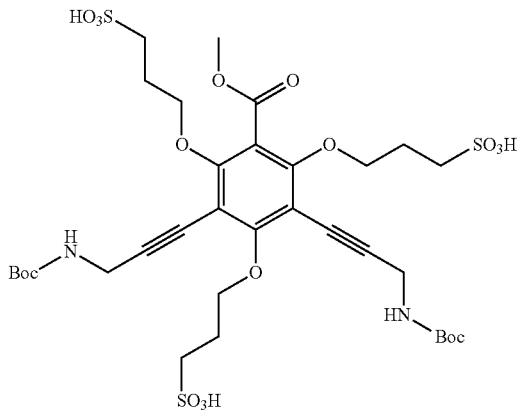

8.3 Synthesis of methyl 3,5-bis(3-(tert-butoxycarbonylamino)prop-1-ynyl)-2,4,6-tris(3-sulfopropoxy) benzoate (8d)

N-Boc-propargylamine (752 mg, 4.85 mmol, 10.00 eq) was added to degassed mixture of 8b (536 mg, 0.485 mmol, 1.00 eq), [PdCl₂(PPh₃)₂](34 mg, 0.048 mmol, 0.10 eq), [Pd(PPh₃)₄](56 mg, 0.048 mmol, 0.10 eq), CuI (19 mg, 0.097 mmol, 0.20 eq), and DIEA (5.0 ml) in DMF (5.0 ml) and the mixture was stirred under Ar and heated to 80° C. for 3.3 h. After cooling to rt the mixture was concentrated in vacuo and diluted with water (30 ml). The solids were separated and the filtrate was purified by reverse phase HPLC (Waters Xterra C18 RP 30×100 column, 0-32% AcN in 0.1 M TEAB, Akta Purifier) to give 8d (209 mg, 37% yield). LCMS: Calculated Mass 856.2, Observed Mass 855.1 (M⁻). Using similar procedure 8e can be prepared from 8c.

8f

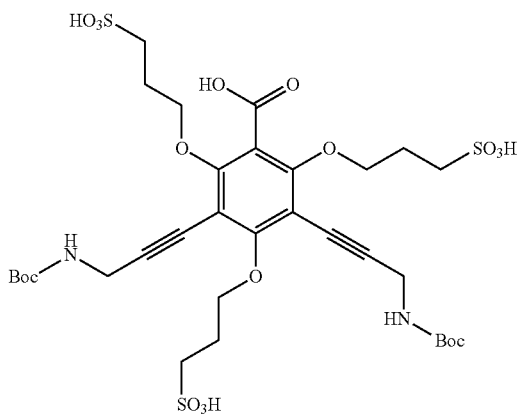

8.4 Synthesis of 3,5-bis(3-(tert-butoxycarbonylamino)prop-1-ynyl)-2,4,6-tris(3-sulfopropoxy) benzoic acid (8f)

Aq. KOH solution (1 M, 793 µl, 0.793 mmol, 5.00 eq) was added to a solution of 8d (184 mg, 0.159 mmol, 1.00 eq) in water (1.00 ml) and the mixture was heated to 55° C. for 15 h. The product was purified by reverse phase HPLC (Waters Xterra C18 RP 30×100 column, 0-27% AcN in 0.1 M TEAB, Akta Purifier) to give 8f (122 mg, 67% yield). LCMS: Calculated Mass 842.2, Observed Mass 841.1 (M⁻).

8k

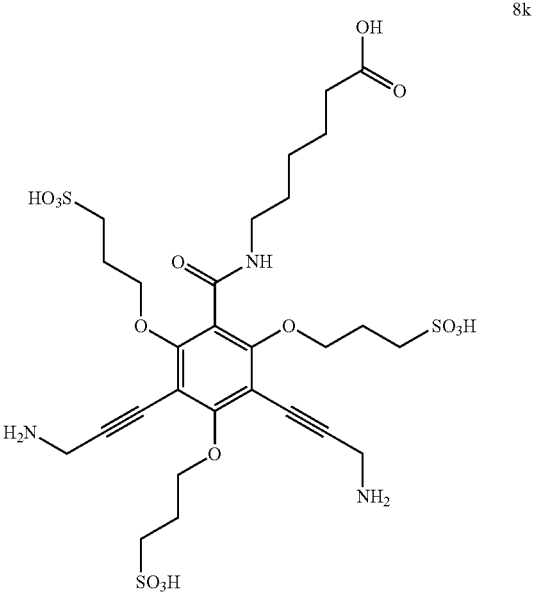 [SMILES: NCC#Cc1c(OCCCS(=O)(=O)O)c(C#CCN)c(OCCCS(=O)(=O)O)c(C(=O)NCCCCCC(=O)O)c1OCCCS(=O)(=O)O]

8.5 Synthesis of 6-(3,5-bis(3-aminoprop-1-ynyl)-2, 4,6-tris(3-sulfopropoxy)benzamido)hexanoic acid (10k)

Carbonyldiimidazole (172 mg, 1.06 mmol, 10.00 eq) was added to a solution of 8f (122 mg, 0.106 mmol, 1.00 eq) in DMF (1.00 ml) and the mixture was stirred at 40° C. for 9 h. Ethyl acetate (30 ml) was added to the reaction mixture and the precipitated solid product 8g was separated by centrifuge and dissolved in DMF (1.00 ml). NHS (244 mg, 2.12 mmol, 20.00 eq) and aq. NaHCO₃ (0.2 M, 1 ml) were added and the mixture was stirred at rt for 15 h. The product 8h was purified by reverse phase HPLC (Waters Xterra C18 RP 30×100 column, 0-32% AcN in 0.1 M TEAB saturated with CO₂, Akta Purifier) and then dissolved in a 2 M solution of 6-aminocaproic acid in 0.4 M aq. NaHCO₃ (1.0 ml). The mixture was stirred at rt for 16 h. The product 8i was purified by reverse phase HPLC (Waters Xterra C18 RP 30×100 column, 0-28% AcN in 0.1 M TEAB, Akta Purifier) and then dissolved in 1 M aq. HCl (3.0 ml). The mixture was heated to 30° C. for 2 h. Purification by reverse phase HPLC (Waters Xterra C18 RP 30×100 column, 0-12% AcN in 0.1 M TEAB, Akta Purifier) yielded product 8k (43.5 mg, 40% yield, DIEA salt). LCMS: Calculated Mass 755.2, Observed Mass 754.3 (M⁻).

The approaches above can be used for preparing a variety of derivatives having an S3 core unit. These include a single S3 core having two different dyes and a single nucleoside phosphate moiety.

Example 9

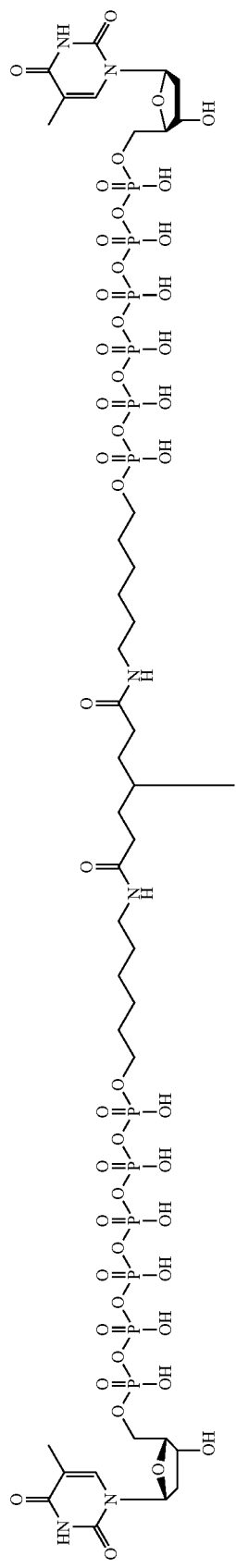
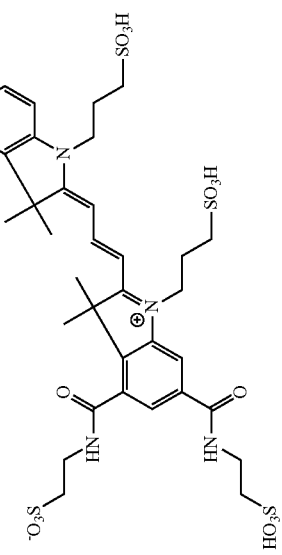

9.1 Multinucleotide Analog Examples

Synthesis of Dinucleotide Analog Dye-DA1-(6C-dT6P)$_2$ (9a)

4-Aminoheptanedioic acid (20 mg, 86.5 µmol, 43.2 eq, prepared by hydrogenation of 4-nitroheptanedioic acid) and aq. NaHCO$_3$ buffer (0.4 M, 20 µl) were added to a solution of Dye NHS ester (2.00 µmol, 1.0 eq) in DMA (20 µl). After complete mixing the solution was kept in dark at 40° C. for 92 h. The product was purified by a reverse phase HPLC (Waters XTerra C18 RP 30×100, 0-30% AcN in 0.1 M TEAB, Akta Purifier) to give diethylester of Dye-DA1 diacid (0.548 µmol, 27% yield).

Aq. potassium carbonate (250 mM, 50 µl) was added to a solution of diethylester of Dye-DA1 diacid (0.548 µmol) in water (150 µl) and the mixture was heated to 40° C. in dark for 17 h. The product was purified by a reverse phase HPLC (Waters XTerra C18 RP 30×100, 0-17% AcN in 0.1 M TEAB, Akta Purifier) to give Dye-DA1 diacid (0.491 µmol, 90% yield). Carbonyldiimidazole (6.4 mg, 39.2 µmol, 80 eq) was added to a solution of Dye-DA1 diacid (0.491 µmol, 1.00 eq) in anhydrous DMF (100 µl) and the mixture was kept at rt in dark for 8 h. N-Hydroxysuccinimide (14.1 mg, 123 µmol, 250 eq) was added and after complete mixing the mixture was kept at rt in dark for 62 h. Ethyl acetate (1.5 ml) was added to the reaction mixture and the precipitated solid was separated by centrifuge. The solid was triturated with ethyl acetate (2×1.5 ml) and dried in HV to give Dye-DA1 bis NHS ester (0.49 µmol, quant. yield).

A solution of NH$_2$-6C-dG6P (18.6 µl, 79 mM, 1.47 µmol, 3.00 eq, DIEA salt) in aq. NaHCO$_3$ buffer (9.2 µl, 0.4 M) was added to a chilled solution of the Dye-DA1 bis NHS ester (0.49 µmol, 1.00 eq) in anhydrous DMA (50 µl). After complete mixing the solution was kept in dark at rt for 43 h. The product was purified by ion exchange chromatography on Q sepharose FF (GE, 0.05-1.5 M TEAB with 20% AcN, Akta Purifier) followed by a reverse phase HPLC (Waters XTerra C18 RP 30×100, 0-18% AcN in 0.1 M TEAB, Akta Purifier) to give 9a (0.278 µmol, 57% yield). LCMS: Calculated Mass 2681.22, Observed Mass 1339.4 (M$^{2-}$/2).

The approaches above can be used to produce, for example, polymerase substrates having two fluorescent dye moieties and one nucleoside phosphate moiety or polymerase substrates having one fluorescent dye moiety and two nucleoside phosphate moieties. The methods can be modified to prepare substrates having more than three substituents.

Example 10

Synthesis of Double Donor DiCytidine FRET Analog

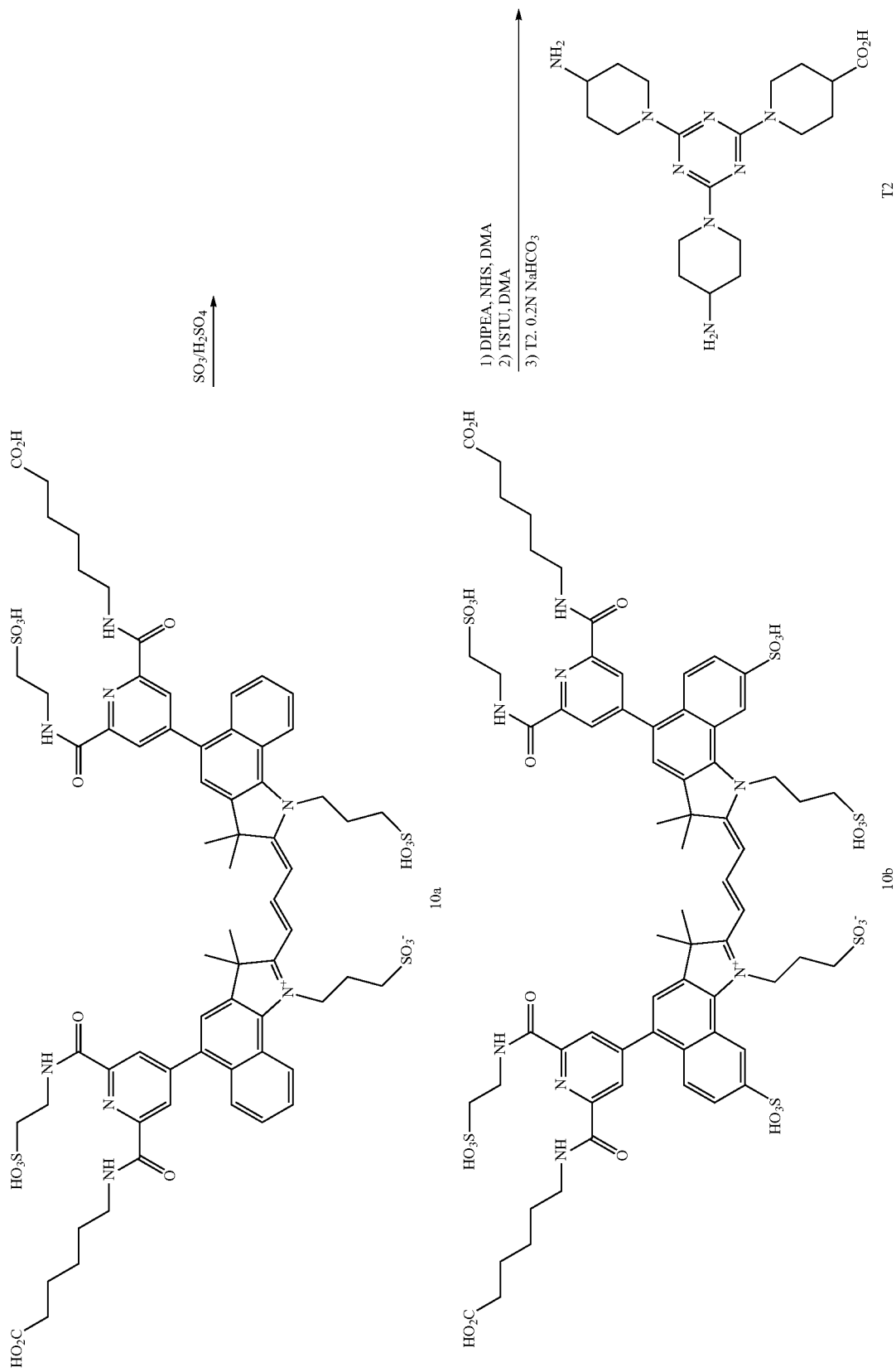

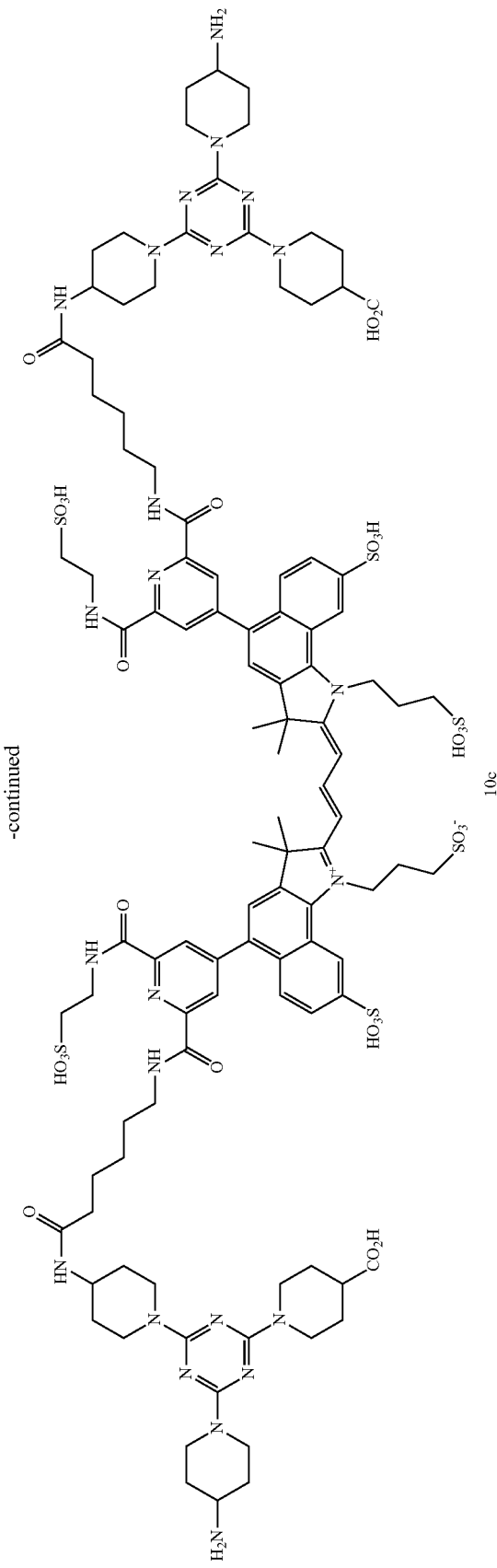
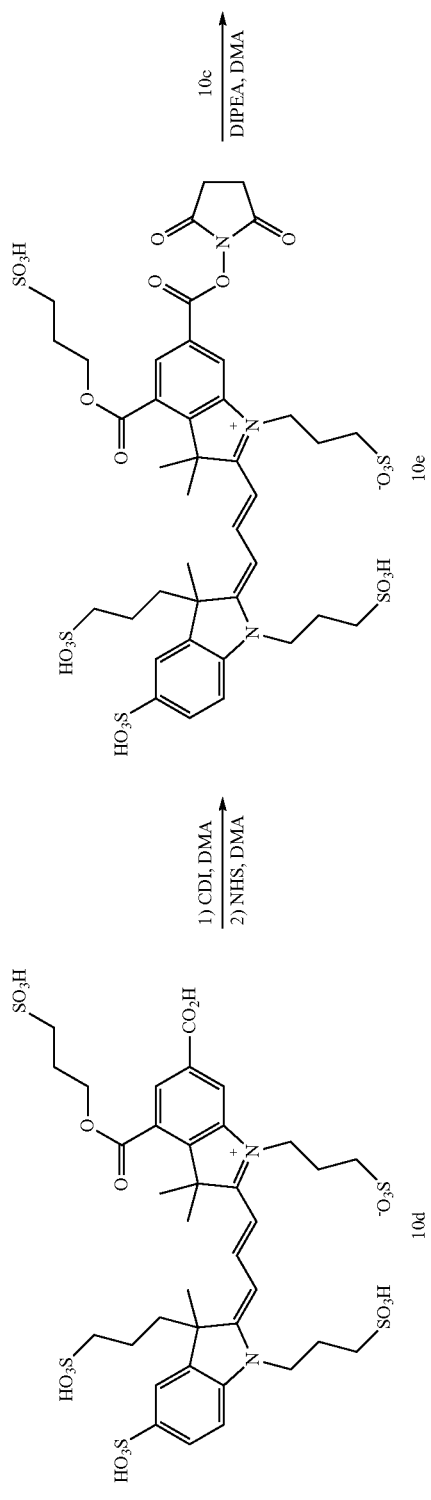

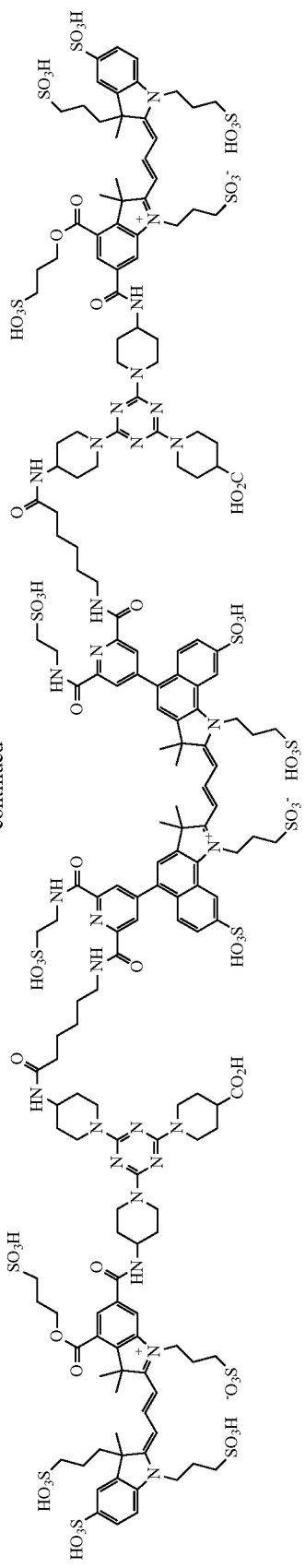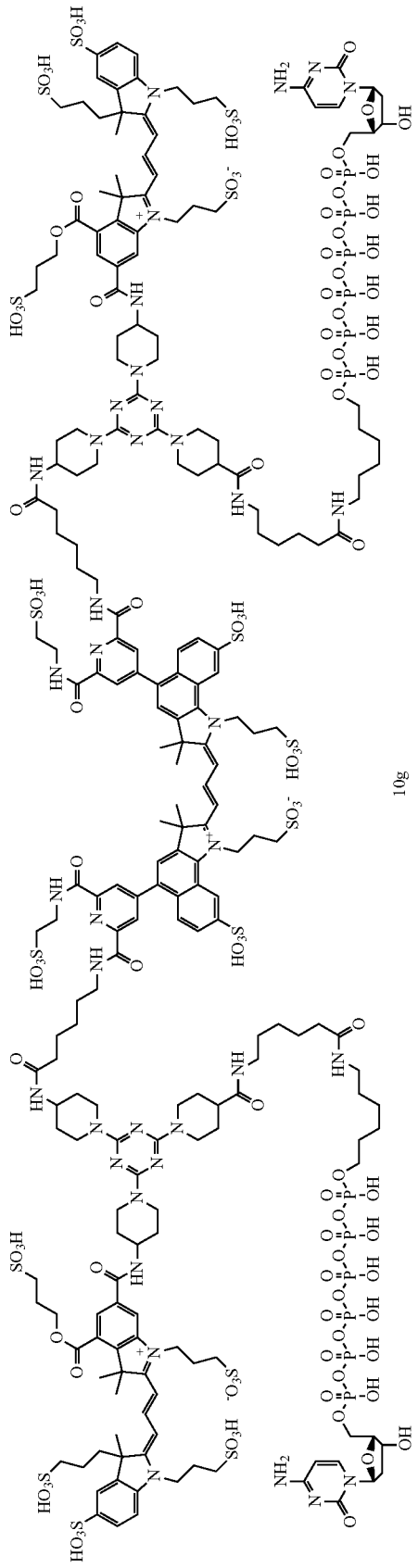

Synthesis of 10b: Fuming sulfuric acid (100 uL) was added to 10a (13.2 mg, 1.3 μmole), the reaction was agitated for 12 min at 25° C. The reaction was diluted with 1 mL EtOAc and 1 mL Et$_2$O, the precipitate was collected by centrifugation and purified by reverse phase HPLC eluted with a gradient of CH$_3$CN over 0.1 N TEAB buffer. The yield of the product, 10b, was 6.4 mg (44%).

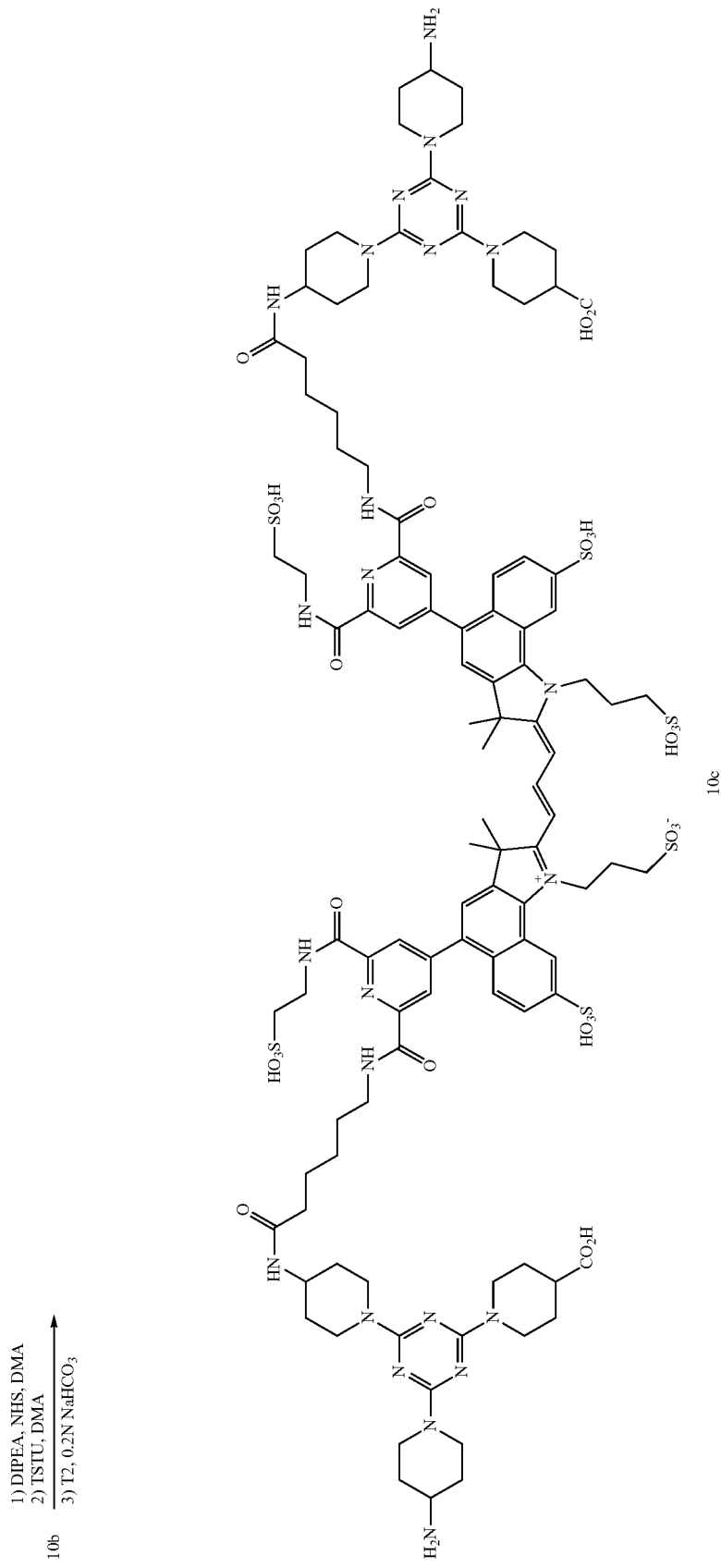

Synthesis of 10c: DIPEA (10 uL) and N-hydroxysuccinimide (1.78 mg, 15.4 μmole) was added to a solution of 10b (3.2 mg, 1.33 μmole) in 140 uL of DMA. The solution was agitated for 5 min and a solution of TSTU (4.1 mg, 14 μmole) in 70 uL of DMA was added. The reaction was agitated for 1 hr at 25° C. The bis-NHS ester was precipitated with 2 mL EtOAc, collected by centrifugation, redissolved in 70 uL of DMA, and added to a solution of T2 (5.1 mg, 12.6 mole) in 53 uL 0.2 N $NaHCO_3$ solution. The reaction was agitated for 1 hr and diluted with 5 mL of 0.1 N TEAB buffer pH 7.0 solution. The product was purified by reverse phase HPLC eluted with a gradient of $CH_3CN$ over 0.1 N TEAB buffer. The yield of the desired product, 10c, was 2.7 mg (0.93 μmole, 68%).

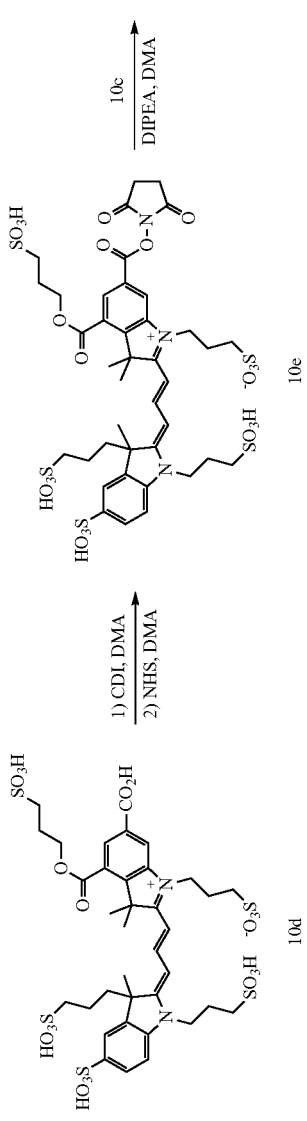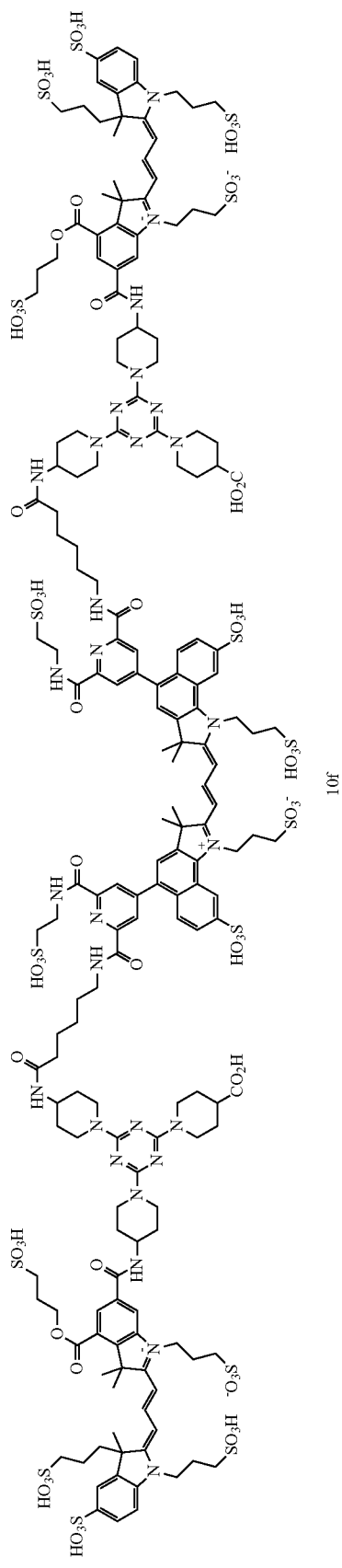

Synthesis of 10f: CDI (4.9 mh, 30 µmole) was added to a solution of 10d (4.1 mg, 2.8 µmole) in 210 uL DMA the reaction was agitated for 30 min follows by N-hydroxysuccinimide (4.6 mg, 40 µmole) the reaction was agitated for another 4 hr. The NHS ester, 10e, was precipitated with 2 mL EtOAc, collected by centrifugation, redissolved in 100 uL DMA, and added to a solution of 10 (2.7 mg, 0.93 pole) in 128 uL DMA and 10 uL DIPEA. The reaction was agitated for 15 hr at 25° C. and diluted with 5 mL of water. The product was purified by ion exchange chromatography eluted with an increasing gradient of 1.5 M TEAB buffer/ACN (4:1) over 0.05 M TEAB buffer/ACN (4:1). Fractions containing desired product were combined and further purified by reverse phase HPLC eluted with a gradient of $CH_3CN$ over 0.1 N TEAB buffer. The yield of the desired product, 10f, was 2.8 mg (0.48 µmole, 52%).

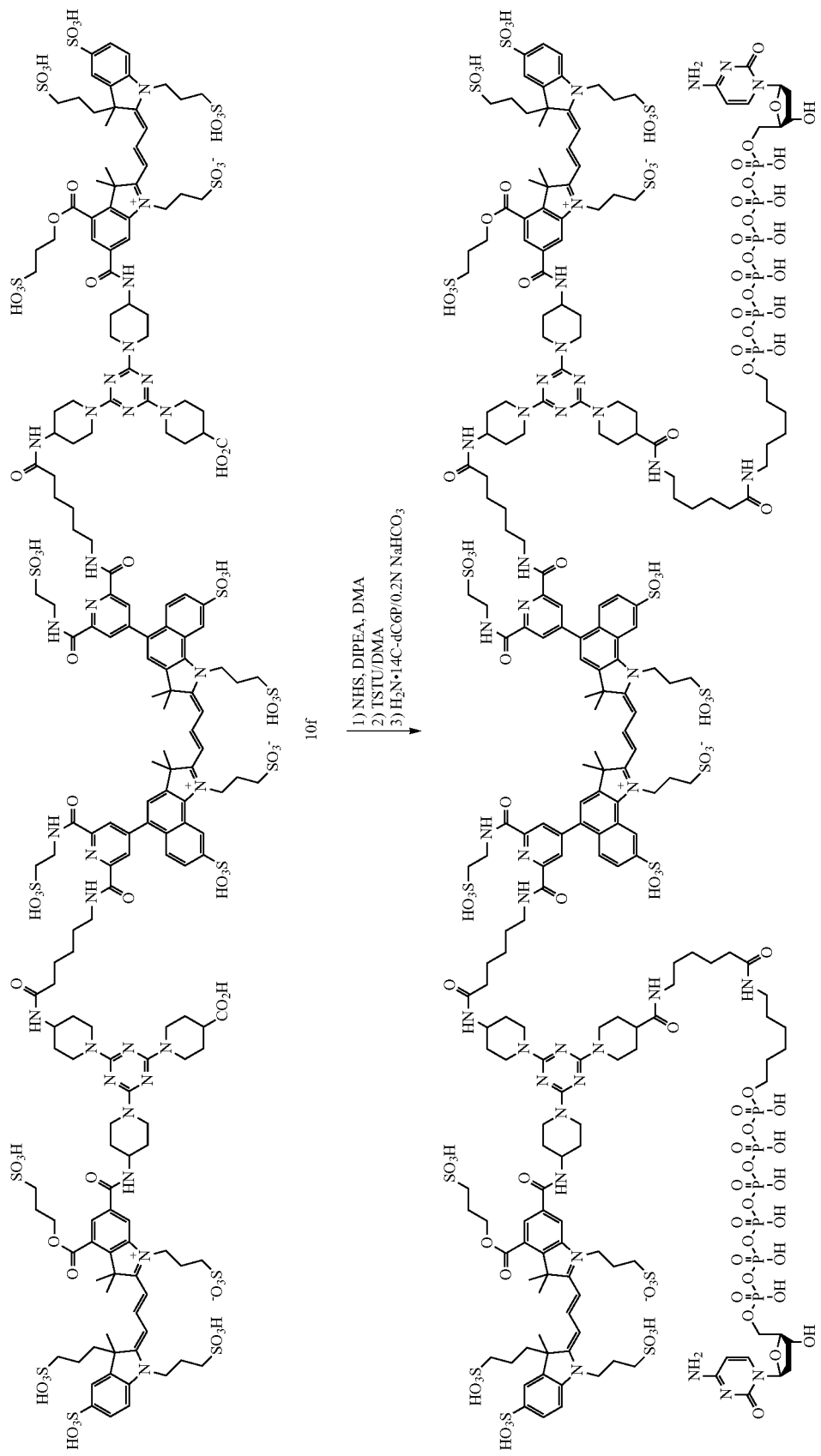

Synthesis of 10g: DIPEA (7 μL) and N-hydroxysuccinimide (1.78 mg, 15.4 μmole) was added to a solution of 10f (1.4 mg, 0.24 μmole) in 140 μL of DMA. The solution was agitated for 5 min and a solution of TSTU (4.1 mg, 14 μmole) in 70 μL of DMA was added. The reaction was agitated for 1 hr at 25° C. The bis-NHS ester was precipitated with 2 mL EtOAc, collected by centrifugation, dissolved in 70 μL of DMA, added to a solution of $H_2N$-14C-dC6P (3.6 μmole) in 30 μL of water and 70 μL of 0.2 N $NaHCO_3$. The reaction was agitated for 2 hr and diluted with 5 mL of water. The product was purified by ion exchange chromatography eluted with an increasing gradient of 1.5 M TEAB buffer/ACN (4:1) over 0.05 M TEAB buffer/ACN (4:1). Fractions containing desired product were combined and further purified by reverse phase HPLC eluted with a gradient of $CH_3CN$ over 0.1 N TEAB buffer. The yield of the desired product, 10g, was 0.10 μmole (42%). The compound 10g was used as a component in a single molecule sequencing reaction such as described in Eid, J. et al., Science, 323(5910), 133-138 (2009)). The compound showed better signal to noise, higher brightness, longer readlength, fewer missing pulses, and shorter interpulse distance than the control run with polymerase enzyme substrates having one dye and one nucleoside phosphate.

Example 11

Synthesis of Double Donor Di-Adenosine FRET Analog

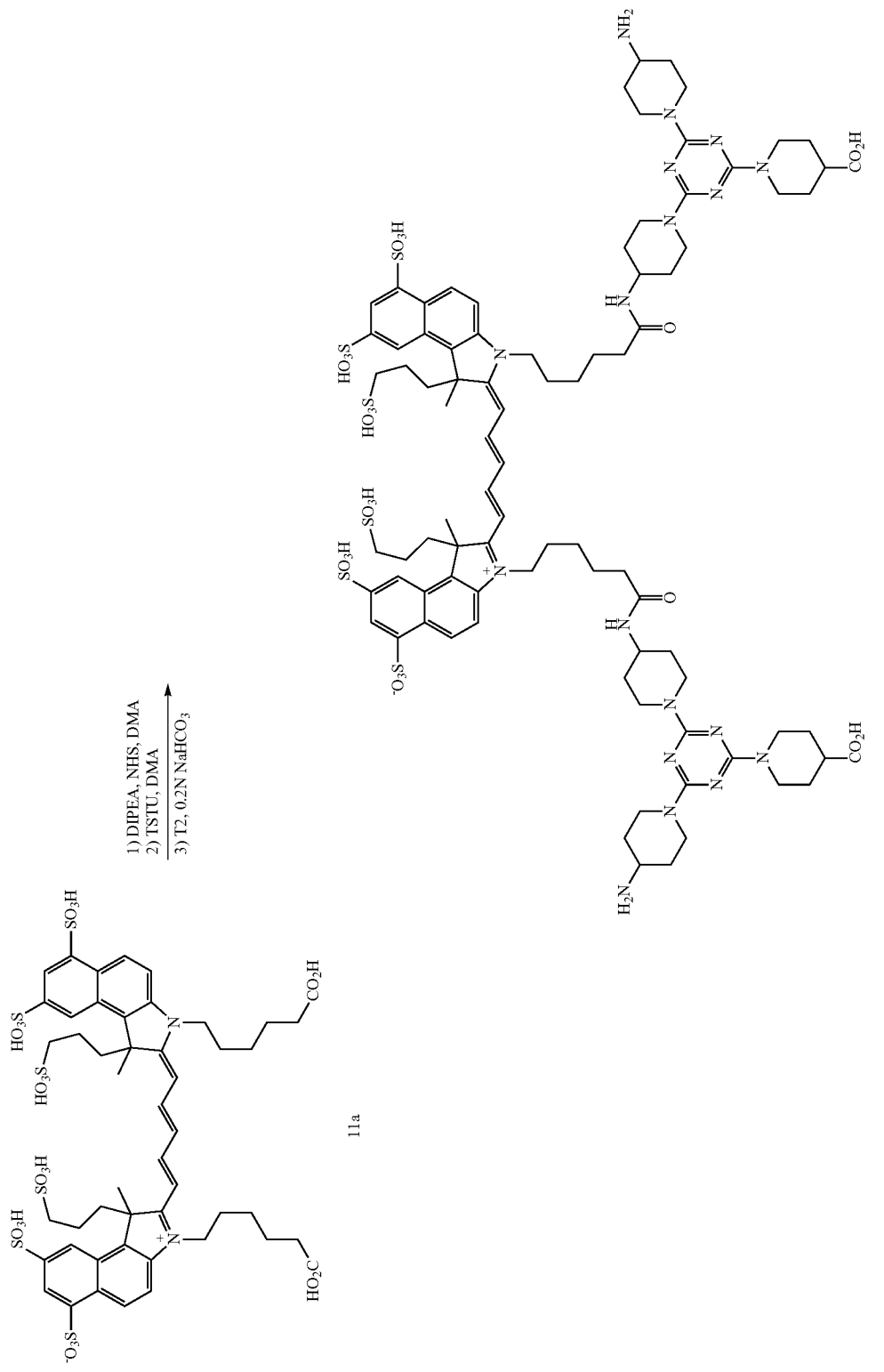

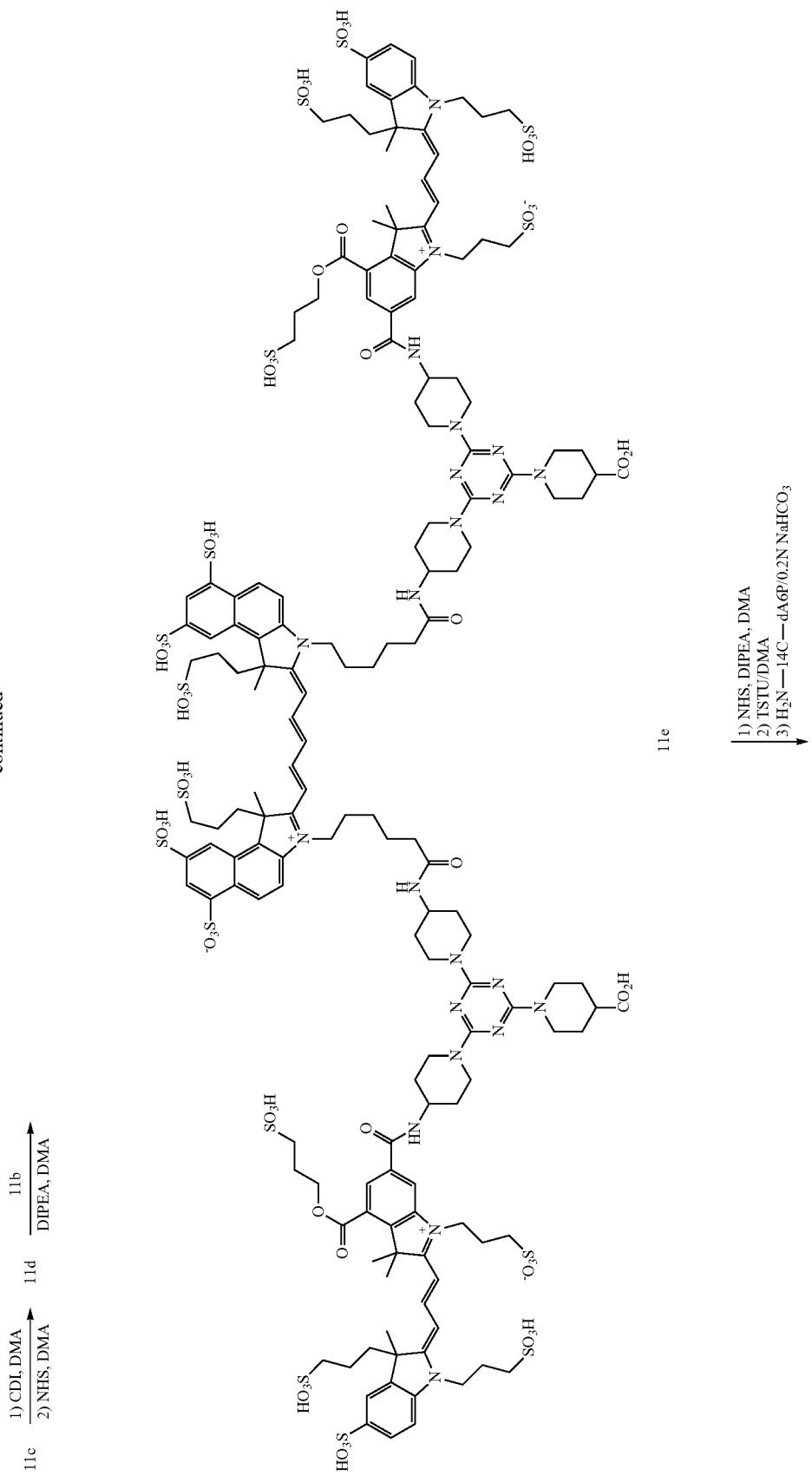

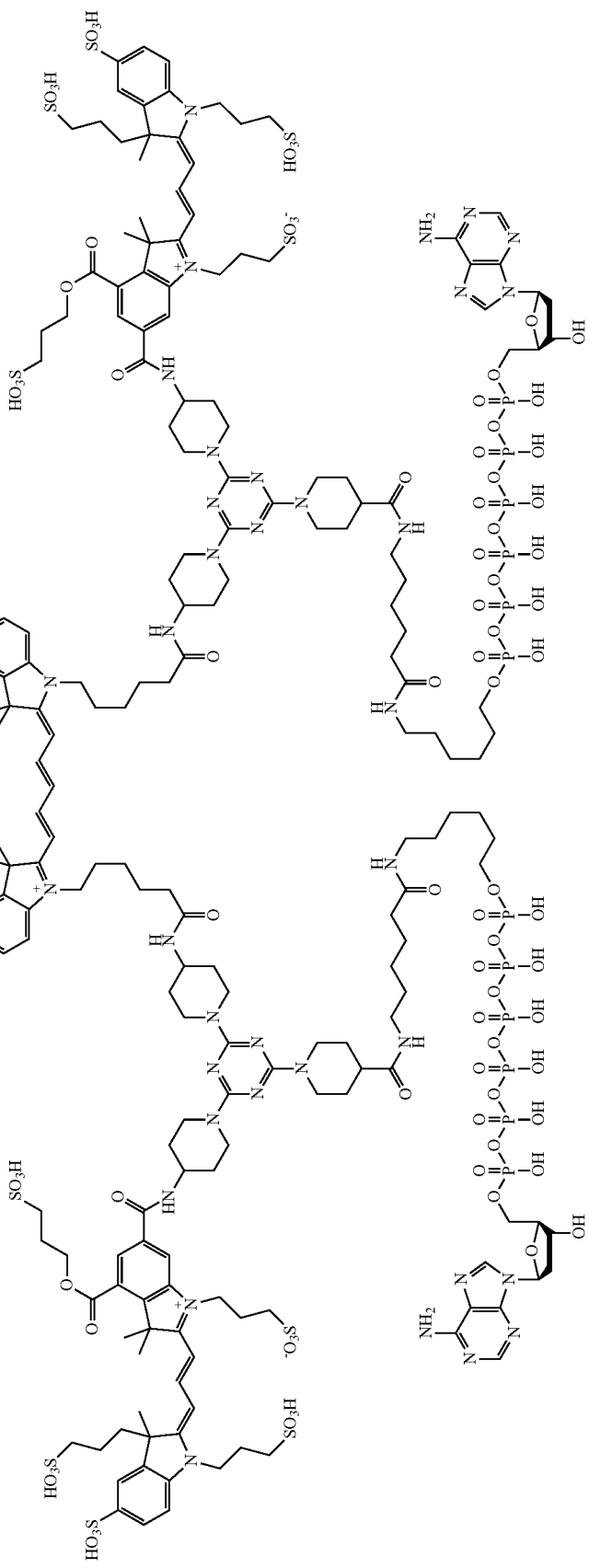
11f

Synthesis of 11f: Similar to the synthesis of 10g, starting from 11a, 11f can be prepared according to the above Scheme.

Example 12

Synthesis of Quadruple Donor TetraCytidine FRET Analog

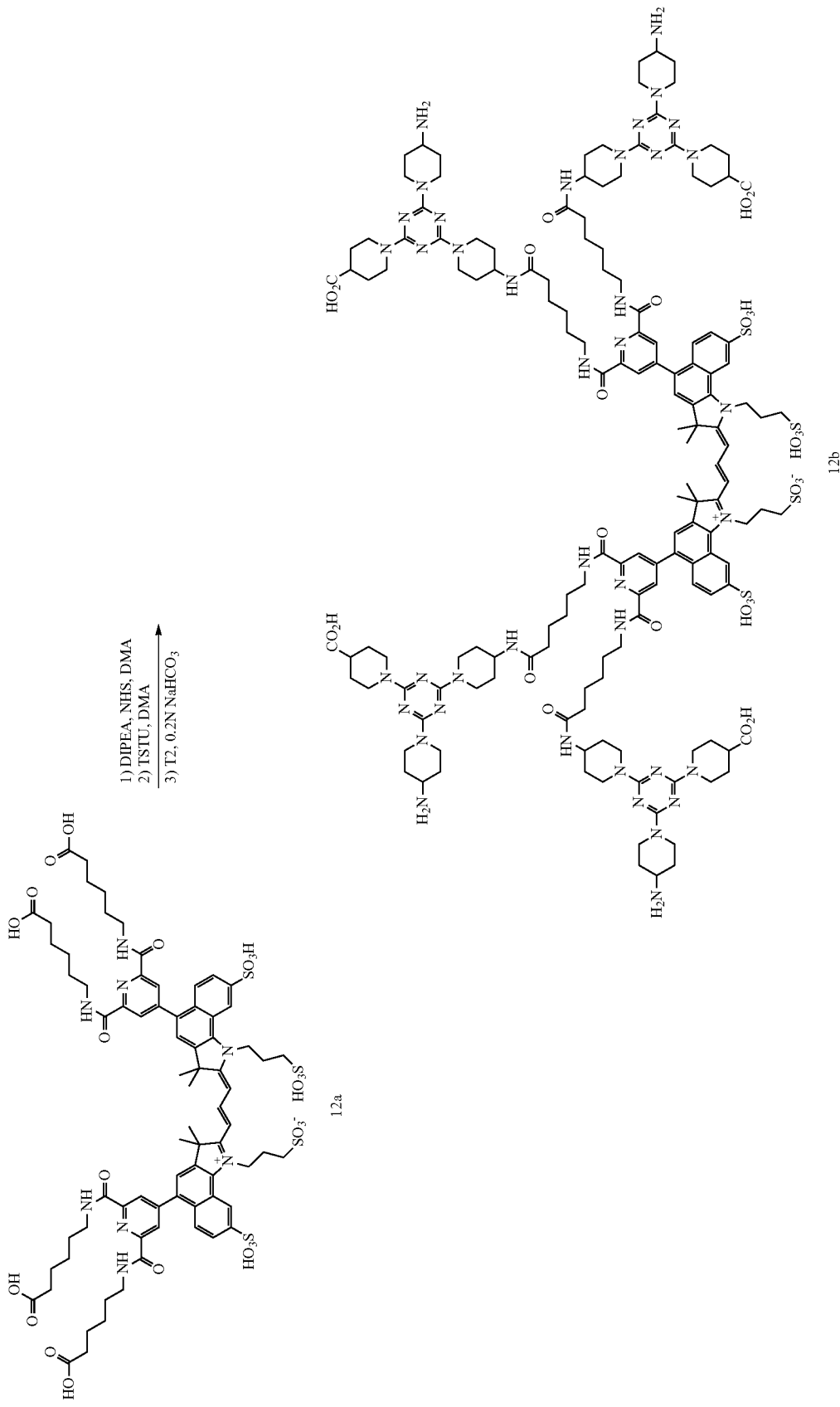

-continued
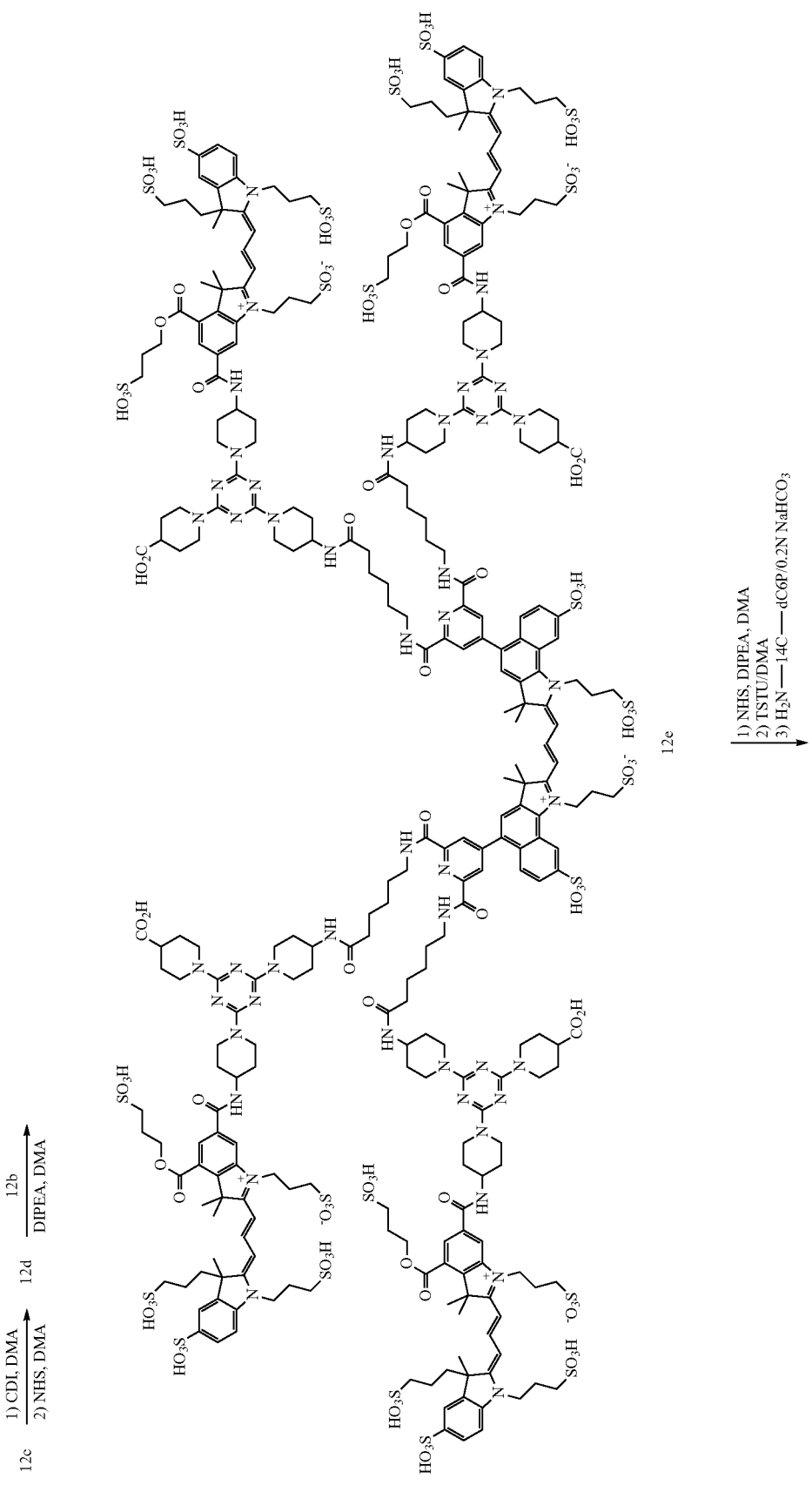

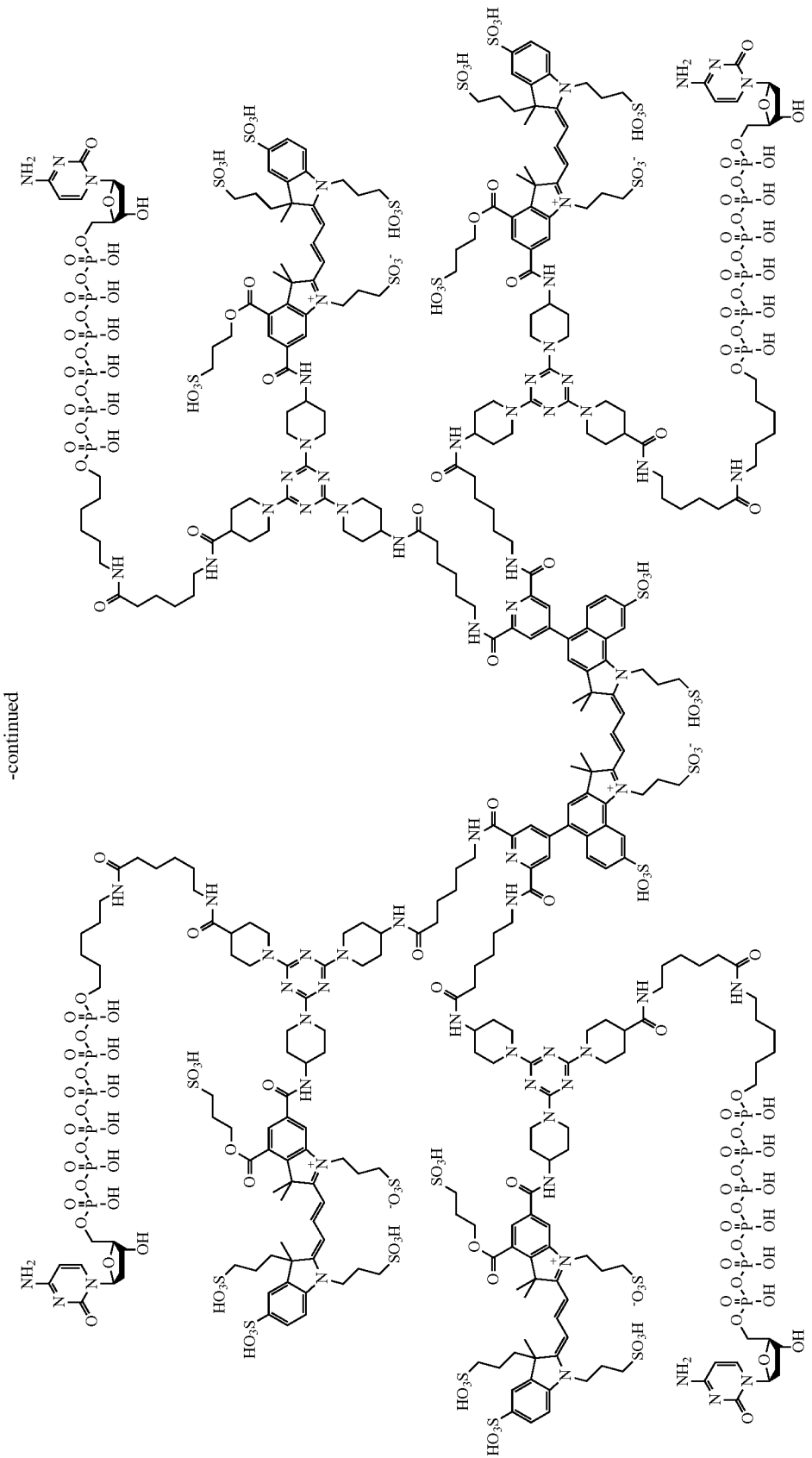

Synthesis of 12f: Similar to the synthesis of 10g, starting from 12a, 12f can be prepared according to the above Scheme.

Example 13

Single Molecule Real Time Sequencing

The polymerase enzyme substrates of the invention can be used for single molecule sequencing. For example, all of the compounds shown in FIGS. 18-22 were evaluated for their performance in single molecule sequencing using the method described in Eid, J. et al., Science, 323(5910), 133-138 (2009)). The compounds having multiple nucleosides were found to be faster substrates than compounds having a single nucleotide.

Example 14

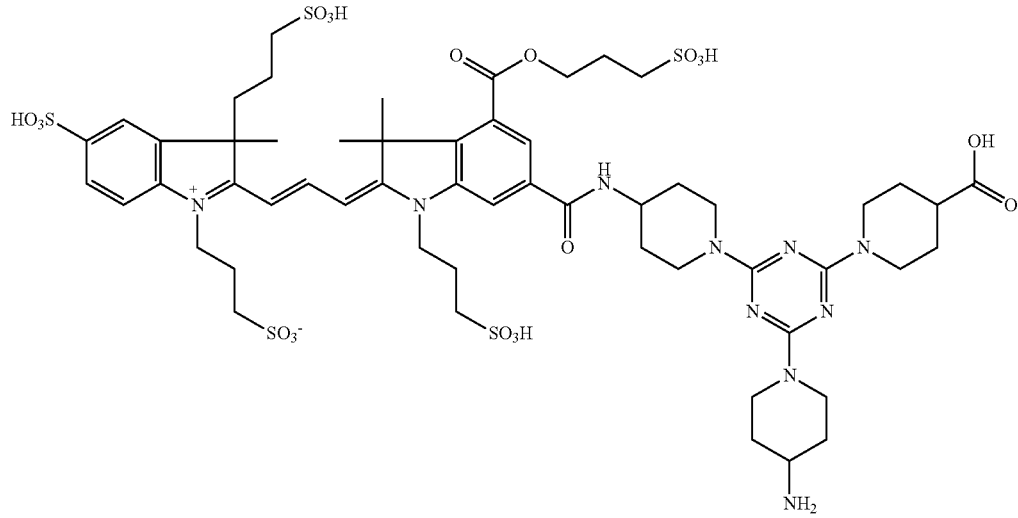

14a

Synthesis of (NH$_2$,Dye1)-T2 (14a). A solution of cyanine NHS ester (10.7 mg, 10.0 µmol, 1.0 eq) in anhydrous DMF (500.0 µl) was added to a chilled solution of (NH$_2$)$_2$-T2-COOH (1d, 50.0 µmol, 5.0 eq) in aq. sodium bicarbonate buffer (500.0 µl, 0.2 M, pH 8.3). After complete mixing, the solution was kept in dark at room temperature for 18 h. The product was purified by reverse phase HPLC (Waters XTerra C18 RP 19×100, 0-30% AcN in 0.1 M TEAB, Akta Purifier) to give 14a (0.900 µmol, 90% yield).

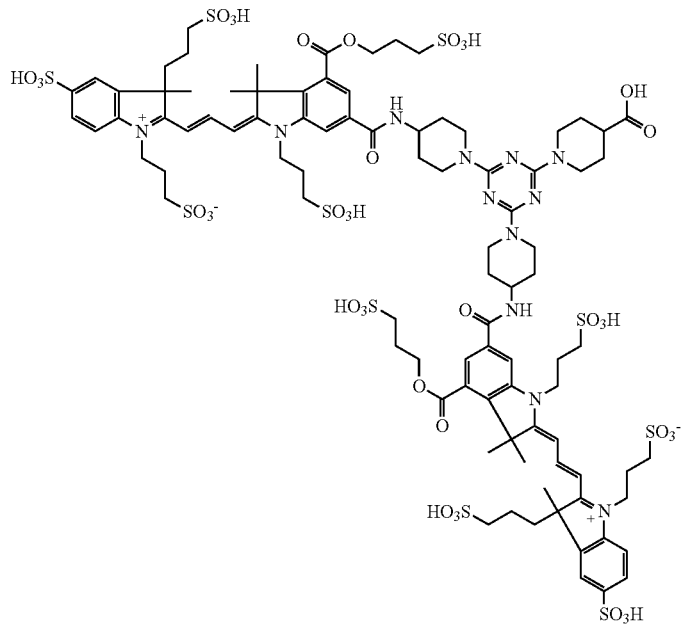

14b

Synthesis of (Dye1)₂-T2 (14). A solution of cyanine dye NHS ester (6.41 mg, 6.00 μmol, 1.2 eq) in anhydrous DMF (300.0 μl) was added to a chilled solution of (NH₂,Dye1)-T2 (14a, 5.00 μmol) in anhydrous DMF (300.0 μl) and aqueous bicarbonate buffer (60.0 μl, 0.2 M, pH 8.3). After complete mixing, the solution was kept in dark at room temperature for 18 h. The product was then purified by reverse phase HPLC (Waters XTerra C18 RP 19×100, 0-30% AcN in 0.1 M TEAB, Akta Purifier) to give 14b (4.60 μmol, 92% yield).

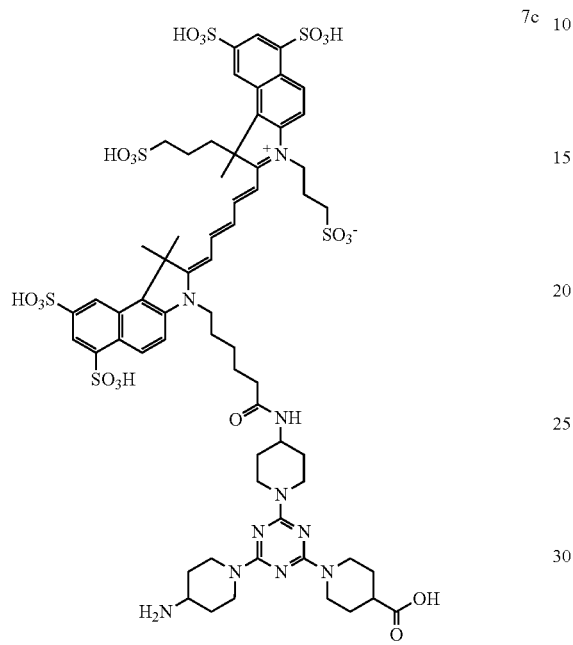

7c

Synthesis of (NH₂,Dye2)-T2 (14c). A solution of cyanine NHS ester (3.65 mg, 3.00 μmol, 1.0 eq) in anhydrous DMF (150.0 μl) was added to a chilled solution of (NH₂)₂-T2-COOH (1d, 15.0 μmol, 5.0 eq) in aq. sodium bicarbonate buffer (150.0 μl, 0.2 M, pH 8.3). After complete mixing, the solution was kept in dark at room temperature for 18 h. The product was purified by reverse phase HPLC (Waters XTerra C18 RP 19×100, 0-30% AcN in 0.1 M TEAB, Akta Purifier) to give 14a (2.55 μmol, 85% yield).

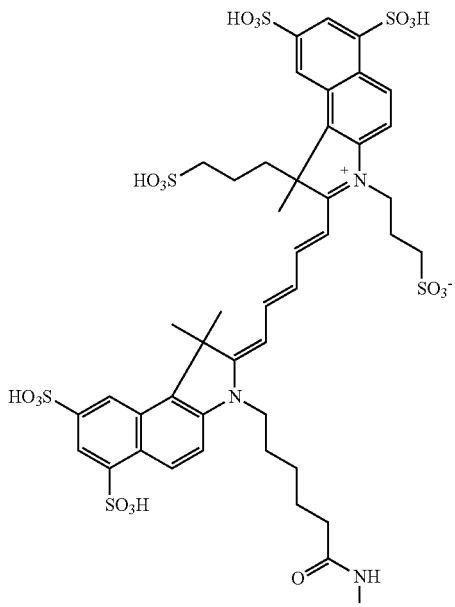

14d

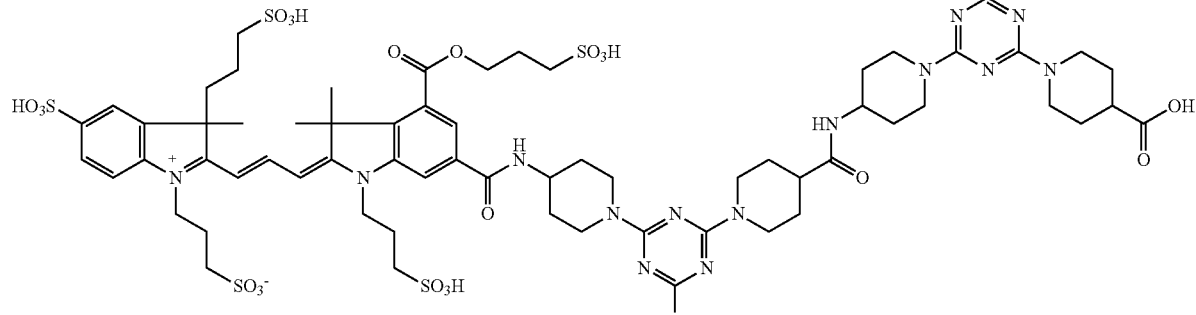

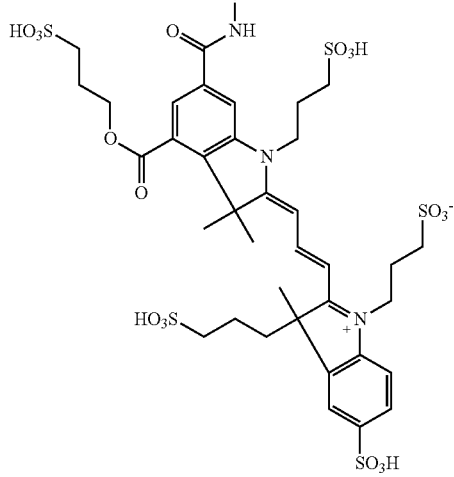

Synthesis of [(Dye1)$_2$-T2,Dye2]-T2 (14d). A solution of (Dye1)$_2$-T2 NHS ester (1.00 µmol), prepared from (Dye1)$_2$-T2 (7b) with carbonyl diimidazole (CDI) and N-hydroxysuccimide (NHS), in anhydrous DMF (100 µl) was added to a chilled solution of (NH$_2$,Dye2)-T2 (14c, 1.00 µmol) in anhydrous DMF (100 µl) and aqueous sodium bicarbonate buffer (40.0 µl, 0.2 M, pH 8.3). After complete mixing, the solution was kept in dark at room temperature for 18 h. The product was purified by reverse phase HPLC (Waters XTerra C18 RP 19×100, 0-30% AcN in 0.1 M TEAB, Akta Purifier) to give 14d (0.58 µmol, 58% yield).

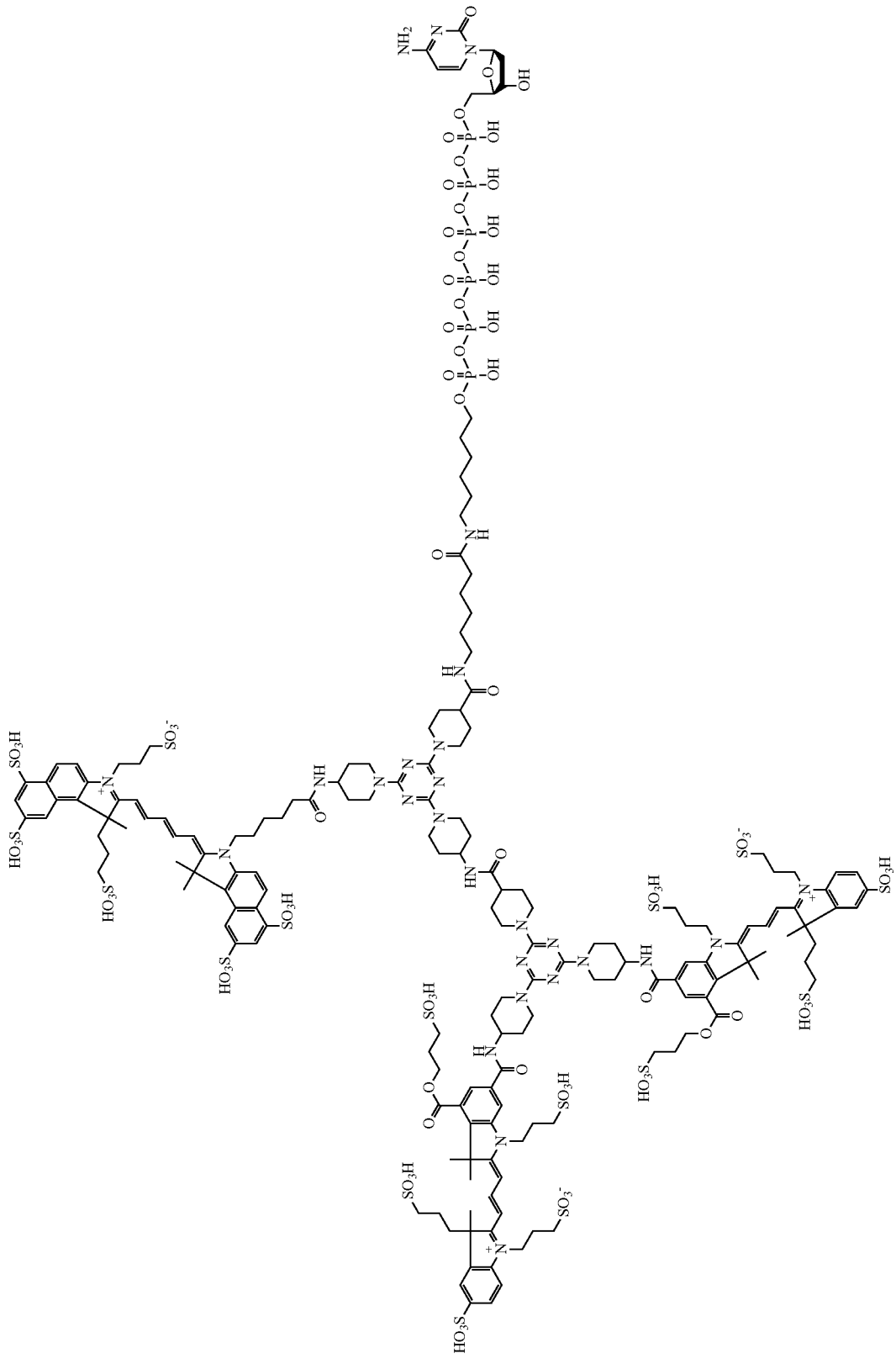

Synthesis of 14e. A solution of [(Dye1)$_2$-T2,Dye2]-T2 NHS ester (0.58 µmol), prepared from [(Dye1)$_2$-T2,Dye2]-T2 (7d) with carbonyl diimidazole (CDI) and N-hydroxysuccimide (NHS), in anhydrous DMF (100 µl) was added to a chilled solution of NH$_2$-14C-dC6P (1.00 µmol) in aq. sodium bicarbonate buffer (100.0 µl, 0.2 M, pH 8.3). After complete mixing, the solution was kept in dark at room temperature for 18 h. The product was then purified by ion exchange chromatography on Q sepharose FF (GE, 0.05-1.5 M TEAB with 20% AcN, Akta Purifier) followed by a reverse phase HPLC (Waters XTerra C18 RP 19×100, 0-33% AcN in 0.1 M TEAB, Akta Purifier) to give 14e (67 nmol, 12% yield, 887 µM, 75 µl).

Example 15

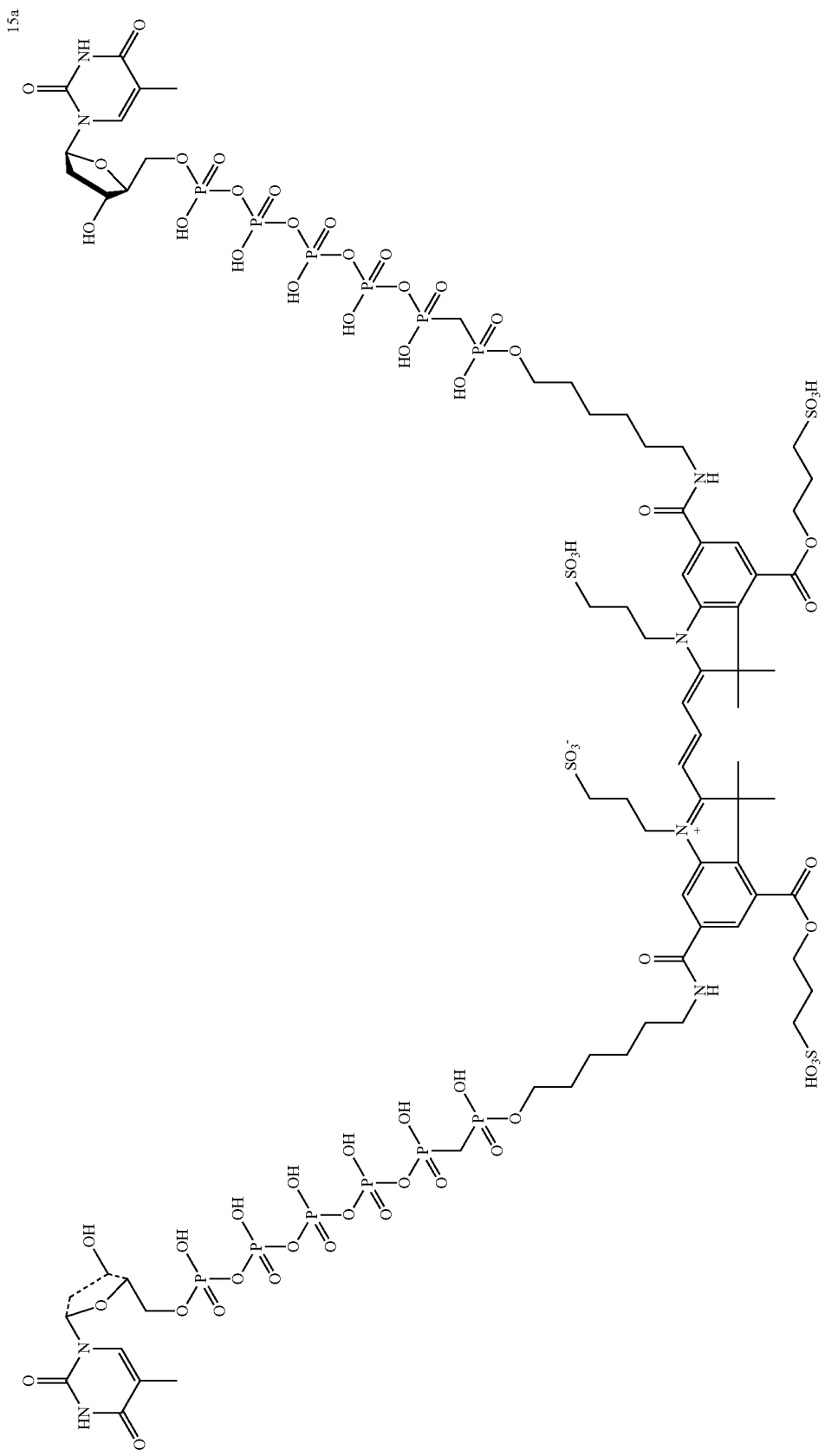

Synthesis of 15a. A solution of the cyanine bis-NHS ester (1.00 μmol), prepared from the corresponding cyanine dicarboxylic acid with carbonyl diimidazole (CDI) and N-hydroxysuccimide (NHS), in anhydrous DMF (100.0 μl) was added to a chilled solution of $NH_2$-14C-dT6P (3.00 μmol) in aq. sodium bicarbonate buffer (100.0 μl, 0.2 M, pH 8.3). After complete mixing, the solution was kept in dark at room temperature for 18 h. The product was then purified by ion exchange chromatography on Q sepharose FF (GE, 0.05-1.5 M TEAB with 20% AcN, Akta Purifier) followed by a reverse phase HPLC (Waters XTerra C18 RP 19×100, 0-33% AcN in 0.1 M TEAB, Akta Purifier) to give 15a (111 nmol, 11% yield, 1106 μM, 100 μl).

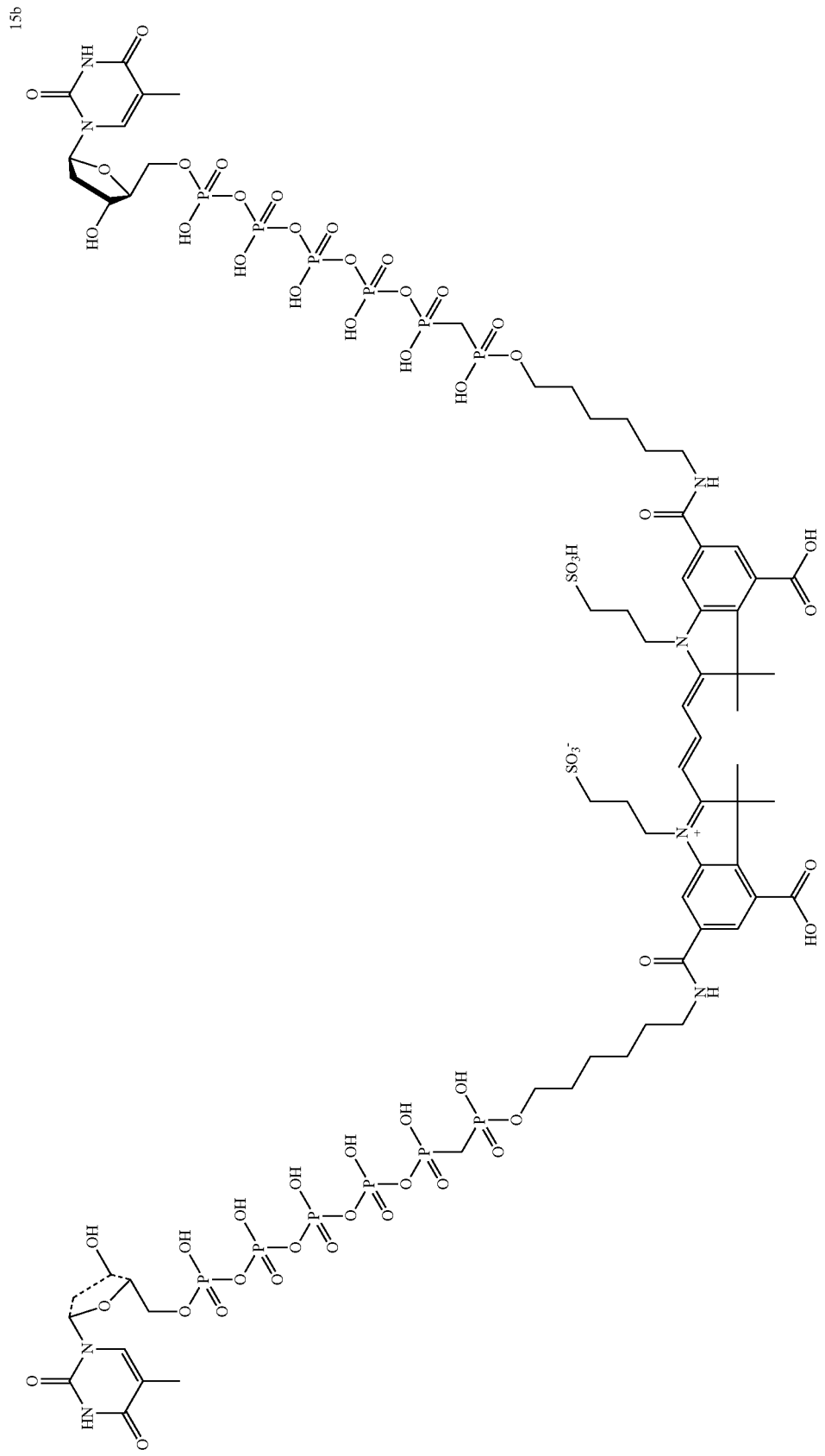

Synthesis of 15b. To the dried 15a (0.053 μmol) was added 10% aqueous sodium carbonate (600 μL) and the solution was kept in dark at room temperature for 18 h. The product was then purified by reverse phase HPLC (Waters XTerra C18 RP 19×100, 0-33% AcN in 0.1 M TEAB, Akta Purifier) to give 15b (35.2 nmol, 67% yield, 882 μM, 40 μl).

The present invention provides, inter alia, novel cyanine dyes, conjugates incorporating these dyes and method of using the dyes and conjugates. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A composition comprising a compound having the structure:

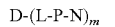

wherein D is a fluorescent dye moiety having m linking sites, L is a linker, P is a polyphosphate moiety having the structure:

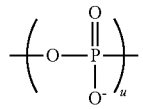

wherein u is from 2 to 10, N is a nucleoside moiety, and m is from 3 to 8.

2. The composition of claim 1 wherein D comprises a cyanine dye.

3. The composition of claim 1 wherein m is 3 or 4.

4. The composition of claim 1 wherein the compound has 2 to 40 sulfonate groups.

5. The composition of claim 1 wherein the compound is water soluble.

6. The composition of claim 1 wherein L is a linker having a linear or branched alkyl chain with 2 to 20 carbons.

7. The composition of claim 1 wherein each L-P-N in the compound is the same.

8. The composition of claim 1 wherein each N is A, G, C, T, or U.

9. The composition of claim 1 wherein D comprises a core having multiple covalently connected dyes.

10. The composition of claim 9 wherein number of dyes in the core is from 1 to about 12.

11. The composition of claim 1 wherein linker groups, L, comprise substituted or unsubstituted $C_6$-$C_{30}$ alkyl groups, polyols, polyethers, polyamines, amino acids, peptides, saccharides, or combinations thereof.

12. The composition of claim 1 wherein at least one of the linker groups, L, comprises one or more proline, pyrrolidine, or alkynyl moiety.

13. A sequencing mixture comprising a set of 4 nucleotide analog substrates, each having one of the bases A, G, C, T, or A, G, C, U, at least two of the substrates having the structure of claim 1, and each substrate having at least one fluorescent dye moiety different from the fluorescent dye moieties on the other three substrates.

14. The sequencing mixture of claim 13 wherein D comprises a cyanine dye.

15. The sequencing mixture of claim 13 wherein the compound has 2 to 40 sulfonate groups.

16. The sequencing mixture of claim 13 wherein L is a linker having a linear or branched alkyl chain with 2 to 20 carbons.

17. The sequencing mixture of claim 13 wherein each L-P-N in the compound is the same.

18. The sequencing mixture of claim 13 wherein D comprises a core having multiple covalently connected dyes.

19. The sequencing mixture of claim 18 wherein number of dyes in the core is from 1 to about 12.

20. The sequencing mixture of claim 13 wherein linker groups, L, comprise substituted or unsubstituted $C_6$-$C_{30}$ alkyl groups, polyols, polyethers, polyamines, amino acids, peptides, saccharides, or combinations thereof.

21. A method for nucleic acid sequencing comprising:
    immobilizing a polymerase enzyme complex comprising a polymerase enzyme and a template nucleic acid;
    exposing the immobilized polymerase enzyme complex to a plurality of labeled nucleotide analog substrates, at least one of the substrates comprising a compound having the structure of claim 1;
    detecting the incorporation of substrates by observing fluorescence from the nucleotide analog substrates; and
    using the detected incorporation over time to obtain sequence information about the template nucleic acid.

22. The method of claim 21 wherein D comprises a cyanine dye.

23. The method of claim 21 wherein the compound has 2 to 40 sulfonate groups.

24. The method of claim 21 wherein L is a linker having a linear or branched alkyl chain with 2 to 20 carbons.

25. The method of claim 21 wherein each L-P-N in the compound is the same.

26. The method of claim 21 wherein D comprises a core having multiple covalently connected dyes.

27. The method of claim 26 wherein number of dyes in the core is from 1 to about 12.

28. The method of claim 21 wherein linker groups, L, comprise substituted or unsubstituted $C_6$-$C_{30}$ alkyl groups, polyols, polyethers, polyamines, amino acids, peptides, saccharides, or combinations thereof.

* * * * *